US010323029B2

(12) United States Patent
Roberts et al.

(10) Patent No.: US 10,323,029 B2

(45) Date of Patent: Jun. 18, 2019

(54) SPHINOGOSINE-1-PHOSPHATE RECEPTOR MODULATORS FOR TREATMENT OF CARDIOPULMONARY DISORDERS

(71) Applicant: THE SCRIPPS RESEARCH INSTITUTE, La Jolla, CA (US)

(72) Inventors: Edward Roberts, Fallbrook, CA (US); Hugh Rosen, La Jolla, CA (US); Mariangela Urbano, Del Mar, CA (US); Miguel A. Guerrero, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/514,891

(22) PCT Filed: Sep. 28, 2015

(86) PCT No.: PCT/US2015/052611

§ 371 (c)(1),
(2) Date: Mar. 28, 2017

(87) PCT Pub. No.: WO2016/053855

PCT Pub. Date: Apr. 7, 2016

(65) Prior Publication Data

US 2017/0217963 A1 Aug. 3, 2017

Related U.S. Application Data

(60) Provisional application No. 62/056,946, filed on Sep. 29, 2014.

(51) Int. Cl.

| | |
|---|---|
| ***C07D 471/04*** | (2006.01) |
| ***C07D 213/61*** | (2006.01) |
| ***C07D 215/12*** | (2006.01) |
| ***C07D 213/38*** | (2006.01) |
| ***C07D 413/12*** | (2006.01) |
| ***C07D 213/40*** | (2006.01) |
| ***C07D 405/12*** | (2006.01) |
| ***C07D 401/12*** | (2006.01) |
| ***C07D 409/12*** | (2006.01) |
| ***C07D 239/30*** | (2006.01) |
| ***C07D 213/75*** | (2006.01) |
| ***C07D 333/20*** | (2006.01) |
| ***C07D 241/16*** | (2006.01) |
| ***C07D 237/08*** | (2006.01) |

(Continued)

(52) U.S. Cl.

CPC .......... *C07D 471/04* (2013.01); *C07C 255/63* (2013.01); *C07D 211/16* (2013.01); *C07D 213/38* (2013.01); *C07D 213/40* (2013.01); *C07D 213/55* (2013.01); *C07D 213/61* (2013.01); *C07D 213/75* (2013.01); *C07D 213/78* (2013.01); *C07D 213/80* (2013.01); *C07D 215/12* (2013.01); *C07D 217/18* (2013.01); *C07D 235/14* (2013.01); *C07D 237/08* (2013.01); *C07D 239/26* (2013.01); *C07D 239/30* (2013.01); *C07D 241/16* (2013.01); *C07D 241/42* (2013.01); *C07D 249/08* (2013.01); *C07D 263/32* (2013.01); *C07D 263/58* (2013.01); *C07D 271/06* (2013.01); *C07D 271/10* (2013.01); *C07D 285/12* (2013.01); *C07D 309/06* (2013.01); *C07D 309/14* (2013.01); *C07D 333/20* (2013.01); *C07D 401/12* (2013.01); *C07D 405/06* (2013.01); *C07D 405/12* (2013.01); *C07D 409/12* (2013.01); *C07D 413/04* (2013.01); *C07D 413/06* (2013.01); *C07D 413/12* (2013.01); *C07D 413/14* (2013.01); *C09B 55/002* (2013.01); *C09B 55/005* (2013.01); *C09B 55/007* (2013.01)

(58) Field of Classification Search

CPC .. C07C 255/63; C07D 471/04; C07D 213/38; C07D 213/40; C07D 213/55; C07D 213/61; C07D 213/75; C07D 213/80; C07D 215/12; C07D 217/18; C07D 235/14; C07D 237/08; C07D 239/26; C07D 239/30; C07D 241/16; C07D 241/42; C07D 249/08; C07D 263/32; C07D 263/58; C07D 271/06; C07D 271/10; C07D 333/20; C07D 401/12; C07D 409/12; C07D 413/04; C07D 413/12; C07D 413/14; C07D 405/12

USPC .......................................................... 514/249

See application file for complete search history.

(56) References Cited

U.S. PATENT DOCUMENTS

| | | | | |
|---|---|---|---|---|
| 7,947,712 B2 * | 5/2011 | Bursavich | ............ | C07D 215/26 514/312 |
| 2011/0065671 A1 * | 3/2011 | Harris | .................. | C07D 239/90 514/80 |
| 2013/0272962 A1 * | 10/2013 | Kugler | ................... | A61K 49/00 424/9.1 |

* cited by examiner

*Primary Examiner* — Kristin A Vajda

(74) *Attorney, Agent, or Firm* — Geoffrey K. Cooper; Thomas Fitting

(57) ABSTRACT

The invention provides compounds effective as sphingosine-1-phosphate receptor modulators for treatment of cardiopulmonary diseases, such as hypertension (including malignant hypertension), angina, myocardial infarction, cardiac arrhythmias, congestive heart failure, coronary heart disease, atherosclerosis, angina pectoris, dysrhythmias, cardiomyothopy (including hypertropic cardiomyothopy), heart failure, cardiac arrest, bronchitis, asthma, chronic obstructive pulmonary disease, cystic fibrosis, croup, emphysema, pleurisy, pulmonary fibrosis, pneumonia, pulmonary embolus, pulmonary hypertension, mesothelioma, ventricular conduction abnormalities, complete heart block, adult respiratory distress syndrome, sepsis syndrome, idiopathic pulmonary fibrosis, scleroderma, systemic sclerosis, retroperitoneal fibrosis, prevention of keloid formation, or cirrhosis.

12 Claims, No Drawings

(51) Int. Cl.

| | |
|---|---|
| ***C07D 239/26*** | (2006.01) |
| ***C07D 213/55*** | (2006.01) |
| ***C07D 235/14*** | (2006.01) |
| ***C07D 213/80*** | (2006.01) |
| ***C07D 263/32*** | (2006.01) |
| ***C07D 217/18*** | (2006.01) |
| ***C07D 249/08*** | (2006.01) |
| ***C07D 263/58*** | (2006.01) |
| ***C07D 241/42*** | (2006.01) |
| ***C07D 413/14*** | (2006.01) |
| ***C07D 413/04*** | (2006.01) |
| ***C07D 271/06*** | (2006.01) |
| ***C07D 271/10*** | (2006.01) |
| ***C07C 255/63*** | (2006.01) |
| ***C09B 55/00*** | (2006.01) |
| ***C07D 213/78*** | (2006.01) |
| ***C07D 309/06*** | (2006.01) |
| ***C07D 309/14*** | (2006.01) |
| ***C07D 405/06*** | (2006.01) |
| ***C07D 413/06*** | (2006.01) |
| ***C07D 285/12*** | (2006.01) |
| ***C07D 211/16*** | (2006.01) |

SPHINOGOSINE-1-PHOSPHATE RECEPTOR MODULATORS FOR TREATMENT OF CARDIOPULMONARY DISORDERS

CROSS-REFERENCE TO RELATED APPLICATION

This application claims the priority of U.S. provisional application Ser. No. 62/056,946, filed Sep. 29, 2014, the disclosure of which is incorporated by reference herein in its entirety.

STATEMENT OF GOVERNMENT SUPPORT

This invention was made with government support under MH084512, awarded by the National Institutes of Health. The government has certain rights in the invention.

BACKGROUND

Antagonism of the subtype 3 of the sphingosine-1-phosphate receptors (S1PRs) is proposed to have therapeutic utility in asthma, chronic obstructive pulmonary diseases, as well as additional therapeutic utilities based upon receptor expression and the effects of pharmacological antagonism of gene deletion. Five high affinity G-protein coupled receptors for sphingosine 1-phosphate (S1P) are identified (1) and the crystal structure of $S1PR_1$ has been solved (2). This cluster of receptors is medically important because the non-selective S1PR agonist fingolimod is an effective oral therapy for the treatment of relapsing-remitting multiple sclerosis by altering lymphocyte function. Various S1P receptor subtypes that differ in spatial distribution, coupling and function can singly or in combination, play complex roles in embryonic formation of the arterial media, blood pressure regulation and cardiac function. FTY720 (fingolimod) in man is associated with significant sinus bradycardia, heart block and a prolongation of QTc interval (3, 4). Atropine reversal of the sinus bradycardia (5) and the demonstration of sinus bradycardia with $S1PR_1$-selective agonists in man (6) as well as rodents (7) suggested that sino-atrial (SA) node effects and those events resulting from alterations in ventricular conduction are distinctly regulated. Mice deficient in $S1PR_3$ are resistant to a variety of pharmacological effects produced by agonists of $S1PR_3$ including pulmonary and cardiac fibrosis (8-10), cardiac arrhythmias (11) as well as being resistant to complex pathologies such as cytokine storm and sepsis syndrome.

Sepsis syndrome, a consequence of infection and characterized by a state of uncontrolled systemic inflammation, kills approximately 200,000 people per year in the US (12, 13). According to global estimates, the incidence of sepsis is believed to range from 140-240 cases per 100,000, with fatality rates as high as 30%. If associated with circulatory collapse and end-organ failures, fatality rates remain in 50-80% range (14, 15). The 1979-2000 epidemiologic sepsis study estimated a 17 billion annual cost of sepsis care in the US (16), a value that is likely to be higher today due to the increased cost of healthcare. Although early intervention and modern supportive care practices in sepsis have slightly increased in overall sepsis survival rates, to 37 to 30% (17-21), there is still an obvious unmet medical need that requires development of new therapeutic strategies to combat this healthcare burden.

Despite measures to alter pathogen burden, and intensive supportive care, sepsis syndrome has high morbidity, mortality and a significant cost burden, reflecting imbalance between pro-inflammatory cytokines and elements of inflammation essential for host protection (22). Recent work defining the signature for key elements regulating systemic inflammation, has defined new, chemically tractable targets for therapeutic intervention that are genetically validated in animal models. Our recent work has demonstrated that blunting not abolishing host responses and cytokine storm provides important protection from immunopathology while sparing antiviral immune responses (23-25). In bacterial infections we have now demonstrated by both genetic deletion of receptor (26), as well as with the use of early selective, neutral antagonists, that S1P signaling via $S1PR_3$ on dendritic cells (DC) exacerbates systemic inflammation and lethality in stringent models of sepsis, i.e. both LPS-induced inflammation and in cecal ligation puncture (CLP) models.

Sepsis syndrome is a significant unmet medical need, as no effective treatment options exist beyond antimicrobial therapies and supportive intensive care. Behind this medical challenge lie multiple, complex pathological endpoints that coalesce in final common pathways of end-organ failure, and prospective identification of patient subsets is a work in progress. None-the-less, the importance of the unmet medical need, coupled with new mechanistic insights into shared critical pathways, offers new opportunities for mechanism-based interventions. Characteristic pathological symptoms of severe sepsis include profound inflammation, dysregulated coagulation, tissue microvascular edema, cardiovascular collapse, renal dysfunction and ultimately death. An additional long-term consequence is pulmonary fibrosis. These symptoms result primarily from the hyper-activation of the host's immune system reacting to the pathogen's invasion (27, 28). Understanding the factor(s) regulating the onset and progression of the host's immune overactivation is relevant for designing novel effective therapies for sepsis. Multiple lines of evidence support crucial roles for S1PRs in the control of immune cell trafficking and cardiovascular functions in physiology and disease (29, 30). S1P, a circulating bioactive lysophospholipid derived from the ceramide pathway binds to and activates five closely related G-protein coupled receptors, referred to as $S1PR_{1-5}$. Interestingly, human diseases with an active inflammatory component, such as multiple sclerosis (MS), coronary atherosclerosis, and lupus, have elevated plasma or local S1P levels (31-34). In the case of sepsis, there is even plasma elevation of a major S1P carrier lipoprotein, Apoprotein M, in disease subjects, and is now a risk factor for poor prognosis (35, 36). Thus it is likely that S1P signaling tone is consequently altered in septicemia. Since discontinuation of Xigris (37), an intended target of the endothelial components of sepsis, and since immunosuppressive corticosteroidal therapy can be controversial due to adrenal insufficiency occurring in sepsis (38, 39), there is a limited arsenal to combat sepsis. Inhibiting, with a systemic selective small molecule antagonist, $S1PR_3$ on DCs, on vascular smooth muscle, coronary artery smooth muscle and bronchial smooth muscle can contribute to improving the therapeutic outcome in multiple clinical syndromes characterized by bronchoconstriction, pulmonary fibrosis, coronary artery constriction, cytokine amplification by dendritic cells, as well as the generation of disseminated intravascular coagulopathy, based upon data showing that $S1PR_3$ signaling contributes to pro-inflammatory signals, fibrosis and to poor sepsis outcome.

Previous findings indicated that $S1PR_3$ deficient DCs (taken from $S1PR_3$ knockouts), significantly enhanced the survival of mice administered with a 90% lethal dose (LD90) of LPS or in mice following the Cecal Ligation Puncture (CLP) model of polymicrobial sepsis (26). Most importantly, the study pointed out that treatment with AUY954, a selective $S1P_1$ agonist that sequesters B- and T-lymphocytes from the blood (40), and is useful for dampening inflammation in animal models of localized inflammation (41), did not infer any protection in the same study. Another report using similar transfer methods has just shown that $S1PR_3$-deficiency in DCs significantly blunted pro-inflammatory mediators in renal ischemia/reperfusion studies and lowered kidney immunopathology in mice (42). Interesting, the authors further implicated IL-4 signaling as a downstream mediator of the $S1PR_3$ deficiency benefits in renal ischemia/reperfusion. Furthermore, siRNA knockdown of $S1PR_3$ in bone marrow derived DCs (BMDC) greatly reduced transwell DC migration, and migration to the mesenteric lymph node (43), suggesting that $S1PR_3$ is directly involved in DC migration. Overall, the available evidence strongly suggests that down-modulating $S1PR_3$ DC signaling, as proposed with a systemic $S1PR_3$ antagonist, may open a new therapeutic opportunity in sepsis syndrome. These data strongly suggest that an $S1PR_3$ antagonist may be valuable during the early management period of sepsis care, characterized as the critical therapeutic window with potential for boosting survival (44) (45).

SUMMARY

The invention provides, in various embodiments, a compound of formula (I)

(I)

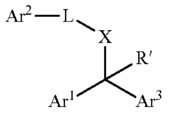

wherein each of $Ar^1$, $Ar^2$, and $Ar^3$ is independently selected (C6-C10)aryl ring system or a (5- to 10-membered) heteroaryl ring system, wherein any aryl or heteroaryl ring system of $Ar^1$, $Ar^2$, or $Ar^3$ is optionally fused with a cycloalkyl or a heterocyclyl ring;

wherein any aryl or heteroaryl of $Ar^1$, $Ar^2$, or $Ar^3$ is each optionally independently mono- or multi-substituted with up to three substituents selected from the group consisting of (C1-C4)alkyl, (C2-C4)alkenyl, halo, halo(C1-C4)alkyl, OH, monohydroxy(C1-C4)alkyl, dihydroxy(C2-C4)alkyl, monohydroxy(C1-C4)alkoxy, dihydroxy(C2-C4)alkoxy, (C1-C4) alkoxy, (C2-C6)acyl, (C1-C6)alkoxycarbonyl$(CH_2)_{0-2}$, carboxy$(CH_2)_{0-2}$, oxo, cyano, $NR_2(CH_2)_{0-2}$, $NR_2C({=}O)(CH_2)_{0-2}$, $NR_2C({=}O)(CH_2)_{0-2}O(CH_2)_{0-2}$, (C1-C4)C(=O)N(R), (C1-C4)OC(=O)N(R), C=NOR, (C3-C10)cycloalkyl, (5- to 10-membered)heterocyclyl, (C6-C10)aryl, and (5- to 10-membered) heteroaryl; wherein any cycloalkyl, heterocyclyl, aryl or heteroaryl substituent of $Ar^1$, $Ar^2$, or $Ar^3$ is itself optionally substituted with up to three secondary substituents selected from the group consisting of (C1-C4)alkyl, (C2-C4)alkenyl, halo, halo(C1-C4) alkyl, OH, monohydroxy(C1-C4)alkyl, dihydroxy(C2-C4) alkyl, monohydroxy(C1-C4)alkoxy, dihydroxy(C2-C4) alkoxy, (C1-C4)alkoxy, (C2-C6)acyl, (C1-C6) alkoxycarbonyl$(CH_2)_{0-2}$, carboxy$(CH_2)_{0-2}$, oxo, cyano, $NR_2(CH_2)_{0-2}$, $NR_2C({=}O)(CH_2)_{0-2}$, $NR_2C({=}O)(CH_2)_{0-2}O(CH_2)_{0-2}$, (C1-C4)C(=O)N(R), (C1-C4)OC(=O)N(R), and C=NOR;

each R is independently H, (C1-C4)alkyl, hydroxy(C2-C4)alkyl, cyano, or $((C1\text{-}C4)alkyl\text{-}O)_{1-2}(C1\text{-}C4)alkyl$, or two R groups together with an atom to which they are both joined can form a ring;

each R' is independently H, (C1-C4)alkyl, hydroxy(C2-C4)alkyl, $(CH_2)_{0-2}C({=}O)O(C1\text{-}C4)alkyl$, or (C3-C6)cycloalkyl;

X is a bond, $(CH_2)_{1-2}$, $(CH_2)_{0-2}N(R)(CH_2)_{0-2}$, $(CH_2)_{0-2}O(CH_2)_{0-2}$, $(CH_2)_{0-2}N(R)C({=}O)(CH_2)_{0-2}$, $(CH_2)_{0-2}C({=}O)N(R)(CH_2)_{0-2}$, $(CH_2)_{0-2}N(R)C({=}O)O(CH_2)_{0-2}$, or $(CH_2)_{0-2}OC({=}O)N(R)(CH_2)_{0-2}$;

L is a bond, NR, $SO_2$, C(=NR), $C({=}O)CR_2$, C(=O)CH(N(R)C(=O)(C1-C4)alkyl, C(=O)CH(N(R)C(=O)O(C1-C4)alkyl, $C({=}O)CH(NR_2)$, C(=O)CR(halo), or is

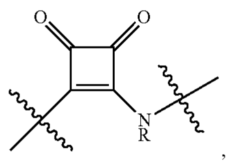

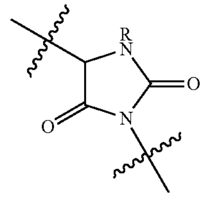

, or wherein wavy lines indicate points of bonding, or a pharmaceutically acceptable salt thereof.

For example, the compound can be of formula (IA)

(IA)

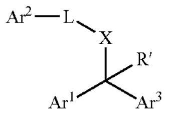

wherein each of $Ar^1$, $Ar^2$, and $Ar^3$ is independently selected aryl; X, L, R, and R' are as defined herein.

For example, the compound can be of formula (IB)

(IB)

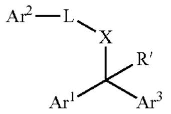

wherein $Ar^1$ and $Ar^2$ are independently selected aryl and $Ar^3$ is heteroaryl; X, L, R, and R' are as defined herein.

For example, the compound can be of formula (IC)

(IC)

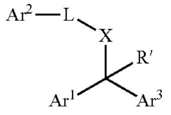

wherein $Ar^1$ is aryl, $Ar^2$ and $Ar^3$ are independently selected heteroaryl; X, L, R, and R' are as defined herein.

For example, the compound can be of formula (ID)

(ID)

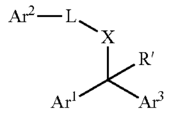

wherein $Ar^1$ and $Ar^3$ are independently selected aryl, and $Ar^2$ is heteroaryl; X, L, R, and R' are as defined herein.

For example, the compound can be of formula (IE)

(IE)

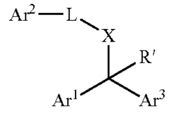

wherein $Ar^1$ and $Ar^3$ are independently selected heteroaryl, and $Ar^2$ is aryl; X, L, R, and R' are as defined herein.

In various embodiments, the invention provides a pharmaceutical composition comprising a compound of the invention and a pharmaceutically acceptable excipient.

The invention further provides, in various embodiments, a method of treatment of a cardiopulmonary disease in a patient afflicted therewith, comprising administering an effective amount of a compound of the invention. For instance, the disease can be asthma or a chronic obstructive pulmonary disease; or, the disease can comprises sepsis; or, wherein the disease is coronary atherosclerosis. In various embodiments, the invention provides a method of treatment wherein the disease comprises a clinical syndrome characterized by bronchoconstriction, pulmonary fibrosis, coronary artery constriction, cytokine amplification by dendritic cells, or the generation of disseminated intravascular coagulopathy. More specifically, the invention provides a method of treatment of a disease in a patient afflicted therewith wherein the disease comprises inflammation by influenza infection, or wherein the disease is cardiovascular disease, hypertension (including malignant hypertension), angina, myocardial infarction, cardiac arrhythmias, congestive heart failure, coronary heart disease, atherosclerosis, angina pectoris, dysrhythmias, cardiomyothopy (including hypertropic cardiomyothopy), heart failure, cardiac arrest, bronchitis, asthma, chronic obstructive pulmonary disease, cystic fibrosis, croup, emphysema, pleurisy, pulmonary fibrosis, pneumonia, pulmonary embolus, pulmonary hypertension, mesothelioma, ventricular conduction abnormalities, complete heart block, adult respiratory distress syndrome, sepsis syndrome, idiopathic pulmonary fibrosis, scleroderma, systemic sclerosis, retroperitoneal fibrosis, prevention of keloid formation, or cirrhosis.

Accordingly, the invention provides, in various embodiments, a medical use comprising use of a compound of the invention, such as in a pharmaceutical composition, for treatment of any of the above-enumerated medical conditions.

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

The term "disease" or "disorder" or "malcondition" are used interchangeably, and are used to refer to diseases or conditions wherein a sphingosine-1-phosphate receptor plays a role in the biochemical mechanisms involved in the disease or malcondition or symptom(s) thereof such that a therapeutically beneficial effect can be achieved by acting on sphingosine-1-phosphate receptor, e.g. with an effective amount or concentration of a synthetic ligand of the invention. "Acting on" a sphingosine-1-phosphate receptor, or "modulating" a sphingosine-1-phosphate receptor, can include binding to the sphingosine-1-phosphate receptor and/or inhibiting the bioactivity of the sphingosine-1-phosphate receptor and/or allosterically regulating the bioactivity of the sphingosine-1-phosphate receptor in vivo.

The expression "effective amount", when used to describe therapy to an individual suffering from a disorder, refers to the quantity or concentration of a compound of the invention that is effective to inhibit or otherwise act on a sphingosine-1-phosphate receptor in the individual's tissues wherein the sphingosine-1-phosphate receptor involved in the disorder, wherein such inhibition or other action occurs to an extent sufficient to produce a beneficial therapeutic effect.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents, or provides prophylaxis for, the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by, the therapeutically beneficial effects.

It is to be further understood that where descriptions of various embodiments use the term "comprising," those skilled in the art would understand that in some specific instances, an embodiment can be alternatively described using language "consisting essentially of" or "consisting of."

By "chemically feasible" is meant a bonding arrangement or a compound where the generally understood rules of organic structure are not violated; for example a structure within a definition of a claim that would contain in certain situations, e.g., a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group is recited, wherein the group can be present in more than a single orientation within a structure resulting in more than single molecular structure, e.g., a carboxamide group C(═O)NR, it is understood that the group can be present in any possible orientation, e.g., X—C(═O)N(R)—Y or X—N(R)C(═O)—Y, unless the context clearly limits the orientation of the group within the molecular structure.

Substituted ring groups such as substituted cycloalkyl, aryl, heterocyclyl and heteroaryl groups also include rings and fused ring systems in which a bond to a hydrogen atom is replaced with a bond to a carbon atom, or to a substituent group as defined above. Therefore, substituted cycloalkyl, aryl, heterocyclyl and heteroaryl groups can also be substituted with alkyl, alkenyl, and alkynyl groups, or with the substituent groups listed above or other substituent groups know to persons of ordinary skill in the art.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

Ring systems can be mono- or independently multi-substituted with substituents as are described above. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

When a number of carbon atoms in a group, e.g., an alkyl, alkenyl, alkynyl, cycloalkyl, aryl, etc., is specified as a range, each individual integral number representing the number of carbon atoms is intended. For example, recitation of a $(C_1$-$C_4)$alkyl group indicates that the alkyl group can be any of methyl, ethyl, propyl, isopropyl, butyl, sec-butyl, isobutyl, or tert-butyl. It is understood that a specification of a number of carbon atoms must be an integer.

When a number of atoms in a ring is specified, e.g., a 3- to 9-membered cycloalkyl or heterocyclyl ring, the cycloalkyl or heterocyclyl ring can include any of 3, 4, 5, 6, 7, 8, or 9 atoms. A cycloalkyl ring is carbocyclic; a heterocyclyl ring can include atoms of any element in addition to carbon capable of forming two or more bonds, e.g., nitrogen, oxygen, sulfur, and the like. The number of atoms in a ring is understood to necessarily be an integer.

Alkyl groups include straight chain and branched carbon-based groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the substituent groups listed above, for example, amino, hydroxy, cyano, carboxy, nitro, thio, alkoxy, and halogen groups. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

Cycloalkyl groups are groups containing one or more carbocyclic ring including, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, $—CH═CH(CH_3)$, $—CH═C(CH_3)_2$, $—C(CH_3)═CH_2$, $—C(CH_3)═CH(CH_3)$, $—C(CH_2CH_3)═CH_2$, cyclohexenyl, cyclopentenyl, cyclohexadienyl, butadienyl, pentadienyl, and hexadienyl among others. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

Aryl groups are cyclic aromatic hydrocarbons that do not contain heteroatoms in the ring. An aromatic compound, as is well-known in the art, is a multiply-unsaturated cyclic system that contains 4n+2 π electrons where n is an integer.

Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl, also termed arylalkyl, groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which one or more ring atom is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. Ring sizes can also be expressed by the total number of atoms in the ring, e.g., a 3- to 10-membered heterocyclyl group, counting both carbon and non-carbon ring atoms. A heterocyclyl ring can also include one or more double bonds. A heteroaryl ring is an embodiment of a heterocyclyl group. The term "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The term also includes polycyclic, e.g., bicyclo- and tricyclo-ring systems containing one or more heteroatom such as, but not limited to, quinuclidyl.

Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure, which is a multiply-unsaturated cyclic system that contains 4n+2 it electrons wherein n is an integer A heteroaryl group designated as a $C_2$-heteroaryl can be a 5-ring (i.e., a 5-membered ring) with two carbon atoms and three heteroatoms, a 6-ring (i.e., a 6-membered ring) with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, thiadiazolyl, pyridinyl, pyrimidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with substituent groups as is discussed above. Representative substituted heteroaryl groups can be substituted one or more times with independently selected groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Any heterocyclyl or heteroaryl comprising nitrogen can be an N-oxide or N-metho salt or other N-quaternarized salt thereof; when a cationic N-quaternarized salt is present, it is understood that an anionic counterion is present for charge balance. Any heterocyclyl or heteroaryl comprising sulfur can be an sulfoxide or sulfone or an S-metho salt or other S-alkylated salt thereof; when a cationic S-alkylated salt is present, it is understood that an anionic counterion is present for charge balance.

The term "alkoxy" or "alkoxyl" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Exemplary alkoxy groups include, but are not limited to, alkoxy groups of 1-6 or 2-6 carbon atoms, referred to herein as $C_{1-6}$alkoxy, and $C_{2-6}$ alkoxy, respectively. Exemplary alkoxy groups include, but are not limited to methoxy, ethoxy, isopropoxy, etc.

An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by the same or differing halogen atoms, such as fluorine and/or chlorine atoms. Examples of haloalkyl include trifluoromethyl, 1,1-dichloroethyl, 1,2-dichloroethyl, 1,3-dibromo-3,3-difluoropropyl, perfluorobutyl, and the like.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen atom, the group is a "formyl" group, also an example of an acyl group as the term is defined herein. An acyl group can include 0 to about 12-20 additional carbon atoms bonded to the carbonyl group. An acyl group can include double or triple bonds within the meaning herein. An acryloyl group is an example of a double bond-containing acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula $N(group)_3$ wherein each group can independently be H or non-H, such as alkyl, aryl, and the like. Amines include but are not limited to $R—NH_2$, wherein R is a carbon-based moiety, for example, alkylamines, arylamines, alkylarylamines; $R_2NH$ wherein each R is independently selected carbon-based moiety, such as dialkylamines, diarylamines, aralkylamines, heterocyclylamines and the like; and $R_3N$ wherein each R is independently selected carbon-based moiety, such as trialkylamines, dialkylarylamines, alkyldiarylamines, triarylamines, and the like. The term "amine" as used herein also includes positively charged (cationic) forms such as amine salts and quaternarized amines.

An "amino" group is a substituent group of the form $—NH_2$, —NHR, $—NR_2$, or $—NR_3^+$, wherein each R is an independently selected carbon-based group, and protonated forms of each, except for $—NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino (trialkylammonium) group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., $—C(O)NR_2$, and —NRC(O)R groups, respectively. Amide groups therefore include but are not limited to primary carboxamide groups ($—C(O)NH_2$) and formamide groups (—NHC(O)H). A "carboxamido" group is a group of the formula $C(O)NR_2$, wherein R can be H, alkyl, aryl, etc.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

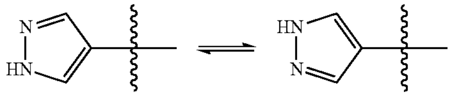 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

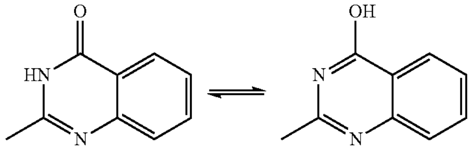

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as single and substantially pure enantiomeric or diastereomeric forms or as racemic mixtures. The present invention therefore includes any possible enantiomers, diastereomers, racemates or mixtures thereof of the compounds of the invention.

The compounds of the invention, or compounds used in practicing methods of the invention, may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the invention, or compounds used in practicing methods of the invention, may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer. The solid wedge indicates that the atom bonded thereby projects toward the viewer out of the plane of the paper, and a dashed wedge indicates that the atom bonded thereby projects away from the viewer out of the plan of the paper, i.e., the plane "of the paper" being defined by atoms A, C, and the chiral carbon atom for the (R) configuration shown below.

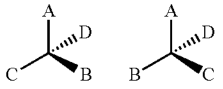

(R) configuration (S) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

There are various conventions for depicting chiral structures using solid and dashed wedges. For example, for the (R) configuration shown above, the following two depictions are equivalent:

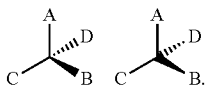

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" or "isolated enantiomer" means a compound which has been substantially purified from the corresponding optical isomer(s) of the same formula. Preferably, the isolated isomer is at least about 80%, more preferably at least 90% enantiomerically pure, even more preferably at least 98% enantiomerically pure, most preferably at least about 99% enantiomerically pure, by weight. By "enantiomeric purity" is meant the percent of the predominant enantiomer in an enantiomeric mixture of optical isomers of a compound. A pure single enantiomer has an enantiomeric purity of 100%.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 μg to about 1250 mg, preferably from about 250 μg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Evaluations

It is within ordinary skill to evaluate any compound disclosed and claimed herein for effectiveness in inhibition of a sphingosine-1-phosphate receptor and in the various cellular assays using the procedures described above or found in the scientific literature. Accordingly, the person of ordinary skill can prepare and evaluate any of the claimed compounds without undue experimentation.

Any compound found to be an effective inhibitor of the sphingosine-1-phosphate receptor can likewise be tested in animal models and in human clinical studies using the skill and experience of the investigator to guide the selection of dosages and treatment regimens.

In various embodiments, the compound is any of those shown in Tables 1, 2, or 3, below. Such compounds can be prepared by synthetic methods disclosed herein in combination with the knowledge of a person of ordinary skill in the art of organic synthesis, including the use of appropriately selected precursors, intermediates, reagents, and reaction mechanisms.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Description

Although published tool compounds provide for a valuable proof-of-concept, sphingolipid analogs that are aminophosphate esters, in general do not have the necessary kinetics and stability for optimal usefulness. Our recent publications have documented key aspects separating the $S1PR_1$ from $S1PR_3$ binding pockets, (7, 46). Although the systemic “immunosuppressive” actions of $S1PR_1$ modulators would be theoretically useful to dampen inflammation in localized environments, eg inflammation of the CNS in EAE or lung inflammation by influenza infection (25, 47), $S1PR_1$ agonists would likely pose risks in sepsis because of bradycardia (6, 7) and their potential to increase lung microvascular permeability (48) (49). Thus, dampening systemic inflammation in sepsis with selective $S1PR_3$ antagonist devoid of $S1P_1$ affinity is desired.

Recently, (Jo et al, 2012 and references therein) we described a model of $S1PR_3$ based upon our published X-ray structure of the very similar $S1PR_1$ subtype (2). Using a combination of site-directed mutagenesis, ligand competition binding, functional assays, and molecular modeling, we demonstrated that the endogenous pan-S1P receptor agonist, S1P binds to the orthosteric site as expected (50), that the novel $S1PR_3$ selective agonist CYM-5541 binds to an allosteric site and is therefore an allosteric agonist and that the $S1PR_3$ selective antagonist, SPM-242 competes for binding to both the orthosteric and allosteric sites and is said to be “bitopic’. The $S1PR_3$ selectivity of SPM-242 and CYM-5541, was concluded to come from binding to the less conserved, (non-orthosteric) regions of the S1P receptor family. In our quest for a drug-like $S1PR_3$ antagonist, we chose to use the allosteric agonist CYM-5541 as our starting point. We hypothesize that by attaching other “drug-friendly’ functional groups (—OH, —NR2, etc) onto the relatively low molecular weight CYM-5541 scaffold, we should be able to pick up accessory binding groups on the receptor such as hydrogen bonding to the peptide backbone or nearby side-chains such as Asn-95, Ser-99, Gln-281, Glu-115 and Arg-114, resulting is a new bitopic ligand with enhanced solubility characteristics.

TABLE 1

| Specific Compounds of the Invention | |
|---|---|
| Cpd. ID | Structure |
| CYM-52146 not I | 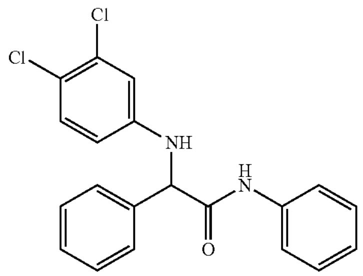 [SMILES: O=C(Nc1ccccc1)C(Nc1ccc(Cl)c(Cl)c1)c1ccccc1] |
| CYM-52147 not I | 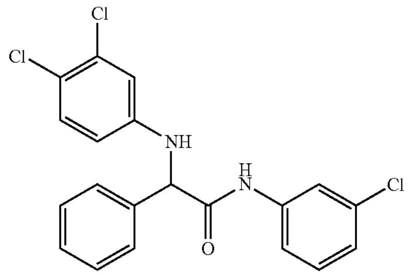 [SMILES: O=C(Nc1cccc(Cl)c1)C(Nc1ccc(Cl)c(Cl)c1)c1ccccc1] |
| CYM-52148 not I | 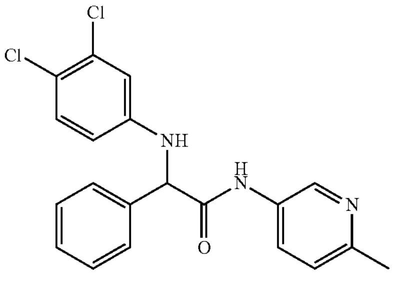 [SMILES: Cc1ccc(NC(=O)C(Nc2ccc(Cl)c(Cl)c2)c2ccccc2)cn1] |

TABLE 1-continued
| Specific Compounds of the Invention | |
|---|---|
| Cpd. ID | Structure |
| CYM-52149 not I | 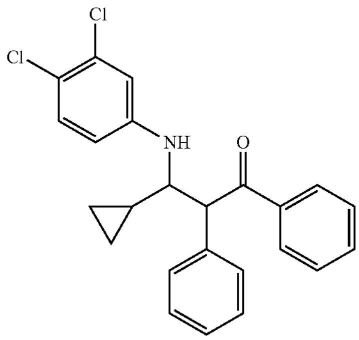 [SMILES: O=C(c1ccccc1)C(c1ccccc1)C(Nc1ccc(Cl)c(Cl)c1)C1CC1] |
| CYM52150 IA | 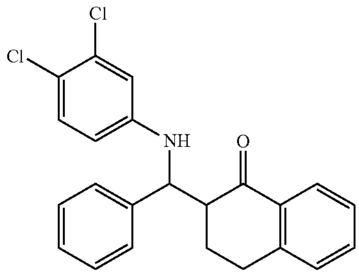 [SMILES: O=C1c2ccccc2CCC1C(Nc1ccc(Cl)c(Cl)c1)c1ccccc1] |
| CYM52151 not I | 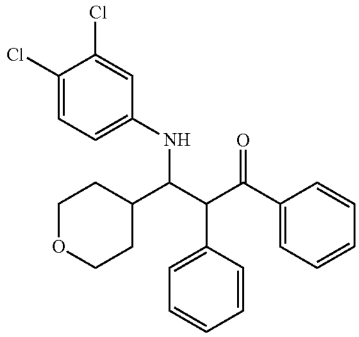 [SMILES: O=C(c1ccccc1)C(c1ccccc1)C(Nc1ccc(Cl)c(Cl)c1)C1CCOCC1] |
| CYM52152 not I | 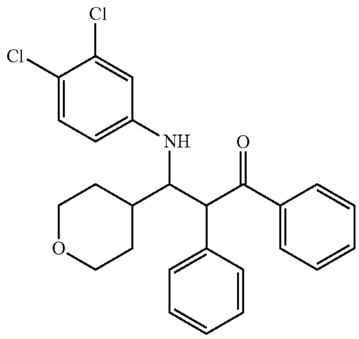 [SMILES: O=C(c1ccccc1)C(c1ccccc1)C(Nc1ccc(Cl)c(Cl)c1)C1CCOCC1] |

TABLE 1-continued
| Specific Compounds of the Invention | |
|---|---|
| Cpd. ID | Structure |
| CYM52153 not I | 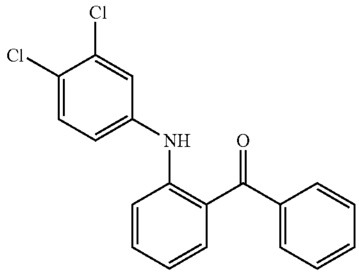 [SMILES: O=C(c1ccccc1)c1ccccc1Nc1ccc(Cl)c(Cl)c1] |
| CYM 52154 not I | 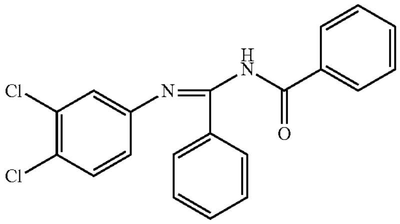 [SMILES: O=C(N/C(=N/c1ccc(Cl)c(Cl)c1)c1ccccc1)c1ccccc1] |
| CYM 52155 not I | 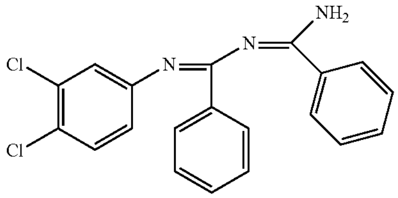 [SMILES: N/C(=N/C(=N/c1ccc(Cl)c(Cl)c1)c1ccccc1)c1ccccc1] |
| CYM 52156 not I | 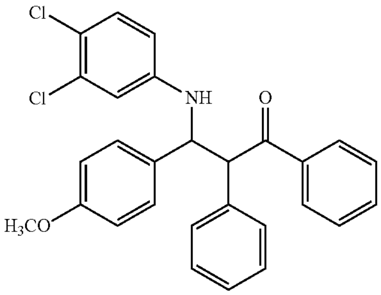 [SMILES: COc1ccc(C(Nc2ccc(Cl)c(Cl)c2)C(C(=O)c2ccccc2)c2ccccc2)cc1] |
| CYM 52157 not I | 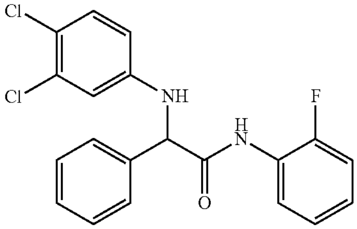 [SMILES: O=C(Nc1ccccc1F)C(Nc1ccc(Cl)c(Cl)c1)c1ccccc1] |
| CYM 52158 not I | 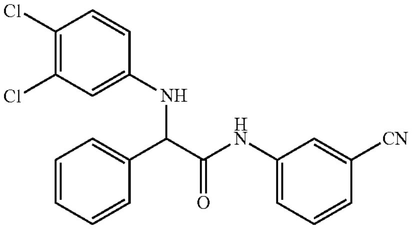 [SMILES: N#Cc1cccc(NC(=O)C(Nc2ccc(Cl)c(Cl)c2)c2ccccc2)c1] |

TABLE 1-continued
| Specific Compounds of the Invention | |
|---|---|
| Cpd. ID | Structure |
| CYM 52159 not I | 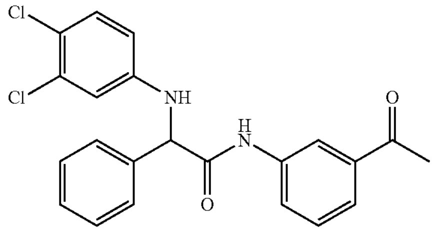 [SMILES: CC(=O)c1cccc(NC(=O)C(Nc2ccc(Cl)c(Cl)c2)c2ccccc2)c1] |
| CYM 52160 not I | 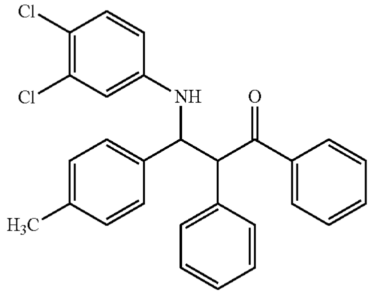 [SMILES: Cc1ccc(C(Nc2ccc(Cl)c(Cl)c2)C(C(=O)c2ccccc2)c2ccccc2)cc1] |
| CYM 52161 not I | 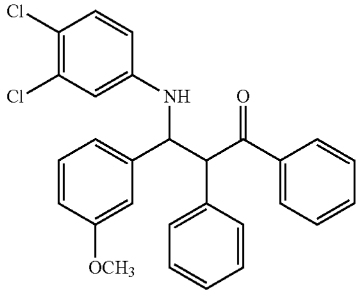 [SMILES: COc1cccc(C(Nc2ccc(Cl)c(Cl)c2)C(C(=O)c2ccccc2)c2ccccc2)c1] |
| CYM 52162 not I | 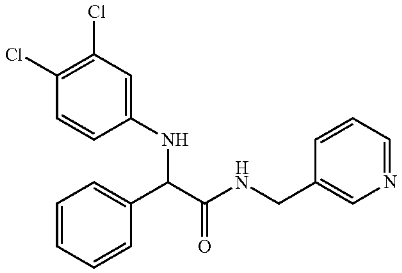 [SMILES: O=C(NCc1cccnc1)C(Nc1ccc(Cl)c(Cl)c1)c1ccccc1] |
| CYM 52163 not I | 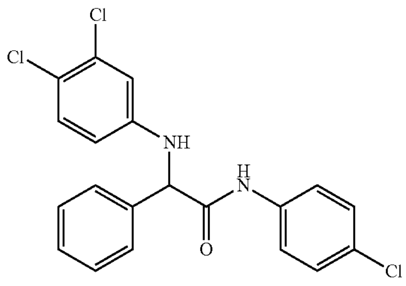 [SMILES: O=C(Nc1ccc(Cl)cc1)C(Nc1ccc(Cl)c(Cl)c1)c1ccccc1] |

TABLE 1-continued
| Specific Compounds of the Invention | |
|---|---|
| Cpd. ID | Structure |
| CYM 52164 not I | 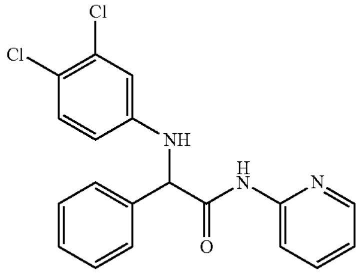 [SMILES: O=C(Nc1ccccn1)C(Nc1ccc(Cl)c(Cl)c1)c1ccccc1] |
| CYM 52165 not I | 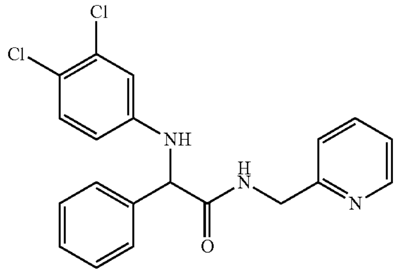 [SMILES: O=C(NCc1ccccn1)C(Nc1ccc(Cl)c(Cl)c1)c1ccccc1] |
| CYM 52166 not I | 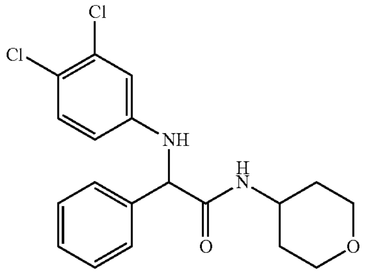 [SMILES: O=C(NC1CCOCC1)C(Nc1ccc(Cl)c(Cl)c1)c1ccccc1] |
| CYM 52167 IB | 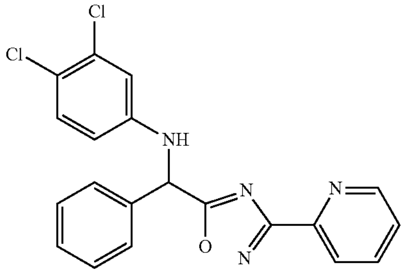 [SMILES: N=C(/N=C(\O)C(Nc1ccc(Cl)c(Cl)c1)c1ccccc1)c1ccccn1] |
| CYM 52184 not I | 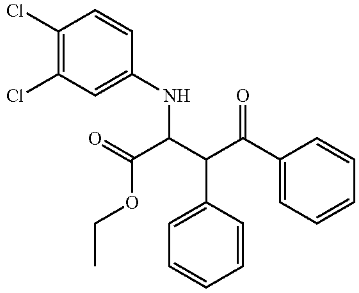 [SMILES: CCOC(=O)C(Nc1ccc(Cl)c(Cl)c1)C(C(=O)c1ccccc1)c1ccccc1] |

TABLE 1-continued
| Specific Compounds of the Invention | |
|---|---|
| Cpd. ID | Structure |
| CYM 52197 not I | 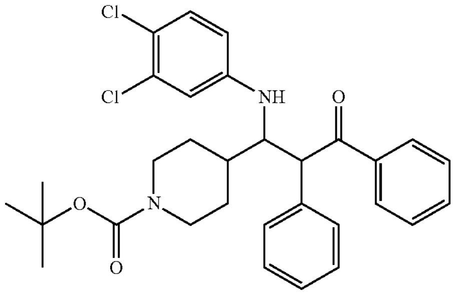 [SMILES: CC(C)(C)OC(=O)N1CCC(C(Nc2ccc(Cl)c(Cl)c2)C(C(=O)c2ccccc2)c2ccccc2)CC1] |
| CYM 52198 not I | 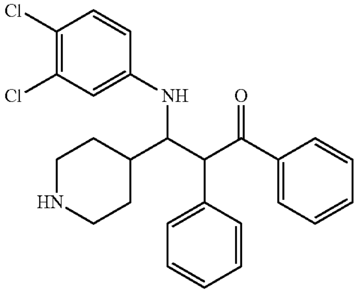 [SMILES: O=C(c1ccccc1)C(c1ccccc1)C(Nc1ccc(Cl)c(Cl)c1)C1CCNCC1] |
| CYM 52199 not I | 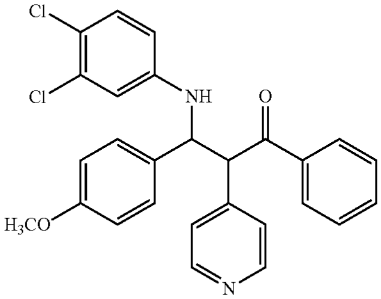 [SMILES: COc1ccc(C(Nc2ccc(Cl)c(Cl)c2)C(C(=O)c2ccccc2)c2ccncc2)cc1] |
| CYM 52200 not I | 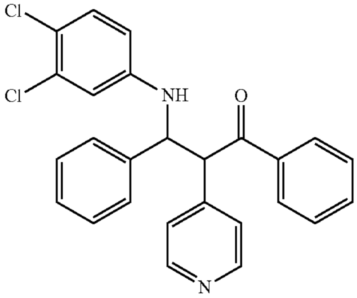 [SMILES: O=C(c1ccccc1)C(c1ccncc1)C(Nc1ccc(Cl)c(Cl)c1)c1ccccc1] |
| CYM 52201 not I | 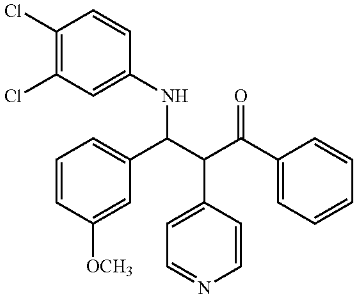 [SMILES: COc1cccc(C(Nc2ccc(Cl)c(Cl)c2)C(C(=O)c2ccccc2)c2ccncc2)c1] |

TABLE 1-continued
| Specific Compounds of the Invention | |
|---|---|
| Cpd. ID | Structure |
| CYM 52202<br>not I | 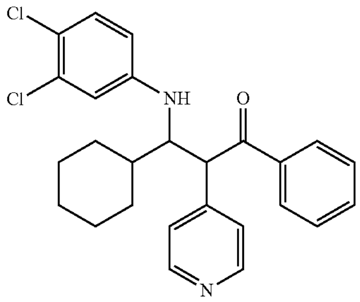 [SMILES: O=C(c1ccccc1)C(c1ccncc1)C(Nc1ccc(Cl)c(Cl)c1)C1CCCCC1] |
| CYM 52203<br>not 1 | 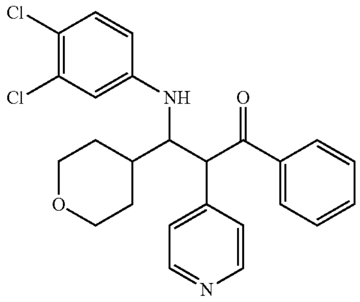 [SMILES: O=C(c1ccccc1)C(c1ccncc1)C(Nc1ccc(Cl)c(Cl)c1)C1CCOCC1] |
| CYM 52204<br>not I | 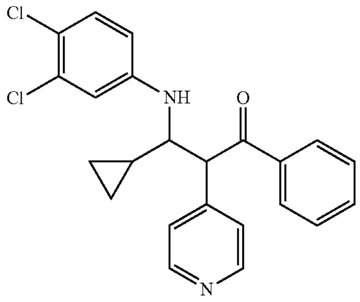 [SMILES: O=C(c1ccccc1)C(c1ccncc1)C(Nc1ccc(Cl)c(Cl)c1)C1CC1] |
| CYM 52205<br>IB | 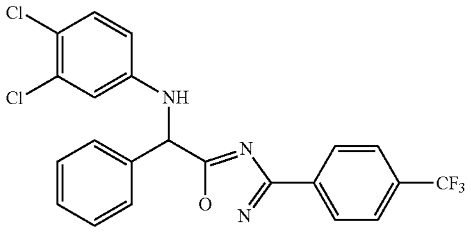 [SMILES: N=C(/N=C(\O)C(Nc1ccc(Cl)c(Cl)c1)c1ccccc1)c1ccc(C(F)(F)F)cc1] |
| CYM 52206<br>not I | 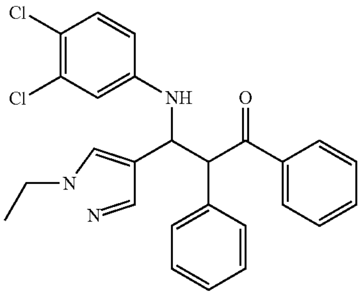 [SMILES: CCN/C=C(\C=N)C(Nc1ccc(Cl)c(Cl)c1)C(C(=O)c1ccccc1)c1ccccc1] |

TABLE 1-continued
| Specific Compounds of the Invention | |
|---|---|
| Cpd. ID | Structure |
| CYM 52207<br>IB | 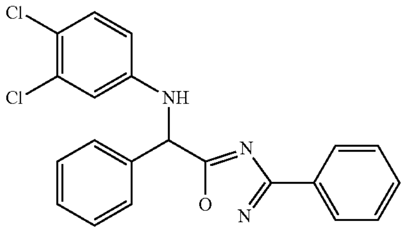 [SMILES: N=C(/N=C(\O)C(Nc1ccc(Cl)c(Cl)c1)c1ccccc1)c1ccccc1] |
| CYM 52208<br>not I | 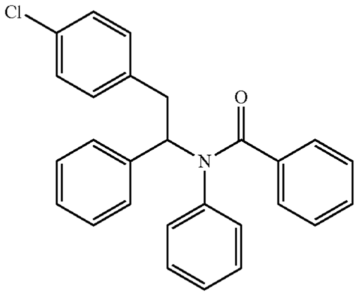 [SMILES: O=C(c1ccccc1)N(c1ccccc1)C(Cc1ccc(Cl)cc1)c1ccccc1] |
| CYM 52209<br>not I | 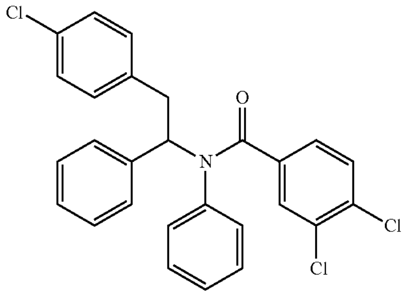 [SMILES: O=C(c1ccc(Cl)c(Cl)c1)N(c1ccccc1)C(Cc1ccc(Cl)cc1)c1ccccc1] |
| CYM 52210<br>not I | 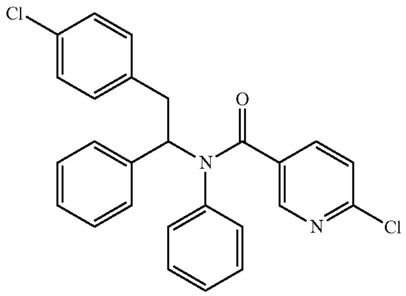 [SMILES: O=C(c1ccc(Cl)nc1)N(c1ccccc1)C(Cc1ccc(Cl)cc1)c1ccccc1] |
| CYM 52211<br>not I | 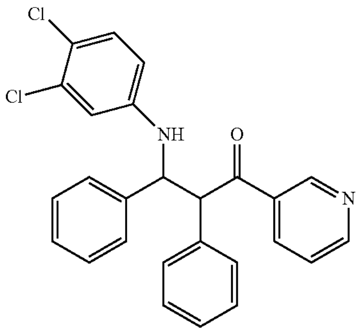 [SMILES: O=C(c1cccnc1)C(c1ccccc1)C(Nc1ccc(Cl)c(Cl)c1)c1ccccc1] |

TABLE 1-continued
| Specific Compounds of the Invention | |
|---|---|
| Cpd. ID | Structure |
| CYM 52212 not I | 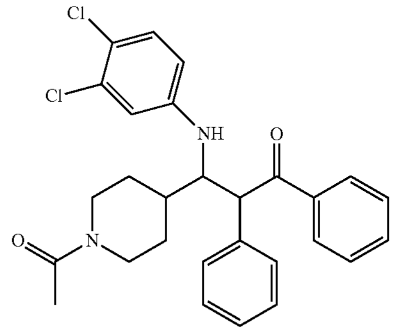 [SMILES: CC(=O)N1CCC(C(Nc2ccc(Cl)c(Cl)c2)C(C(=O)c2ccccc2)c2ccccc2)CC1] |
| CYM 52213 not I | 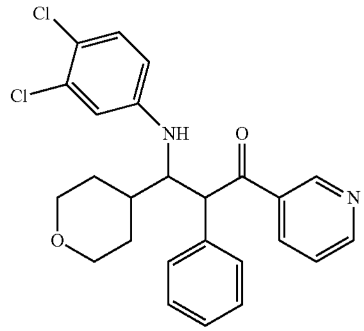 [SMILES: O=C(c1cccnc1)C(c1ccccc1)C(Nc1ccc(Cl)c(Cl)c1)C1CCOCC1] |
| CYM 52214 not I | 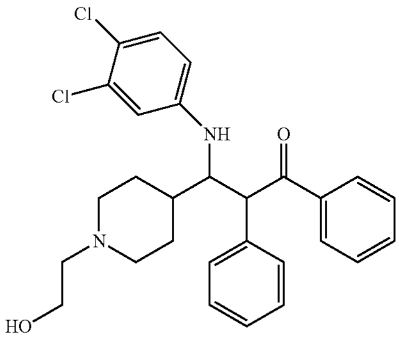 [SMILES: O=C(c1ccccc1)C(c1ccccc1)C(Nc1ccc(Cl)c(Cl)c1)C1CCN(CCO)CC1] |
| CYM 52215 not I | 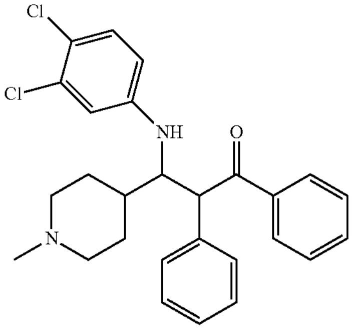 [SMILES: CN1CCC(C(Nc2ccc(Cl)c(Cl)c2)C(C(=O)c2ccccc2)c2ccccc2)CC1] |

TABLE 1-continued
| Specific Compounds of the Invention | |
|---|---|
| Cpd. ID | Structure |
| CYM 52216 not I | 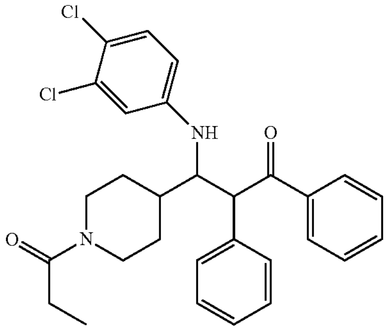 [SMILES: CCC(=O)N1CCC(C(Nc2ccc(Cl)c(Cl)c2)C(C(=O)c2ccccc2)c2ccccc2)CC1] |
| CYM 52217 not I | 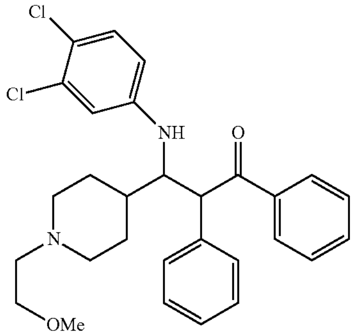 [SMILES: COCCN1CCC(C(Nc2ccc(Cl)c(Cl)c2)C(C(=O)c2ccccc2)c2ccccc2)CC1] |
| CYM 52218 not I | 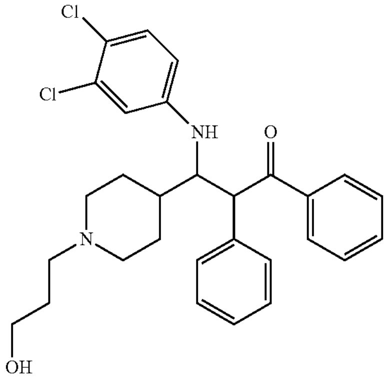 [SMILES: O=C(c1ccccc1)C(c1ccccc1)C(Nc1ccc(Cl)c(Cl)c1)C1CCN(CCCO)CC1] |
| CYM 52219 not I | 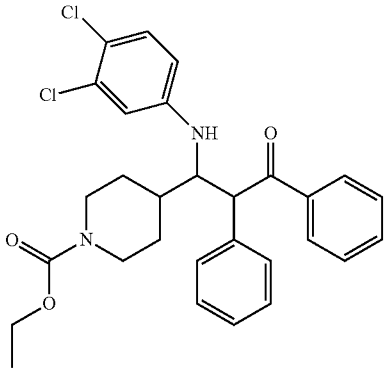 [SMILES: CCOC(=O)N1CCC(C(Nc2ccc(Cl)c(Cl)c2)C(C(=O)c2ccccc2)c2ccccc2)CC1] |

TABLE 1-continued
| Specific Compounds of the Invention | |
|---|---|
| Cpd. ID | Structure |
| CYM 52246 IB | 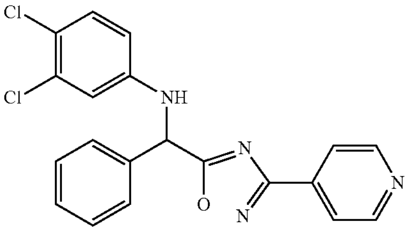 [SMILES: N=C(/N=C(\O)C(Nc1ccc(Cl)c(Cl)c1)c1ccccc1)c1ccncc1] |
| CYM 52247 IB | 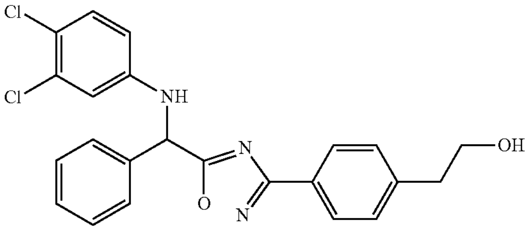 [SMILES: N=C(/N=C(\O)C(Nc1ccc(Cl)c(Cl)c1)c1ccccc1)c1ccc(CCO)cc1] |
| CYM 52248 IB | 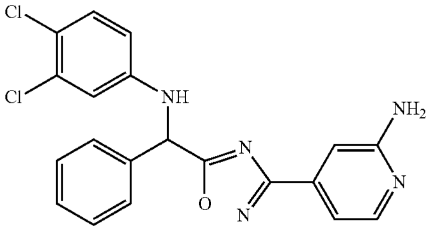 [SMILES: N=C(/N=C(\O)C(Nc1ccc(Cl)c(Cl)c1)c1ccccc1)c1ccnc(N)c1] |
| CYM 52249 IB | 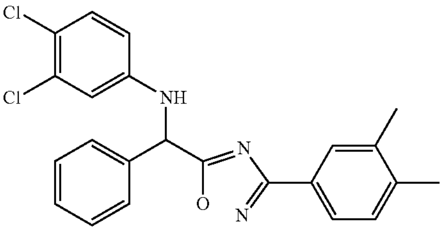 [SMILES: Cc1ccc(C(=N)/N=C(\O)C(Nc2ccc(Cl)c(Cl)c2)c2ccccc2)cc1C] |
| CYM 52250 IB | 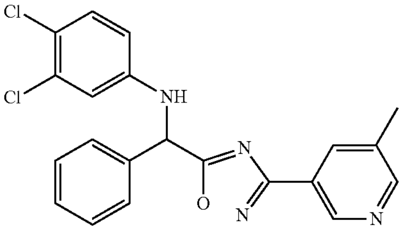 [SMILES: Cc1cncc(C(=N)/N=C(\O)C(Nc2ccc(Cl)c(Cl)c2)c2ccccc2)c1] |
| CYM 52251 IB | 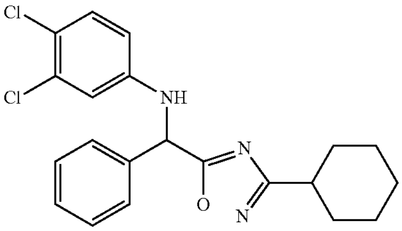 [SMILES: N=C(/N=C(\O)C(Nc1ccc(Cl)c(Cl)c1)c1ccccc1)C1CCCCC1] |

TABLE 1-continued
| Specific Compounds of the Invention | |
|---|---|
| Cpd. ID | Structure |
| CYM 52252 IA | 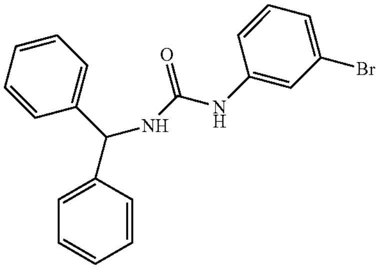 [SMILES: O=C(Nc1cccc(Br)c1)NC(c1ccccc1)c1ccccc1] |
| CYM 52253 IA | 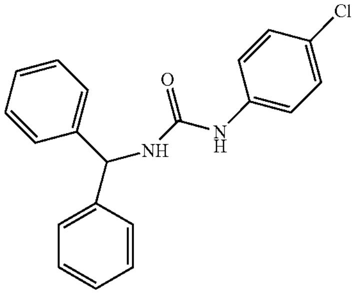 [SMILES: O=C(Nc1ccc(Cl)cc1)NC(c1ccccc1)c1ccccc1] |
| CYM 52254 IA | 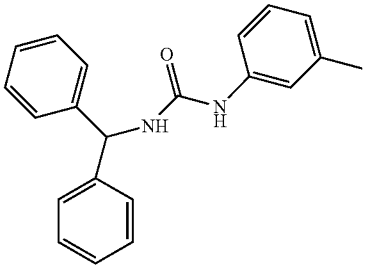 [SMILES: Cc1cccc(NC(=O)NC(c2ccccc2)c2ccccc2)c1] |
| CYM 52255 IB | 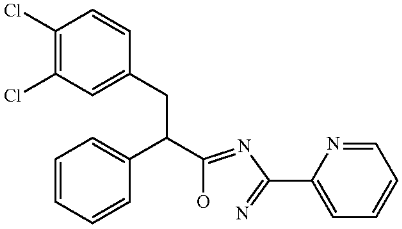 [SMILES: N=C(/N=C(\O)C(Cc1ccc(Cl)c(Cl)c1)c1ccccc1)c1ccccn1] |
| CYM 52256 IB | 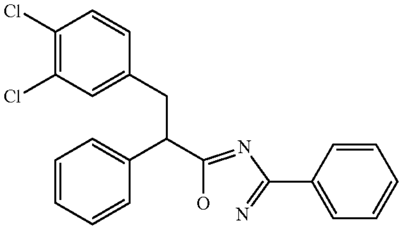 [SMILES: N=C(/N=C(\O)C(Cc1ccc(Cl)c(Cl)c1)c1ccccc1)c1ccccc1] |

TABLE 1-continued
| Specific Compounds of the Invention | |
|---|---|
| Cpd. ID | Structure |
| CYM 52257<br>IB | 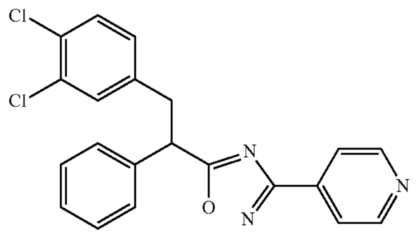 [SMILES: N=C(/N=C(\O)C(Cc1ccc(Cl)c(Cl)c1)c1ccccc1)c1ccncc1] |
| CYM 52258<br>IB | 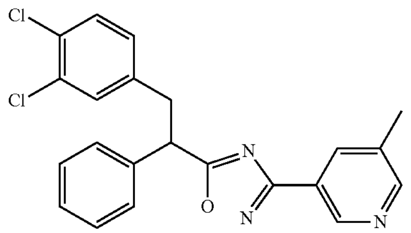 [SMILES: Cc1cncc(C(=N)/N=C(\O)C(Cc2ccc(Cl)c(Cl)c2)c2ccccc2)c1] |
| CYM 52259<br>60<br>IA | 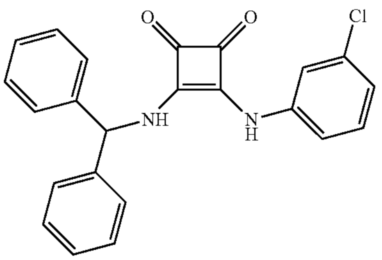 [SMILES: O=c1c(Nc2cccc(Cl)c2)c(NC(c2ccccc2)c2ccccc2)c1=O] |
| CYM 52260<br>not I | 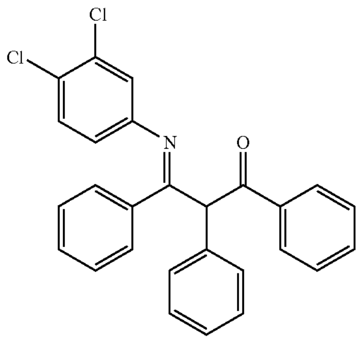 [SMILES: O=C(c1ccccc1)C(/C(=N/c1ccc(Cl)c(Cl)c1)c1ccccc1)c1ccccc1] |
| CYM 52264<br>IB | 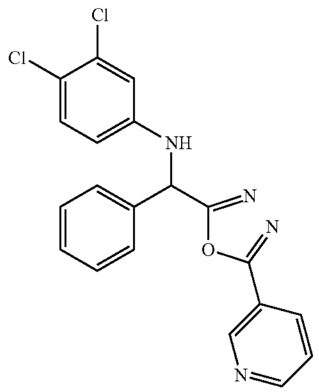 [SMILES: N=C(OC(=N)C(Nc1ccc(Cl)c(Cl)c1)c1ccccc1)c1cccnc1] |

TABLE 1-continued
| Specific Compounds of the Invention | |
|---|---|
| Cpd. ID | Structure |
| CYM 52266 IB | 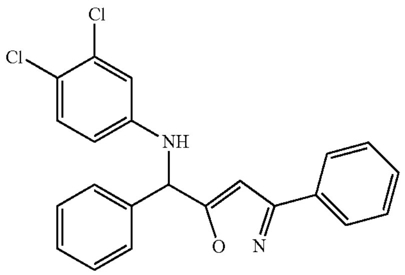 [SMILES: N=C(/C=C(\O)C(Nc1ccc(Cl)c(Cl)c1)c1ccccc1)c1ccccc1] |
| CYM 52267 IB | 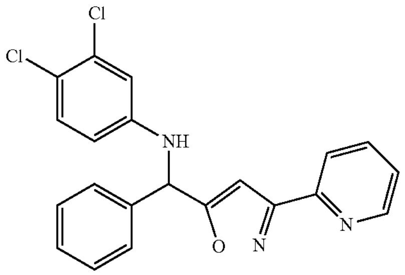 [SMILES: N=C(/C=C(\O)C(Nc1ccc(Cl)c(Cl)c1)c1ccccc1)c1ccccn1] |
| CYM 52268 IB | 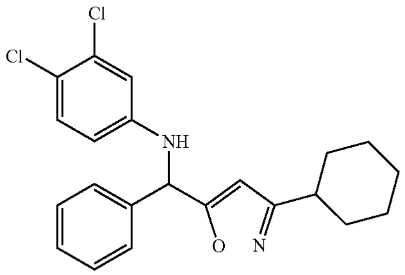 [SMILES: N=C(/C=C(\O)C(Nc1ccc(Cl)c(Cl)c1)c1ccccc1)C1CCCCC1] |
| CYM 52269 not I | 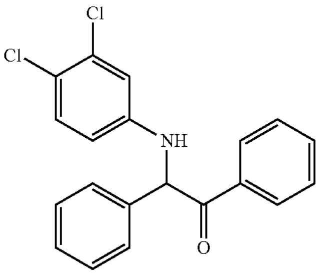 [SMILES: O=C(c1ccccc1)C(Nc1ccc(Cl)c(Cl)c1)c1ccccc1] |
| CYM 52270 not I | 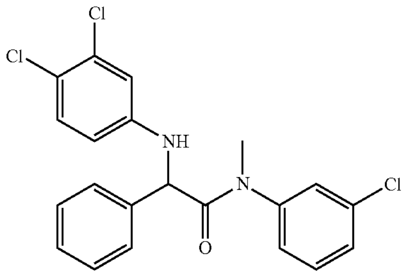 [SMILES: CN(C(=O)C(Nc1ccc(Cl)c(Cl)c1)c1ccccc1)c1cccc(Cl)c1] |

TABLE 1-continued
| Specific Compounds of the Invention | |
|---|---|
| Cpd. ID | Structure |
| CYM 52271<br>not I | 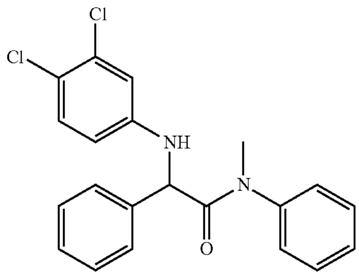 [SMILES: CN(C(=O)C(Nc1ccc(Cl)c(Cl)c1)c1ccccc1)c1ccccc1] |
| CYM 52272<br>not I | 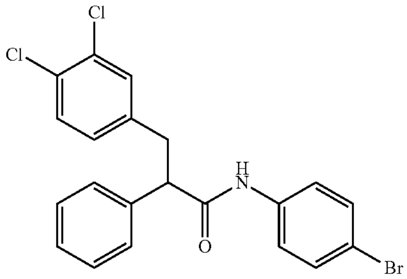 [SMILES: O=C(Nc1ccc(Br)cc1)C(Cc1ccc(Cl)c(Cl)c1)c1ccccc1] |
| CYM 52273<br>not I | 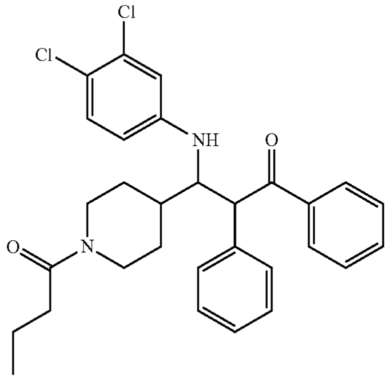 [SMILES: CCCC(=O)N1CCC(C(Nc2ccc(Cl)c(Cl)c2)C(C(=O)c2ccccc2)c2ccccc2)CC1] |
| CYM 52274<br>IB | 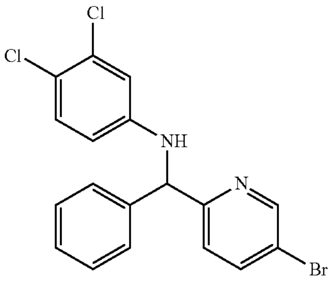 |
| CYM 52276<br>IB | 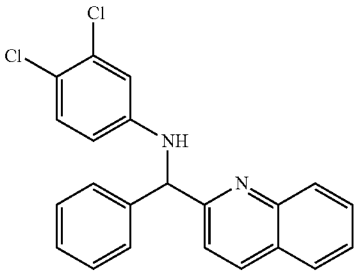 [SMILES: Clc1ccc(NC(c2ccccc2)c2ccc3ccccc3n2)cc1Cl] |

TABLE 1-continued
| Specific Compounds of the Invention | |
|---|---|
| Cpd. ID | Structure |
| CYM 52289 IB | 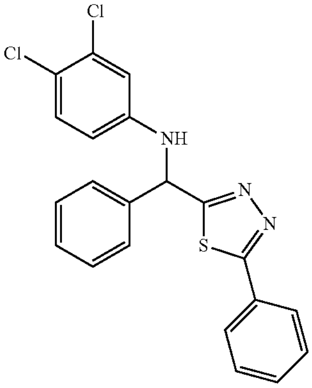 [SMILES: Clc1ccc(NC(c2ccccc2)c2nnc(-c3ccccc3)s2)cc1Cl] |
| CYM 52290 not I | 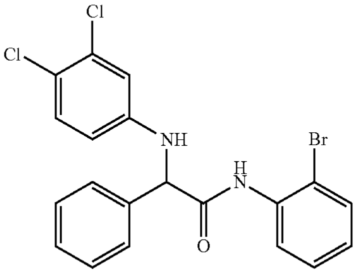 [SMILES: O=C(Nc1ccccc1Br)C(Nc1ccc(Cl)c(Cl)c1)c1ccccc1] |
| CYM 52291 not I | 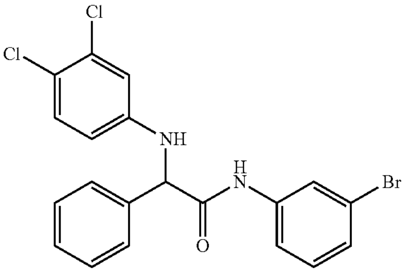 [SMILES: O=C(Nc1cccc(Br)c1)C(Nc1ccc(Cl)c(Cl)c1)c1ccccc1] |
| CYM 52294 IB | 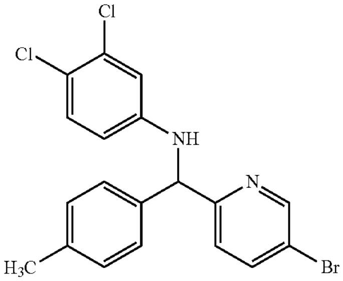 [SMILES: Cc1ccc(C(Nc2ccc(Cl)c(Cl)c2)c2ccc(Br)cn2)cc1] |
| CYM 52295 not I | 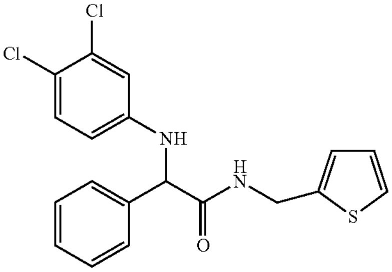 [SMILES: O=C(NCc1cccs1)C(Nc1ccc(Cl)c(Cl)c1)c1ccccc1] |

TABLE 1-continued
| Specific Compounds of the Invention | |
|---|---|
| Cpd. ID | Structure |
| CYM 52296 IB | 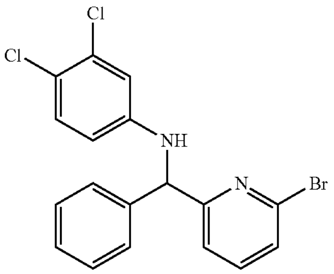 [SMILES: Clc1ccc(NC(c2ccccc2)c2cccc(Br)n2)cc1Cl] |
| CYM 52297 IB | 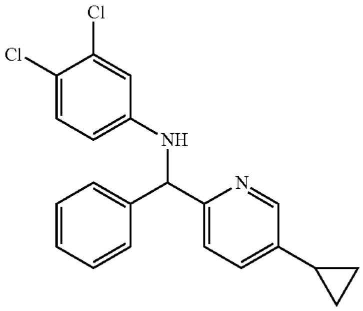 [SMILES: Clc1ccc(NC(c2ccccc2)c2ccc(C3CC3)cn2)cc1Cl] |
| CYM 52298 IB | 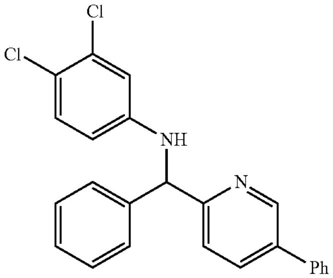 [SMILES: Clc1ccc(NC(c2ccccc2)c2ccc(-c3ccccc3)cn2)cc1Cl] |
| CYM 52299 IB | 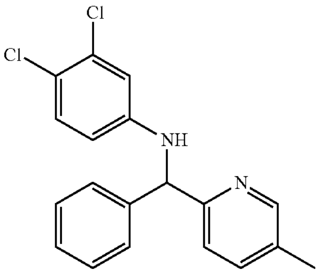 [SMILES: Cc1ccc(C(Nc2ccc(Cl)c(Cl)c2)c2ccccc2)nc1] |
| CYM 52300 IB | 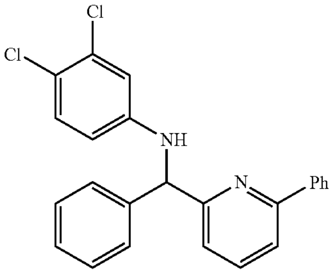 [SMILES: Clc1ccc(NC(c2ccccc2)c2cccc(-c3ccccc3)n2)cc1Cl] |

TABLE 1-continued
| Specific Compounds of the Invention | |
|---|---|
| Cpd. ID | Structure |
| CYM 52301 IB | 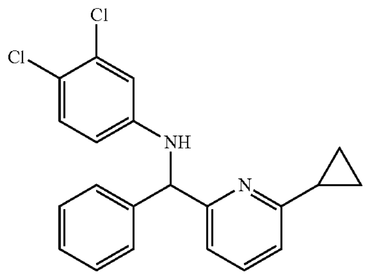 [SMILES: Clc1ccc(NC(c2ccccc2)c2cccc(C3CC3)n2)cc1Cl] |
| CYM 52302 IB | 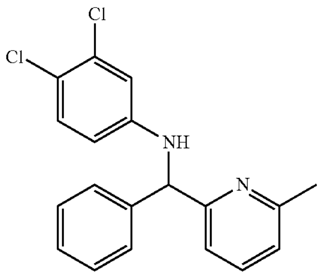 [SMILES: Cc1cccc(C(Nc2ccc(Cl)c(Cl)c2)c2ccccc2)n1] |
| CYM 52303 not I | 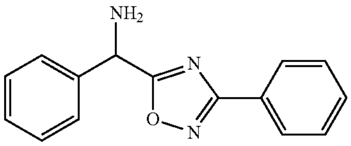 [SMILES: NC(c1ccccc1)c1nc(-c2ccccc2)no1] |
| CYM 52304 IB | 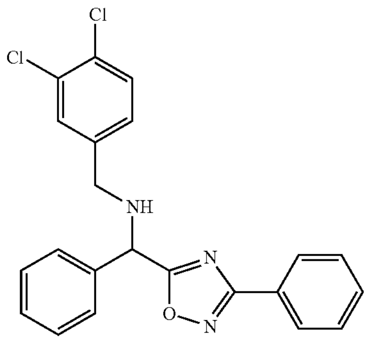 [SMILES: Clc1ccc(CNC(c2ccccc2)c2nc(-c3ccccc3)no2)cc1Cl] |
| CYM 52305 IB | 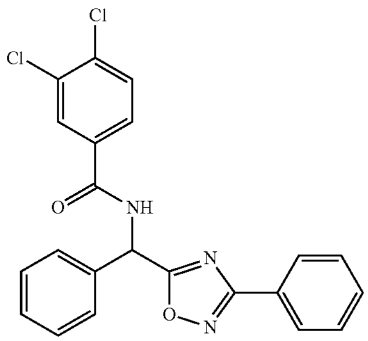 [SMILES: O=C(NC(c1ccccc1)c1nc(-c2ccccc2)no1)c1ccc(Cl)c(Cl)c1] |

TABLE 1-continued
| Specific Compounds of the Invention | |
|---|---|
| Cpd. ID | Structure |
| CYM 52306 IB | 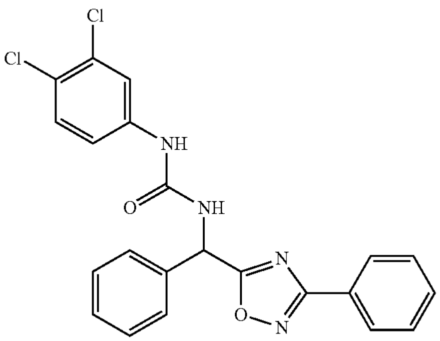 |
| CYM 52307 IC | 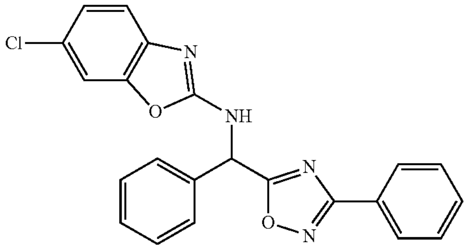 [SMILES: Clc1ccc2nc(NC(c3ccccc3)c3nc(-c4ccccc4)no3)oc2c1] |
| CYM 52308 IB | 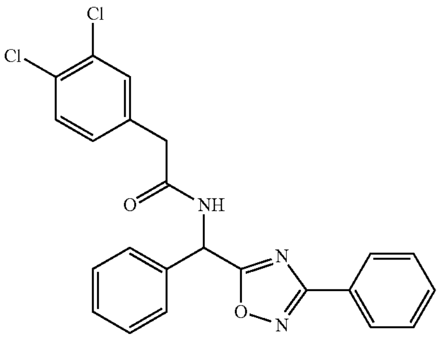 [SMILES: O=C(Cc1ccc(Cl)c(Cl)c1)NC(c1ccccc1)c1nc(-c2ccccc2)no1] |
| CYM 52309 IC | 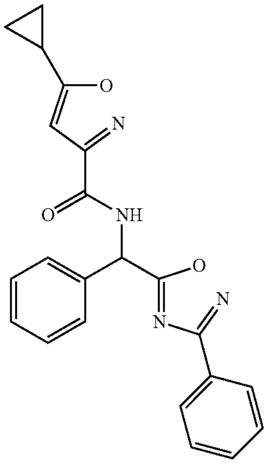 [SMILES: N=C(/C=C(\O)C1CC1)C(=O)NC(/C(O)=N/C(=N)c1ccccc1)c1ccccc1] |

TABLE 1-continued
| Specific Compounds of the Invention | |
|---|---|
| Cpd. ID | Structure |
| CYM 52310<br>IB | 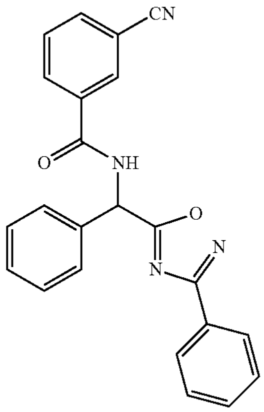 [SMILES: N#Cc1cccc(C(=O)NC(/C(O)=N/C(=N)c2ccccc2)c2ccccc2)c1] |
| CYM 52311<br>IB | 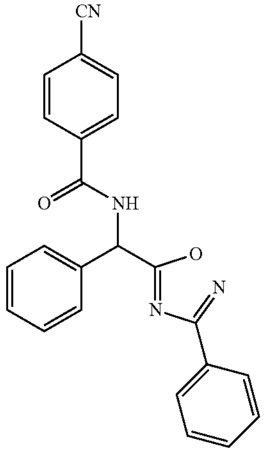 [SMILES: N#Cc1ccc(C(=O)NC(/C(O)=N/C(=N)c2ccccc2)c2ccccc2)cc1] |
| CYM 52312<br>IB | 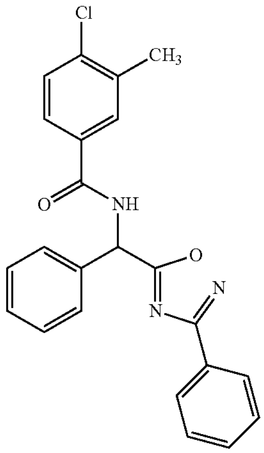 [SMILES: Cc1cc(C(=O)NC(/C(O)=N/C(=N)c2ccccc2)c2ccccc2)ccc1Cl] |

TABLE 1-continued
| Specific Compounds of the Invention | |
|---|---|
| Cpd. ID | Structure |
| CYM 52313<br>IB | 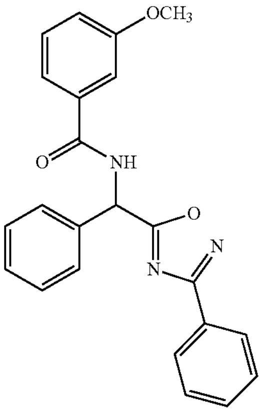 [SMILES: COc1cccc(C(=O)NC(/C(O)=N/C(=N)c2ccccc2)c2ccccc2)c1] |
| CYM 52314<br>IB | 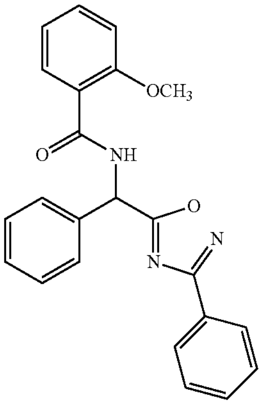 [SMILES: COc1ccccc1C(=O)NC(/C(O)=N/C(=N)c1ccccc1)c1ccccc1] |
| CYM 52315<br>IC | 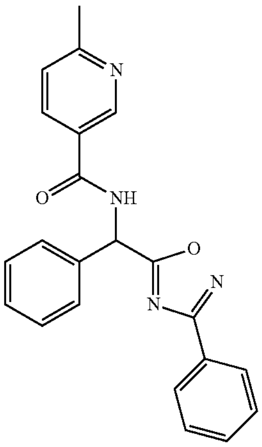 [SMILES: Cc1ccc(C(=O)NC(/C(O)=N/C(=N)c2ccccc2)c2ccccc2)cn1] |

TABLE 1-continued
| Specific Compounds of the Invention | |
|---|---|
| Cpd. ID | Structure |
| CYM 52316 IC | 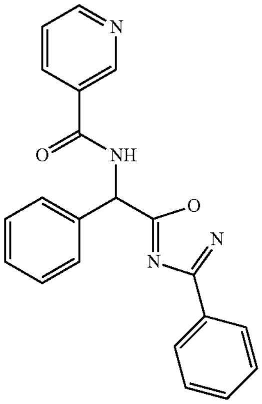 [SMILES: N=C(/N=C(\O)C(NC(=O)c1cccnc1)c1ccccc1)c1ccccc1] |
| CYM 52317 IC | 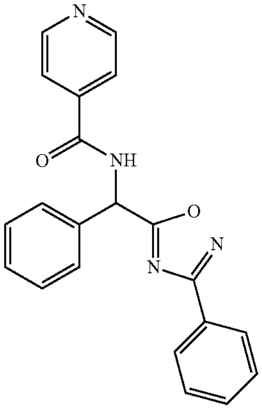 [SMILES: N=C(/N=C(\O)C(NC(=O)c1ccncc1)c1ccccc1)c1ccccc1] |
| CYM 52318 not I | 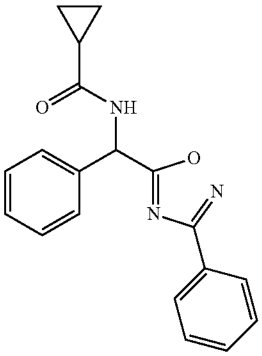 [SMILES: N=C(/N=C(\O)C(NC(=O)C1CC1)c1ccccc1)c1ccccc1] |
| CYM 52319 not I | 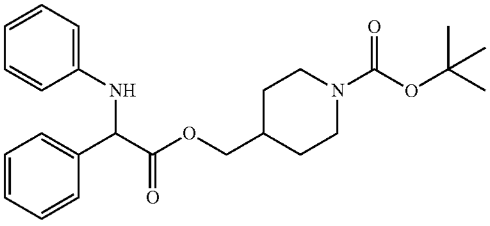 [SMILES: CC(C)(C)OC(=O)N1CCC(COC(=O)C(Nc2ccccc2)c2ccccc2)CC1] |

TABLE 1-continued
| Specific Compounds of the Invention | |
|---|---|
| Cpd. ID | Structure |
| CYM 52320 IB | 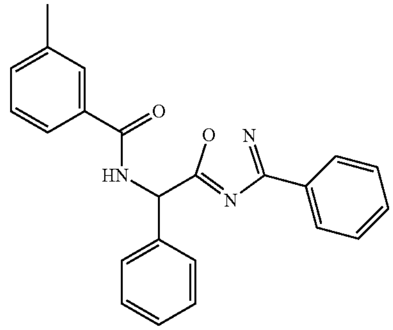 [SMILES: Cc1cccc(C(=O)NC(/C(O)=N/C(=N)c2ccccc2)c2ccccc2)c1] |
| CYM 52321 IB | 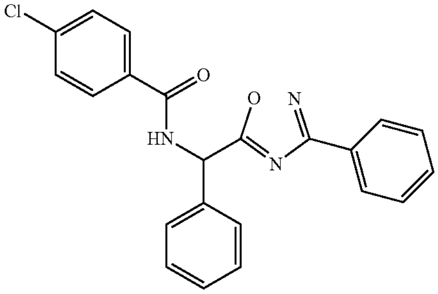 [SMILES: N=C(/N=C(\O)C(NC(=O)c1ccc(Cl)cc1)c1ccccc1)c1ccccc1] |
| CYM 52322 IC | 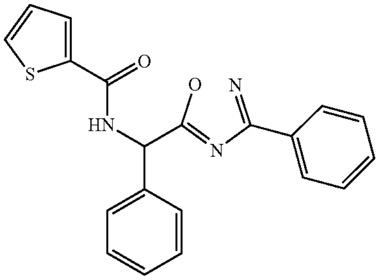 [SMILES: N=C(/N=C(\O)C(NC(=O)c1cccs1)c1ccccc1)c1ccccc1] |
| CYM 52323 IB | 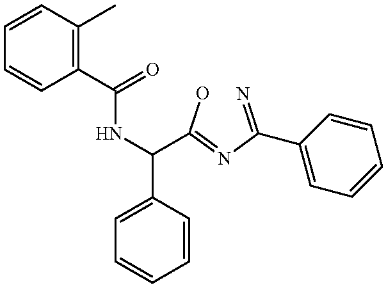 [SMILES: Cc1ccccc1C(=O)NC(/C(O)=N/C(=N)c1ccccc1)c1ccccc1] |
| CYM 52324 not I | 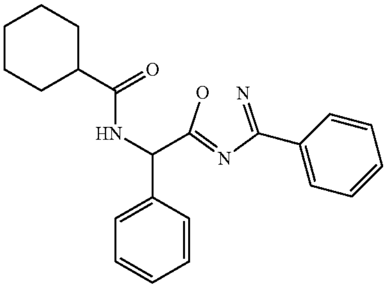 [SMILES: N=C(/N=C(\O)C(NC(=O)C1CCCCC1)c1ccccc1)c1ccccc1] |

TABLE 1-continued
| Specific Compounds of the Invention | |
|---|---|
| Cpd. ID | Structure |
| CYM 52325<br>IB | 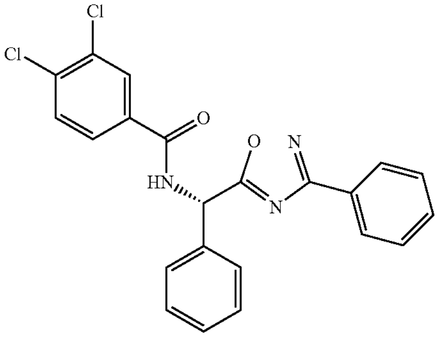 [SMILES: N=C(/N=C(\O)[C@@H](NC(=O)c1ccc(Cl)c(Cl)c1)c1ccccc1)c1ccccc1] |
| CYM 52326<br>IB | 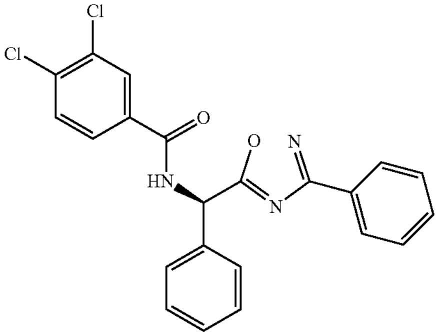 [SMILES: N=C(/N=C(\O)[C@H](NC(=O)c1ccc(Cl)c(Cl)c1)c1ccccc1)c1ccccc1] |
| CYM 52327<br>not I | 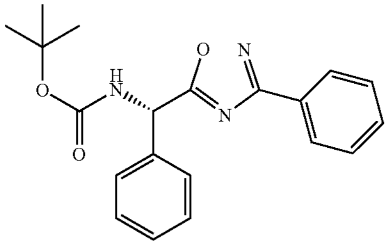 [SMILES: CC(C)(C)OC(=O)N[C@H](/C(O)=N/C(=N)c1ccccc1)c1ccccc1] |
| CYM 52328<br>not I | 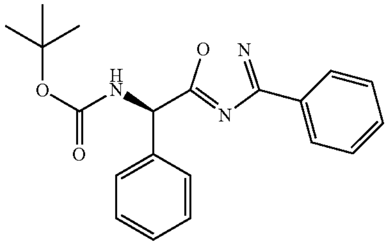 [SMILES: CC(C)(C)OC(=O)N[C@@H](/C(O)=N/C(=N)c1ccccc1)c1ccccc1] |
| CYM 52329<br>IB | 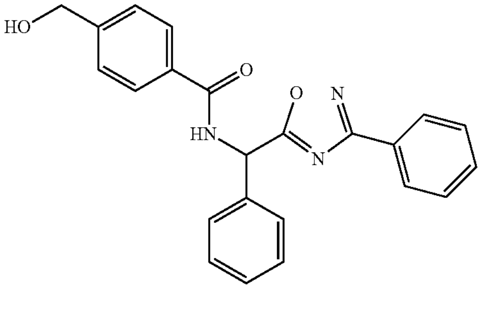 [SMILES: N=C(/N=C(\O)C(NC(=O)c1ccc(CO)cc1)c1ccccc1)c1ccccc1] |

TABLE 1-continued
| Specific Compounds of the Invention | |
|---|---|
| Cpd. ID | Structure |
| CYM 52330 IB | 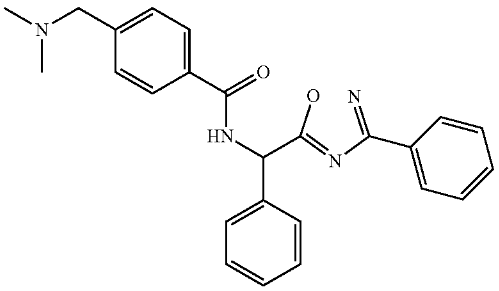 [SMILES: CN(C)Cc1ccc(C(=O)NC(/C(O)=N/C(=N)c2ccccc2)c2ccccc2)cc1] |
| CYM 52331 IB | 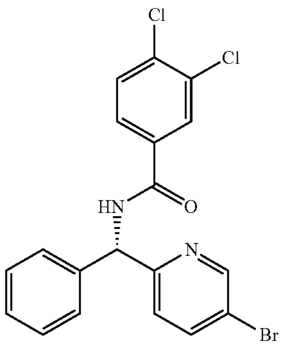 [SMILES: O=C(N[C@@H](c1ccccc1)c1ccc(Br)cn1)c1ccc(Cl)c(Cl)c1] |
| CYM 52332 IB | 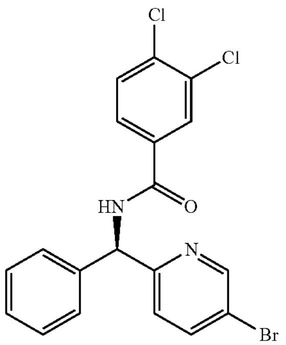 [SMILES: O=C(N[C@H](c1ccccc1)c1ccc(Br)cn1)c1ccc(Cl)c(Cl)c1] |
| CYM 52333 IB | 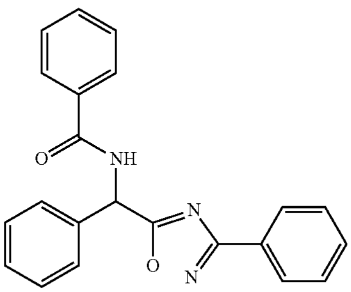 [SMILES: N=C(/N=C(\O)C(NC(=O)c1ccccc1)c1ccccc1)c1ccccc1] |

TABLE 1-continued
| Specific Compounds of the Invention | |
|---|---|
| Cpd. ID | Structure |
| CYM 52334 IB | 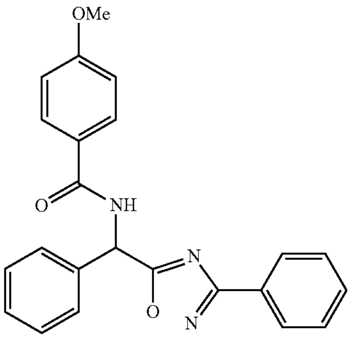 [SMILES: COc1ccc(C(=O)NC(/C(O)=N/C(=N)c2ccccc2)c2ccccc2)cc1] |
| CYM 52335 IB | 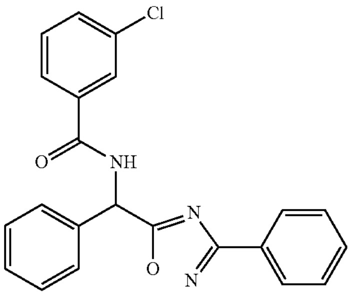 |
| CYM 52336 IB | 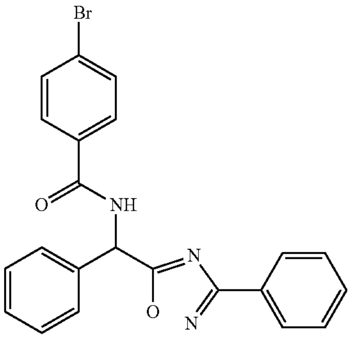 [SMILES: N=C(/N=C(\O)C(NC(=O)c1ccc(Br)cc1)c1ccccc1)c1ccccc1] |
| CYM 52337 IC | 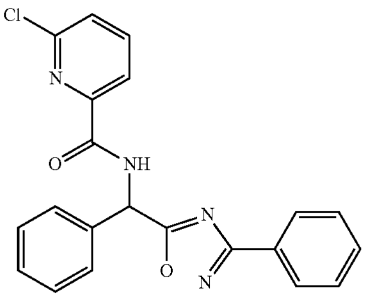 [SMILES: N=C(/N=C(\O)C(NC(=O)c1cccc(Cl)n1)c1ccccc1)c1ccccc1] |

TABLE 1-continued
| Specific Compounds of the Invention | |
|---|---|
| Cpd. ID | Structure |
| CYM 52338<br>IC | 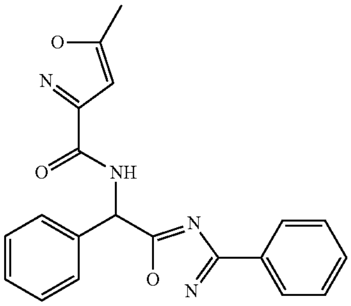 [SMILES: C/C(O)=C/C(=N)C(=O)NC(/C(O)=N/C(=N)c1ccccc1)c1ccccc1] |
| CYM 52339<br>IC | 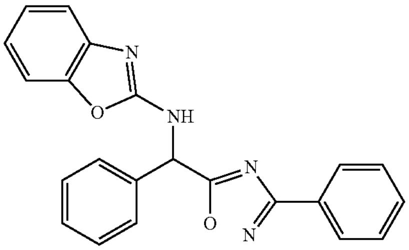 [SMILES: N=C(/N=C(\O)C(Nc1nc2ccccc2o1)c1ccccc1)c1ccccc1] |
| CYM 52340<br>not I | 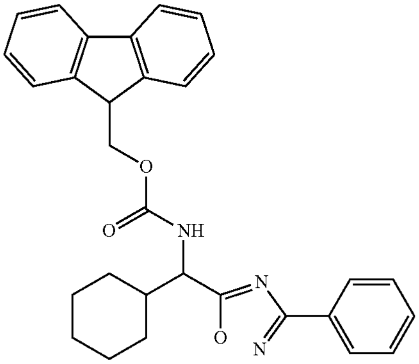 [SMILES: N=C(/N=C(\O)C(NC(=O)OCC1c2ccccc2-c2ccccc21)C1CCCCC1)c1ccccc1] |
| CYM 52341<br>not I | 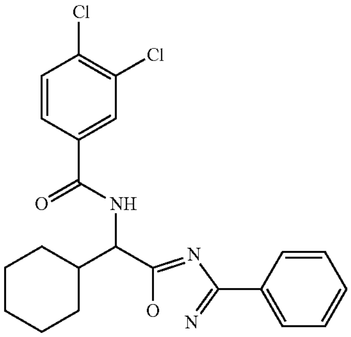 [SMILES: N=C(/N=C(\O)C(NC(=O)c1ccc(Cl)c(Cl)c1)C1CCCCC1)c1ccccc1] |
| CYM 52342<br>not I | 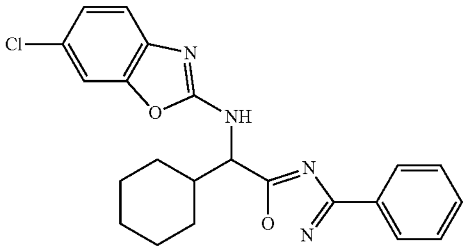 [SMILES: N=C(/N=C(\O)C(Nc1nc2ccc(Cl)cc2o1)C1CCCCC1)c1ccccc1] |

TABLE 1-continued
| Specific Compounds of the Invention | |
|---|---|
| Cpd. ID | Structure |
| CYM 52343<br>IB | 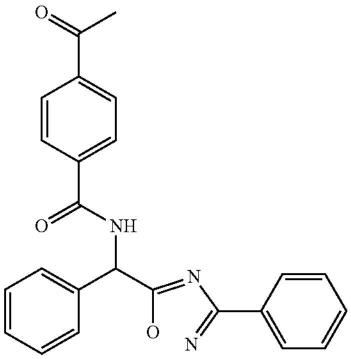 [SMILES: CC(=O)c1ccc(C(=O)NC(/C(O)=N/C(=N)c2ccccc2)c2ccccc2)cc1] |
| CYM 52344<br>IB | 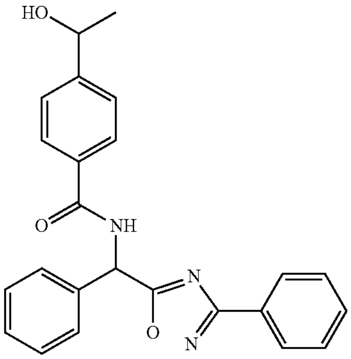 [SMILES: CC(O)c1ccc(C(=O)NC(/C(O)=N/C(=N)c2ccccc2)c2ccccc2)cc1] |
| CYM 52345<br>not I | 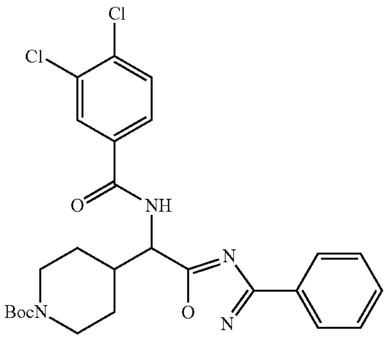 [SMILES: CC(C)(C)OC(=O)N1CCC(C(NC(=O)c2ccc(Cl)c(Cl)c2)/C(O)=N/C(=N)c2ccccc2)CC1] |
| CYM 52346<br>not I | 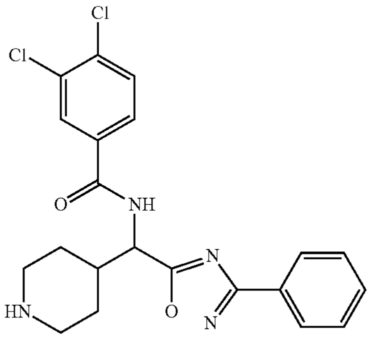 [SMILES: N=C(/N=C(\O)C(NC(=O)c1ccc(Cl)c(Cl)c1)C1CCNCC1)c1ccccc1] |

TABLE 1-continued
| Specific Compounds of the Invention | |
|---|---|
| Cpd. ID | Structure |
| CYM 52347<br>not I<br>not I | 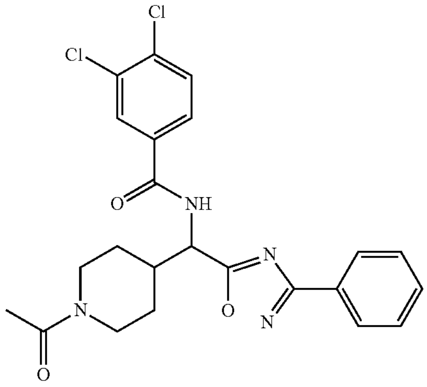 [SMILES: CC(=O)N1CCC(C(NC(=O)c2ccc(Cl)c(Cl)c2)/C(O)=N/C(=N)c2ccccc2)CC1] |
| CYM 52348<br>not I | 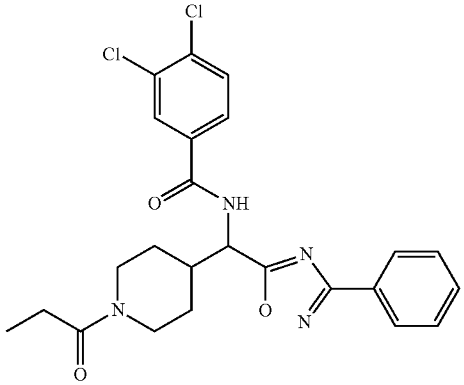 [SMILES: CCC(=O)N1CCC(C(NC(=O)c2ccc(Cl)c(Cl)c2)/C(O)=N/C(=N)c2ccccc2)CC1] |
| CYM 52349<br>not I | 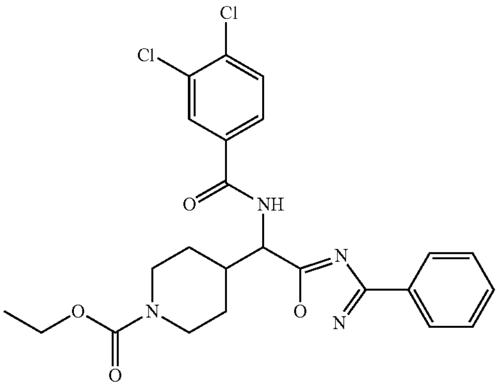 [SMILES: CCOC(=O)N1CCC(C(NC(=O)c2ccc(Cl)c(Cl)c2)/C(O)=N/C(=N)c2ccccc2)CC1] |
| CYM 52350<br>not I | 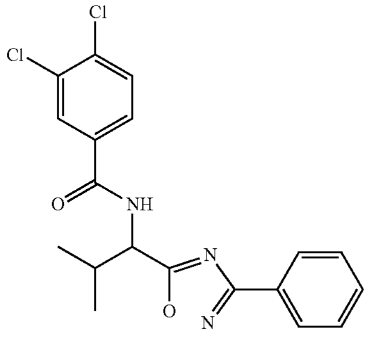 [SMILES: CC(C)C(NC(=O)c1ccc(Cl)c(Cl)c1)/C(O)=N/C(=N)c1ccccc1] |

TABLE 1-continued
| Specific Compounds of the Invention | |
|---|---|
| Cpd. ID | Structure |
| CYM 52351 IC | 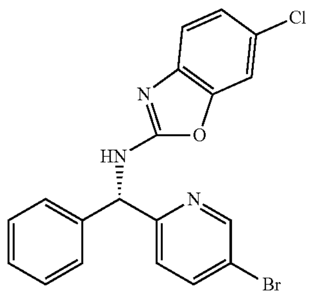 [SMILES: Clc1ccc2nc(N[C@@H](c3ccccc3)c3ccc(Br)cn3)oc2c1] |
| CYM 52352 IC | 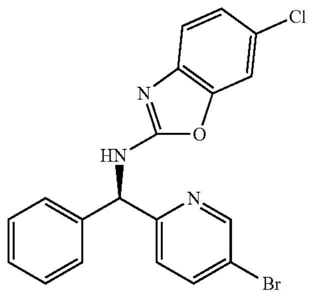 [SMILES: Clc1ccc2nc(N[C@H](c3ccccc3)c3ccc(Br)cn3)oc2c1] |
| CYM 52353 IB | 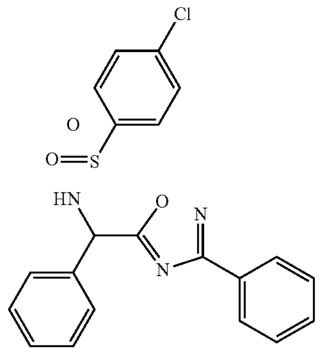 |
| CYM 52354 IC | 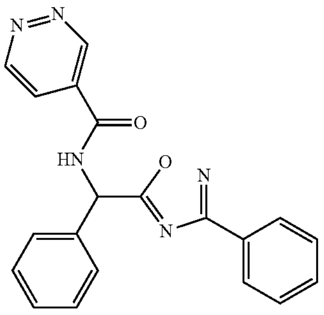 [SMILES: N=C(/N=C(\O)C(NC(=O)c1ccnnc1)c1ccccc1)c1ccccc1] |

TABLE 1-continued
| Specific Compounds of the Invention | |
|---|---|
| Cpd. ID | Structure |
| CYM 52355<br>IB | 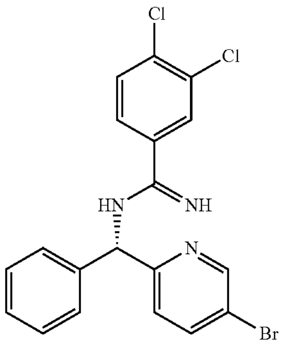 [SMILES: N=C(N[C@@H](c1ccccc1)c1ccc(Br)cn1)c1ccc(Cl)c(Cl)c1] |
| CYM 52356<br>IB | 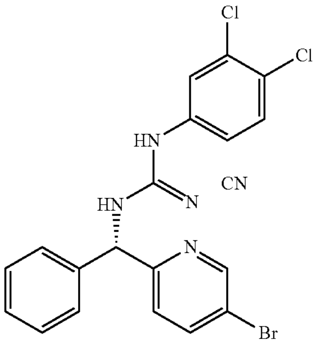 |
| CYM 52357<br>not I | 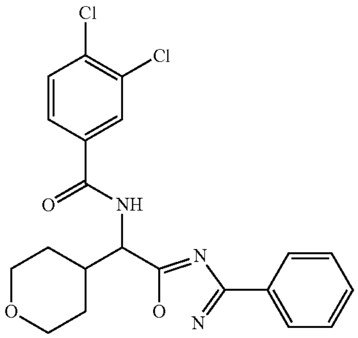 [SMILES: N=C(/N=C(\O)C(NC(=O)c1ccc(Cl)c(Cl)c1)C1CCOCC1)c1ccccc1] |
| CYM 52358<br>not I | 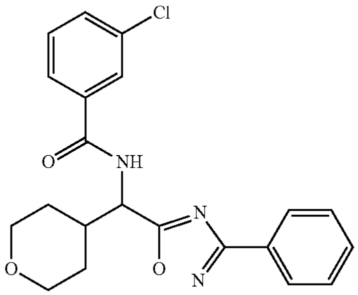 [SMILES: N=C(/N=C(\O)C(NC(=O)c1cccc(Cl)c1)C1CCOCC1)c1ccccc1] |

TABLE 1-continued
| Specific Compounds of the Invention | |
|---|---|
| Cpd. ID | Structure |
| CYM 52359<br>IB | 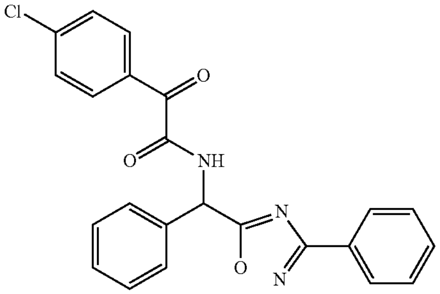 [SMILES: N=C(/N=C(\O)C(NC(=O)C(=O)c1ccc(Cl)cc1)c1ccccc1)c1ccccc1] |
| CYM 52360<br>not I | 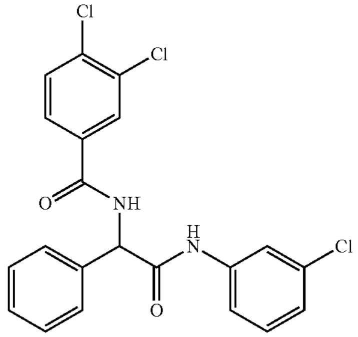 [SMILES: O=C(NC(C(=O)Nc1cccc(Cl)c1)c1ccccc1)c1ccc(Cl)c(Cl)c1] |
| CYM 52361<br>not I | 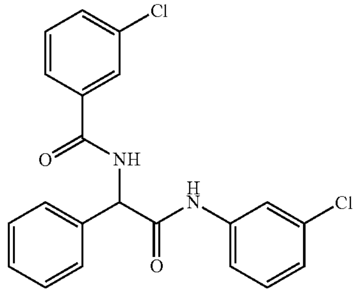 [SMILES: O=C(NC(C(=O)Nc1cccc(Cl)c1)c1ccccc1)c1cccc(Cl)c1] |
| CYM 52362<br>not I | 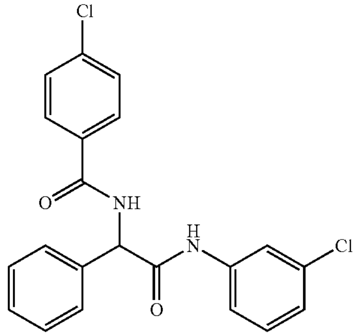 [SMILES: O=C(NC(C(=O)Nc1cccc(Cl)c1)c1ccccc1)c1ccc(Cl)cc1] |
| CYM 52363<br>not I | 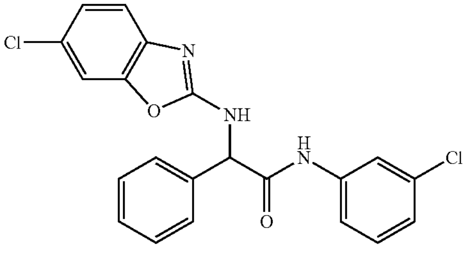 [SMILES: O=C(Nc1cccc(Cl)c1)C(Nc1nc2ccc(Cl)cc2o1)c1ccccc1] |

TABLE 1-continued
| Specific Compounds of the Invention | |
|---|---|
| Cpd. ID | Structure |
| CYM 52364 IB | 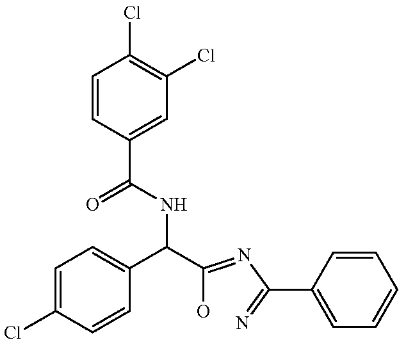 [SMILES: N=C(/N=C(\O)C(NC(=O)c1ccc(Cl)c(Cl)c1)c1ccc(Cl)cc1)c1ccccc1] |
| CYM 52365 IB | 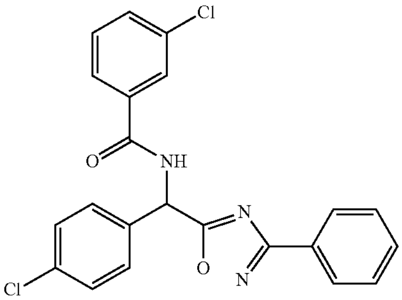 [SMILES: N=C(/N=C(\O)C(NC(=O)c1cccc(Cl)c1)c1ccc(Cl)cc1)c1ccccc1] |
| CYM 52366 IC | 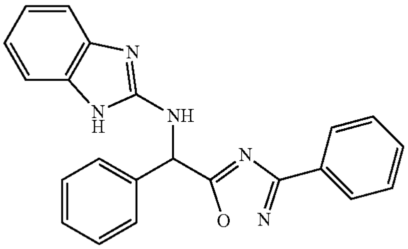 [SMILES: N=C(/N=C(\O)C(Nc1nc2ccccc2[nH]1)c1ccccc1)c1ccccc1] |
| CYM 52367 IC | 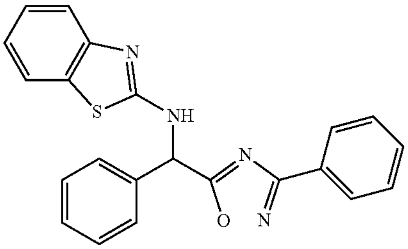 [SMILES: N=C(/N=C(\O)C(Nc1nc2ccccc2s1)c1ccccc1)c1ccccc1] |
| CYM 52368 IC | 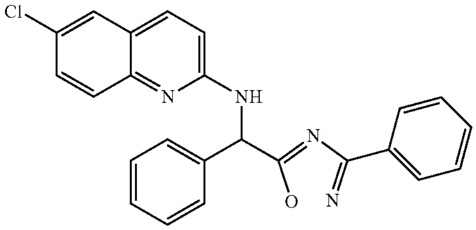 [SMILES: N=C(/N=C(\O)C(Nc1ccc2cc(Cl)ccc2n1)c1ccccc1)c1ccccc1] |

TABLE 1-continued
| Specific Compounds of the Invention | |
|---|---|
| Cpd. ID | Structure |
| CYM 52369 IC | 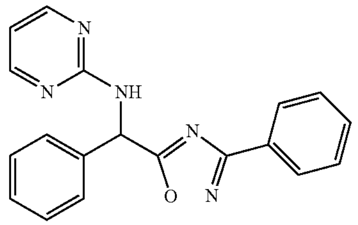 [SMILES: N=C(/N=C(\O)C(Nc1ncccn1)c1ccccc1)c1ccccc1] |
| CYM 52370 IC | 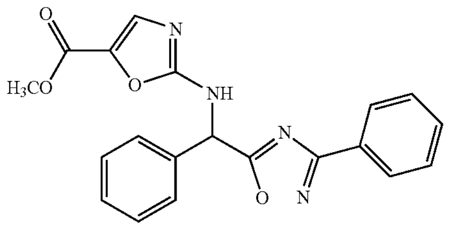 [SMILES: COC(=O)c1cnc(NC(/C(O)=N/C(=N)c2ccccc2)c2ccccc2)o1] |
| CYM 52371 IC | 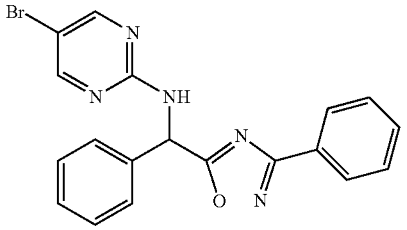 [SMILES: N=C(/N=C(\O)C(Nc1ncc(Br)cn1)c1ccccc1)c1ccccc1] |
| CYM 52372 IB | 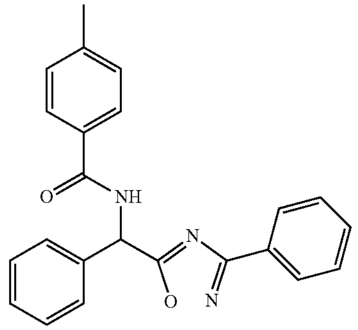 [SMILES: Cc1ccc(C(=O)NC(/C(O)=N/C(=N)c2ccccc2)c2ccccc2)cc1] |
| CYM 52373 IC | 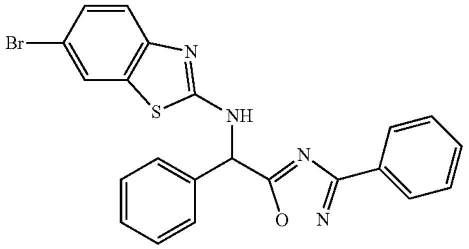 [SMILES: N=C(/N=C(\O)C(Nc1nc2ccc(Br)cc2s1)c1ccccc1)c1ccccc1] |
| CYM 52374 IC | 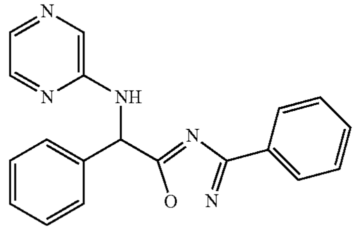 [SMILES: N=C(/N=C(\O)C(Nc1cnccn1)c1ccccc1)c1ccccc1] |

TABLE 1-continued
| Specific Compounds of the Invention | |
|---|---|
| Cpd. ID | Structure |
| CYM 52375 IB | 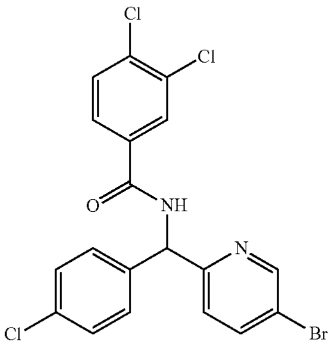 [SMILES: O=C(NC(c1ccc(Cl)cc1)c1ccc(Br)cn1)c1ccc(Cl)c(Cl)c1] |
| CYM 52376 IB | 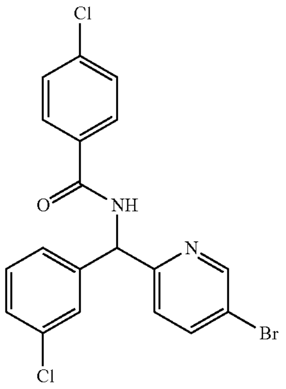 [SMILES: O=C(NC(c1cccc(Cl)c1)c1ccc(Br)cn1)c1ccc(Cl)cc1] |
| CYM 52377 IB | 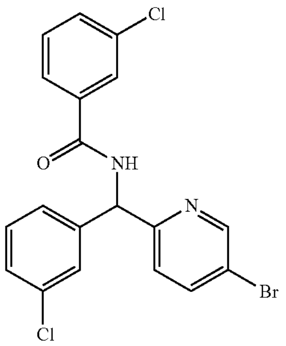 [SMILES: O=C(NC(c1cccc(Cl)c1)c1ccc(Br)cn1)c1cccc(Cl)c1] |
| CYM 52378 IB | 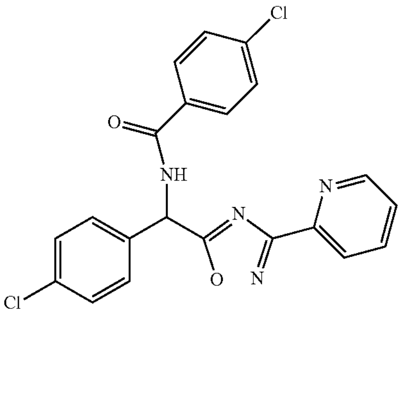 [SMILES: N=C(/N=C(\O)C(NC(=O)c1ccc(Cl)cc1)c1ccc(Cl)cc1)c1ccccn1] |

TABLE 1-continued
| Specific Compounds of the Invention | |
|---|---|
| Cpd. ID | Structure |
| CYM 52379 IB | 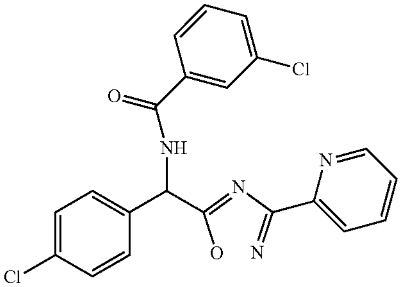 [SMILES: N=C(/N=C(\O)C(NC(=O)c1cccc(Cl)c1)c1ccc(Cl)cc1)c1ccccn1] |
| CYM 52380 IB | 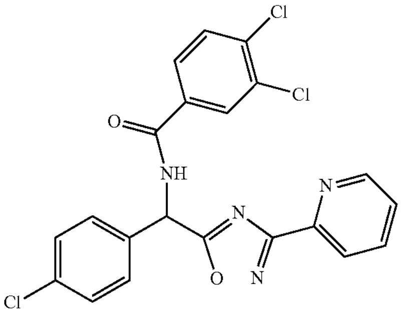 [SMILES: N=C(/N=C(\O)C(NC(=O)c1ccc(Cl)c(Cl)c1)c1ccc(Cl)cc1)c1ccccn1] |
| CYM 52381 IB | 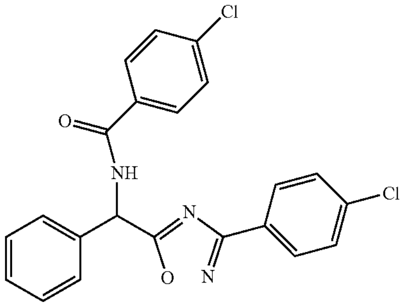 [SMILES: N=C(/N=C(\O)C(NC(=O)c1ccc(Cl)cc1)c1ccccc1)c1ccc(Cl)cc1] |
| CYM 52382 IB | 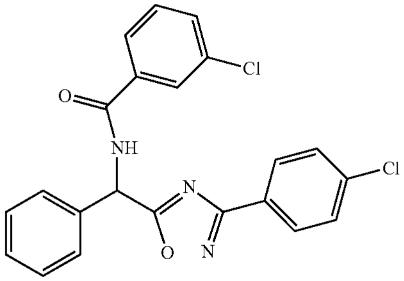 [SMILES: N=C(/N=C(\O)C(NC(=O)c1cccc(Cl)c1)c1ccccc1)c1ccc(Cl)cc1] |
| CYM 52383 IB | 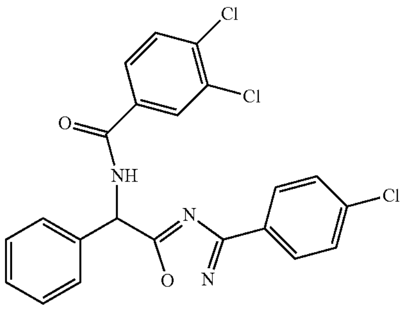 [SMILES: N=C(/N=C(\O)C(NC(=O)c1ccc(Cl)c(Cl)c1)c1ccccc1)c1ccc(Cl)cc1] |

TABLE 1-continued
| Specific Compounds of the Invention | |
|---|---|
| Cpd. ID | Structure |
| CYM 52384<br>IC | 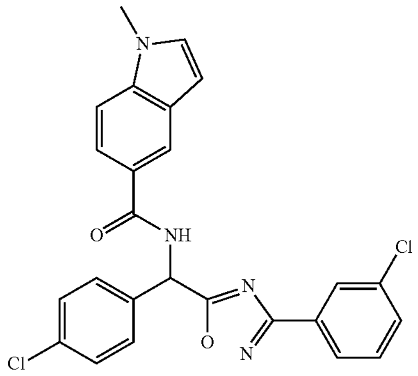 [SMILES: Cn1ccc2cc(C(=O)NC(/C(O)=N/C(=N)c3cccc(Cl)c3)c3ccc(Cl)cc3)ccc21] |
| CYM 52385<br>not I | 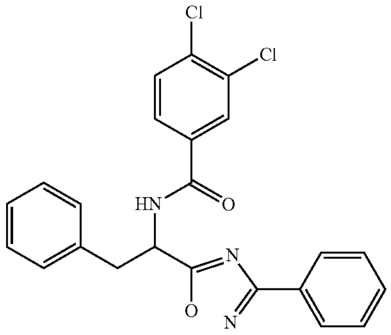 [SMILES: N=C(/N=C(\O)C(Cc1ccccc1)NC(=O)c1ccc(Cl)c(Cl)c1)c1ccccc1] |
| CYM 52386<br>not I | 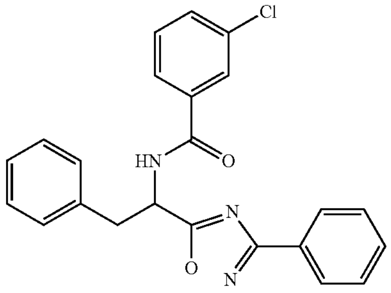 [SMILES: N=C(/N=C(\O)C(Cc1ccccc1)NC(=O)c1cccc(Cl)c1)c1ccccc1] |
| CYM 52387<br>IB | 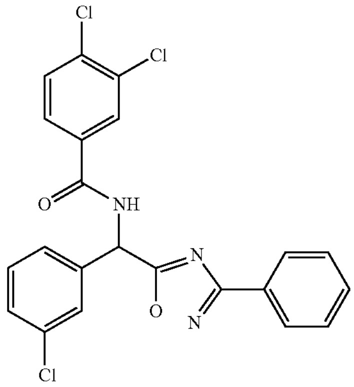 [SMILES: N=C(/N=C(\O)C(NC(=O)c1ccc(Cl)c(Cl)c1)c1cccc(Cl)c1)c1ccccc1] |

TABLE 1-continued
| Specific Compounds of the Invention | |
|---|---|
| Cpd. ID | Structure |
| CYM 52388<br>IB | 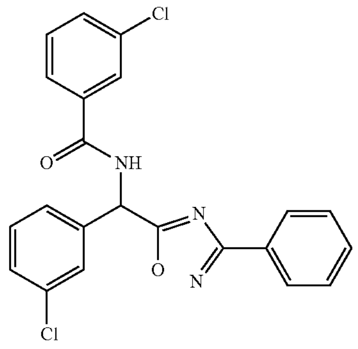 [SMILES: N=C(/N=C(\O)C(NC(=O)c1cccc(Cl)c1)c1cccc(Cl)c1)c1ccccc1] |
| CYM 52389<br>IB | 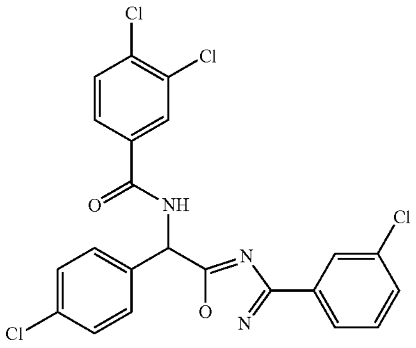 [SMILES: N=C(/N=C(\O)C(NC(=O)c1ccc(Cl)c(Cl)c1)c1ccc(Cl)cc1)c1cccc(Cl)c1] |
| CYM 52390<br>IB | 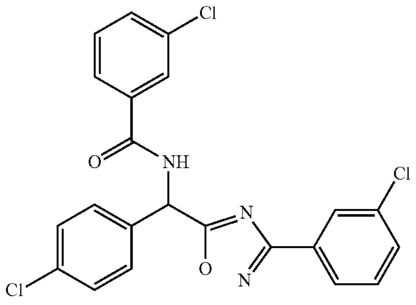 [SMILES: N=C(/N=C(\O)C(NC(=O)c1cccc(Cl)c1)c1ccc(Cl)cc1)c1cccc(Cl)c1] |
| CYM 52391<br>IB | 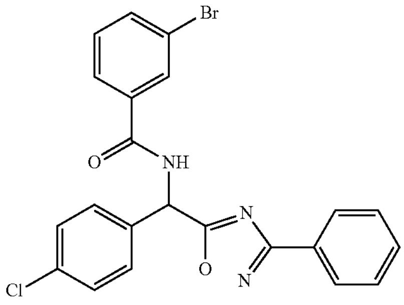 |

TABLE 1-continued
| Specific Compounds of the Invention | |
|---|---|
| Cpd. ID | Structure |
| CYM 52392<br>IB | 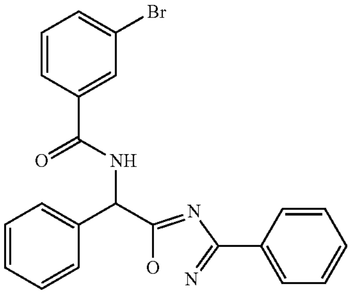 |
| CYM 52393<br>IC | 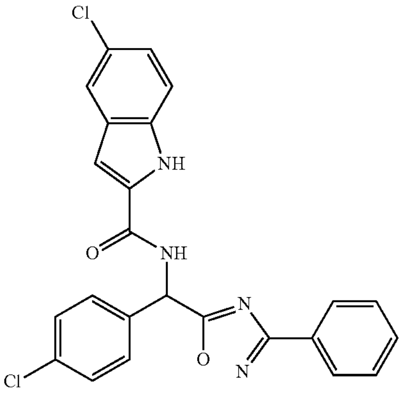 [SMILES: N=C(/N=C(\O)C(NC(=O)c1cc2cc(Cl)ccc2[nH]1)c1ccc(Cl)cc1)c1ccccc1] |
| CYM 52394<br>IB | 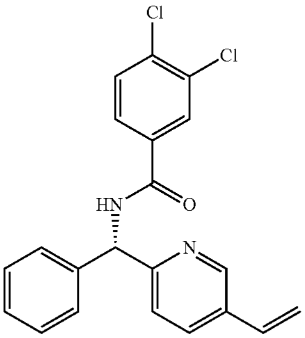 [SMILES: C=Cc1ccc([C@@H](NC(=O)c2ccc(Cl)c(Cl)c2)c2ccccc2)nc1] |
| CYM 52395<br>IB | 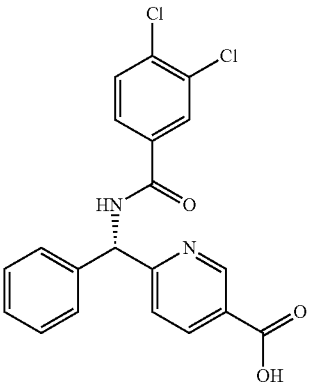 [SMILES: O=C(O)c1ccc([C@@H](NC(=O)c2ccc(Cl)c(Cl)c2)c2ccccc2)nc1] |

TABLE 1-continued
| Specific Compounds of the Invention | |
|---|---|
| Cpd. ID | Structure |
| CYM 52396 IB | 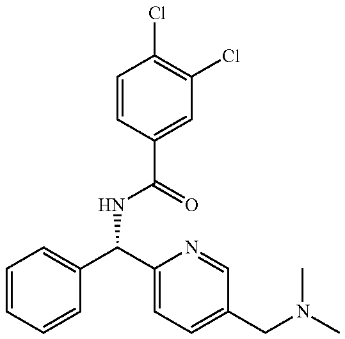 [SMILES: CN(C)Cc1ccc([C@@H](NC(=O)c2ccc(Cl)c(Cl)c2)c2ccccc2)nc1] |
| CYM 52397 IB | 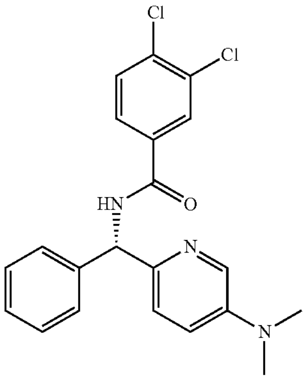 [SMILES: CN(C)c1ccc([C@@H](NC(=O)c2ccc(Cl)c(Cl)c2)c2ccccc2)nc1] |
| CYM 52398 IB | 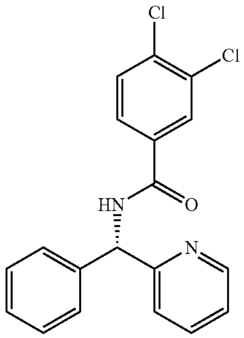 [SMILES: O=C(N[C@@H](c1ccccc1)c1ccccn1)c1ccc(Cl)c(Cl)c1] |
| CYM 52399 IB | 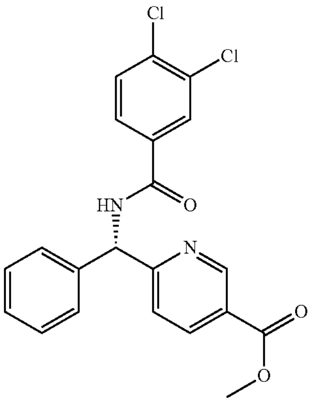 [SMILES: COC(=O)c1ccc([C@@H](NC(=O)c2ccc(Cl)c(Cl)c2)c2ccccc2)nc1] |

TABLE 1-continued
| Specific Compounds of the Invention | |
|---|---|
| Cpd. ID | Structure |
| CYM 52400<br>IB | 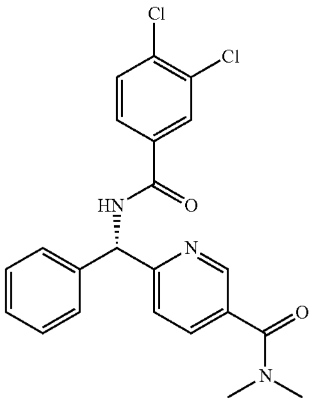 [SMILES: CN(C)C(=O)c1ccc([C@@H](NC(=O)c2ccc(Cl)c(Cl)c2)c2ccccc2)nc1] |
| CYM 52401<br>IB | 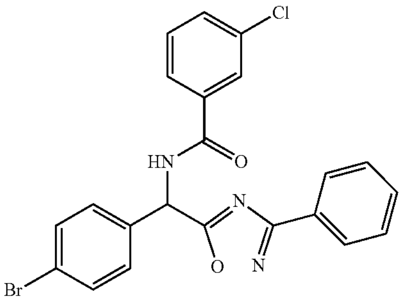 [SMILES: N=C(/N=C(\O)C(NC(=O)c1cccc(Cl)c1)c1ccc(Br)cc1)c1ccccc1] |
| CYM 52402<br>IB | 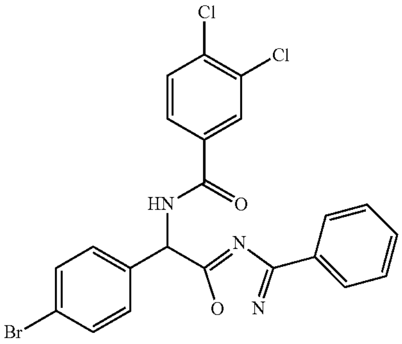 [SMILES: N=C(/N=C(\O)C(NC(=O)c1ccc(Cl)c(Br)c1)c1ccc(Cl)cc1)c1ccccc1] |
| CYM 52403<br>IB | 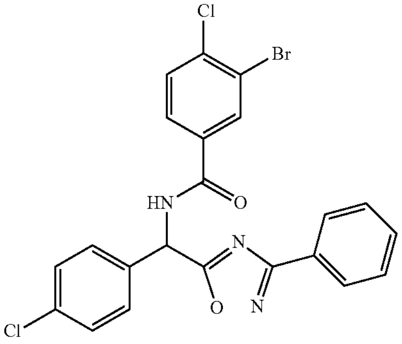 [SMILES: N=C(/N=C(\O)C(NC(=O)c1ccc(Cl)c(Br)c1)c1ccc(Cl)cc1)c1ccccc1] |

TABLE 1-continued
| Specific Compounds of the Invention | |
|---|---|
| Cpd. ID | Structure |
| CYM 52404 IB | 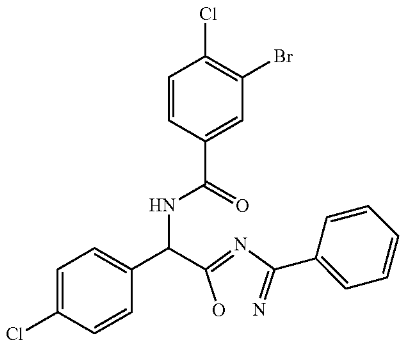 |
| CYM 52405 IB | 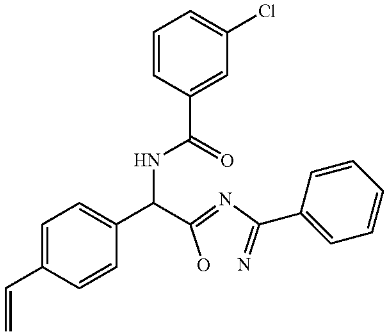 [SMILES: C=Cc1ccc(C(NC(=O)c2cccc(Cl)c2)/C(O)=N/C(=N)c2ccccc2)cc1] |
| CYM 52406 IB | 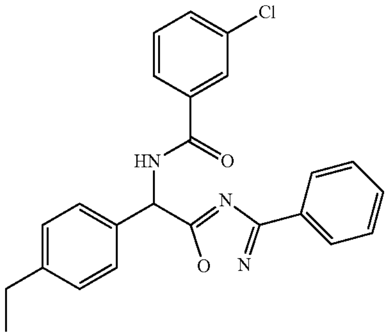 [SMILES: CCc1ccc(C(NC(=O)c2cccc(Cl)c2)/C(O)=N/C(=N)c2ccccc2)cc1] |
| CYM 52407 IB | 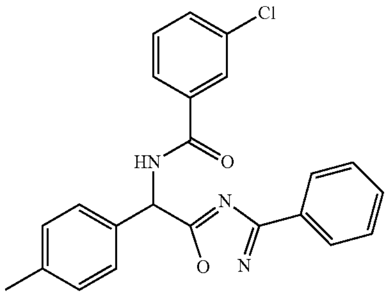 [SMILES: Cc1ccc(C(NC(=O)c2cccc(Cl)c2)/C(O)=N/C(=N)c2ccccc2)cc1] |

TABLE 1-continued
| Specific Compounds of the Invention | |
|---|---|
| Cpd. ID | Structure |
| CYM 52408<br>IB | 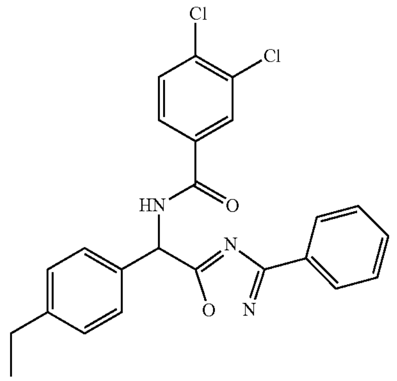 [SMILES: CCc1ccc(C(NC(=O)c2ccc(Cl)c(Cl)c2)/C(O)=N/C(=N)c2ccccc2)cc1] |
| CYM 52409<br>IB | 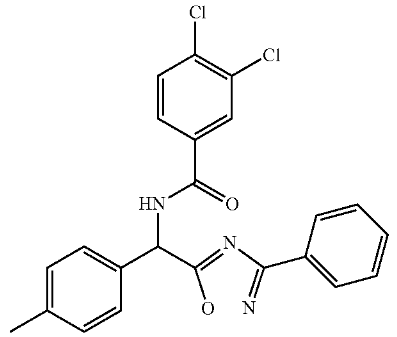 [SMILES: Cc1ccc(C(NC(=O)c2ccc(Cl)c(Cl)c2)/C(O)=N/C(=N)c2ccccc2)cc1] |
| CYM 52410<br>IB | 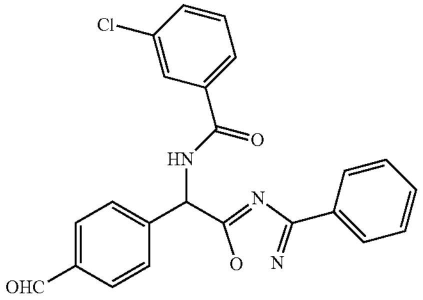 [SMILES: N=C(/N=C(\O)C(NC(=O)c1cccc(Cl)c1)c1ccc(C=O)cc1)c1ccccc1] |
| CYM 52411<br>IB | 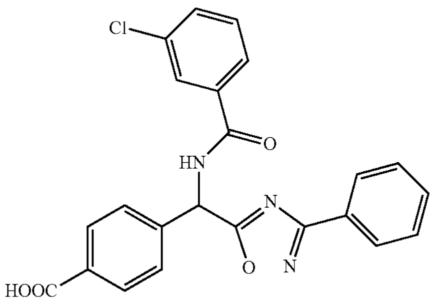 [SMILES: N=C(/N=C(\O)C(NC(=O)c1cccc(Cl)c1)c1ccc(C(=O)O)cc1)c1ccccc1] |

TABLE 1-continued
| Specific Compounds of the Invention | |
|---|---|
| Cpd. ID | Structure |
| CYM 52412 IB | 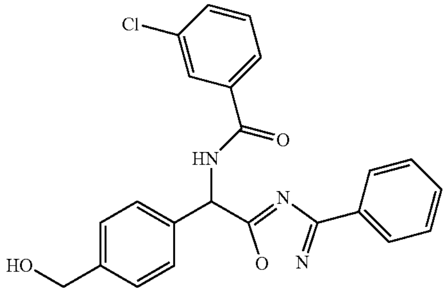 [SMILES: N=C(/N=C(\O)C(NC(=O)c1cccc(Cl)c1)c1ccc(CO)cc1)c1ccccc1] |
| CYM 52413 IB | 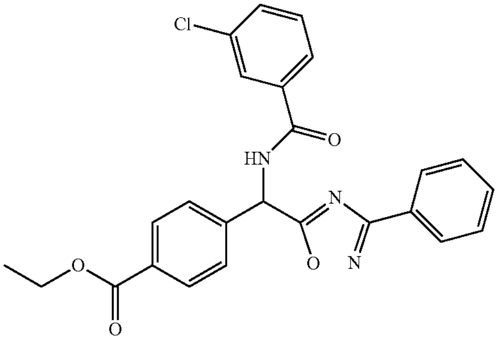 [SMILES: CCOC(=O)c1ccc(C(NC(=O)c2cccc(Cl)c2)/C(O)=N/C(=N)c2ccccc2)cc1] |
| CYM 52414 IB | 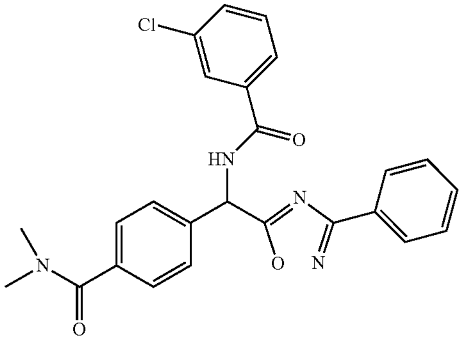 [SMILES: CN(C)C(=O)c1ccc(C(NC(=O)c2cccc(Cl)c2)/C(O)=N/C(=N)c2ccccc2)cc1] |
| CYM 52415 IC | 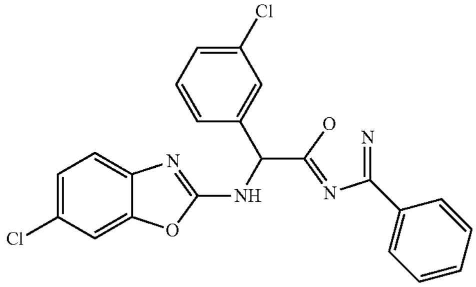 [SMILES: N=C(/N=C(\O)C(Nc1nc2ccc(Cl)cc2o1)c1cccc(Cl)c1)c1ccccc1] |
| CYM 52416 IC | 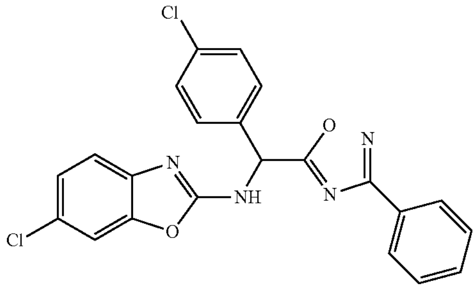 [SMILES: N=C(/N=C(\O)C(Nc1nc2ccc(Cl)cc2o1)c1ccc(Cl)cc1)c1ccccc1] |

TABLE 1-continued
| Specific Compounds of the Invention | |
|---|---|
| Cpd. ID | Structure |
| CYM 52417<br>IB | 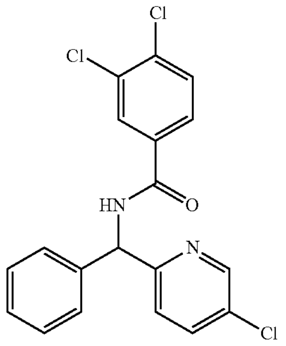 [SMILES: O=C(NC(c1ccccc1)c1ccc(Cl)cn1)c1ccc(Cl)c(Cl)c1] |
| CYM 52418<br>IB | 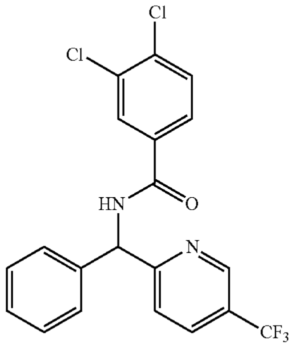 [SMILES: O=C(NC(c1ccccc1)c1ccc(C(F)(F)F)cn1)c1ccc(Cl)c(Cl)c1] |
| CYM 52419<br>IB | 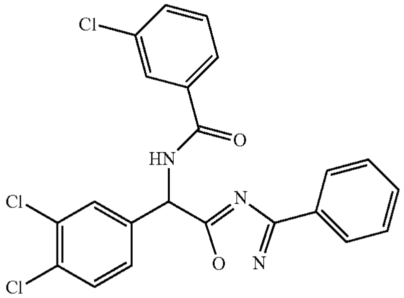 [SMILES: N=C(/N=C(\O)C(NC(=O)c1cccc(Cl)c1)c1ccc(Cl)c(Cl)c1)c1ccccc1] |
| CYM 52420<br>IB | 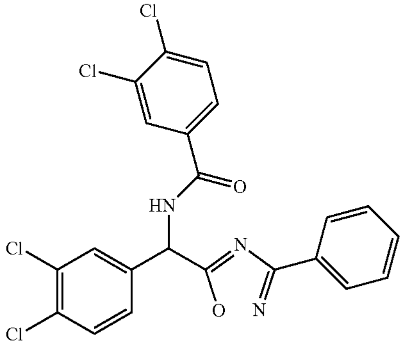 [SMILES: N=C(/N=C(\O)C(NC(=O)c1ccc(Cl)c(Cl)c1)c1ccc(Cl)c(Cl)c1)c1ccccc1] |

TABLE 1-continued
| Specific Compounds of the Invention | |
|---|---|
| Cpd. ID | Structure |
| CYM 52421<br>IB | 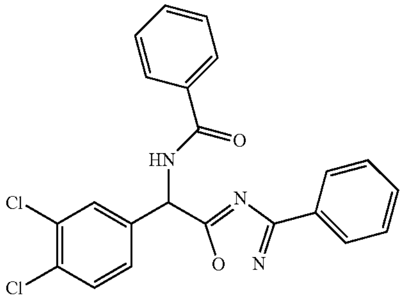 [SMILES: N=C(/N=C(\O)C(NC(=O)c1ccccc1)c1ccc(Cl)c(Cl)c1)c1ccccc1] |
| CYM 52422<br>not I | 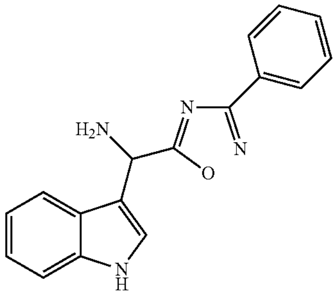 [SMILES: N=C(/N=C(\O)C(N)c1c[nH]c2ccccc12)c1ccccc1] |
| CYM 52423<br>IE | 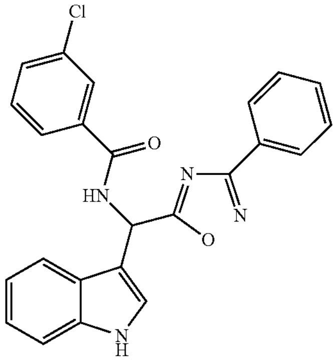 [SMILES: N=C(/N=C(\O)C(NC(=O)c1cccc(Cl)c1)c1c[nH]c2ccccc12)c1ccccc1] |
| CYM 52424<br>IE | 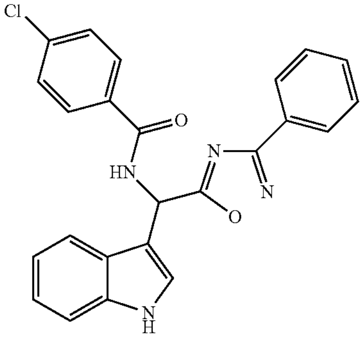 [SMILES: N=C(/N=C(\O)C(NC(=O)c1ccc(Cl)cc1)c1c[nH]c2ccccc12)c1ccccc1] |

TABLE 1-continued
| Specific Compounds of the Invention | |
|---|---|
| Cpd. ID | Structure |
| CYM 52425 IE | 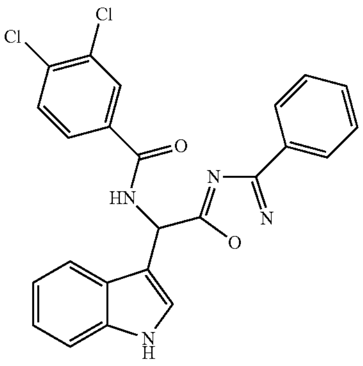 [SMILES: N=C(/N=C(\O)C(NC(=O)c1ccc(Cl)c(Cl)c1)c1c[nH]c2ccccc12)c1ccccc1] |
| CYM 52426 IB | 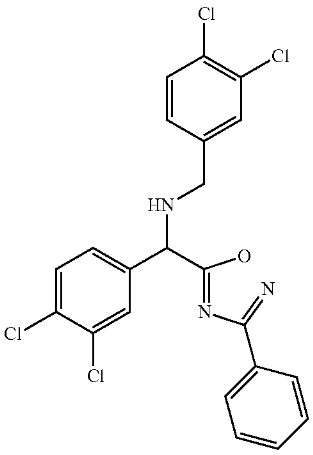 [SMILES: N=C(/N=C(\O)C(NCc1ccc(Cl)c(Cl)c1)c1ccc(Cl)c(Cl)c1)c1ccccc1] |
| CYM 52427 IB | 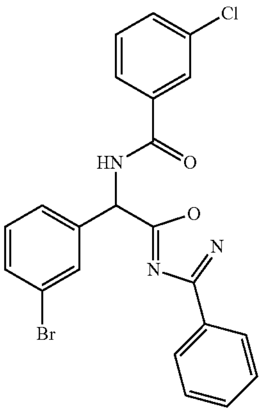 [SMILES: N=C(/N=C(\O)C(NC(=O)c1cccc(Cl)c1)c1cccc(Br)c1)c1ccccc1] |

TABLE 1-continued
| Specific Compounds of the Invention | |
|---|---|
| Cpd. ID | Structure |
| CYM 52428<br>IB | 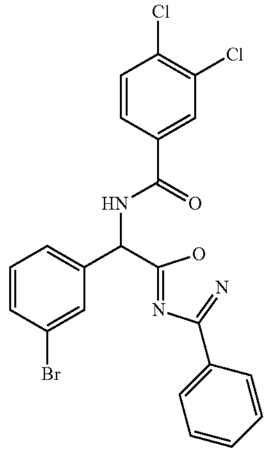 [SMILES: N=C(/N=C(\O)C(NC(=O)c1ccc(Cl)c(Cl)c1)c1cccc(Br)c1)c1ccccc1] |
| CYM 52429<br>IB | 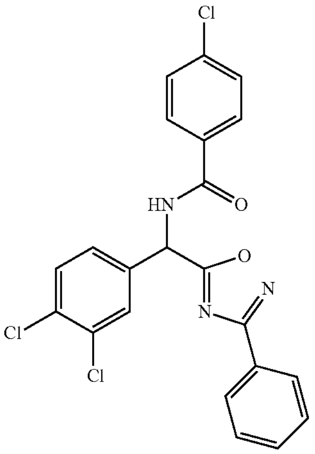 [SMILES: N=C(/N=C(\O)C(NC(=O)c1ccc(Cl)cc1)c1ccc(Cl)c(Cl)c1)c1ccccc1] |
| CYM 52430<br>IB | 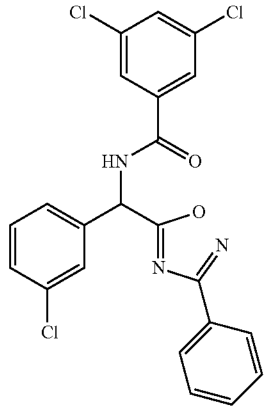 [SMILES: N=C(/N=C(\O)C(NC(=O)c1cc(Cl)cc(Cl)c1)c1cccc(Cl)c1)c1ccccc1] |

TABLE 1-continued
| Specific Compounds of the Invention | |
|---|---|
| Cpd. ID | Structure |
| CYM 52431<br>IB | 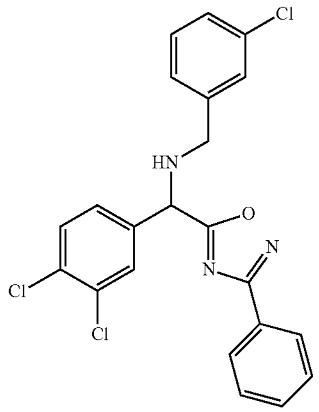 [SMILES: N=C(/N=C(\O)C(NCc1cccc(Cl)c1)c1ccc(Cl)c(Cl)c1)c1ccccc1] |
| CYM 52432<br>IB | 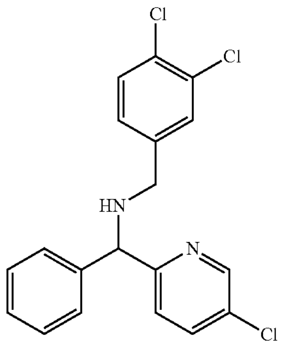 [SMILES: Clc1ccc(C(NCc2ccc(Cl)c(Cl)c2)c2ccccc2)nc1] |
| CYM 52433<br>IB | 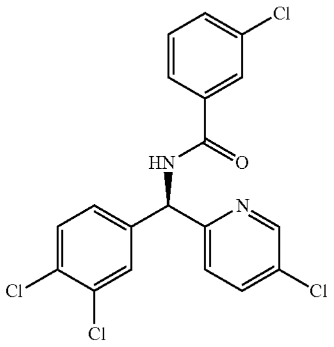 [SMILES: O=C(N[C@H](c1ccc(Cl)c(Cl)c1)c1ccc(Cl)cn1)c1cccc(Cl)c1] |
| CYM 52434<br>IB | 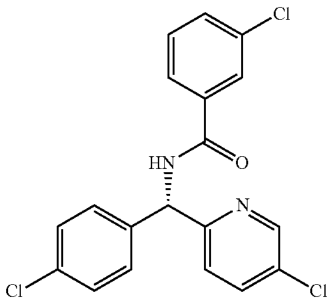 [SMILES: O=C(N[C@@H](c1ccc(Cl)cc1)c1ccc(Cl)cn1)c1cccc(Cl)c1] |

TABLE 1-continued
| Specific Compounds of the Invention | |
|---|---|
| Cpd. ID | Structure |
| CYM 52435 IB | 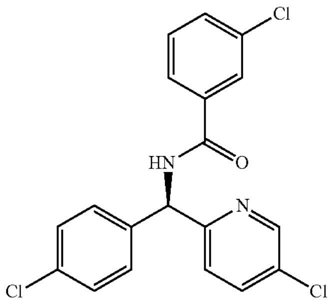 [SMILES: O=C(N[C@H](c1ccc(Cl)cc1)c1ccc(Cl)cn1)c1cccc(Cl)c1] |
| CYM 52436 IB | 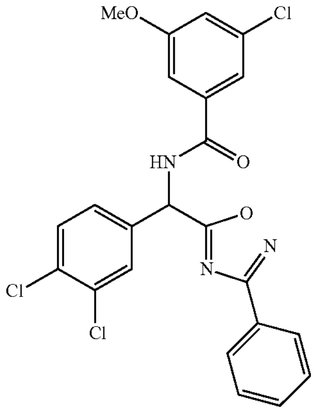 [SMILES: COc1cc(Cl)cc(C(=O)NC(/C(O)=N/C(=N)c2ccccc2)c2ccc(Cl)c(Cl)c2)c1] |
| CYM 52437 IB | 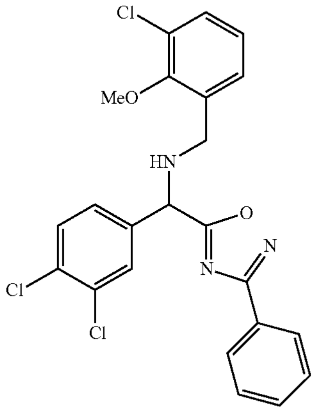 [SMILES: COc1c(Cl)cccc1CNC(/C(O)=N/C(=N)c1ccccc1)c1ccc(Cl)c(Cl)c1] |
| CYM 52438 IB | 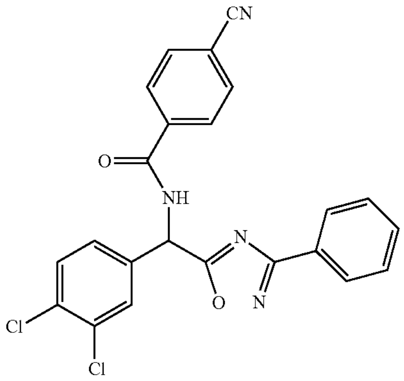 [SMILES: N#Cc1ccc(C(=O)NC(/C(O)=N/C(=N)c2ccccc2)c2ccc(Cl)c(Cl)c2)cc1] |

TABLE 1-continued
| Specific Compounds of the Invention | |
|---|---|
| Cpd. ID | Structure |
| CYM 52439<br>IB | 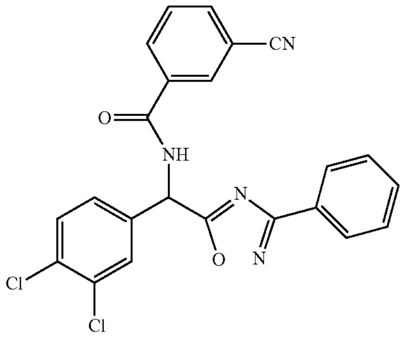 [SMILES: N#Cc1cccc(C(=O)NC(/C(O)=N/C(=N)c2ccccc2)c2ccc(Cl)c(Cl)c2)c1] |
| CYM 52440<br>IB | 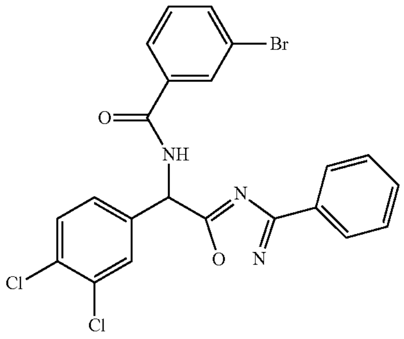 [SMILES: N=C(/N=C(\O)C(NC(=O)c1cccc(Br)c1)c1ccc(Cl)c(Cl)c1)c1ccccc1] |
| CYM 52441<br>IC | 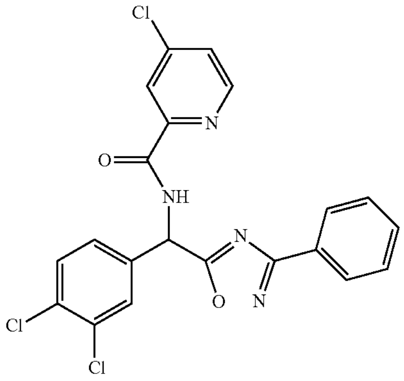 [SMILES: N=C(/N=C(\O)C(NC(=O)c1cc(Cl)ccn1)c1ccc(Cl)c(Cl)c1)c1ccccc1] |
| CYM 52442<br>IB | 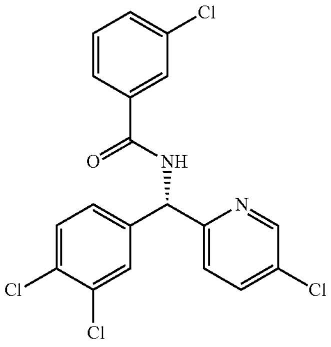 [SMILES: O=C(N[C@@H](c1ccc(Cl)c(Cl)c1)c1ccc(Cl)cn1)c1cccc(Cl)c1] |

TABLE 1-continued
| Specific Compounds of the Invention | |
|---|---|
| Cpd. ID | Structure |
| CYM 52443 IB | 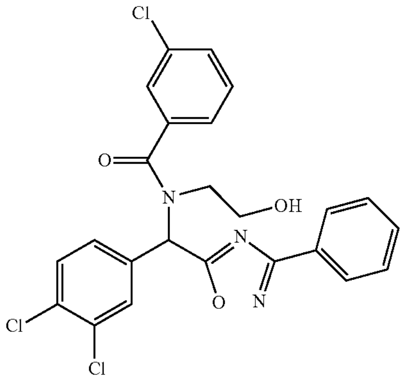 [SMILES: N=C(/N=C(\O)C(c1ccc(Cl)c(Cl)c1)N(CCO)C(=O)c1cccc(Cl)c1)c1ccccc1] |
| CYM 52444 IB | 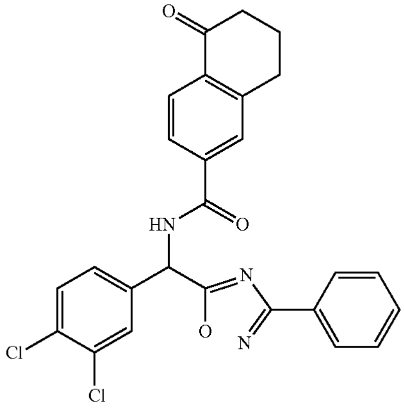 [SMILES: N=C(/N=C(\O)C(NC(=O)c1ccc2c(c1)CCCC2=O)c1ccc(Cl)c(Cl)c1)c1ccccc1] |
| CYM 52445 IB | 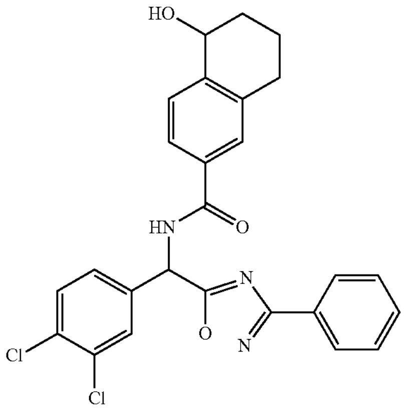 [SMILES: N=C(/N=C(\O)C(NC(=O)c1ccc2c(c1)CCCC2O)c1ccc(Cl)c(Cl)c1)c1ccccc1] |

TABLE 1-continued
| Specific Compounds of the Invention | |
|---|---|
| Cpd. ID | Structure |
| CYM 52446<br>IC | 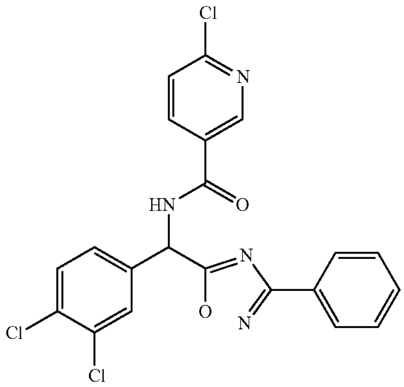 [SMILES: N=C(/N=C(\O)C(NC(=O)c1ccc(Cl)nc1)c1ccc(Cl)c(Cl)c1)c1ccccc1] |
| CYM 52447<br>IB | 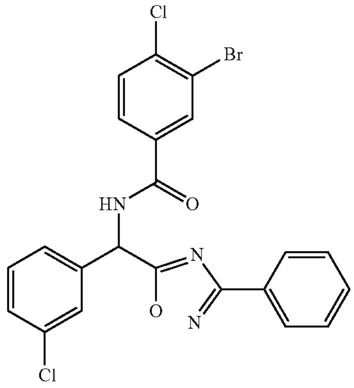 |
| CYM 52448<br>IB | 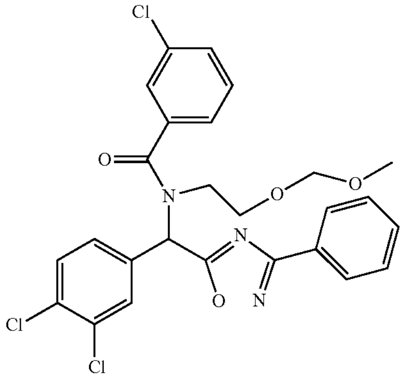 [SMILES: COCOCCN(C(=O)c1cccc(Cl)c1)C(/C(O)=N/C(=N)c1ccccc1)c1ccc(Cl)c(Cl)c1] |
| CYM 52449<br>IB | 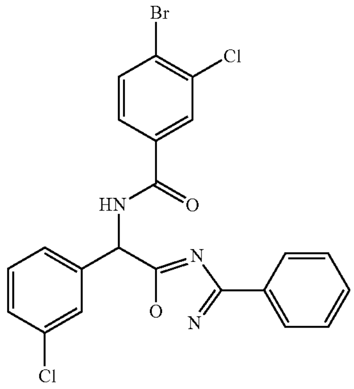 |

TABLE 1-continued
| Specific Compounds of the Invention | |
|---|---|
| Cpd. ID | Structure |
| CYM 52450 IB | 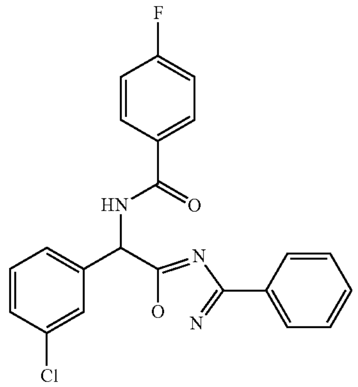 [SMILES: N=C(/N=C(\O)C(NC(=O)c1ccc(F)cc1)c1cccc(Cl)c1)c1ccccc1] |
| CYM 52451 IB | 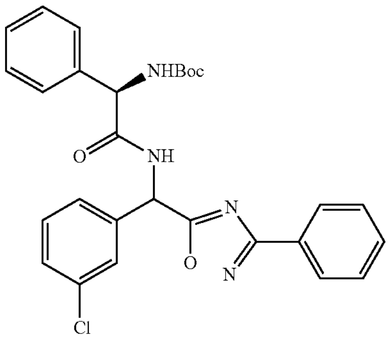 [SMILES: CC(C)(C)OC(=O)N[C@@H](C(=O)NC(/C(O)=N/C(=N)c1ccccc1)c1cccc(Cl)c1)c1ccccc1] |
| CYM 52452 IB | 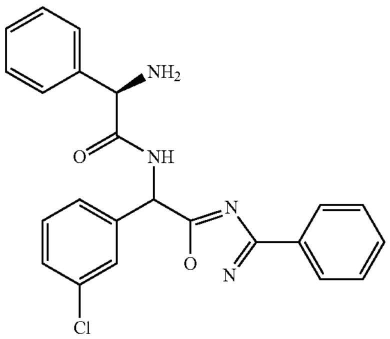 [SMILES: N=C(/N=C(\O)C(NC(=O)[C@H](N)c1ccccc1)c1cccc(Cl)c1)c1ccccc1] |
| CYM 52453 IB | 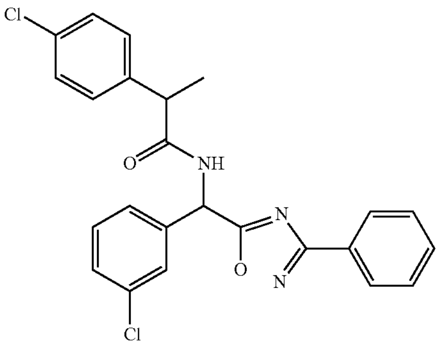 [SMILES: CC(C(=O)NC(/C(O)=N/C(=N)c1ccccc1)c1cccc(Cl)c1)c1ccc(Cl)cc1] |

TABLE 1-continued
| Specific Compounds of the Invention | |
|---|---|
| Cpd. ID | Structure |
| CYM 52454 IB | 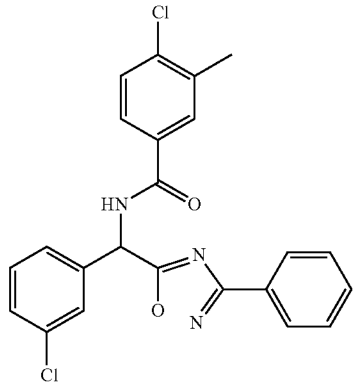 [SMILES: Cc1cc(C(=O)NC(/C(O)=N/C(=N)c2ccccc2)c2cccc(Cl)c2)ccc1Cl] |
| CYM 52455 IB | 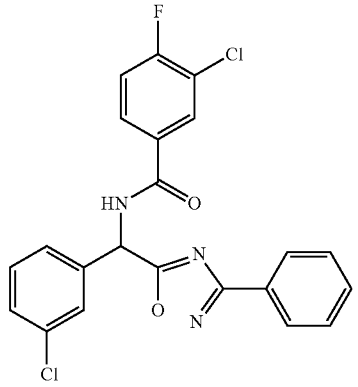 [SMILES: N=C(/N=C(\O)C(NC(=O)c1ccc(F)c(Cl)c1)c1cccc(Cl)c1)c1ccccc1] |
| CYM 52456 IB | 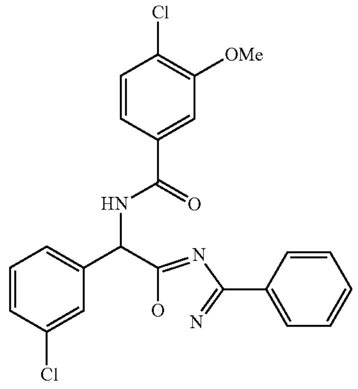 [SMILES: COc1cc(C(=O)NC(/C(O)=N/C(=N)c2ccccc2)c2cccc(Cl)c2)ccc1Cl] |
| CYM 52457 IB | 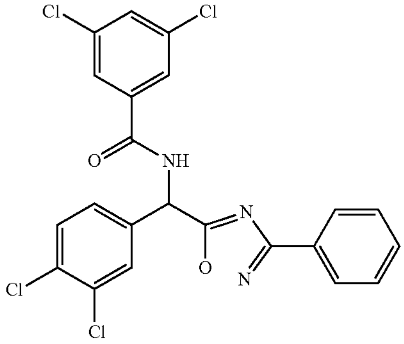 [SMILES: N=C(/N=C(\O)C(NC(=O)c1cc(Cl)cc(Cl)c1)c1ccc(Cl)c(Cl)c1)c1ccccc1] |

TABLE 1-continued
| Specific Compounds of the Invention | |
|---|---|
| Cpd. ID | Structure |
| CYM 52458 IB | 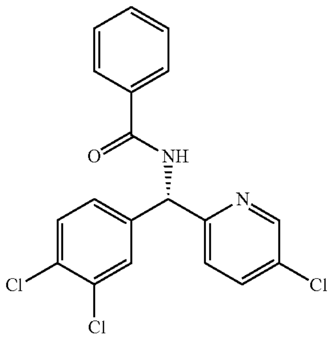 [SMILES: O=C(N[C@@H](c1ccc(Cl)c(Cl)c1)c1ccc(Cl)cn1)c1ccccc1] |
| CYM 52459 IB | 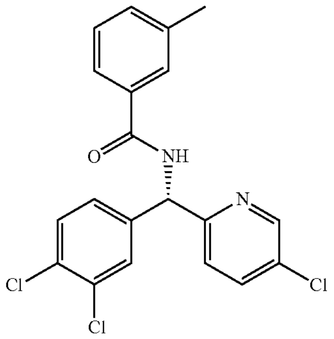 [SMILES: Cc1cccc(C(=O)N[C@@H](c2ccc(Cl)c(Cl)c2)c2ccc(Cl)cn2)c1] |
| CYM 52460 IB | 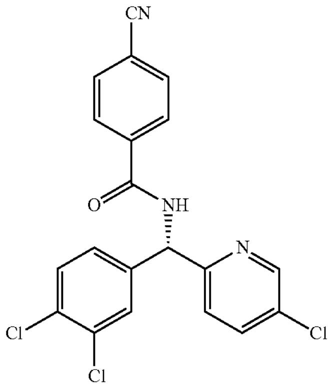 [SMILES: N#Cc1ccc(C(=O)N[C@@H](c2ccc(Cl)c(Cl)c2)c2ccc(Cl)cn2)cc1] |
| CYM 52461 IC | 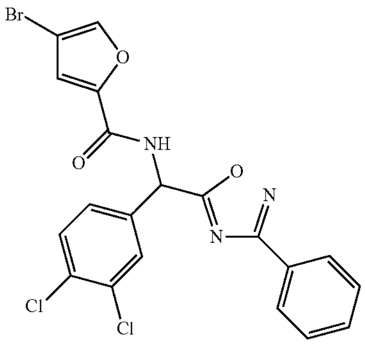 [SMILES: N=C(/N=C(\O)C(NC(=O)c1cc(Br)co1)c1ccc(Cl)c(Cl)c1)c1ccccc1] |

TABLE 1-continued
| Specific Compounds of the Invention | |
| --- | --- |
| Cpd. ID | Structure |
| CYM 52462 IC | 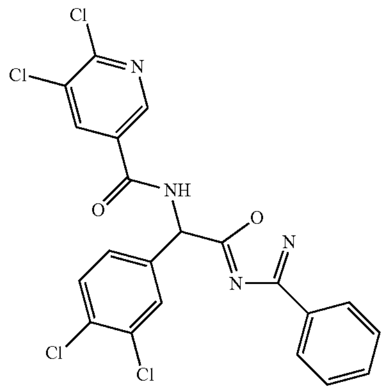 [SMILES: N=C(/N=C(\O)C(NC(=O)c1cnc(Cl)c(Cl)c1)c1ccc(Cl)c(Cl)c1)c1ccccc1] |
| CYM 52463 IB | 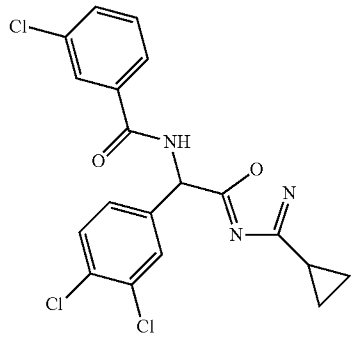 [SMILES: N=C(/N=C(\O)C(NC(=O)c1cccc(Cl)c1)c1ccc(Cl)c(Cl)c1)C1CC1] |
| CYM 52464 IB | 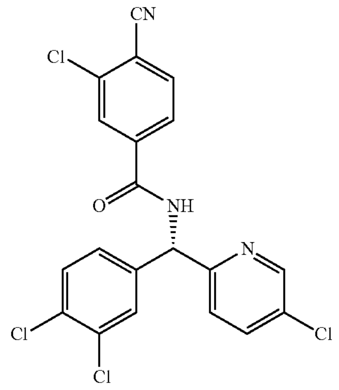 [SMILES: N#Cc1ccc(C(=O)N[C@@H](c2ccc(Cl)c(Cl)c2)c2ccc(Cl)cn2)cc1Cl] |
| CYM 52465 IB | 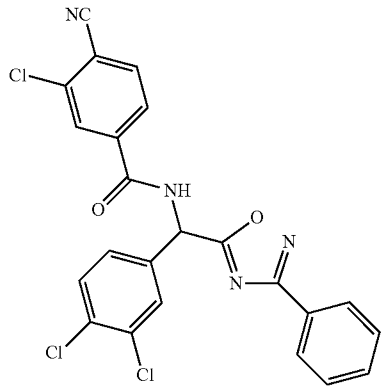 [SMILES: N#Cc1ccc(C(=O)NC(/C(O)=N/C(=N)c2ccccc2)c2ccc(Cl)c(Cl)c2)cc1Cl] |

TABLE 1-continued
| Specific Compounds of the Invention | |
|---|---|
| Cpd. ID | Structure |
| CYM 52466 IC | 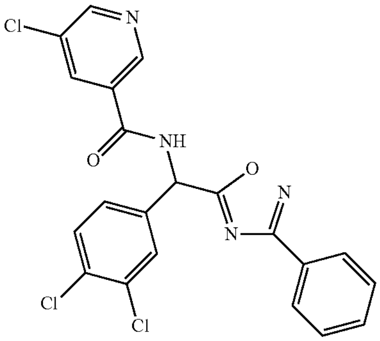 [SMILES: N=C(/N=C(\O)C(NC(=O)c1cncc(Cl)c1)c1ccc(Cl)c(Cl)c1)c1ccccc1] |
| CYM 52467 IC | 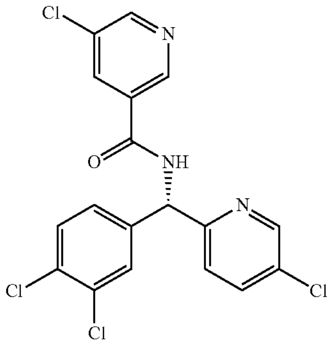 [SMILES: O=C(N[C@@H](c1ccc(Cl)c(Cl)c1)c1ccc(Cl)cn1)c1cncc(Cl)c1] |
| CYM 52468 IC | 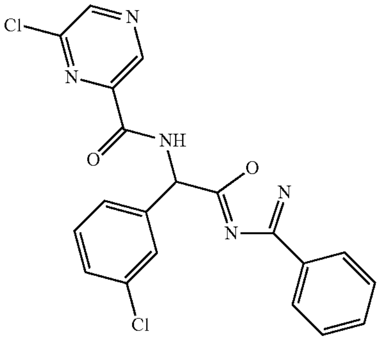 [SMILES: N=C(/N=C(\O)C(NC(=O)c1cncc(Cl)n1)c1cccc(Cl)c1)c1ccccc1] |
| CYM 52469 IB | 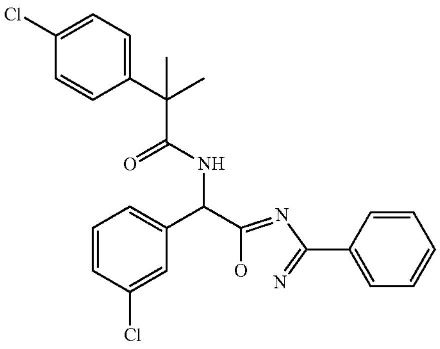 [SMILES: CC(C)(C(=O)NC(/C(O)=N/C(=N)c1ccccc1)c1cccc(Cl)c1)c1ccc(Cl)cc1] |

TABLE 1-continued
| Specific Compounds of the Invention | |
|---|---|
| Cpd. ID | Structure |
| CYM 52470 IB | 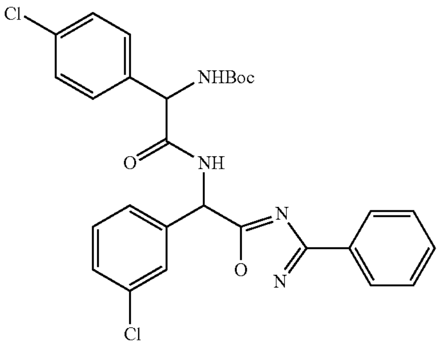 [SMILES: CC(C)(C)OC(=O)NC(C(=O)NC(/C(O)=N/C(=N)c1ccccc1)c1cccc(Cl)c1)c1ccc(Cl)cc1] |
| CYM 52471 IB | 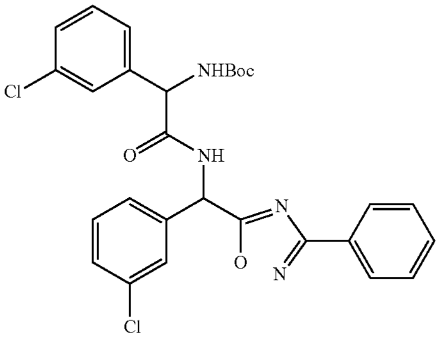 [SMILES: CC(C)(C)OC(=O)NC(C(=O)NC(/C(O)=N/C(=N)c1ccccc1)c1cccc(Cl)c1)c1cccc(Cl)c1] |
| CYM 52472 IB | 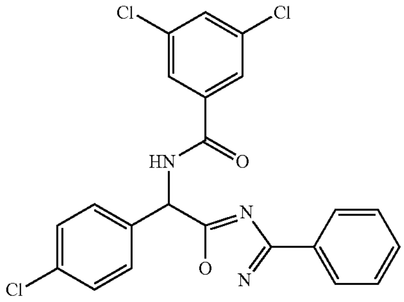 [SMILES: N=C(/N=C(\O)C(NC(=O)c1cc(Cl)cc(Cl)c1)c1ccc(Cl)cc1)c1ccccc1] |
| CYM 52473 IB | 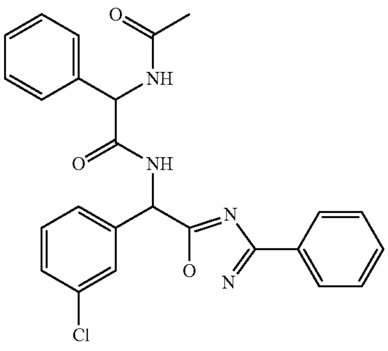 [SMILES: CC(=O)NC(C(=O)NC(/C(O)=N/C(=N)c1ccccc1)c1cccc(Cl)c1)c1ccccc1] |

TABLE 1-continued
| Specific Compounds of the Invention | |
|---|---|
| Cpd. ID | Structure |
| CYM 52474<br>IB | 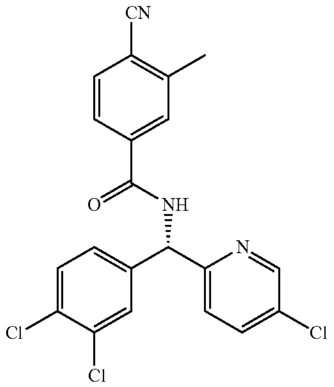 [SMILES: Cc1cc(C(=O)N[C@@H](c2ccc(Cl)c(Cl)c2)c2ccc(Cl)cn2)ccc1C#N] |
| CYM 52475<br>IB | 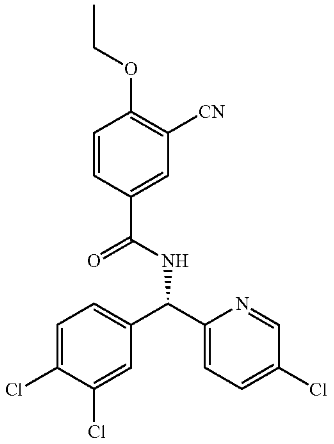 [SMILES: CCOc1ccc(C(=O)N[C@@H](c2ccc(Cl)c(Cl)c2)c2ccc(Cl)cn2)cc1C#N] |
| CYM 52476<br>IA | 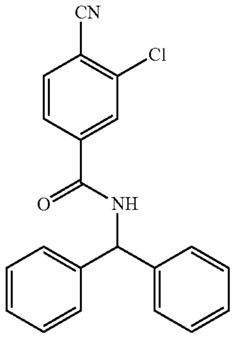 [SMILES: N#Cc1ccc(C(=O)NC(c2ccccc2)c2ccccc2)cc1Cl] |
| CYM 52477<br>IB | 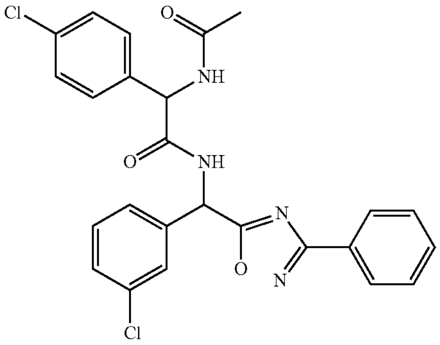 [SMILES: CC(=O)NC(C(=O)NC(/C(O)=N/C(=N)c1ccccc1)c1cccc(Cl)c1)c1ccc(Cl)cc1] |

TABLE 1-continued
| Specific Compounds of the Invention | |
|---|---|
| Cpd. ID | Structure |
| CYM 52478 IB | 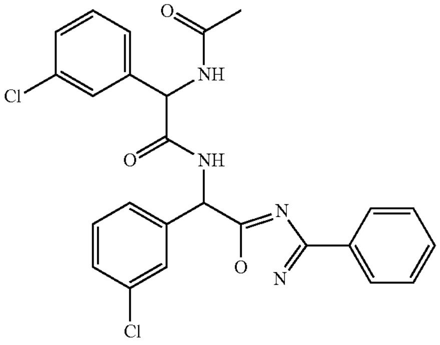 [SMILES: CC(=O)NC(C(=O)NC(/C(O)=N/C(=N)c1ccccc1)c1cccc(Cl)c1)c1cccc(Cl)c1] |
| CYM 52479 IB | 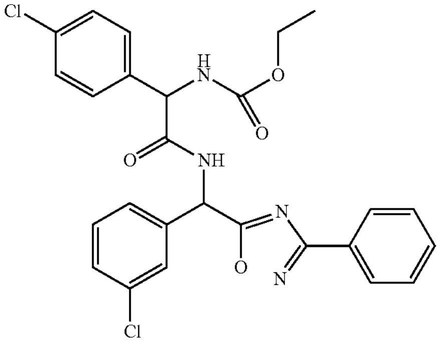 [SMILES: CCOC(=O)NC(C(=O)NC(/C(O)=N/C(=N)c1ccccc1)c1cccc(Cl)c1)c1ccc(Cl)cc1] |
| CYM 52480 IB | 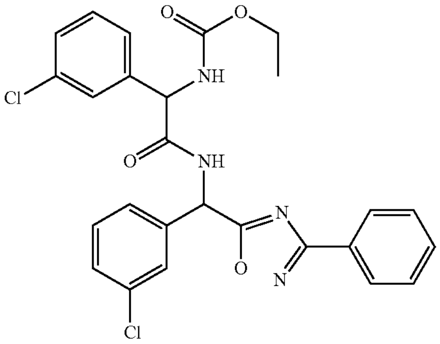 [SMILES: CCOC(=O)NC(C(=O)NC(/C(O)=N/C(=N)c1ccccc1)c1cccc(Cl)c1)c1cccc(Cl)c1] |
| CYM 52481 IB | 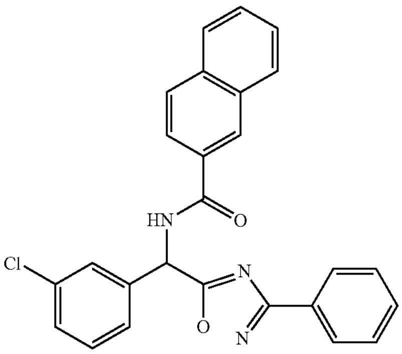 [SMILES: N=C(/N=C(\O)C(NC(=O)c1ccc2ccccc2c1)c1cccc(Cl)c1)c1ccccc1] |

TABLE 1-continued
Specific Compounds of the Invention
| Cpd. ID | Structure |
|---|---|
| CYM 52482 IB | 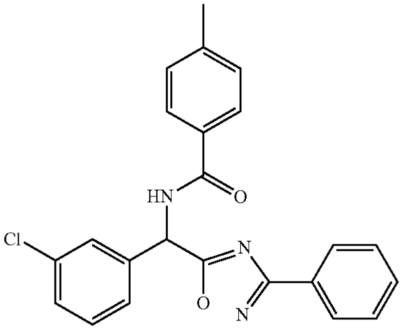 [SMILES: Cc1ccc(C(=O)NC(/C(O)=N/C(=N)c2ccccc2)c2cccc(Cl)c2)cc1] |
| CYM 52483 IB | 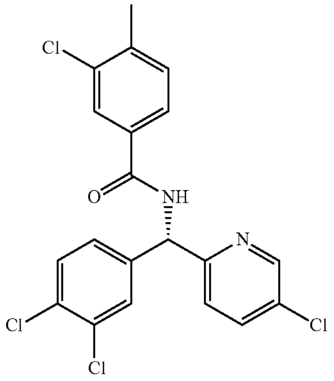 [SMILES: Cc1ccc(C(=O)N[C@@H](c2ccc(Cl)c(Cl)c2)c2ccc(Cl)cn2)cc1Cl] |
| CYM 52484 IB | 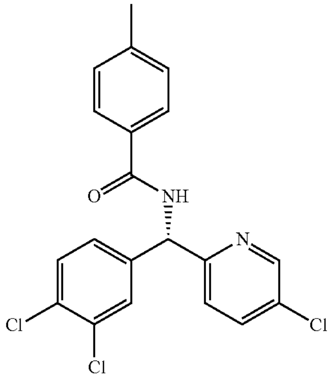 [SMILES: Cc1ccc(C(=O)N[C@@H](c2ccc(Cl)c(Cl)c2)c2ccc(Cl)cn2)cc1] |
| CYM 52485 IC | 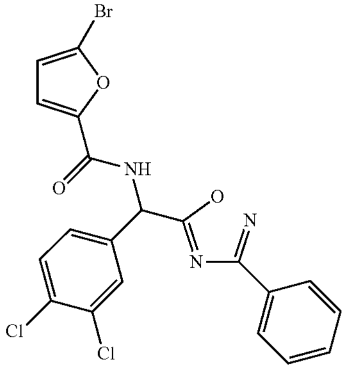 [SMILES: N=C(/N=C(\O)C(NC(=O)c1ccc(Br)o1)c1ccc(Cl)c(Cl)c1)c1ccccc1] |

TABLE 1-continued
| Specific Compounds of the Invention | |
|---|---|
| Cpd. ID | Structure |
| CYM 52486 IB | 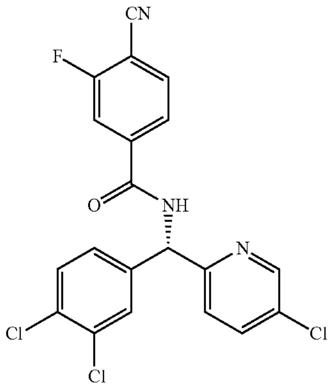 [SMILES: N#Cc1ccc(C(=O)N[C@@H](c2ccc(Cl)c(Cl)c2)c2ccc(Cl)cn2)cc1F] |
| CYM 52487 IB | 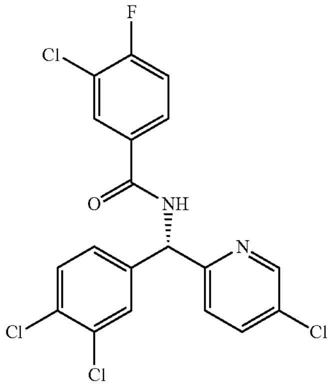 [SMILES: O=C(N[C@@H](c1ccc(Cl)c(Cl)c1)c1ccc(Cl)cn1)c1ccc(F)c(Cl)c1] |
| CYM 52488 IB | 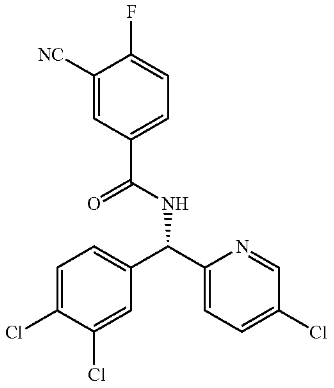 [SMILES: N#Cc1cc(C(=O)N[C@@H](c2ccc(Cl)c(Cl)c2)c2ccc(Cl)cn2)ccc1F] |
| CYM 52489 IC | 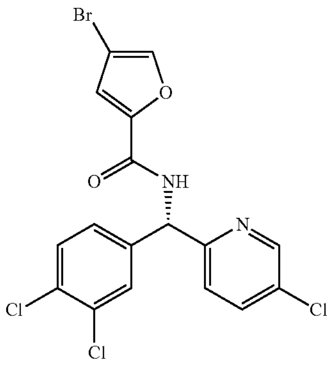 [SMILES: O=C(N[C@@H](c1ccc(Cl)c(Cl)c1)c1ccc(Cl)cn1)c1cc(Br)co1] |

TABLE 1-continued
| Specific Compounds of the Invention | |
|---|---|
| Cpd. ID | Structure |
| CYM 52490 IB | 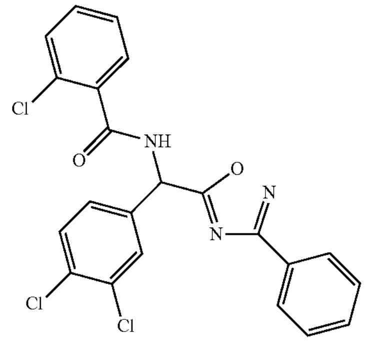 [SMILES: N=C(/N=C(\O)C(NC(=O)c1ccccc1Cl)c1ccc(Cl)c(Cl)c1)c1ccccc1] |
| CYM 52491 IB | 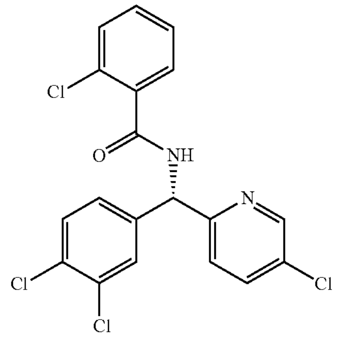 [SMILES: O=C(N[C@@H](c1ccc(Cl)c(Cl)c1)c1ccc(Cl)cn1)c1ccccc1Cl] |
| CYM 52492 IB | 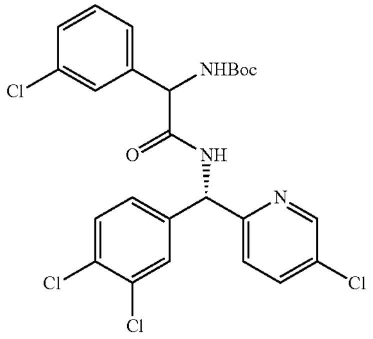 [SMILES: CC(C)(C)OC(=O)NC(C(=O)N[C@@H](c1ccc(Cl)c(Cl)c1)c1ccc(Cl)cn1)c1cccc(Cl)c1] |
| CYM 52493 IB | 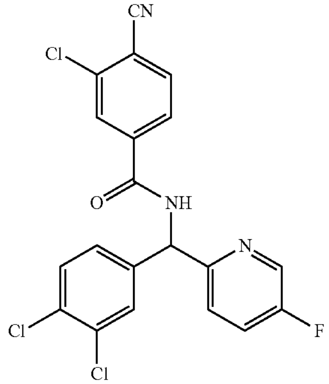 [SMILES: N#Cc1ccc(C(=O)NC(c2ccc(Cl)c(Cl)c2)c2ccc(F)cn2)cc1Cl] |

TABLE 1-continued
| Specific Compounds of the Invention | |
|---|---|
| Cpd. ID | Structure |
| CYM 52494 IB | 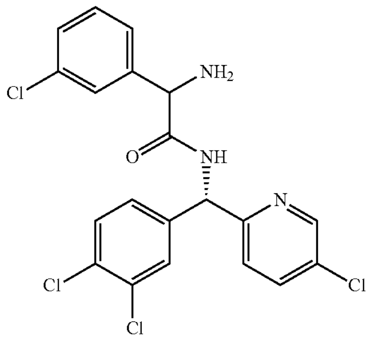 [SMILES: NC(C(=O)N[C@@H](c1ccc(Cl)c(Cl)c1)c1ccc(Cl)cn1)c1cccc(Cl)c1] |
| CYM 52495 IB | 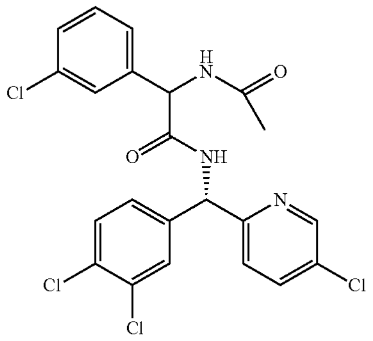 [SMILES: CC(=O)NC(C(=O)N[C@@H](c1ccc(Cl)c(Cl)c1)c1ccc(Cl)cn1)c1cccc(Cl)c1] |
| CYM 52496 IB | 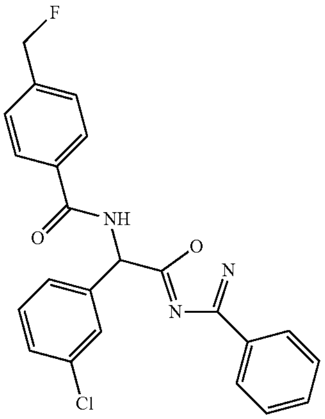 [SMILES: N=C(/N=C(\O)C(NC(=O)c1ccc(CF)cc1)c1cccc(Cl)c1)c1ccccc1] |
| CYM 52497 IB | 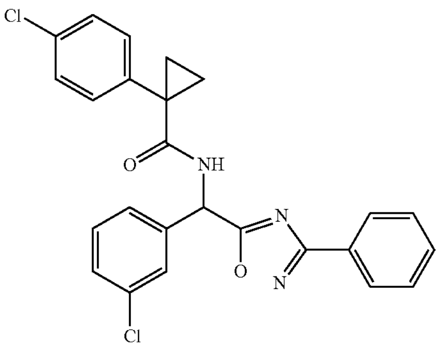 [SMILES: N=C(/N=C(\O)C(NC(=O)C1(c2ccc(Cl)cc2)CC1)c1cccc(Cl)c1)c1ccccc1] |

TABLE 1-continued
| Specific Compounds of the Invention | |
|---|---|
| Cpd. ID | Structure |
| CYM 52498 IB | 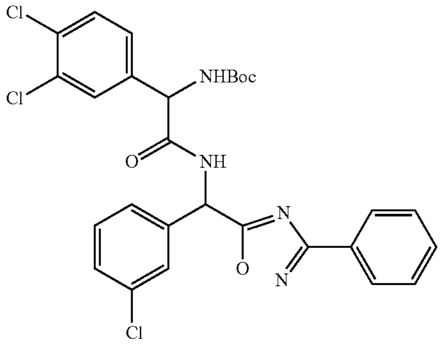 [SMILES: CC(C)(C)OC(=O)NC(C(=O)NC(/C(O)=N/C(=N)c1ccccc1)c1cccc(Cl)c1)c1ccc(Cl)c(Cl)c1] |
| CYM 52499 IB | 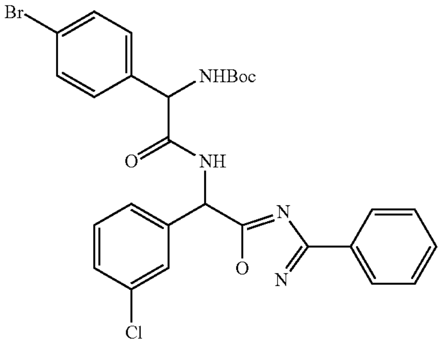 |
| CYM 52500 IB | 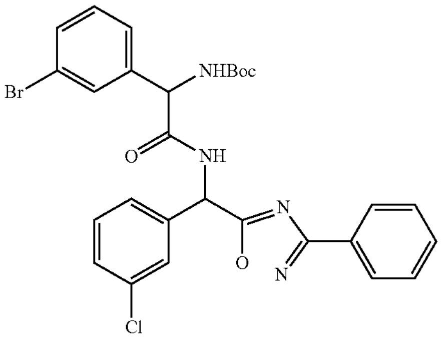 |
| CYM 52501 IB | 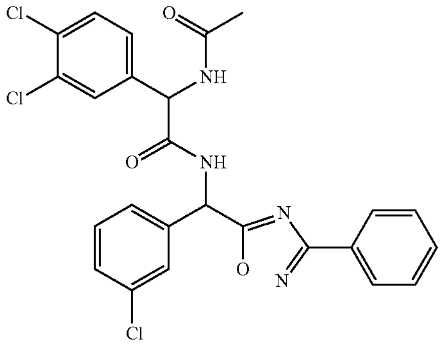 [SMILES: CC(=O)NC(C(=O)NC(/C(O)=N/C(=N)c1ccccc1)c1cccc(Cl)c1)c1ccc(Cl)c(Cl)c1] |

TABLE 1-continued
| Specific Compounds of the Invention | |
|---|---|
| Cpd. ID | Structure |
| CYM 52502 IB | 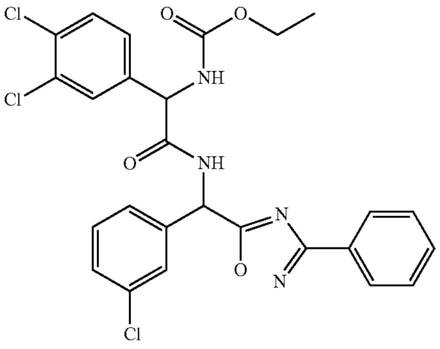 [SMILES: CCOC(=O)NC(C(=O)NC(/C(O)=N/C(=N)c1ccccc1)c1cccc(Cl)c1)c1ccc(Cl)c(Cl)c1] |
| CYM 52503 IB | 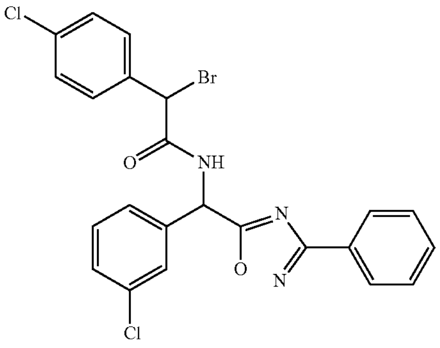 [SMILES: N=C(/N=C(\O)C(NC(=O)C(Br)c1ccc(Cl)cc1)c1cccc(Cl)c1)c1ccccc1] |
| CYM 52504 IB | 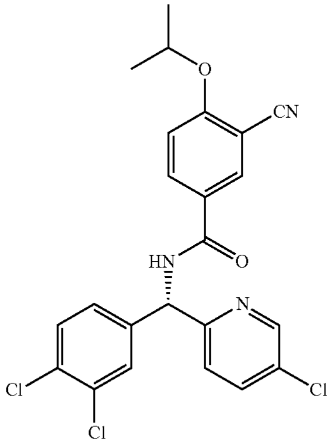 [SMILES: CC(C)Oc1ccc(C(=O)N[C@@H](c2ccc(Cl)c(Cl)c2)c2ccc(Cl)cn2)cc1C#N] |

TABLE 1-continued
| Specific Compounds of the Invention | |
|---|---|
| Cpd. ID | Structure |
| CYM 52505<br>IB | 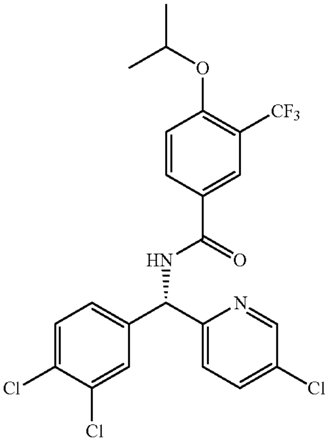 [SMILES: CC(C)Oc1ccc(C(=O)N[C@@H](c2ccc(Cl)c(Cl)c2)c2ccc(Cl)cn2)cc1C(F)(F)F] |
| CYM 52506<br>IB | 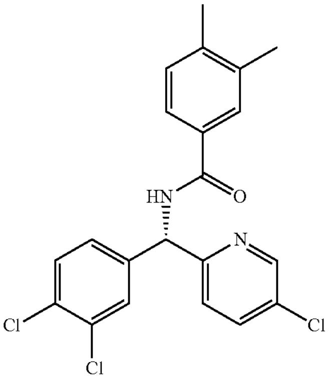 [SMILES: Cc1ccc(C(=O)N[C@@H](c2ccc(Cl)c(Cl)c2)c2ccc(Cl)cn2)cc1C] |
| CYM 52507<br>IB | 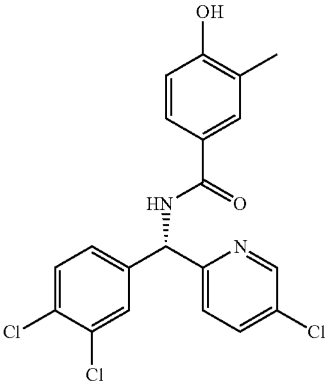 |

TABLE 1-continued
| Specific Compounds of the Invention | |
|---|---|
| Cpd. ID | Structure |
| CYM 52508 IB | 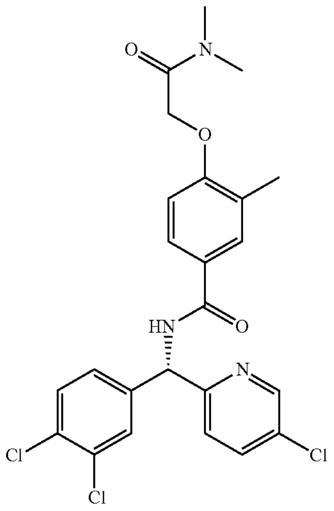 [SMILES: Cc1cc(C(=O)N[C@@H](c2ccc(Cl)c(Cl)c2)c2ccc(Cl)cn2)ccc1OCC(=O)N(C)C] |
| CYM 52509 IB | 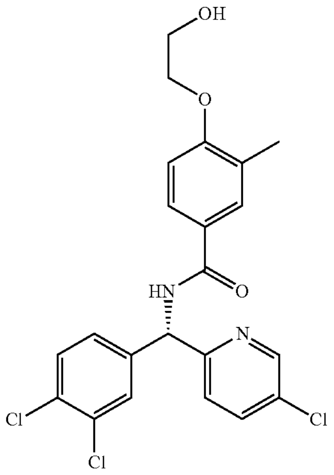 [SMILES: Cc1cc(C(=O)N[C@@H](c2ccc(Cl)c(Cl)c2)c2ccc(Cl)cn2)ccc1OCCO] |
| CYM 52510 IB | 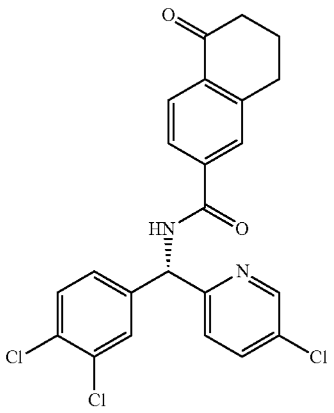 [SMILES: O=C(N[C@@H](c1ccc(Cl)c(Cl)c1)c1ccc(Cl)cn1)c1ccc2c(c1)CCCC2=O] |

TABLE 1-continued
| Specific Compounds of the Invention | |
|---|---|
| Cpd. ID | Structure |
| CYM 52511 IC | 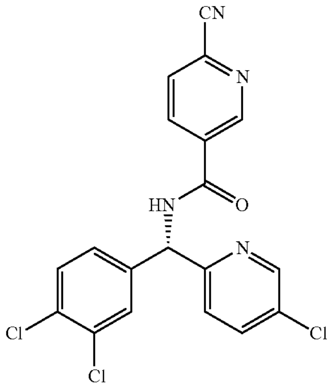 [SMILES: N#Cc1ccc(C(=O)N[C@@H](c2ccc(Cl)c(Cl)c2)c2ccc(Cl)cn2)cn1] |
| CYM 52512 IB | 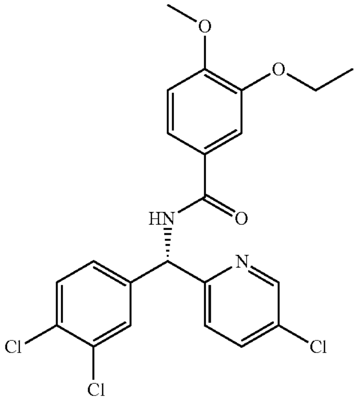 [SMILES: CCOc1cc(C(=O)N[C@@H](c2ccc(Cl)c(Cl)c2)c2ccc(Cl)cn2)ccc1OC] |
| CYM 52513 not I | 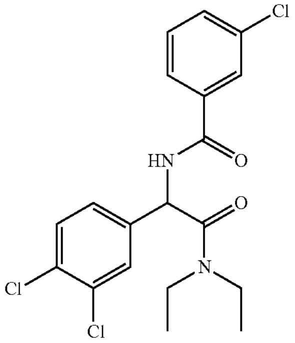 [SMILES: CCN(CC)C(=O)C(NC(=O)c1cccc(Cl)c1)c1ccc(Cl)c(Cl)c1] |
| CYM 52514 IB | 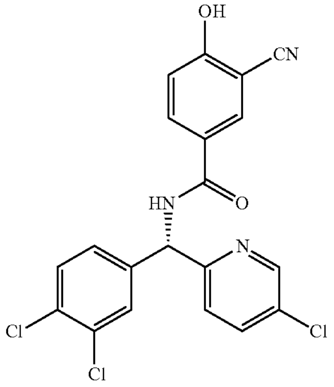 [SMILES: N#Cc1cc(C(=O)N[C@@H](c2ccc(Cl)c(Cl)c2)c2ccc(Cl)cn2)ccc1O] |

TABLE 1-continued
| Specific Compounds of the Invention | |
|---|---|
| Cpd. ID | Structure |
| CYM 52515<br>IB | 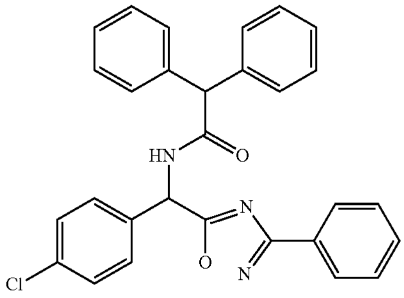 [SMILES: N=C(/N=C(\O)C(NC(=O)C(c1ccccc1)c1ccccc1)c1ccc(Cl)cc1)c1ccccc1] |
| CYM 52516<br>IB | 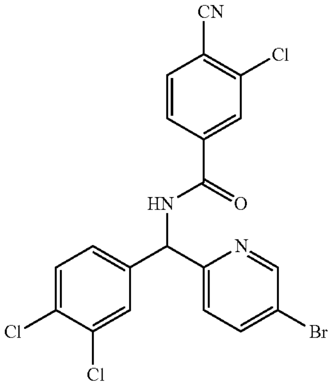 [SMILES: N#Cc1ccc(C(=O)NC(c2ccc(Cl)c(Cl)c2)c2ccc(Br)cn2)cc1Cl] |
| CYM 52517<br>IC | 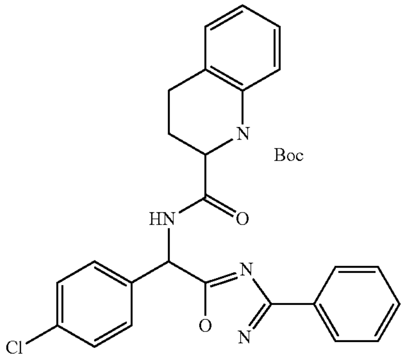 [SMILES: N=C(/N=C(\O)C(NC(=O)C1CCc2ccccc2N1)c1ccc(Cl)cc1)c1ccccc1 ; "Boc"] |
| CYM 52518<br>IC | 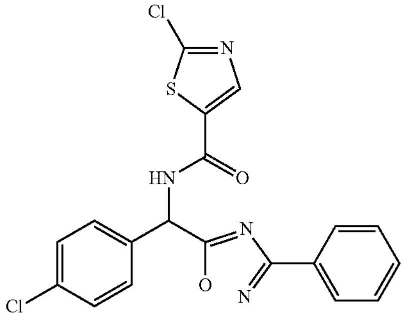 [SMILES: N=C(/N=C(\O)C(NC(=O)c1cnc(Cl)s1)c1ccc(Cl)cc1)c1ccccc1] |

TABLE 1-continued
| Specific Compounds of the Invention | |
|---|---|
| Cpd. ID | Structure |
| CYM 52519<br>IB | 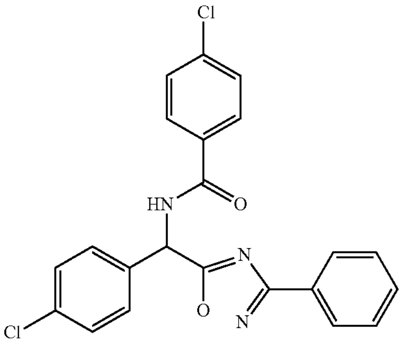 [SMILES: N=C(/N=C(\O)C(NC(=O)c1ccc(Cl)cc1)c1ccc(Cl)cc1)c1ccccc1] |
| CYM 52520<br>IB | 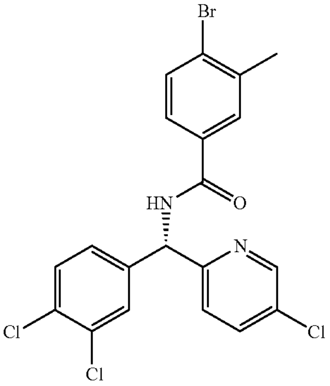 [SMILES: Cc1cc(C(=O)N[C@@H](c2ccc(Cl)c(Cl)c2)c2ccc(Cl)cn2)ccc1Br] |
| CYM52521<br>IB | 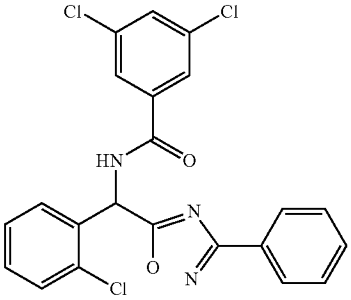 [SMILES: N=C(/N=C(\O)C(NC(=O)c1cc(Cl)cc(Cl)c1)c1ccccc1Cl)c1ccccc1] |
| CYM52522<br>IB | 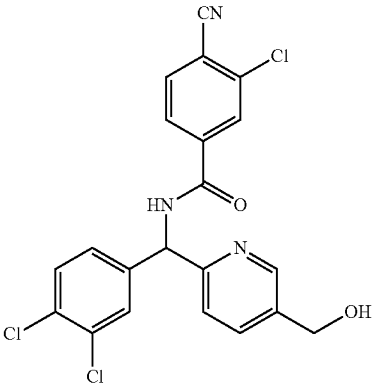 [SMILES: N#Cc1ccc(C(=O)NC(c2ccc(Cl)c(Cl)c2)c2ccc(CO)cn2)cc1Cl] |

TABLE 1-continued
| Specific Compounds of the Invention | |
|---|---|
| Cpd. ID | Structure |
| CYM52523 IB | 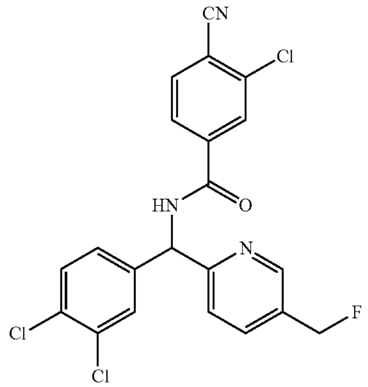 [SMILES: N#Cc1ccc(C(=O)NC(c2ccc(Cl)c(Cl)c2)c2ccc(CF)cn2)cc1Cl] |
| CYM52524 IB | 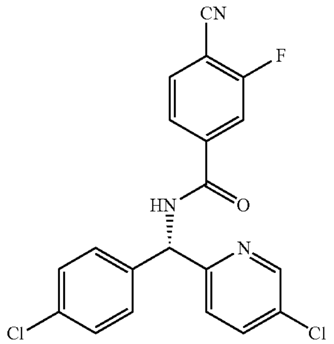 [SMILES: N#Cc1ccc(C(=O)N[C@@H](c2ccc(Cl)cc2)c2ccc(Cl)cn2)cc1F] |
| CYM52525 IB | 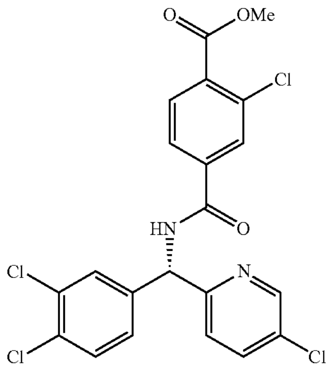 [SMILES: COC(=O)c1ccc(C(=O)N[C@@H](c2ccc(Cl)c(Cl)c2)c2ccc(Cl)cn2)cc1Cl] |
| CYM52526 IB | 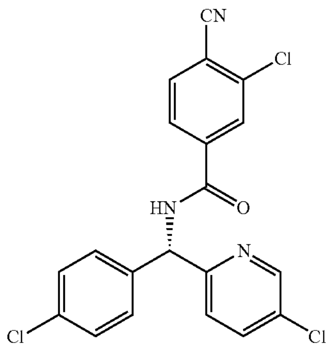 [SMILES: N#Cc1ccc(C(=O)N[C@@H](c2ccc(Cl)cc2)c2ccc(Cl)cn2)cc1Cl] |

TABLE 1-continued
| Specific Compounds of the Invention | |
|---|---|
| Cpd. ID | Structure |
| CYM52527 IB | 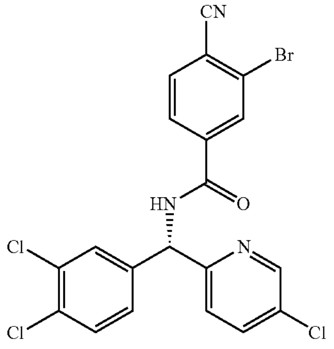 [SMILES: N#Cc1ccc(C(=O)N[C@@H](c2ccc(Cl)c(Cl)c2)c2ccc(Cl)cn2)cc1Br] |
| CYM52528 IB | 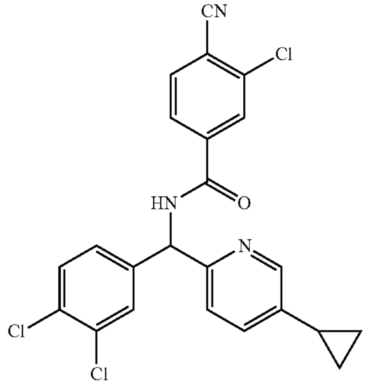 [SMILES: N#Cc1ccc(C(=O)NC(c2ccc(Cl)c(Cl)c2)c2ccc(C3CC3)cn2)cc1Cl] |
| CYM52529 IB | 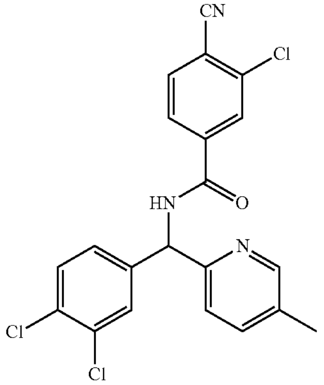 [SMILES: Cc1ccc(C(NC(=O)c2ccc(C#N)c(Cl)c2)c2ccc(Cl)c(Cl)c2)nc1] |
| CYM52530 IB | 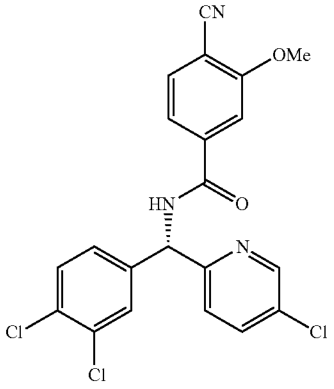 [SMILES: COc1cc(C(=O)N[C@@H](c2ccc(Cl)c(Cl)c2)c2ccc(Cl)cn2)ccc1C#N] |

TABLE 1-continued
| Specific Compounds of the Invention | |
|---|---|
| Cpd. ID | Structure |
| CYM52531<br>IC | 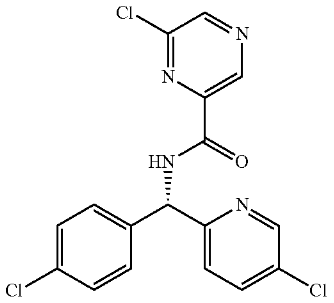 [SMILES: O=C(N[C@@H](c1ccc(Cl)cc1)c1ccc(Cl)cn1)c1cncc(Cl)n1] |
| CYM52532<br>IB | 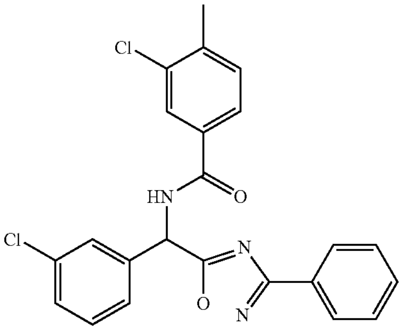 [SMILES: Cc1ccc(C(=O)NC(/C(O)=N/C(=N)c2ccccc2)c2cccc(Cl)c2)cc1Cl] |
| CYM 52533<br>IB | 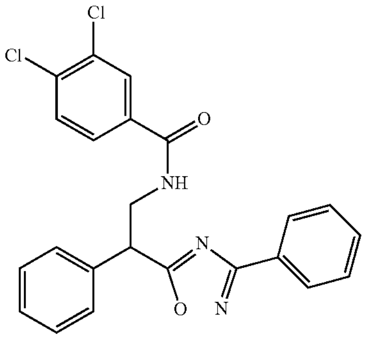 [SMILES: N=C(/N=C(\O)C(CNC(=O)c1ccc(Cl)c(Cl)c1)c1ccccc1)c1ccccc1] |
| CYM 52534<br>IB | 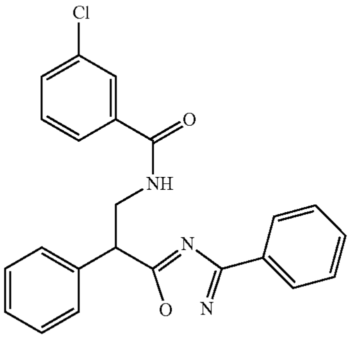 [SMILES: N=C(/N=C(\O)C(CNC(=O)c1cccc(Cl)c1)c1ccccc1)c1ccccc1] |

TABLE 1-continued
| Specific Compounds of the Invention | |
|---|---|
| Cpd. ID | Structure |
| CYM 52535<br>IB | 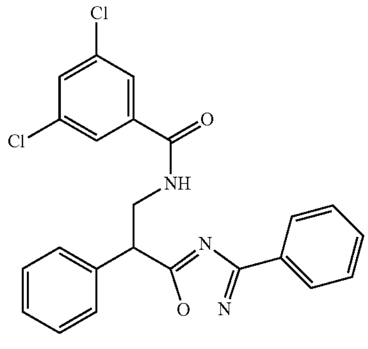 [SMILES: N=C(/N=C(\O)C(CNC(=O)c1cc(Cl)cc(Cl)c1)c1ccccc1)c1ccccc1] |
| CYM 52536<br>IC | 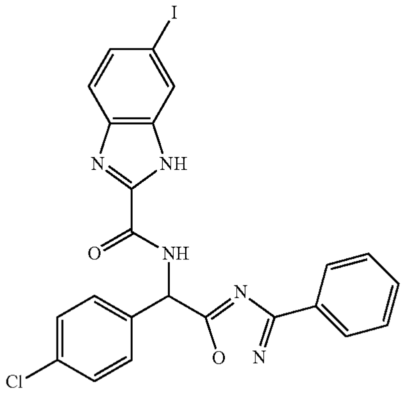 [SMILES: N=C(/N=C(\O)C(NC(=O)c1nc2ccc(I)cc2[nH]1)c1ccc(Cl)cc1)c1ccccc1] |
| CYM 52542<br>IB | 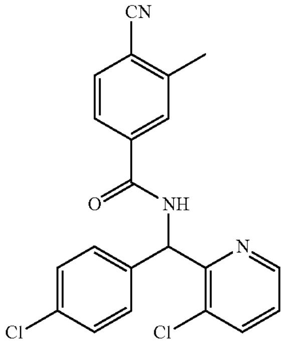 [SMILES: Cc1cc(C(=O)NC(c2ccc(Cl)cc2)c2ncccc2Cl)ccc1C#N] |
| CYM 52543<br>IB | 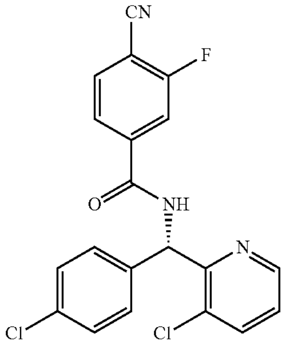 [SMILES: N#Cc1ccc(C(=O)N[C@@H](c2ccc(Cl)cc2)c2ncccc2Cl)cc1F] |

TABLE 1-continued
| Specific Compounds of the Invention | |
|---|---|
| Cpd. ID | Structure |
| CYM 52544 IB | 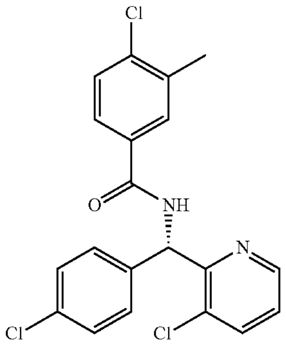 [SMILES: Cc1cc(C(=O)N[C@@H](c2ccc(Cl)cc2)c2ncccc2Cl)ccc1Cl] |
| CYM 52545 IB | 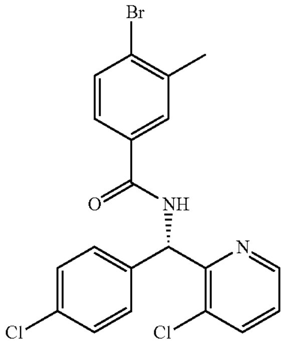 [SMILES: Cc1cc(C(=O)N[C@@H](c2ccc(Cl)cc2)c2ncccc2Cl)ccc1Br] |
| CYM 52546 IB | 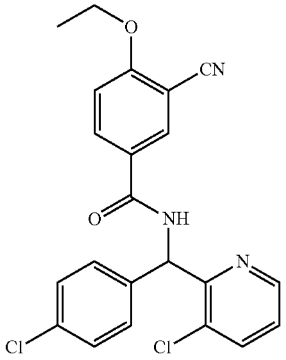 [SMILES: CCOc1ccc(C(=O)NC(c2ccc(Cl)cc2)c2ncccc2Cl)cc1C#N] |
| CYM 52547 IB | 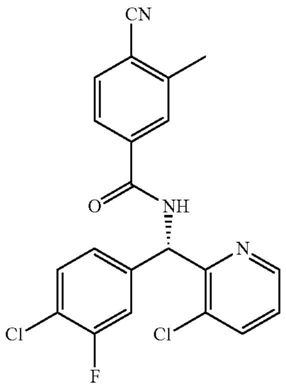 [SMILES: Cc1cc(C(=O)N[C@@H](c2ccc(Cl)c(F)c2)c2ncccc2Cl)ccc1C#N] |

TABLE 1-continued
| Specific Compounds of the Invention | |
|---|---|
| Cpd. ID | Structure |
| CYM 52548<br>IB | 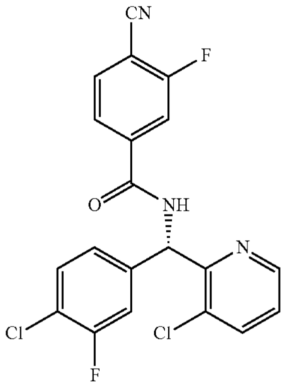 [SMILES: N#Cc1ccc(C(=O)N[C@@H](c2ccc(Cl)c(F)c2)c2ncccc2Cl)cc1F] |
| CYM 52549<br>IB | 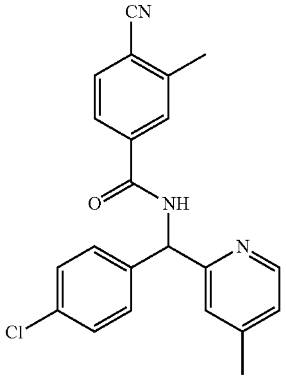 [SMILES: Cc1ccnc(C(NC(=O)c2ccc(C#N)c(C)c2)c2ccc(Cl)cc2)c1] |
| CYM 52550<br>IB | 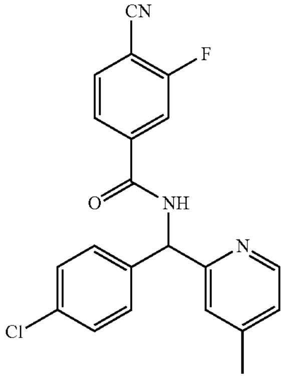 [SMILES: Cc1ccnc(C(NC(=O)c2ccc(C#N)c(F)c2)c2ccc(Cl)cc2)c1] |

TABLE 1-continued
| Specific Compounds of the Invention | |
|---|---|
| Cpd. ID | Structure |
| CYM 52551 IB | 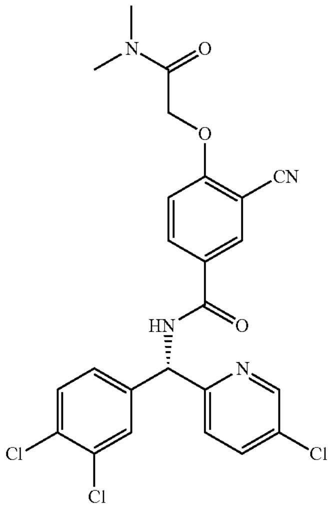 [SMILES: CN(C)C(=O)COc1ccc(C(=O)N[C@@H](c2ccc(Cl)c(Cl)c2)c2ccc(Cl)cn2)cc1C#N] |
| CYM 52552 IB | 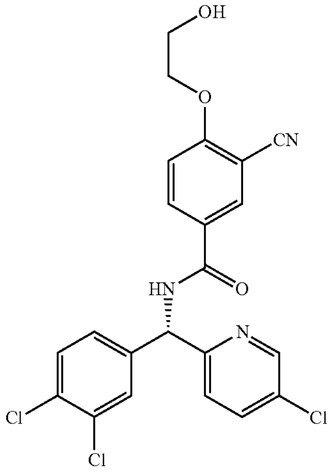 [SMILES: N#Cc1cc(C(=O)N[C@@H](c2ccc(Cl)c(Cl)c2)c2ccc(Cl)cn2)ccc1OCCO] |
| CYM 52553 IB | 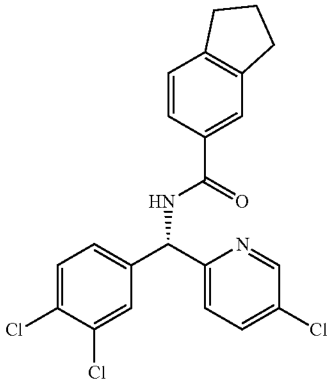 [SMILES: O=C(N[C@@H](c1ccc(Cl)c(Cl)c1)c1ccc(Cl)cn1)c1ccc2c(c1)CCC2] |

TABLE 1-continued
| Specific Compounds of the Invention | |
|---|---|
| Cpd. ID | Structure |
| CYM 52554 IC | 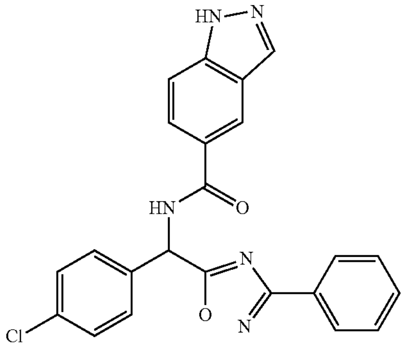 [SMILES: N=C(/N=C(\O)C(NC(=O)c1ccc2[nH]ncc2c1)c1ccc(Cl)cc1)c1ccccc1] |
| CYM 52555 IB | 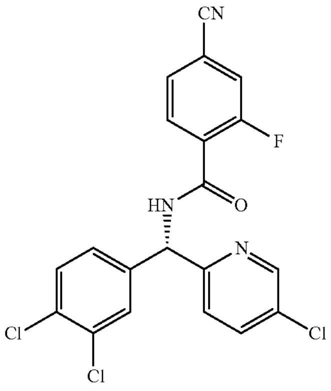 [SMILES: N#Cc1ccc(C(=O)N[C@@H](c2ccc(Cl)c(Cl)c2)c2ccc(Cl)cn2)c(F)c1] |
| CYM 52556 IB | 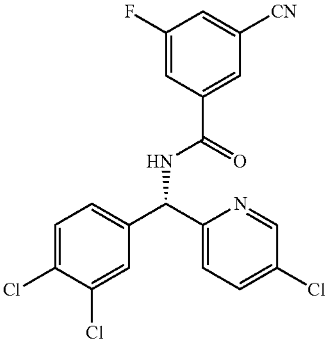 [SMILES: N#Cc1cc(F)cc(C(=O)N[C@@H](c2ccc(Cl)c(Cl)c2)c2ccc(Cl)cn2)c1] |
| CYM 52557 IB | 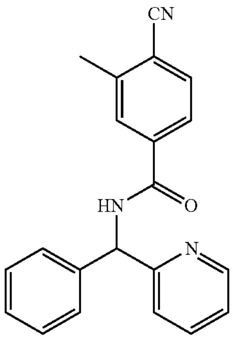 [SMILES: Cc1cc(C(=O)NC(c2ccccc2)c2ccccn2)ccc1C#N] |

TABLE 1-continued
| Specific Compounds of the Invention | |
|---|---|
| Cpd. ID | Structure |
| CYM 52558<br>IB | 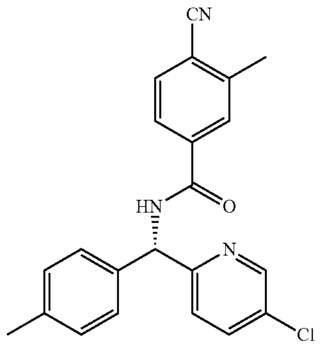 [SMILES: Cc1ccc([C@H](NC(=O)c2ccc(C#N)c(C)c2)c2ccc(Cl)cn2)cc1] |
| CYM 52559<br>IB | 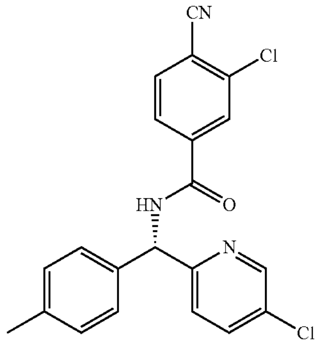 [SMILES: Cc1ccc([C@H](NC(=O)c2ccc(C#N)c(Cl)c2)c2ccc(Cl)cn2)cc1] |
| CYM 52560<br>IB | 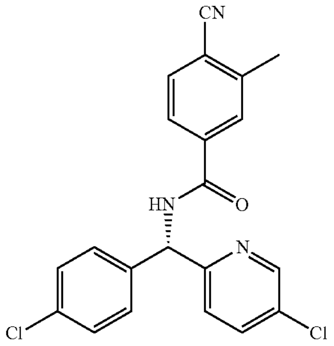 [SMILES: Cc1cc(C(=O)N[C@@H](c2ccc(Cl)cc2)c2ccc(Cl)cn2)ccc1C#N] |
| CYM 52561<br>not I | 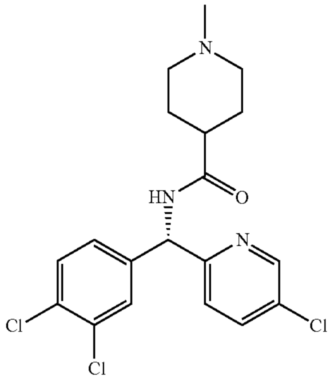 [SMILES: CN1CCC(C(=O)N[C@@H](c2ccc(Cl)c(Cl)c2)c2ccc(Cl)cn2)CC1] |

TABLE 1-continued
| Specific Compounds of the Invention | |
|---|---|
| Cpd. ID | Structure |
| CYM 52562 IB | 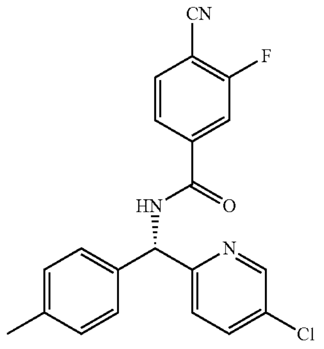 |
| CYM 52563 IB | 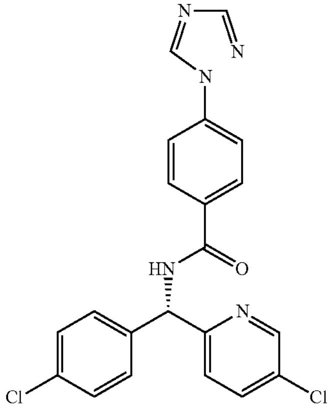 [SMILES: N=C/N=C\Nc1ccc(C(=O)N[C@@H](c2ccc(Cl)cc2)c2ccc(Cl)cn2)cc1] |
| CYM 52564 IB | 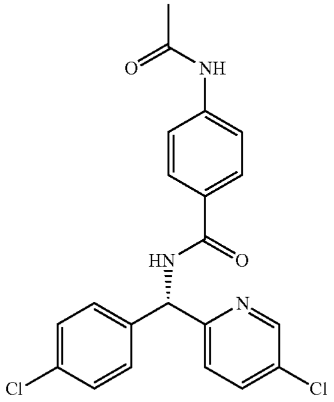 [SMILES: CC(=O)Nc1ccc(C(=O)N[C@@H](c2ccc(Cl)cc2)c2ccc(Cl)cn2)cc1] |
| CYM 52565 IB | 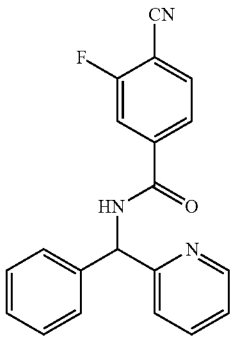 |

TABLE 1-continued
| Specific Compounds of the Invention | |
|---|---|
| Cpd. ID | Structure |
| CYM 52566<br>IB | 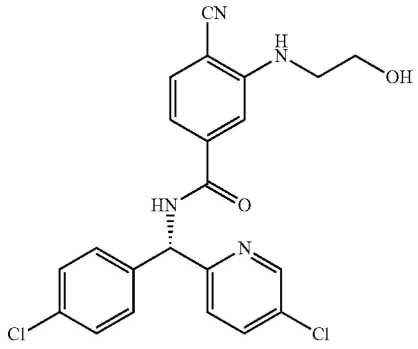 [SMILES: N#Cc1ccc(C(=O)N[C@@H](c2ccc(Cl)cc2)c2ccc(Cl)cn2)cc1NCCO] |
| CYM 52567<br>IB | 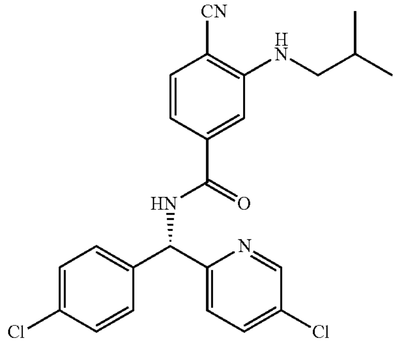 [SMILES: CC(C)CNc1cc(C(=O)N[C@@H](c2ccc(Cl)cc2)c2ccc(Cl)cn2)ccc1C#N] |
| CYM 52568<br>IC | 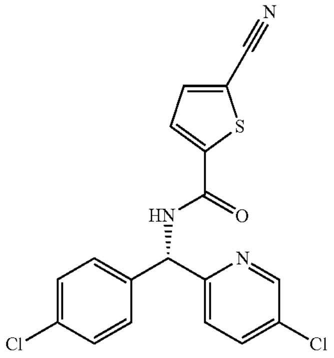 [SMILES: N#Cc1ccc(C(=O)N[C@@H](c2ccc(Cl)cc2)c2ccc(Cl)cn2)s1] |
| CYM 52569<br>IB | 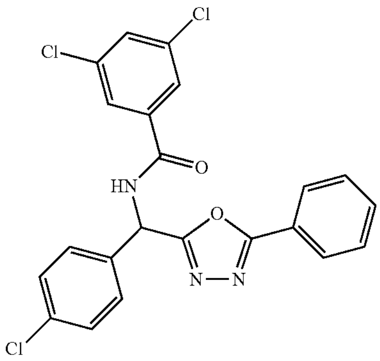 [SMILES: O=C(NC(c1ccc(Cl)cc1)c1nnc(-c2ccccc2)o1)c1cc(Cl)cc(Cl)c1] |

TABLE 1-continued
| Specific Compounds of the Invention | |
|---|---|
| Cpd. ID | Structure |
| CYM 52570 IB | 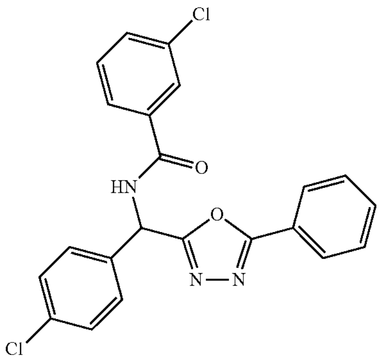 [SMILES: O=C(NC(c1ccc(Cl)cc1)c1nnc(-c2ccccc2)o1)c1cccc(Cl)c1] |
| CYM 52571 IB | 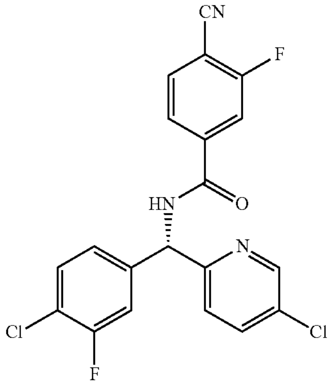 |
| CYM 52572 IB | 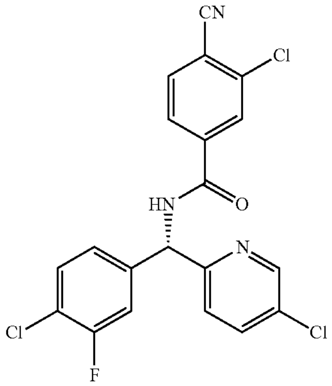 [SMILES: N#Cc1ccc(C(=O)N[C@@H](c2ccc(Cl)c(F)c2)c2ccc(Cl)cn2)cc1Cl] |
| CYM 52573 IB | 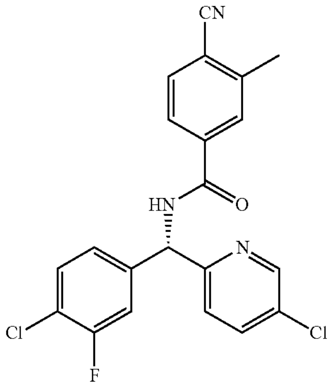 [SMILES: Cc1cc(C(=O)N[C@@H](c2ccc(Cl)c(F)c2)c2ccc(Cl)cn2)ccc1C#N] |

TABLE 1-continued
| Specific Compounds of the Invention | |
|---|---|
| Cpd. ID | Structure |
| CYM 52574 IB | 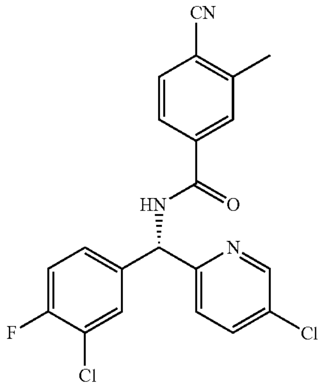 [SMILES: Cc1cc(C(=O)N[C@@H](c2ccc(F)c(Cl)c2)c2ccc(Cl)cn2)ccc1C#N] |
| CYM 52575 IB | 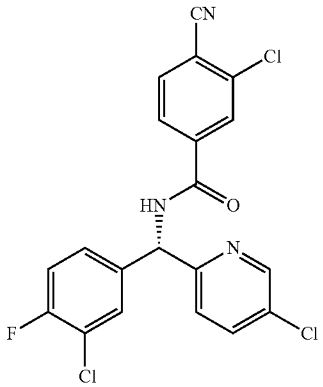 [SMILES: N#Cc1ccc(C(=O)N[C@@H](c2ccc(F)c(Cl)c2)c2ccc(Cl)cn2)cc1Cl] |
| CYM 52576 IB | 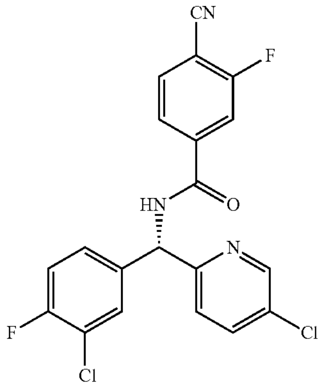 [SMILES: N#Cc1ccc(C(=O)N[C@@H](c2ccc(F)c(Cl)c2)c2ccc(Cl)cn2)cc1F] |
| CYM 52577 IB | 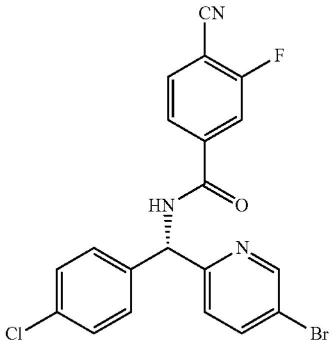 [SMILES: N#Cc1ccc(C(=O)N[C@@H](c2ccc(Cl)cc2)c2ccc(Br)cn2)cc1F] |

TABLE 1-continued
| Specific Compounds of the Invention | |
|---|---|
| Cpd. ID | Structure |
| CYM 52578<br>IB | 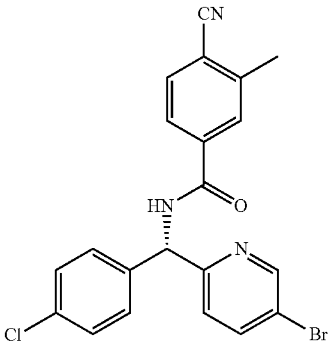 [SMILES: Cc1cc(C(=O)N[C@@H](c2ccc(Cl)cc2)c2ccc(Br)cn2)ccc1C#N] |
| CYM 52579<br>IB | 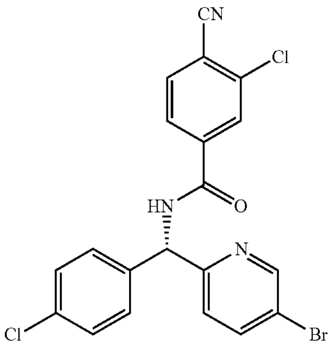 [SMILES: N#Cc1ccc(C(=O)N[C@@H](c2ccc(Cl)cc2)c2ccc(Br)cn2)cc1Cl] |
| CYM 52580<br>IB | 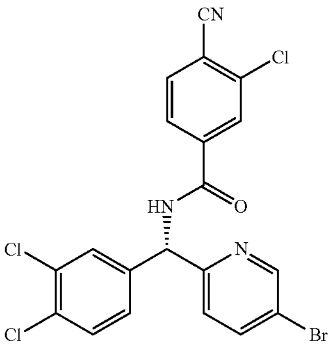 [SMILES: N#Cc1ccc(C(=O)N[C@@H](c2ccc(Cl)c(Cl)c2)c2ccc(Br)cn2)cc1Cl] |
| CYM 52581<br>IB | 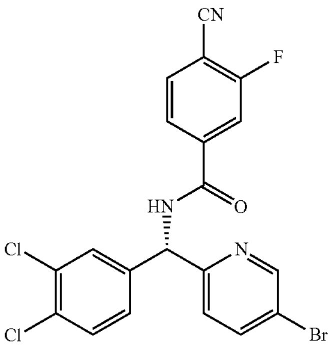 [SMILES: N#Cc1ccc(C(=O)N[C@@H](c2ccc(Cl)c(Cl)c2)c2ccc(Br)cn2)cc1F] |

TABLE 1-continued
| Specific Compounds of the Invention | |
|---|---|
| Cpd. ID | Structure |
| CYM 52582 IB | 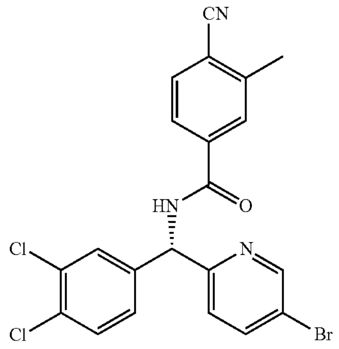 [SMILES: Cc1cc(C(=O)N[C@@H](c2ccc(Cl)c(Cl)c2)c2ccc(Br)cn2)ccc1C#N] |
| CYM 52583 IB | 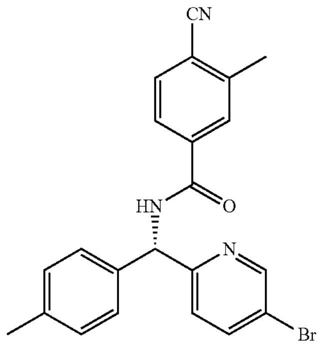 [SMILES: Cc1ccc([C@H](NC(=O)c2ccc(C#N)c(C)c2)c2ccc(Br)cn2)cc1] |
| CYM 52584 IB | 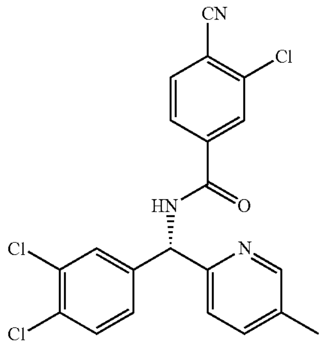 [SMILES: Cc1ccc([C@@H](NC(=O)c2ccc(C#N)c(Cl)c2)c2ccc(Cl)c(Cl)c2)nc1] |
| CYM 52585 IB | 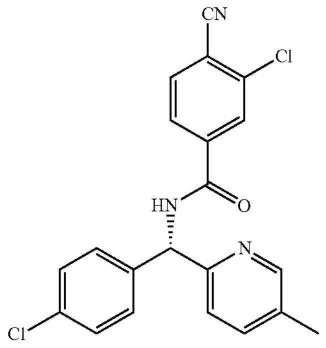 [SMILES: Cc1ccc([C@@H](NC(=O)c2ccc(C#N)c(Cl)c2)c2ccc(Cl)cc2)nc1] |

TABLE 1-continued
| Specific Compounds of the Invention | |
|---|---|
| Cpd. ID | Structure |
| CYM 52586<br>IB | 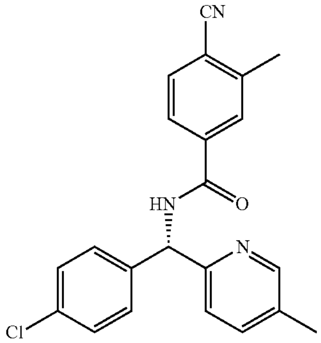 [SMILES: Cc1ccc([C@@H](NC(=O)c2ccc(C#N)c(C)c2)c2ccc(Cl)cc2)nc1] |
| CYM 52587<br>IB | 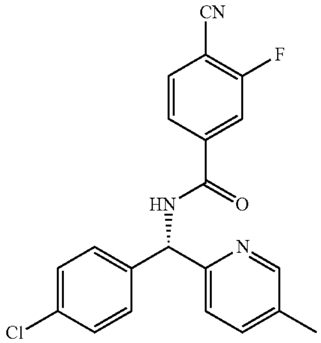 [SMILES: Cc1ccc([C@@H](NC(=O)c2ccc(C#N)c(F)c2)c2ccc(Cl)cc2)nc1] |
| CYM 52588<br>IB | 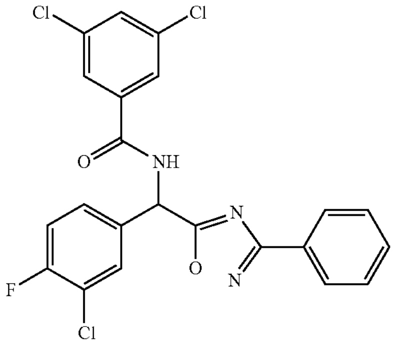 [SMILES: N=C(/N=C(\O)C(NC(=O)c1cc(Cl)cc(Cl)c1)c1ccc(F)c(Cl)c1)c1ccccc1] |
| CYM 52589<br>IB | 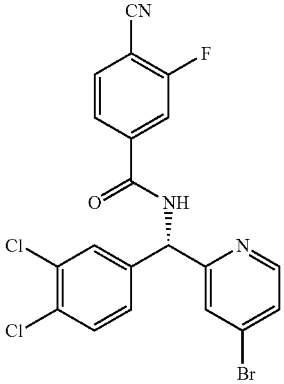 [SMILES: N#Cc1ccc(C(=O)N[C@@H](c2ccc(Cl)c(Cl)c2)c2cc(Br)ccn2)cc1F] |

TABLE 1-continued
| Specific Compounds of the Invention | |
|---|---|
| Cpd. ID | Structure |
| CYM 52590<br>IB | 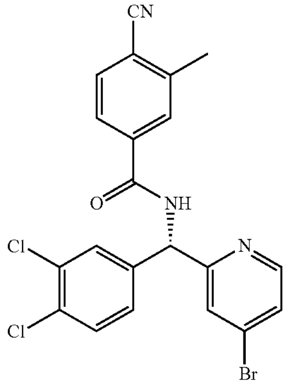 [SMILES: Cc1cc(C(=O)N[C@@H](c2ccc(Cl)c(Cl)c2)c2cc(Br)ccn2)ccc1C#N] |
| CYM 52591<br>IB | 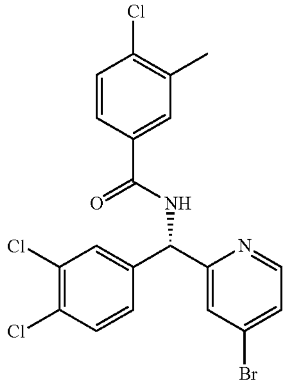 [SMILES: Cc1cc(C(=O)N[C@@H](c2ccc(Cl)c(Cl)c2)c2cc(Br)ccn2)ccc1Cl] |
| CYM 52592<br>IB | 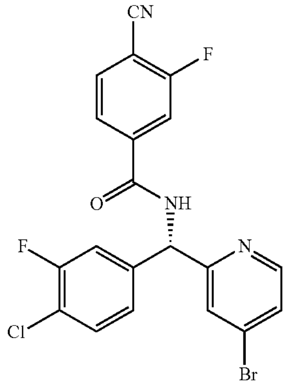 [SMILES: N#Cc1ccc(C(=O)N[C@@H](c2ccc(Cl)c(F)c2)c2cc(Br)ccn2)cc1F] |
| CYM 52593<br>IB | 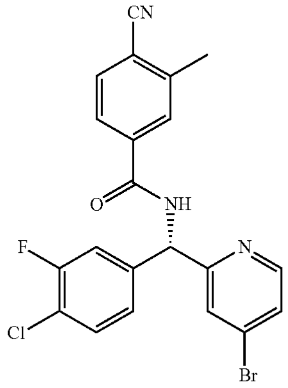 [SMILES: Cc1cc(C(=O)N[C@@H](c2ccc(Cl)c(F)c2)c2cc(Br)ccn2)ccc1C#N] |

TABLE 1-continued
| Specific Compounds of the Invention | |
|---|---|
| Cpd. ID | Structure |
| CYM 52594 IB | 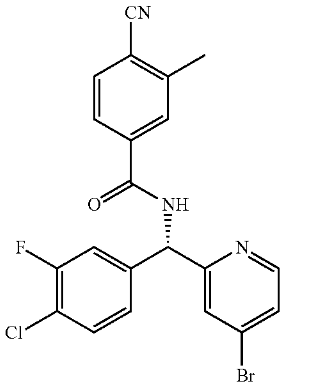 [SMILES: Cc1cc(C(=O)N[C@@H](c2ccc(Cl)c(F)c2)c2cc(Br)ccn2)ccc1C#N] |
| CYM 52595 IB | 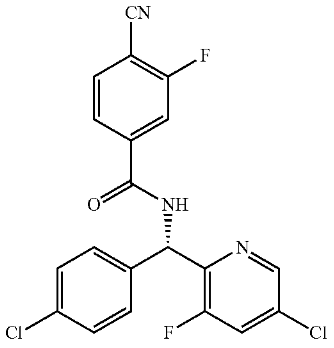 [SMILES: N#Cc1ccc(C(=O)N[C@@H](c2ccc(Cl)cc2)c2ncc(Cl)cc2F)cc1F] |
| CYM 52596 IB | 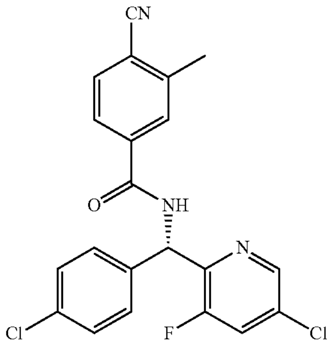 [SMILES: Cc1cc(C(=O)N[C@@H](c2ccc(Cl)cc2)c2ncc(Cl)cc2F)ccc1C#N] |
| CYM 52597 IB | 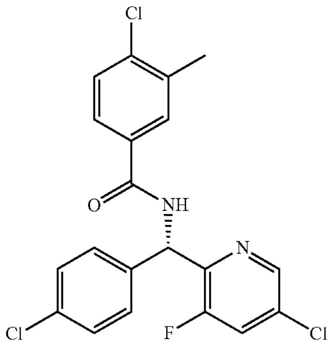 [SMILES: Cc1cc(C(=O)N[C@@H](c2ccc(Cl)cc2)c2ncc(Cl)cc2F)ccc1Cl] |

TABLE 1-continued
| Specific Compounds of the Invention | |
|---|---|
| Cpd. ID | Structure |
| CYM 52598<br>IB | 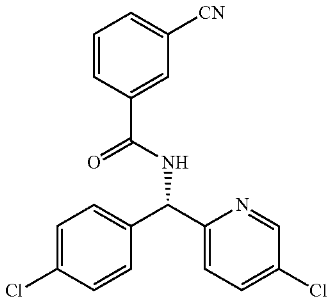 [SMILES: N#Cc1cccc(C(=O)N[C@@H](c2ccc(Cl)cc2)c2ccc(Cl)cn2)c1] |
| CYM 52599<br>IB | 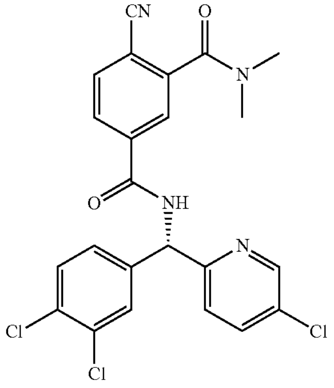 [SMILES: CN(C)C(=O)c1cc(C(=O)N[C@@H](c2ccc(Cl)c(Cl)c2)c2ccc(Cl)cn2)ccc1C#N] |
| CYM 52600<br>IB | 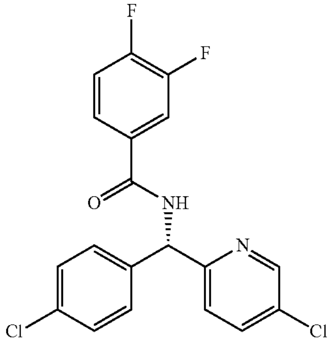 [SMILES: O=C(N[C@@H](c1ccc(Cl)cc1)c1ccc(Cl)cn1)c1ccc(F)c(F)c1] |
| CYM 52601<br>IB | 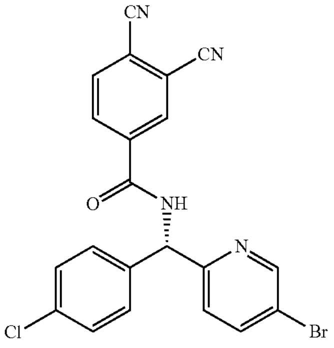 [SMILES: N#Cc1ccc(C(=O)N[C@@H](c2ccc(Cl)cc2)c2ccc(Br)cn2)cc1C#N] |

TABLE 1-continued
| Specific Compounds of the Invention | |
|---|---|
| Cpd. ID | Structure |
| CYM 52602<br>IB | 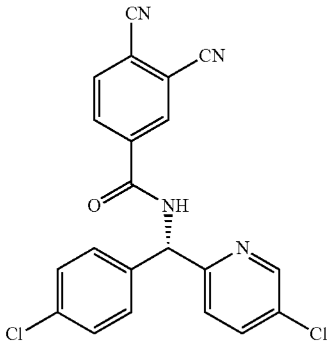 [SMILES: N#Cc1ccc(C(=O)N[C@@H](c2ccc(Cl)cc2)c2ccc(Cl)cn2)cc1C#N] |
| CYM 52603<br>IB | 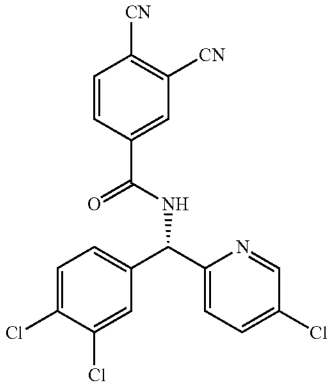 [SMILES: N#Cc1ccc(C(=O)N[C@@H](c2ccc(Cl)c(Cl)c2)c2ccc(Cl)cn2)cc1C#N] |
| CYM 52604<br>IB | 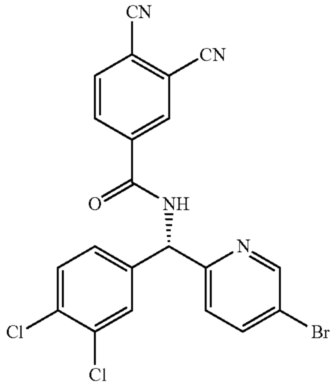 [SMILES: N#Cc1ccc(C(=O)N[C@@H](c2ccc(Cl)c(Cl)c2)c2ccc(Br)cn2)cc1C#N] |
| CYM 52605<br>IB | 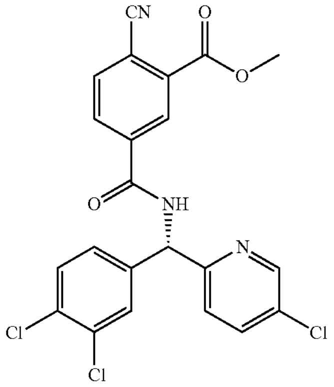 [SMILES: COC(=O)c1cc(C(=O)N[C@@H](c2ccc(Cl)c(Cl)c2)c2ccc(Cl)cn2)ccc1C#N] |

TABLE 1-continued
| Specific Compounds of the Invention | |
|---|---|
| Cpd. ID | Structure |
| CYM 52606<br>IB | 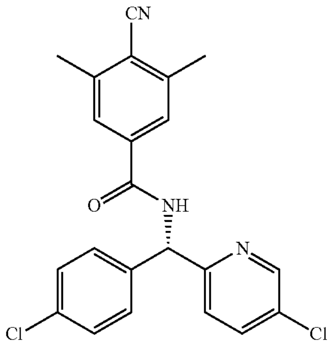 [SMILES: Cc1cc(C(=O)N[C@@H](c2ccc(Cl)cc2)c2ccc(Cl)cn2)cc(C)c1C#N] |
| CYM 52607<br>IB | 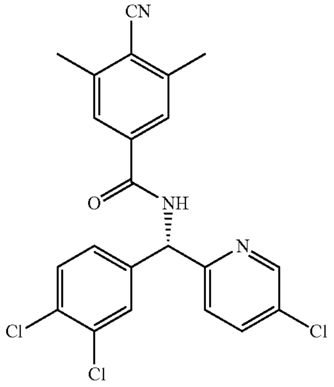 [SMILES: Cc1cc(C(=O)N[C@@H](c2ccc(Cl)c(Cl)c2)c2ccc(Cl)cn2)cc(C)c1C#N] |
| CYM 52608<br>IB | 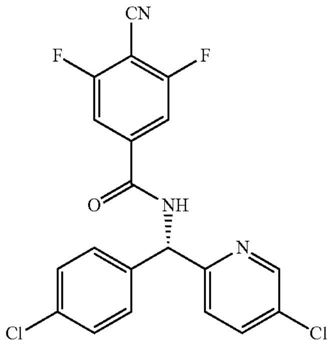 [SMILES: N#Cc1c(F)cc(C(=O)N[C@@H](c2ccc(Cl)cc2)c2ccc(Cl)cn2)cc1F] |
| CYM 52609<br>IB | 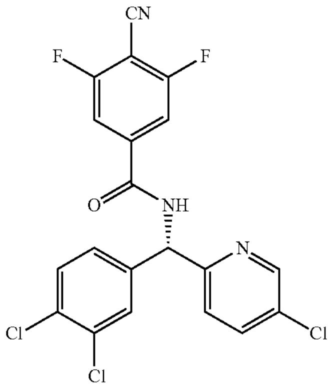 [SMILES: N#Cc1c(F)cc(C(=O)N[C@@H](c2ccc(Cl)c(Cl)c2)c2ccc(Cl)cn2)cc1F] |

TABLE 1-continued
| Specific Compounds of the Invention | |
|---|---|
| Cpd. ID | Structure |
| CYM 52610<br>IB | 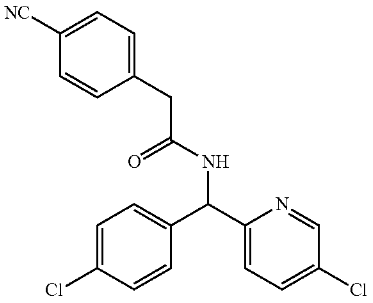 [SMILES: N#Cc1ccc(CC(=O)NC(c2ccc(Cl)cc2)c2ccc(Cl)cn2)cc1] |
| CYM 52611<br>IA | 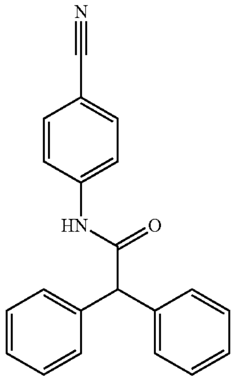 [SMILES: N#Cc1ccc(NC(=O)C(c2ccccc2)c2ccccc2)cc1] |
| CYM 52612<br>IB | 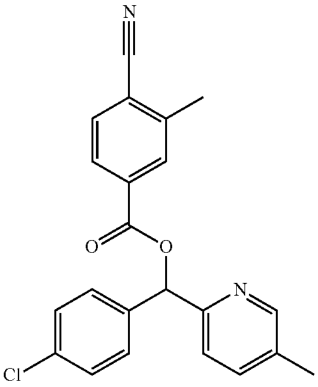 [SMILES: Cc1ccc(C(OC(=O)c2ccc(C#N)c(C)c2)c2ccc(Cl)cc2)nc1] |
| CYM 52613<br>IC | 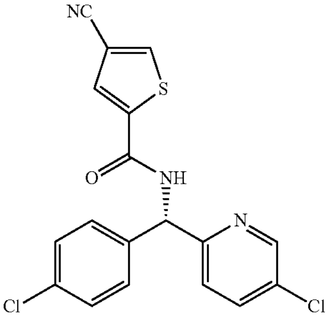 [SMILES: N#Cc1csc(C(=O)N[C@@H](c2ccc(Cl)cc2)c2ccc(Cl)cn2)c1] |

TABLE 1-continued
| Specific Compounds of the Invention | |
|---|---|
| Cpd. ID | Structure |
| CYM 52614<br>IB | 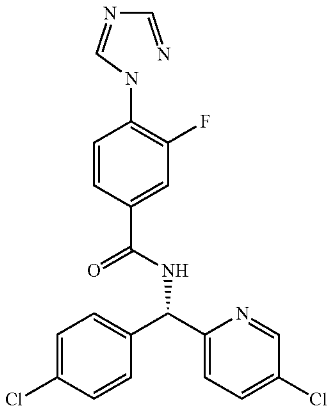 [SMILES: N=C/N=C\Nc1ccc(C(=O)N[C@@H](c2ccc(Cl)cc2)c2ccc(Cl)cn2)cc1F] |
| CYM 52615<br>IC | 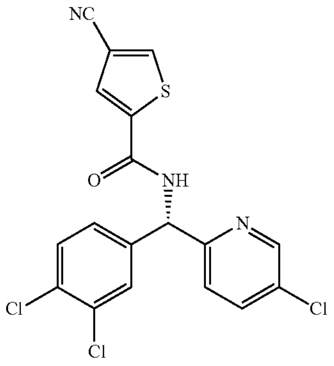 |
| CYM 52616<br>IB | 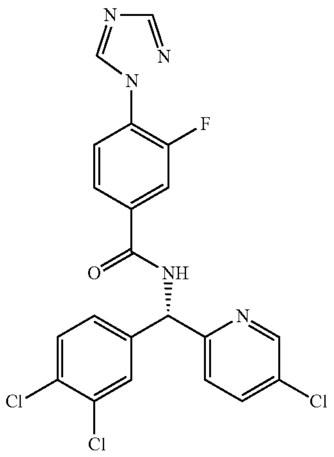 [SMILES: N=C/N=C\Nc1ccc(C(=O)N[C@@H](c2ccc(Cl)c(Cl)c2)c2ccc(Cl)cn2)cc1F] |

TABLE 1-continued
| Specific Compounds of the Invention | |
|---|---|
| Cpd. ID | Structure |
| CYM 52617<br>IB | 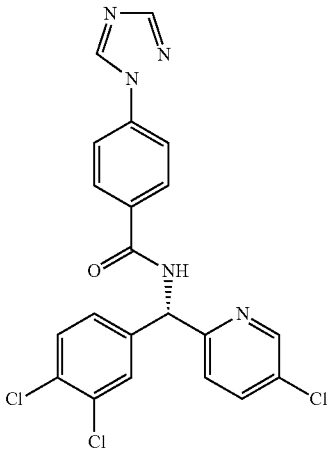 [SMILES: N=C/N=C\Nc1ccc(C(=O)N[C@@H](c2ccc(Cl)c(Cl)c2)c2ccc(Cl)cn2)cc1] |
| CYM 52618<br>IB | 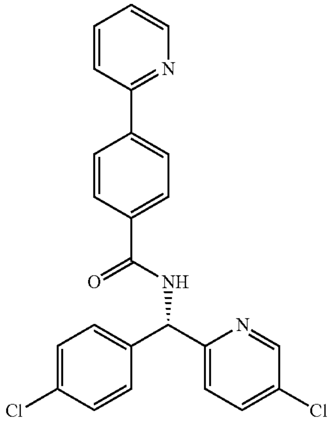 [SMILES: O=C(N[C@@H](c1ccc(Cl)cc1)c1ccc(Cl)cn1)c1ccc(-c2ccccn2)cc1] |
| CYM 52619<br>IB | 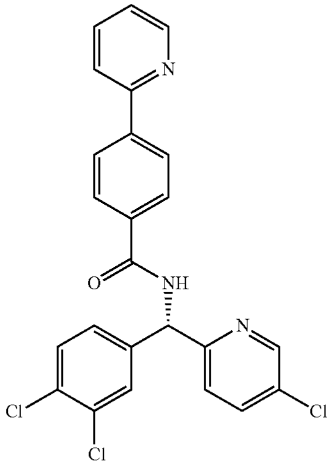 [SMILES: O=C(N[C@@H](c1ccc(Cl)c(Cl)c1)c1ccc(Cl)cn1)c1ccc(-c2ccccn2)cc1] |

TABLE 1-continued
| Specific Compounds of the Invention | |
|---|---|
| Cpd. ID | Structure |
| CYM 52620<br>IB | 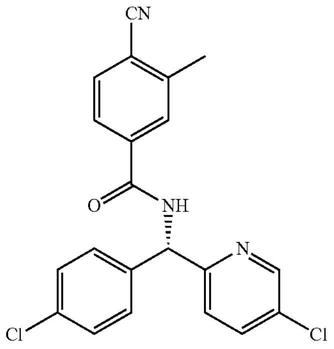 [SMILES: Cc1cc(C(=O)N[C@@H](c2ccc(Cl)cc2)c2ccc(Cl)cn2)ccc1C#N] |
| CYM 52621<br>IB | 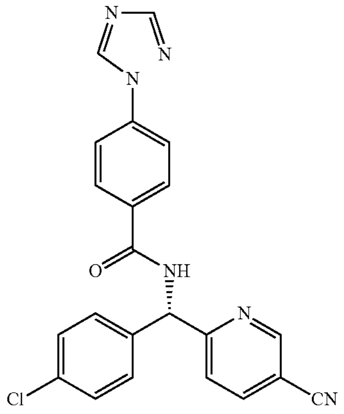 [SMILES: N#Cc1ccc([C@@H](NC(=O)c2ccc(N/C=N\C=N)cc2)c2ccc(Cl)cc2)nc1] |
| CYM 52622<br>IB | 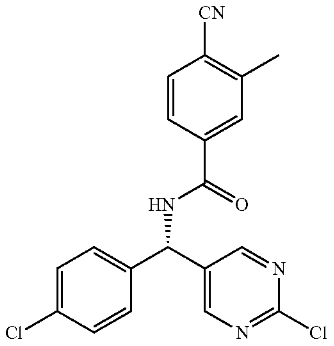 [SMILES: Cc1cc(C(=O)N[C@@H](c2ccc(Cl)cc2)c2cnc(Cl)nc2)ccc1C#N] |
| CYM 52623<br>IB | 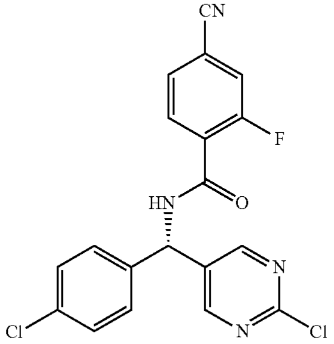 [SMILES: N#Cc1ccc(C(=O)N[C@@H](c2ccc(Cl)cc2)c2cnc(Cl)nc2)c(F)c1] |

TABLE 1-continued
| Specific Compounds of the Invention | |
|---|---|
| Cpd. ID | Structure |
| CYM 52624 IB | 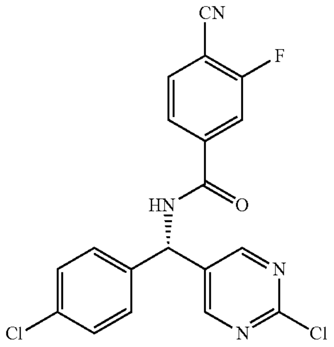 [SMILES: N#Cc1ccc(C(=O)N[C@@H](c2ccc(Cl)cc2)c2cnc(Cl)nc2)cc1F] |
| CYM 52625 IA | 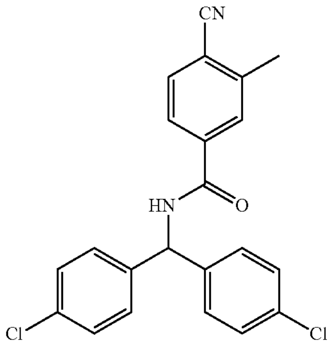 [SMILES: Cc1cc(C(=O)NC(c2ccc(Cl)cc2)c2ccc(Cl)cc2)ccc1C#N] |
| CYM 52626 IA | 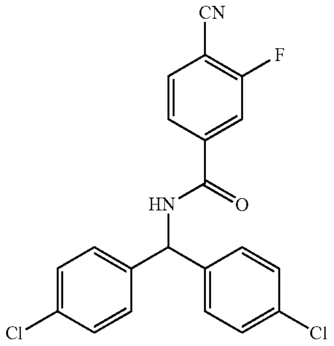 |
| CYM 52627 IB | 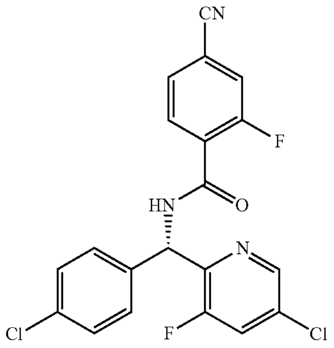 [SMILES: N#Cc1ccc(C(=O)N[C@@H](c2ccc(Cl)cc2)c2ncc(Cl)cc2F)c(F)c1] |

TABLE 1-continued
| Specific Compounds of the Invention | |
|---|---|
| Cpd. ID | Structure |
| CYM 52628<br>IB | 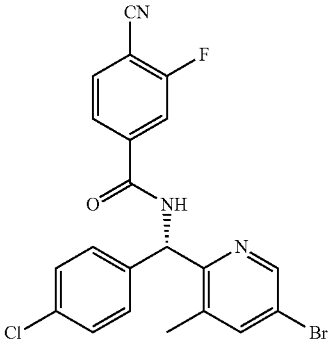 |
| CYM 52629<br>IB | 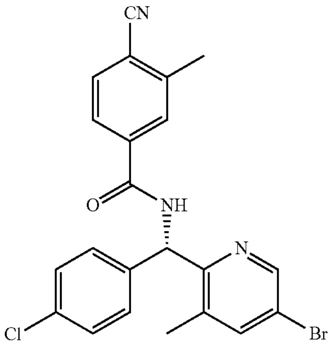 [SMILES: Cc1cc(C(=O)N[C@@H](c2ccc(Cl)cc2)c2ncc(Br)cc2C)ccc1C#N] |
| CYM 52630<br>IB | 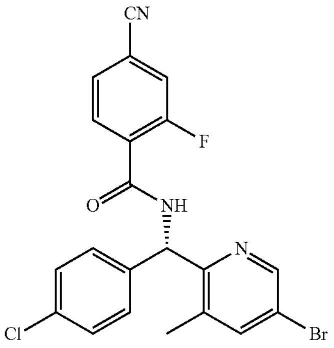 [SMILES: Cc1cc(Br)cnc1[C@@H](NC(=O)c1ccc(C#N)cc1F)c1ccc(Cl)cc1] |
| CYM 52631<br>IB | 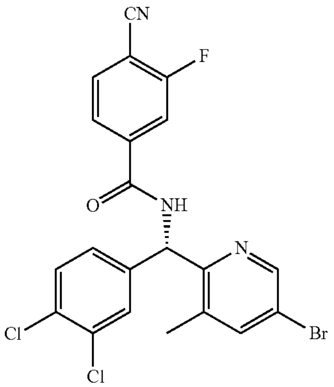 |

TABLE 1-continued
| Specific Compounds of the Invention | |
|---|---|
| Cpd. ID | Structure |
| CYM 52632<br>IB | 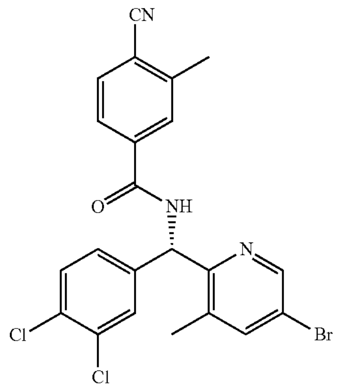 [SMILES: Cc1cc(C(=O)N[C@@H](c2ccc(Cl)c(Cl)c2)c2ncc(Br)cc2C)ccc1C#N] |
| CYM 52633<br>IB | 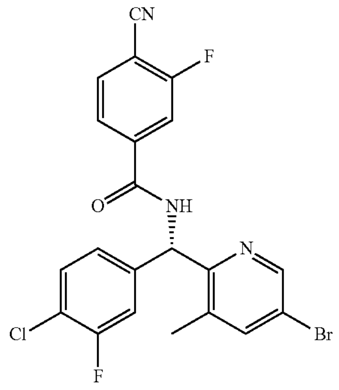 [SMILES: Cc1cc(Br)cnc1[C@@H](NC(=O)c1ccc(C#N)c(F)c1)c1ccc(Cl)c(F)c1] |
| CYM 52634<br>IB | 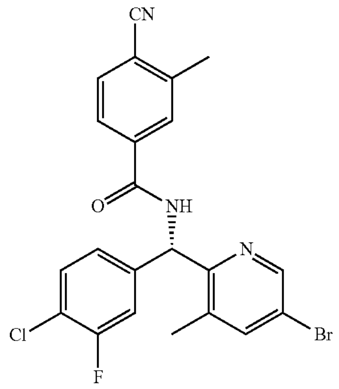 [SMILES: Cc1cc(C(=O)N[C@@H](c2ccc(Cl)c(F)c2)c2ncc(Br)cc2C)ccc1C#N] |
| CYM 52635<br>IC | 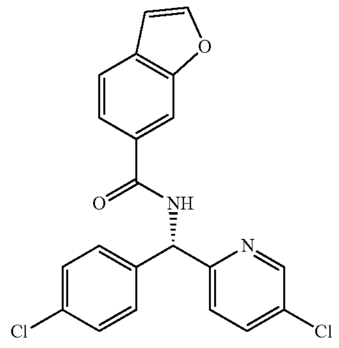 [SMILES: O=C(N[C@@H](c1ccc(Cl)cc1)c1ccc(Cl)cn1)c1ccc2ccoc2c1] |

TABLE 1-continued
Specific Compounds of the Invention
| Cpd. ID | Structure |
| --- | --- |
| CYM 52636 IB | 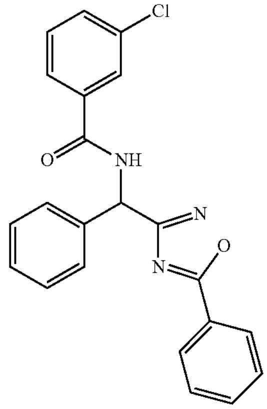 [SMILES: N=C(/N=C(\O)c1ccccc1)C(NC(=O)c1cccc(Cl)c1)c1ccccc1] |
| CYM 52637 IB | 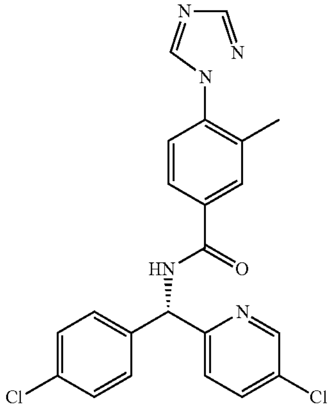 [SMILES: Cc1cc(C(=O)N[C@@H](c2ccc(Cl)cc2)c2ccc(Cl)cn2)ccc1N/C=N\C=N] |
| CYM 52638 IE | 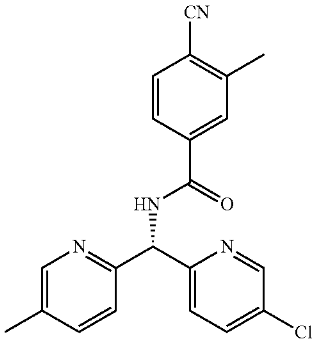 [SMILES: Cc1ccc([C@H](NC(=O)c2ccc(C#N)c(C)c2)c2ccc(Cl)cn2)nc1] |
| CYM 52639 IE | 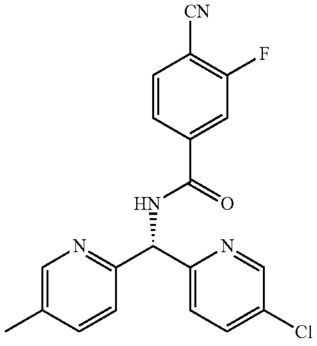 [SMILES: Cc1ccc([C@H](NC(=O)c2ccc(C#N)c(F)c2)c2ccc(Cl)cn2)nc1] |

TABLE 1-continued
| Specific Compounds of the Invention | |
|---|---|
| Cpd. ID | Structure |
| CYM 52640 IB | 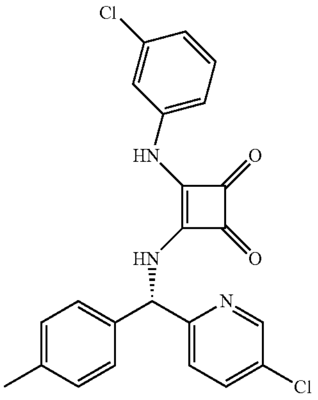 [SMILES: Cc1ccc([C@H](Nc2c(Nc3cccc(Cl)c3)c(=O)c2=O)c2ccc(Cl)cn2)cc1] |
| CYM 52641 IA | 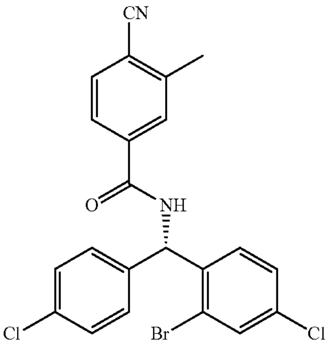 [SMILES: Cc1cc(C(=O)N[C@@H](c2ccc(Cl)cc2)c2ccc(Cl)cc2Br)ccc1C#N] |
| CYM 52642 ID | 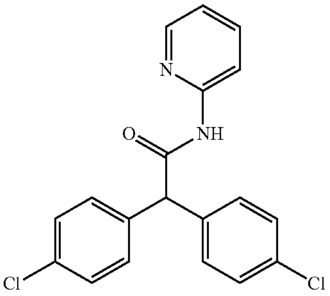 [SMILES: O=C(Nc1ccccn1)C(c1ccc(Cl)cc1)c1ccc(Cl)cc1] |
| CYM 52643 IB | 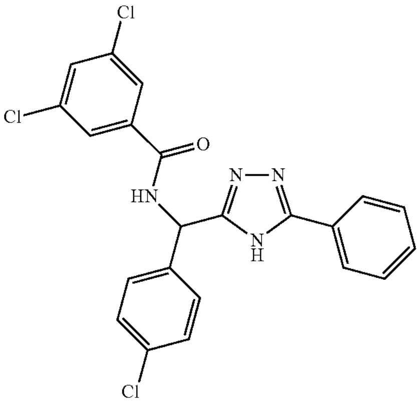 [SMILES: O=C(NC(c1ccc(Cl)cc1)c1nnc(-c2ccccc2)[nH]1)c1cc(Cl)cc(Cl)c1] |

TABLE 1-continued
| Specific Compounds of the Invention | |
|---|---|
| Cpd. ID | Structure |
| CYM 52644<br>IC | 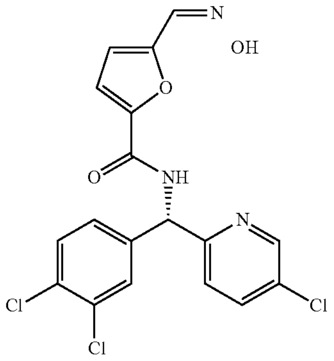 |
| CYM 52645<br>IC | 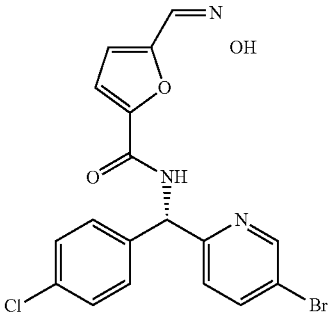 |
| CYM 52646<br>IC | 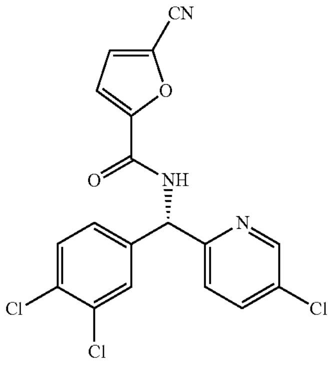 [SMILES: N#Cc1ccc(C(=O)N[C@@H](c2ccc(Cl)c(Cl)c2)c2ccc(Cl)cn2)o1] |
| CYM 52647<br>IC | 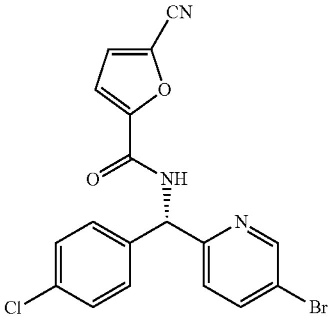 [SMILES: N#Cc1ccc(C(=O)N[C@@H](c2ccc(Cl)cc2)c2ccc(Br)cn2)o1] |

TABLE 1-continued
| Specific Compounds of the Invention | |
|---|---|
| Cpd. ID | Structure |
| CYM 52648 IB | 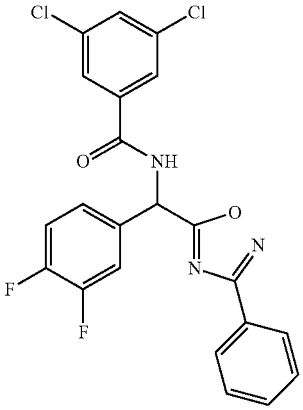 [SMILES: N=C(/N=C(\O)C(NC(=O)c1cc(Cl)cc(Cl)c1)c1ccc(F)c(F)c1)c1ccccc1] |
| CYM 52649 IB | 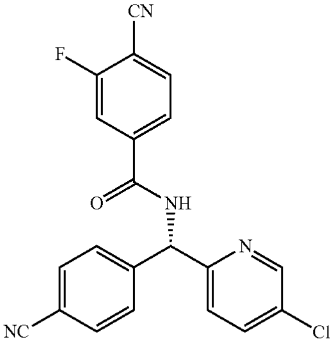 [SMILES: N#Cc1ccc([C@H](NC(=O)c2ccc(C#N)c(F)c2)c2ccc(Cl)cn2)cc1] |
| CYM 52650 IB | 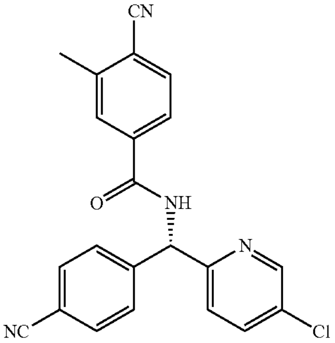 [SMILES: Cc1cc(C(=O)N[C@@H](c2ccc(C#N)cc2)c2ccc(Cl)cn2)ccc1C#N] |
| CYM 52651 IB | 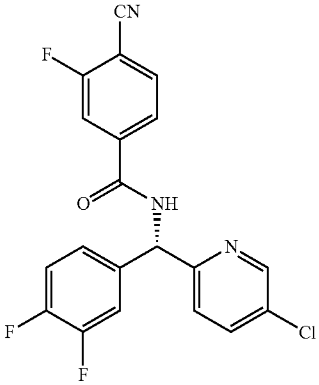 [SMILES: N#Cc1ccc(C(=O)N[C@@H](c2ccc(F)c(F)c2)c2ccc(Cl)cn2)cc1F] |

TABLE 1-continued
Specific Compounds of the Invention
| Cpd. ID | Structure |
|---|---|
| CYM 52652 IB | 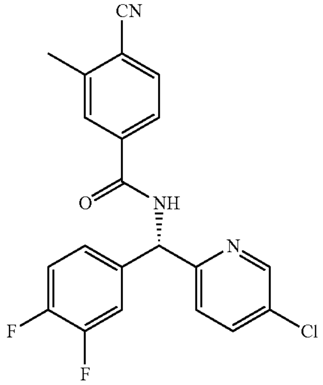 [SMILES: Cc1cc(C(=O)N[C@@H](c2ccc(F)c(F)c2)c2ccc(Cl)cn2)ccc1C#N] |
| CYM 52653 IB | 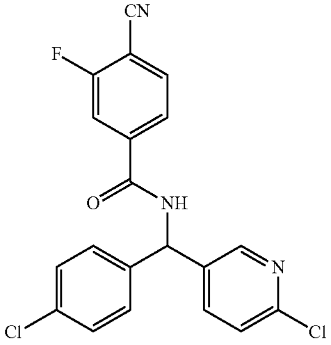 [SMILES: N#Cc1ccc(C(=O)NC(c2ccc(Cl)cc2)c2ccc(Cl)nc2)cc1F] |
| CYM 52654 IE | 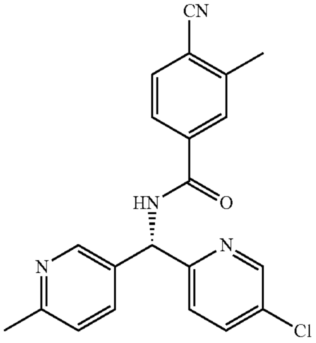 [SMILES: Cc1ccc([C@H](NC(=O)c2ccc(C#N)c(C)c2)c2ccc(Cl)cn2)cn1] |
| CYM 52655 IE | 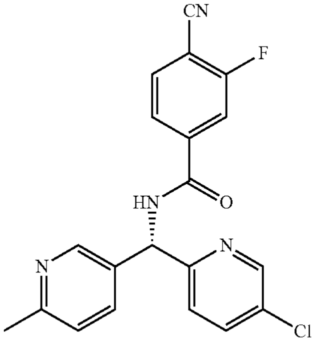 [SMILES: Cc1ccc([C@H](NC(=O)c2ccc(C#N)c(F)c2)c2ccc(Cl)cn2)cn1] |

TABLE 1-continued
| Specific Compounds of the Invention | |
|---|---|
| Cpd. ID | Structure |
| CYM 52656<br>IB | 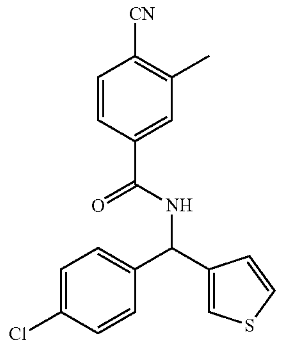 [SMILES: Cc1cc(C(=O)NC(c2ccc(Cl)cc2)c2ccsc2)ccc1C#N] |
| CYM 52657<br>IB | 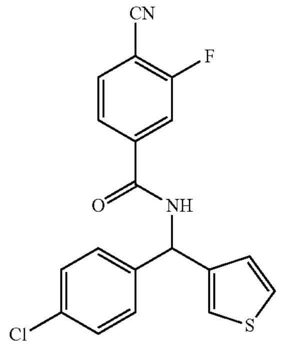 |
| CYM 52658<br>IB | 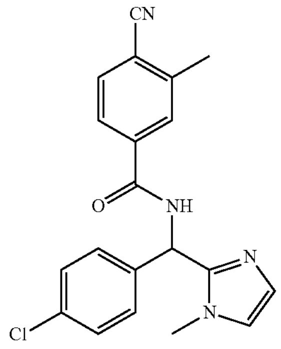 [SMILES: Cc1cc(C(=O)NC(c2ccc(Cl)cc2)c2nccn2C)ccc1C#N] |
| CYM 52659<br>IB | 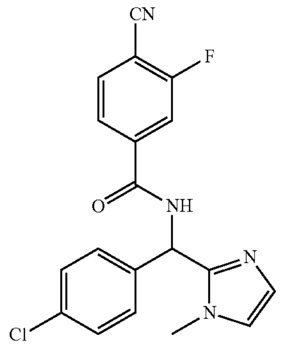 [SMILES: Cn1ccnc1C(NC(=O)c1ccc(C#N)c(F)c1)c1ccc(Cl)cc1] |

TABLE 1-continued
| Specific Compounds of the Invention | |
|---|---|
| Cpd. ID | Structure |
| CYM 52660<br>IE | 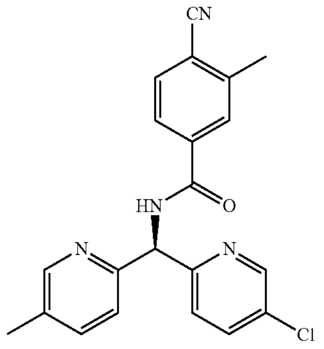 [SMILES: Cc1ccc([C@@H](NC(=O)c2ccc(C#N)c(C)c2)c2ccc(Cl)cn2)nc1] |
| CYM 52661<br>IE | 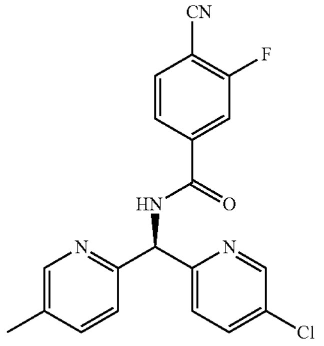 [SMILES: Cc1ccc([C@@H](NC(=O)c2ccc(C#N)c(F)c2)c2ccc(Cl)cn2)nc1] |
| CYM 52662<br>IE | 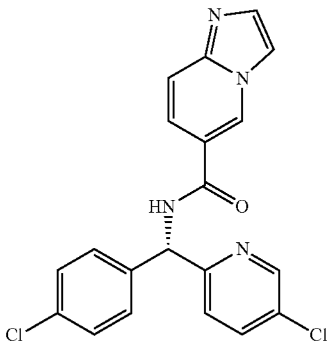 [SMILES: O=C(N[C@@H](c1ccc(Cl)cc1)c1ccc(Cl)cn1)c1ccc2nccn2c1] |
| CYM 52663<br>IB | 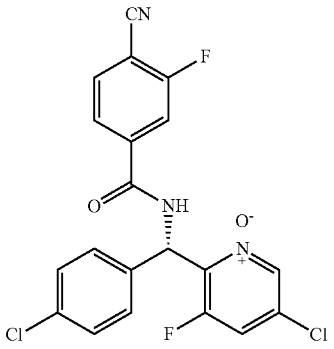 |

TABLE 1-continued
| Specific Compounds of the Invention | |
|---|---|
| Cpd. ID | Structure |
| CYM 52664<br>IB | 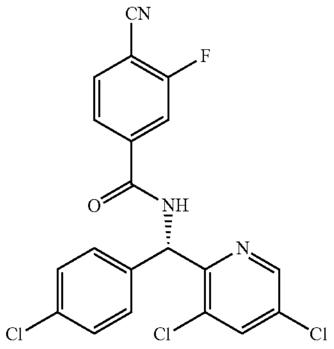 |
| CYM 52665<br>IB | 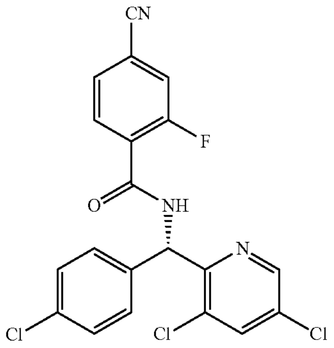 [SMILES: N#Cc1ccc(C(=O)N[C@@H](c2ccc(Cl)cc2)c2ncc(Cl)cc2Cl)c(F)c1] |
| CYM 52666<br>IB | 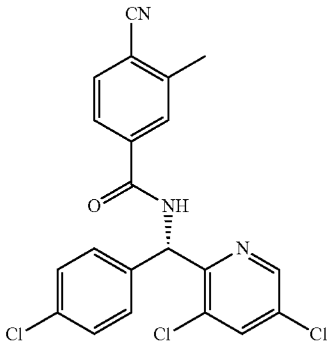 |
| CYM 52667<br>IB | 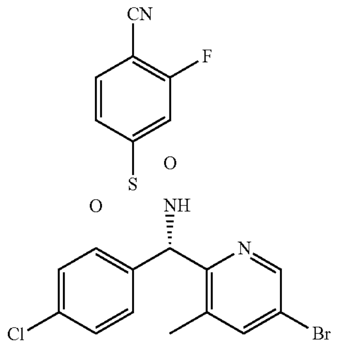 |

TABLE 1-continued
| Specific Compounds of the Invention | |
|---|---|
| Cpd. ID | Structure |
| CYM 52668<br>IA | 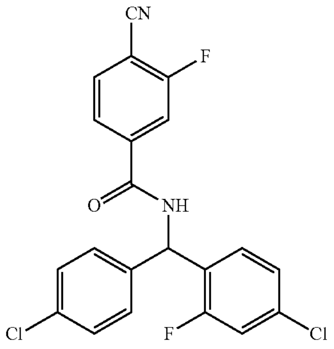 |
| CYM 52669<br>IA | 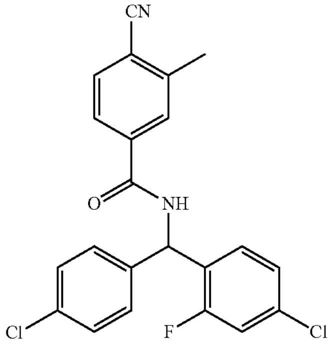 [SMILES: Cc1cc(C(=O)NC(c2ccc(Cl)cc2)c2ccc(Cl)cc2F)ccc1C#N] |
| CYM 52670<br>IB | 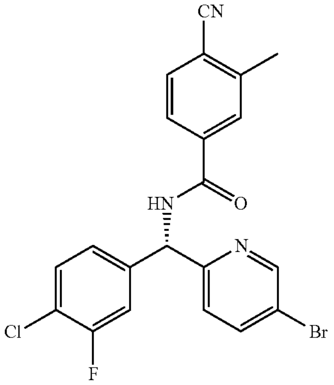 [SMILES: Cc1cc(C(=O)N[C@@H](c2ccc(Cl)c(F)c2)c2ccc(Br)cn2)ccc1C#N] |
| CYM 52671<br>IB | 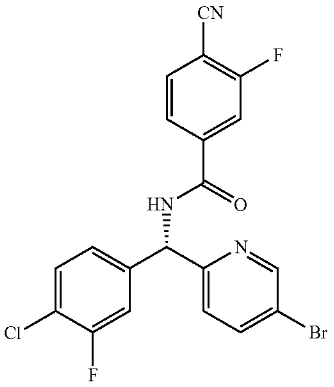 [SMILES: N#Cc1ccc(C(=O)N[C@@H](c2ccc(Cl)c(F)c2)c2ccc(Br)cn2)cc1F] |

TABLE 1-continued
| Specific Compounds of the Invention | |
|---|---|
| Cpd. ID | Structure |
| CYM 52672 IB | 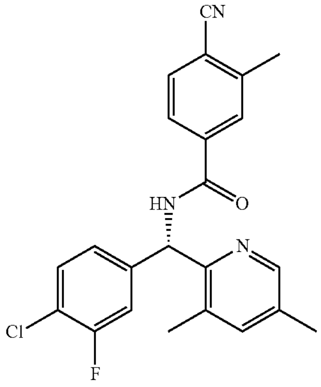 [SMILES: Cc1cnc([C@@H](NC(=O)c2ccc(C#N)c(C)c2)c2ccc(Cl)c(F)c2)c(C)c1] |
| CYM 52673 IB | 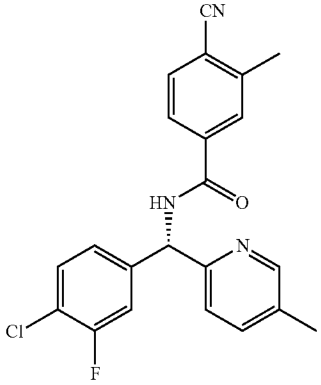 [SMILES: Cc1ccc([C@@H](NC(=O)c2ccc(C#N)c(C)c2)c2ccc(Cl)c(F)c2)nc1] |
| CYM 52674 IB | 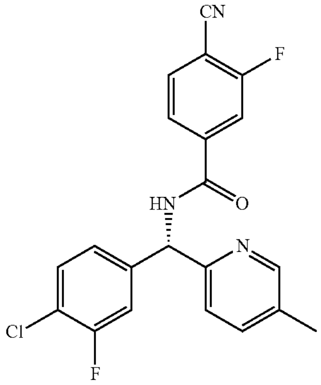 |
| CYM 52675 IB | 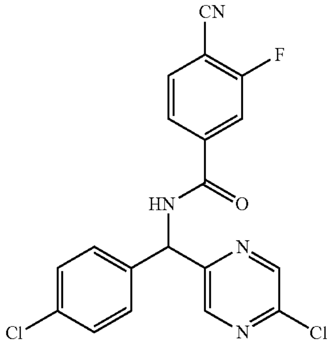 [SMILES: N#Cc1ccc(C(=O)NC(c2ccc(Cl)cc2)c2cnc(Cl)cn2)cc1F] |

TABLE 1-continued
| Specific Compounds of the Invention | |
|---|---|
| Cpd. ID | Structure |
| CYM 52676<br>IB | 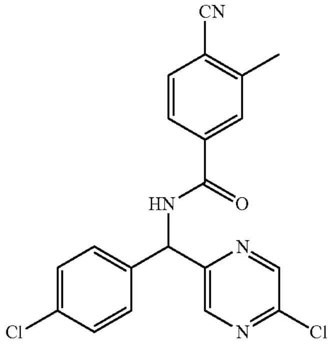 [SMILES: Cc1cc(C(=O)NC(c2ccc(Cl)cc2)c2cnc(Cl)cn2)ccc1C#N] |
| CYM 52677<br>IB | 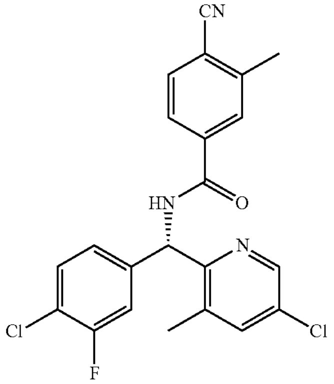 [SMILES: Cc1cc(C(=O)N[C@@H](c2ccc(Cl)c(F)c2)c2ncc(Cl)cc2C)ccc1C#N] |
| CYM 52678<br>IB | 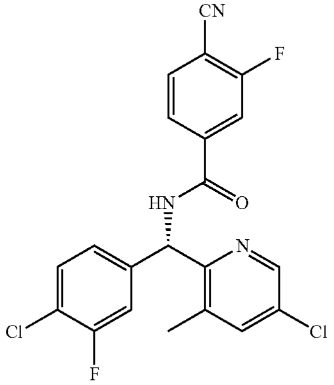 [SMILES: Cc1cc(Cl)cnc1[C@@H](NC(=O)c1ccc(C#N)c(F)c1)c1ccc(Cl)c(F)c1] |
| CYM 52679<br>IB | 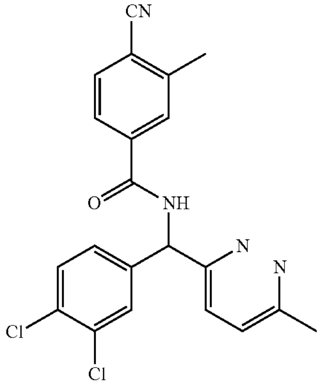 [SMILES: C/C(N)=C/C=C(\N)C(NC(=O)c1ccc(C#N)c(C)c1)c1ccc(Cl)c(Cl)c1] |

TABLE 1-continued
| Specific Compounds of the Invention | |
|---|---|
| Cpd. ID | Structure |
| CYM 52680<br>IA | 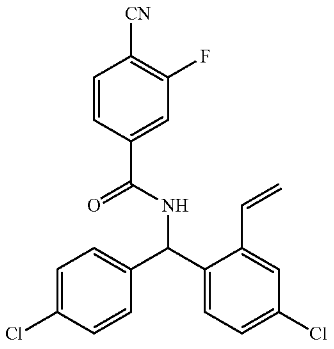 [SMILES: C=Cc1cc(Cl)ccc1C(NC(=O)c1ccc(C#N)c(F)c1)c1ccc(Cl)cc1] |
| CYM 52681<br>IA | 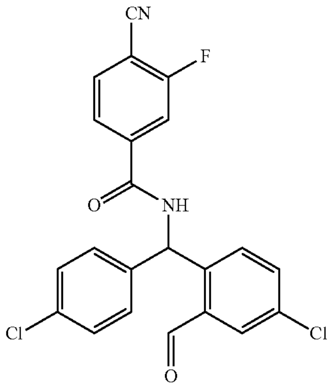 [SMILES: N#Cc1ccc(C(=O)NC(c2ccc(Cl)cc2)c2ccc(Cl)cc2C=O)cc1F] |
| CYM 52682<br>IA | 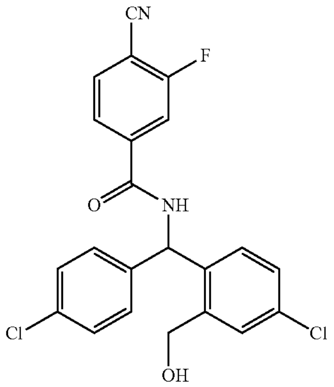 [SMILES: N#Cc1ccc(C(=O)NC(c2ccc(Cl)cc2)c2ccc(Cl)cc2CO)cc1F] |
| CYM 52683<br>IB | 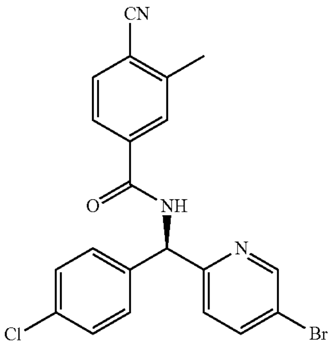 [SMILES: Cc1cc(C(=O)N[C@H](c2ccc(Cl)cc2)c2ccc(Br)cn2)ccc1C#N] |

TABLE 1-continued
| Specific Compounds of the Invention | |
|---|---|
| Cpd. ID | Structure |
| CYM 52684<br>IB | 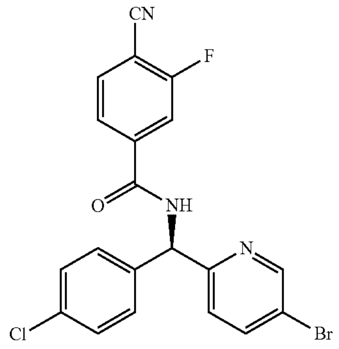 |
| CYM 52685<br>IB | 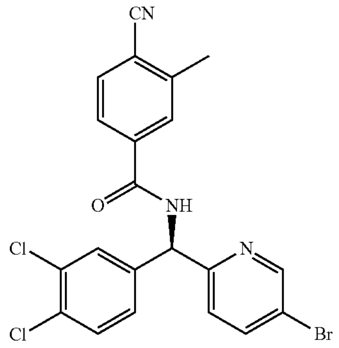 [SMILES: Cc1cc(C(=O)N[C@H](c2ccc(Cl)c(Cl)c2)c2ccc(Br)cn2)ccc1C#N] |
| CYM 52686<br>IB | 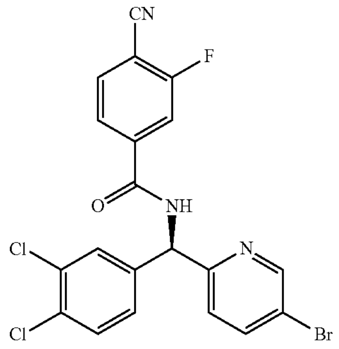 |
| CYM 52687<br>IA | 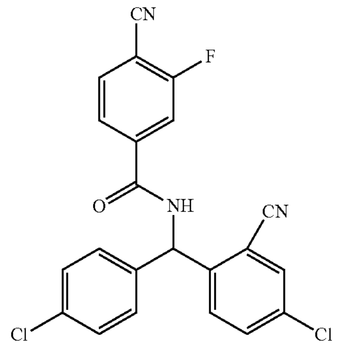 [SMILES: N#Cc1ccc(C(=O)NC(c2ccc(Cl)cc2)c2ccc(Cl)cc2C#N)cc1F] |

TABLE 1-continued
| Specific Compounds of the Invention | |
|---|---|
| Cpd. ID | Structure |
| CYM 52688<br>IA | 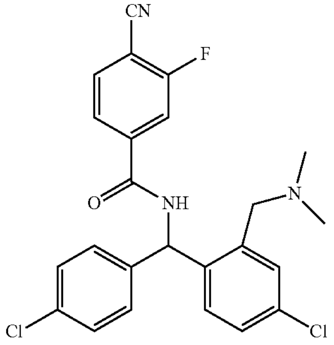 [SMILES: CN(C)Cc1cc(Cl)ccc1C(NC(=O)c1ccc(C#N)c(F)c1)c1ccc(Cl)cc1] |
| CYM 52689<br>IB | 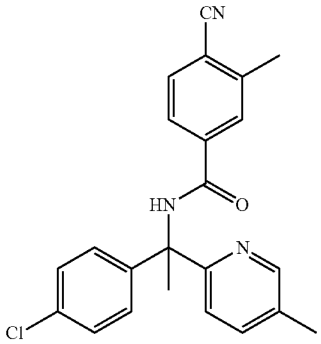 [SMILES: Cc1ccc(C(C)(NC(=O)c2ccc(C#N)c(C)c2)c2ccc(Cl)cc2)nc1] |
| CYM 52690<br>IB | 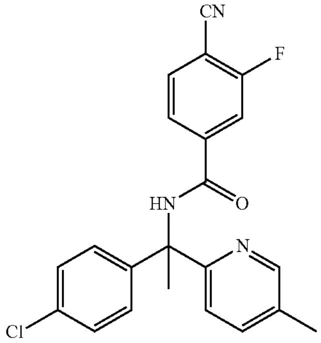 [SMILES: Cc1ccc(C(C)(NC(=O)c2ccc(C#N)c(F)c2)c2ccc(Cl)cc2)nc1] |
| CYM 52691<br>IB | 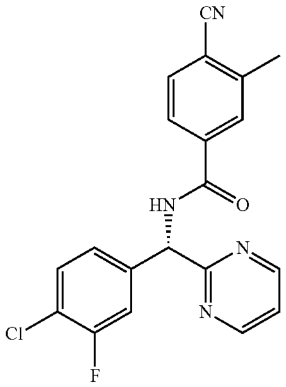 [SMILES: Cc1cc(C(=O)N[C@@H](c2ccc(Cl)c(F)c2)c2ncccn2)ccc1C#N] |

TABLE 1-continued
| Specific Compounds of the Invention | |
|---|---|
| Cpd. ID | Structure |
| CYM 52692<br>IB | 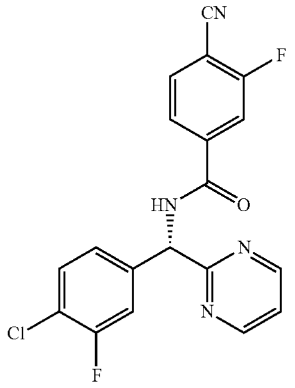 [SMILES: N#Cc1ccc(C(=O)N[C@@H](c2ccc(Cl)c(F)c2)c2ncccn2)cc1F] |
| CYM 52693<br>IB | 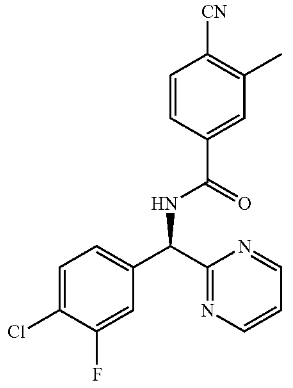 [SMILES: Cc1cc(C(=O)N[C@H](c2ccc(Cl)c(F)c2)c2ncccn2)ccc1C#N] |
| CYM 52694<br>IB | 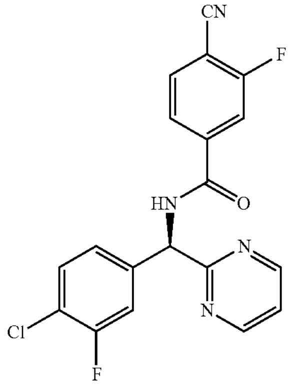 [SMILES: N#Cc1ccc(C(=O)N[C@H](c2ccc(Cl)c(F)c2)c2ncccn2)cc1F] |
| CYM 52695<br>IB | 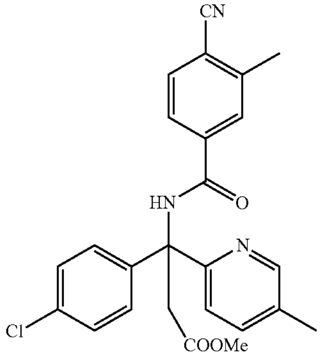 [SMILES: COC(=O)CC(NC(=O)c1ccc(C#N)c(C)c1)(c1ccc(Cl)cc1)c1ccc(C)cn1] |

TABLE 1-continued
| Specific Compounds of the Invention | |
|---|---|
| Cpd. ID | Structure |
| CYM 52696 IB | 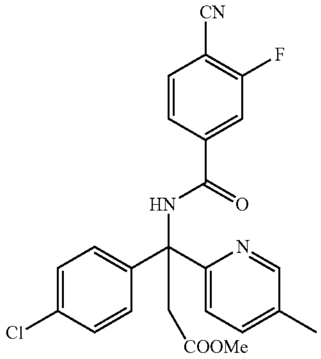 [SMILES: COC(=O)CC(NC(=O)c1ccc(C#N)c(F)c1)(c1ccc(Cl)cc1)c1ccc(C)cn1] |
| CYM 52697 IB | 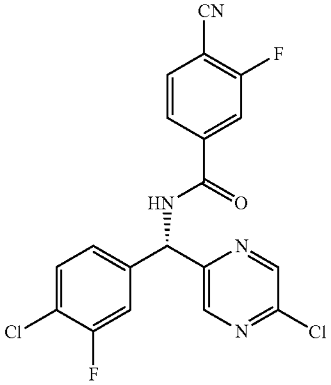 [SMILES: N#Cc1ccc(C(=O)N[C@@H](c2ccc(Cl)c(F)c2)c2cnc(Cl)cn2)cc1F] |
| CYM 52698 IB | 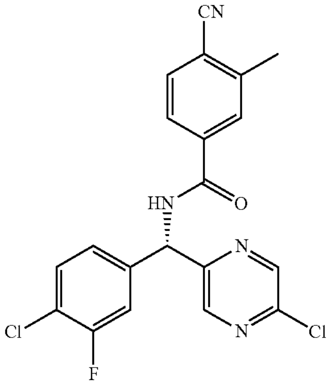 [SMILES: Cc1cc(C(=O)N[C@@H](c2ccc(Cl)c(F)c2)c2cnc(Cl)cn2)ccc1C#N] |
| CYM 52699 IB | 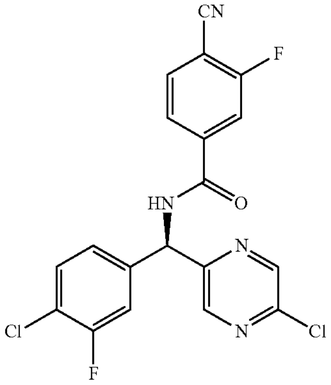 [SMILES: N#Cc1ccc(C(=O)N[C@H](c2ccc(Cl)c(F)c2)c2cnc(Cl)cn2)cc1F] |

TABLE 1-continued
| Specific Compounds of the Invention | |
|---|---|
| Cpd. ID | Structure |
| CYM 52700<br>IB | 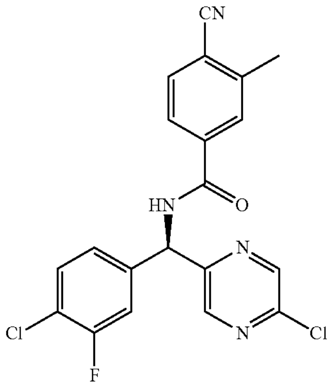 [SMILES: Cc1cc(C(=O)N[C@H](c2ccc(Cl)c(F)c2)c2cnc(Cl)cn2)ccc1C#N] |
| CYM 52701<br>Isomer 2<br>IB | 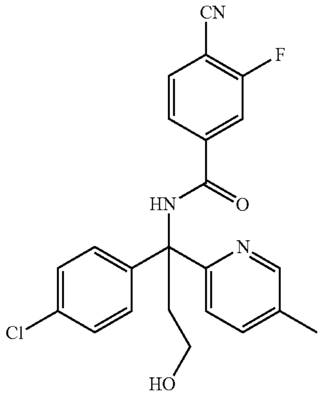 [SMILES: Cc1ccc(C(CCO)(NC(=O)c2ccc(C#N)c(F)c2)c2ccc(Cl)cc2)nc1] |
| CYM 52702<br>IB | 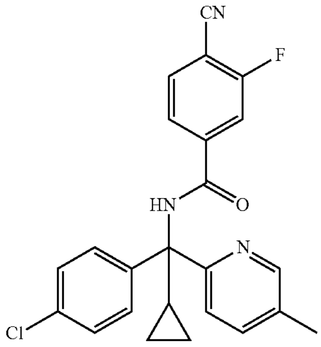 [SMILES: Cc1ccc(C(NC(=O)c2ccc(C#N)c(F)c2)(c2ccc(Cl)cc2)C2CC2)nc1] |
| CY 52703<br>IB | 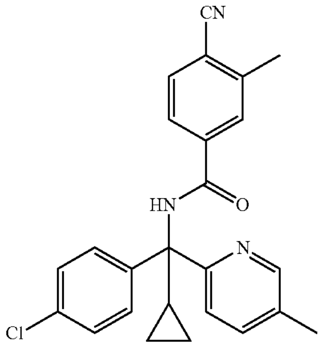 [SMILES: Cc1ccc(C(NC(=O)c2ccc(C#N)c(C)c2)(c2ccc(Cl)cc2)C2CC2)nc1] |

TABLE 1-continued
| Specific Compounds of the Invention | |
|---|---|
| Cpd. ID | Structure |
| CYM 52704<br>not I | 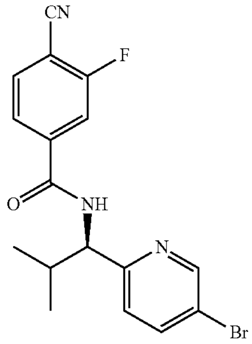 [SMILES: CC(C)[C@@H](NC(=O)c1ccc(C#N)c(F)c1)c1ccc(Br)cn1] |
| CYM 52705<br>IB | 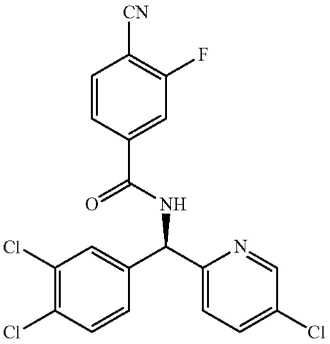 [SMILES: N#Cc1ccc(C(=O)N[C@H](c2ccc(Cl)c(Cl)c2)c2ccc(Cl)cn2)cc1F] |
| CYM-52706<br>IB | 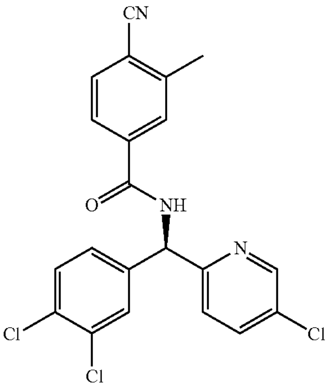 [SMILES: Cc1cc(C(=O)N[C@H](c2ccc(Cl)c(Cl)c2)c2ccc(Cl)cn2)ccc1C#N] |
| CYM-52707<br>IB | 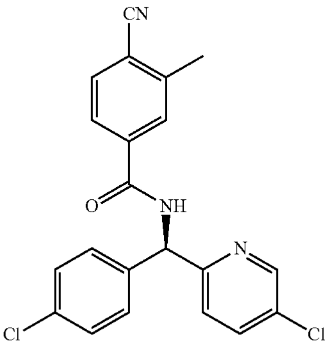 [SMILES: Cc1cc(C(=O)N[C@H](c2ccc(Cl)cc2)c2ccc(Cl)cn2)ccc1C#N] |

TABLE 1-continued
| Specific Compounds of the Invention | |
|---|---|
| Cpd. ID | Structure |
| CYM-52708<br>IB | 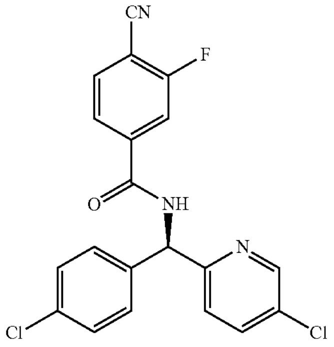 [SMILES: N#Cc1ccc(C(=O)N[C@H](c2ccc(Cl)cc2)c2ccc(Cl)cn2)cc1F] |
| CYM-52709<br>IB | 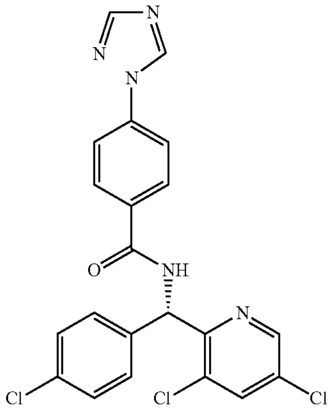 [SMILES: N=C/N=C\Nc1ccc(C(=O)N[C@@H](c2ccc(Cl)cc2)c2ncc(Cl)cc2Cl)cc1] |
| CYM-52710<br>IB | 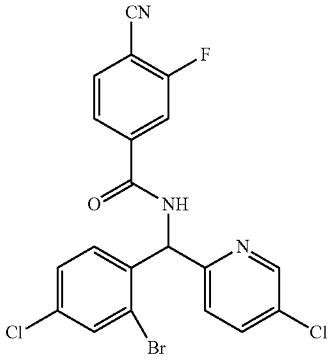 [SMILES: N#Cc1ccc(C(=O)NC(c2ccc(Cl)cn2)c2ccc(Cl)cc2Br)cc1F] |
| CYM-52711<br>IB | 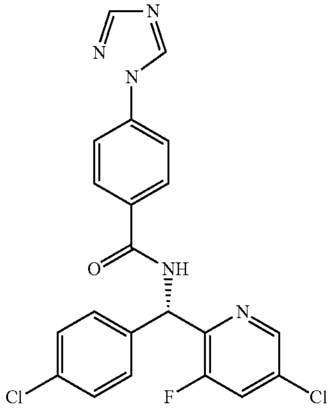 [SMILES: N=C/N=C\Nc1ccc(C(=O)N[C@@H](c2ccc(Cl)cc2)c2ncc(Cl)cc2F)cc1] |

TABLE 1-continued
| Specific Compounds of the Invention | |
|---|---|
| Cpd. ID | Structure |
| CYM-52712<br>IA | 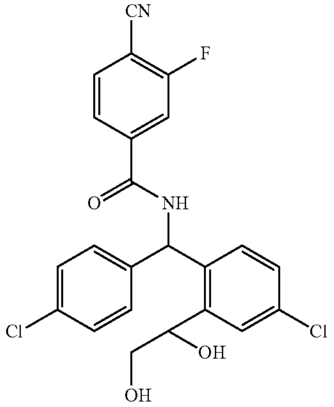 [SMILES: N#Cc1ccc(C(=O)NC(c2ccc(Cl)cc2)c2ccc(Cl)cc2C(O)CO)cc1F] |
| CYM-52713<br>IC | 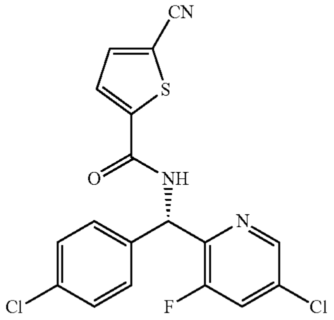 [SMILES: N#Cc1ccc(C(=O)N[C@@H](c2ccc(Cl)cc2)c2ncc(Cl)cc2F)s1] |
| CYM-52714<br>ID OR IB | 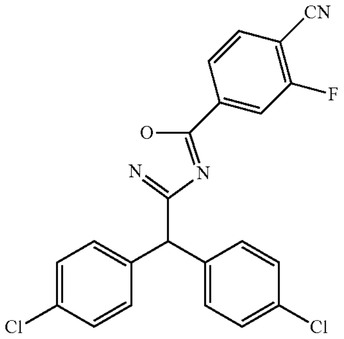 [SMILES: N#Cc1ccc(/C(O)=N/C(=N)C(c2ccc(Cl)cc2)c2ccc(Cl)cc2)cc1F] |
| CYM-52715<br>IB | 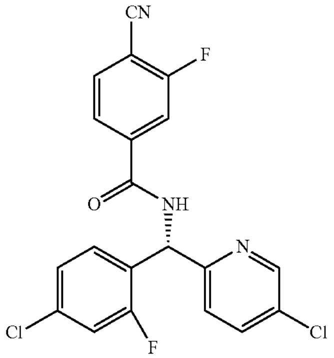 [SMILES: N#Cc1ccc(C(=O)N[C@H](c2ccc(Cl)cn2)c2ccc(Cl)cc2F)cc1F] |

TABLE 1-continued
| Specific Compounds of the Invention | |
|---|---|
| Cpd. ID | Structure |
| CYM52716 IB | 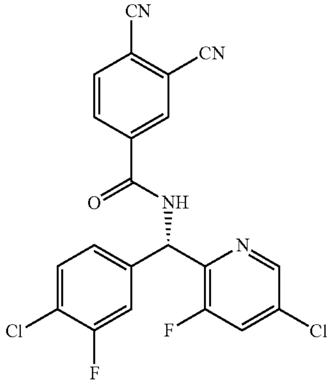 [SMILES: N#Cc1ccc(C(=O)N[C@@H](c2ccc(Cl)c(F)c2)c2ncc(Cl)cc2F)cc1C#N] |
| CYM52717 IB | 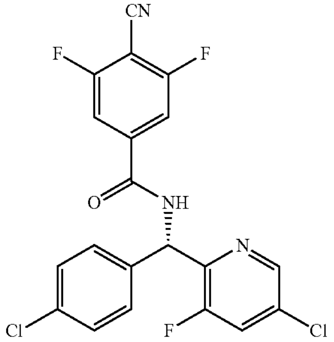 [SMILES: N#Cc1c(F)cc(C(=O)N[C@@H](c2ccc(Cl)cc2)c2ncc(Cl)cc2F)cc1F] |
| CYM52718 IB | 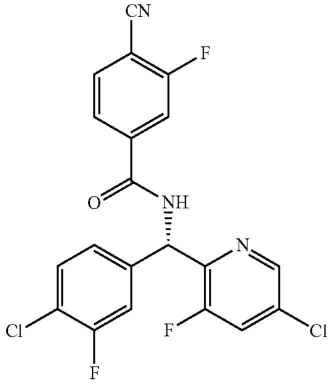 [SMILES: N#Cc1ccc(C(=O)N[C@@H](c2ccc(Cl)c(F)c2)c2ncc(Cl)cc2F)cc1F] |
| CYM52719 isomer 1 IB | 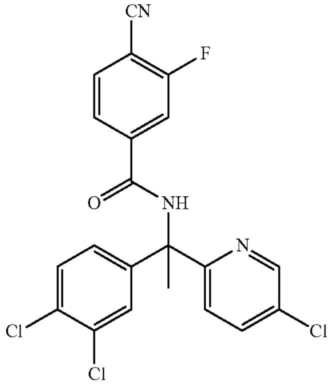 [SMILES: CC(NC(=O)c1ccc(C#N)c(F)c1)(c1ccc(Cl)c(Cl)c1)c1ccc(Cl)cn1] |

TABLE 1-continued
| Specific Compounds of the Invention | |
|---|---|
| Cpd. ID | Structure |
| CYM52720 isomer 2 IB | 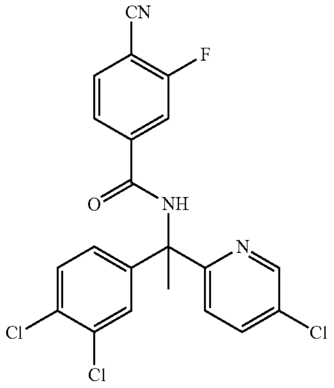 [SMILES: CC(NC(=O)c1ccc(C#N)c(F)c1)(c1ccc(Cl)c(Cl)c1)c1ccc(Cl)cn1] |
| CYM 52721 IB | 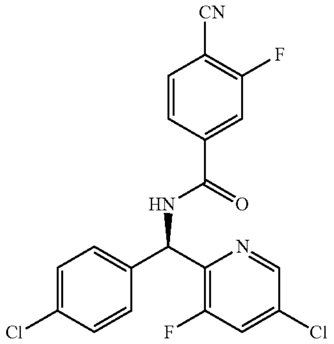 [SMILES: N#Cc1ccc(C(=O)N[C@H](c2ccc(Cl)cc2)c2ncc(Cl)cc2F)cc1F] |
| CYM 52722 IB | 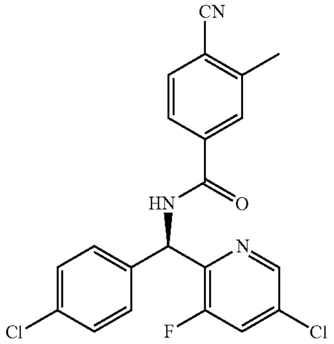 [SMILES: Cc1cc(C(=O)N[C@H](c2ccc(Cl)cc2)c2ncc(Cl)cc2F)ccc1C#N] |
| CYM 52723 IB | 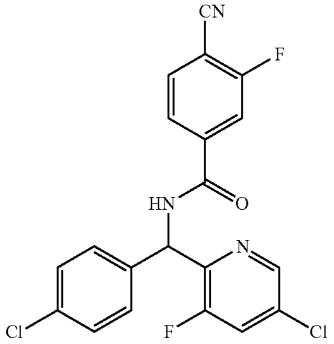 [SMILES: N#Cc1ccc(C(=O)NC(c2ccc(Cl)cc2)c2ncc(Cl)cc2F)cc1F] |

TABLE 1-continued
| Specific Compounds of the Invention | |
|---|---|
| Cpd. ID | Structure |
| CYM 52724<br>IB | 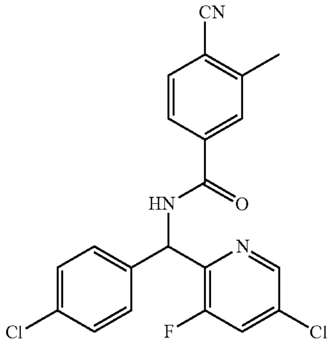 [SMILES: Cc1cc(C(=O)NC(c2ccc(Cl)cc2)c2ncc(Cl)cc2F)ccc1C#N] |
| CYM 52725<br>IB | 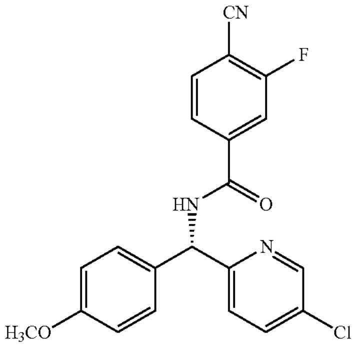 [SMILES: COc1ccc([C@H](NC(=O)c2ccc(C#N)c(F)c2)c2ccc(Cl)cn2)cc1] |
| CYM 52726<br>IA | 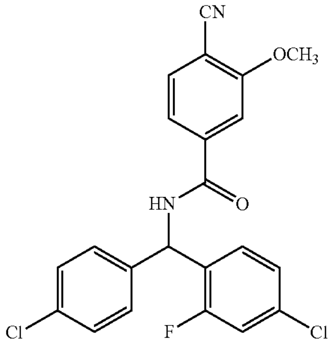 [SMILES: COc1cc(C(=O)NC(c2ccc(Cl)cc2)c2ccc(Cl)cc2F)ccc1C#N] |
| CYM 52727<br>IB | 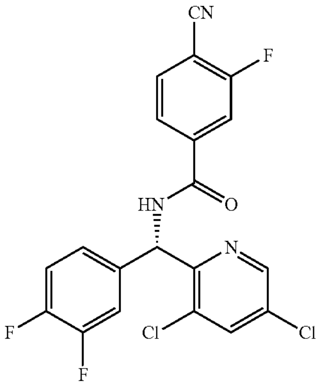 [SMILES: N#Cc1ccc(C(=O)N[C@@H](c2ccc(F)c(F)c2)c2ncc(Cl)cc2Cl)cc1F] |

TABLE 1-continued
| Specific Compounds of the Invention | |
|---|---|
| Cpd. ID | Structure |
| CYM 52728 IA | 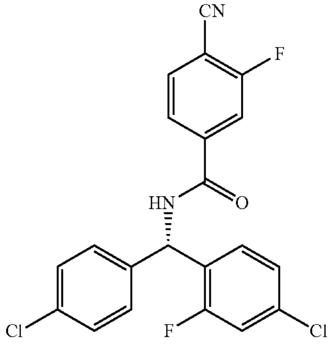 [SMILES: N#Cc1ccc(C(=O)N[C@@H](c2ccc(Cl)cc2)c2ccc(Cl)cc2F)cc1F] |
| CYM 52729 IB | 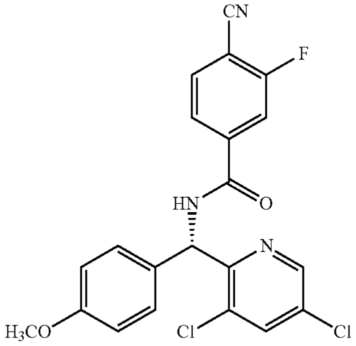 [SMILES: COc1ccc([C@H](NC(=O)c2ccc(C#N)c(F)c2)c2ncc(Cl)cc2Cl)cc1] |
| CYM 52730 IB | 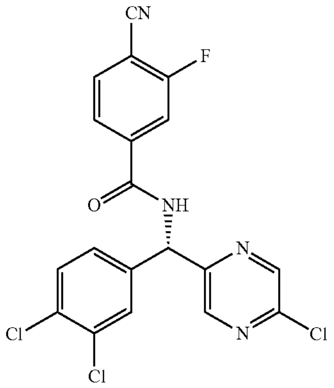 [SMILES: N#Cc1ccc(C(=O)N[C@@H](c2ccc(Cl)c(Cl)c2)c2cnc(Cl)cn2)cc1F] |
| CYM 52731 IB | 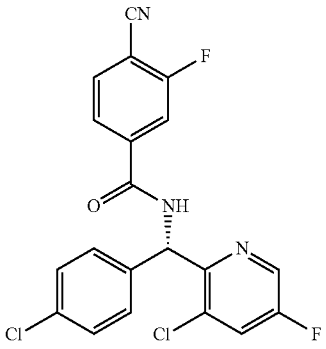 [SMILES: N#Cc1ccc(C(=O)N[C@@H](c2ccc(Cl)cc2)c2ncc(F)cc2Cl)cc1F] |

TABLE 1-continued
| Specific Compounds of the Invention | |
|---|---|
| Cpd. ID | Structure |
| CYM 52732 IB | 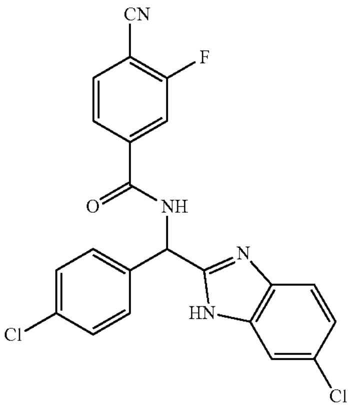 [SMILES: N#Cc1ccc(C(=O)NC(c2ccc(Cl)cc2)c2nc3ccc(Cl)cc3[nH]2)cc1F] |
| CYM 52733 IA | 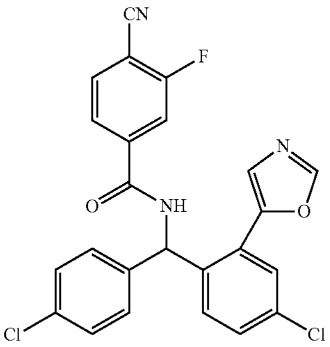 [SMILES: N#Cc1ccc(C(=O)NC(c2ccc(Cl)cc2)c2ccc(Cl)cc2-c2cnco2)cc1F] |
| CYM 52734 IB | 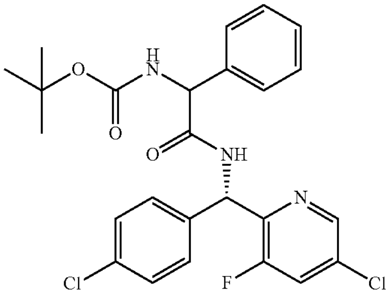 [SMILES: CC(C)(C)OC(=O)NC(C(=O)N[C@@H](c1ccc(Cl)cc1)c1ncc(Cl)cc1F)c1ccccc1] |
| CYM 52735 IB | 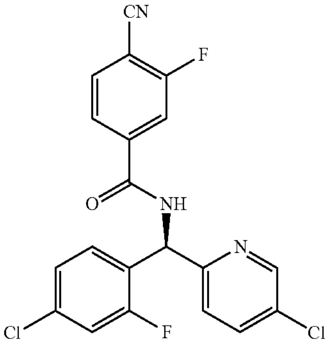 [SMILES: N#Cc1ccc(C(=O)N[C@@H](c2ccc(Cl)cn2)c2ccc(Cl)cc2F)cc1F] |

TABLE 1-continued
| Specific Compounds of the Invention | |
|---|---|
| Cpd. ID | Structure |
| CYM 52736 IB | 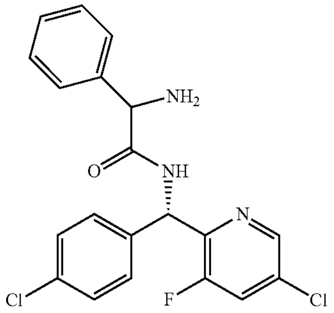 [SMILES: NC(C(=O)N[C@@H](c1ccc(Cl)cc1)c1ncc(Cl)cc1F)c1ccccc1] |
| CYM 52737 IB | 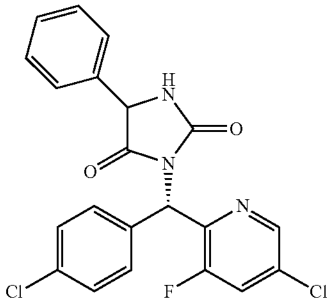 [SMILES: O=C1NC(c2ccccc2)C(=O)N1[C@@H](c1ccc(Cl)cc1)c1ncc(Cl)cc1F] |
| CYM 52738 not I | 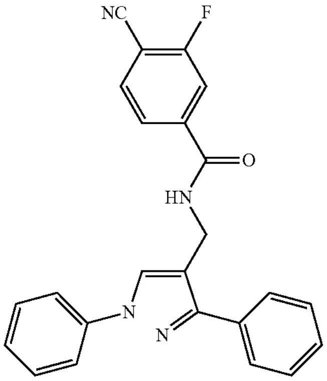 [SMILES: N#Cc1ccc(C(=O)NC/C(=C/Nc2ccccc2)C(=N)c2ccccc2)cc1F] |
| CYM 52739 IB | 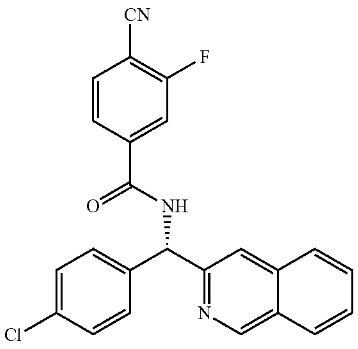 |

TABLE 1-continued
| Specific Compounds of the Invention | |
|---|---|
| Cpd. ID | Structure |
| CYM 52740 IB | 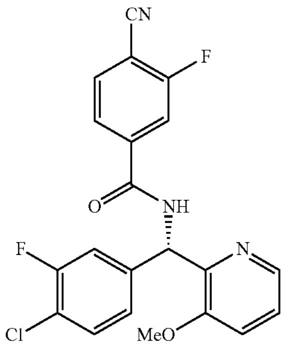 [SMILES: COc1cccnc1[C@@H](NC(=O)c1ccc(C#N)c(F)c1)c1ccc(Cl)c(F)c1] |
| CYM 52741 IA | 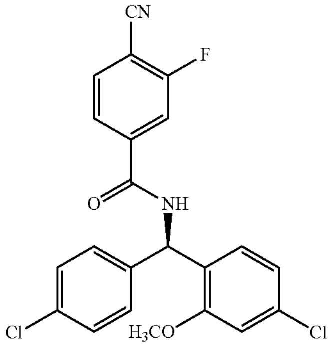 [SMILES: COc1cc(Cl)ccc1[C@H](NC(=O)c1ccc(C#N)c(F)c1)c1ccc(Cl)cc1] |
| CYM 52742 IA | 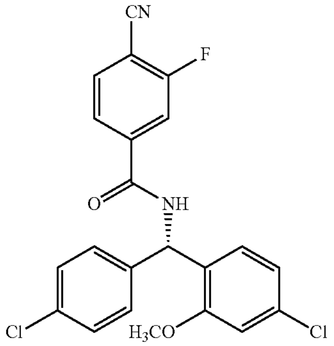 [SMILES: COc1cc(Cl)ccc1[C@@H](NC(=O)c1ccc(C#N)c(F)c1)c1ccc(Cl)cc1] |
| CYM 52743 IA | 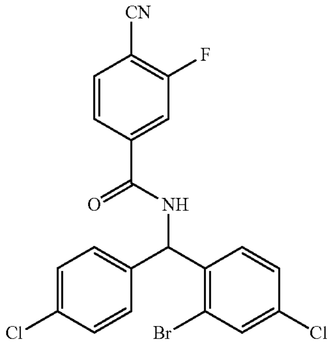 [SMILES: N#Cc1ccc(C(=O)NC(c2ccc(Cl)cc2)c2ccc(Cl)cc2Br)cc1F] |

TABLE 1-continued
| Specific Compounds of the Invention | |
|---|---|
| Cpd. ID | Structure |
| CYM 52744 IB | 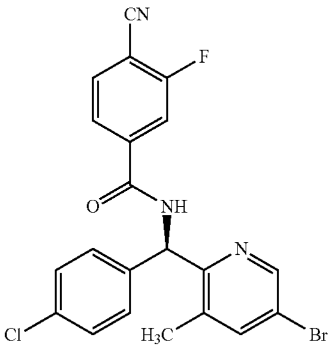 [SMILES: Cc1cc(Br)cnc1[C@H](NC(=O)c1ccc(C#N)c(F)c1)c1ccc(Cl)cc1] |
| CYM 52745 IA | 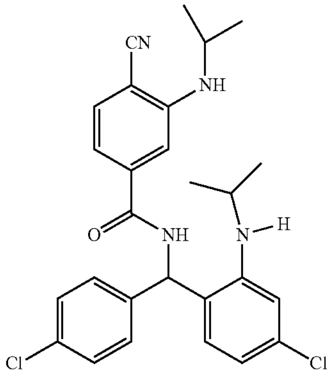 [SMILES: CC(C)Nc1cc(C(=O)NC(c2ccc(Cl)cc2)c2ccc(Cl)cc2NC(C)C)ccc1C#N] |
| CYM 52746 IB | 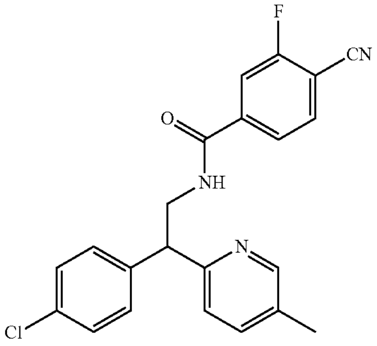 [SMILES: Cc1ccc(C(CNC(=O)c2ccc(C#N)c(F)c2)c2ccc(Cl)cc2)nc1] |
| CYM 52747 IB | 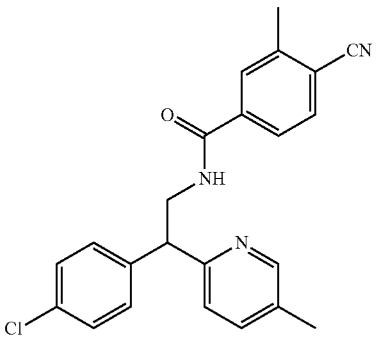 [SMILES: Cc1ccc(C(CNC(=O)c2ccc(C#N)c(C)c2)c2ccc(Cl)cc2)nc1] |

TABLE 1-continued
| Specific Compounds of the Invention | |
|---|---|
| Cpd. ID | Structure |
| CYM 52748<br>IB | 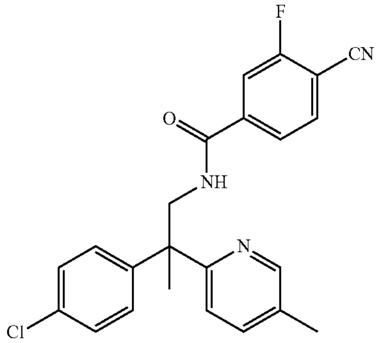 [SMILES: Cc1ccc(C(C)(CNC(=O)c2ccc(C#N)c(F)c2)c2ccc(Cl)cc2)nc1] |
| CYM52749<br>IC | 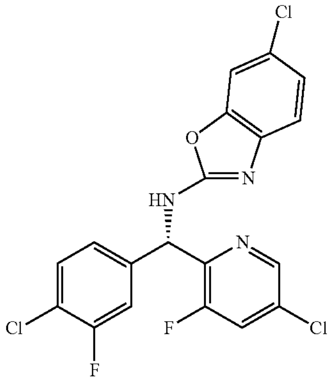 [SMILES: Fc1cc([C@H](Nc2nc3ccc(Cl)cc3o2)c2ncc(Cl)cc2F)ccc1Cl] |
| CYM52750<br>IB | 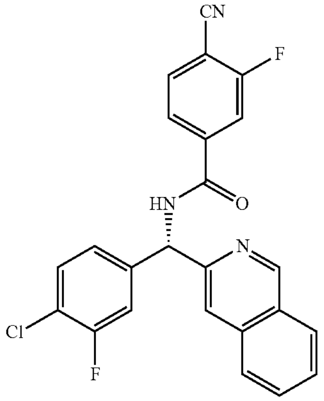 [SMILES: N#Cc1ccc(C(=O)N[C@@H](c2ccc(Cl)c(F)c2)c2cc3ccccc3cn2)cc1F] |
| CYM52751<br>IA | 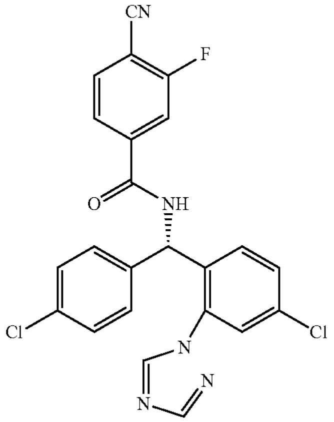 [SMILES: N#Cc1ccc(C(=O)N[C@@H](c2ccc(Cl)cc2)c2ccc(Cl)cc2N/C=N\C=N)cc1F] |

TABLE 1-continued
| Specific Compounds of the Invention | |
|---|---|
| Cpd. ID | Structure |
| CYM52752<br>IB | 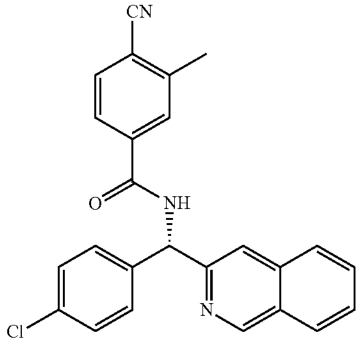 |
| CYM52753<br>not I | 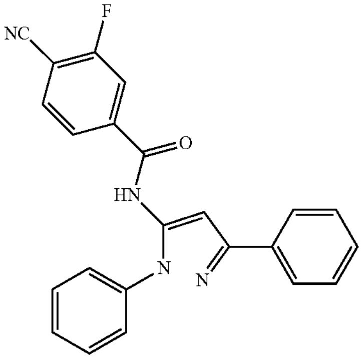 [SMILES: N#Cc1ccc(C(=O)N/C(=C/C(=N)c2ccccc2)Nc2ccccc2)cc1F] |
| CYM52754<br>IB | 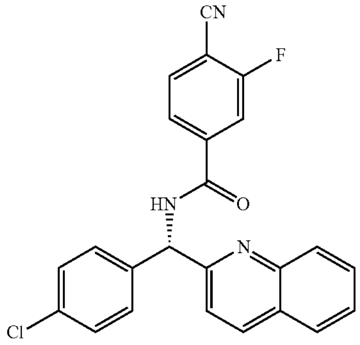 [SMILES: N#Cc1ccc(C(=O)N[C@@H](c2ccc(Cl)cc2)c2ccc3ccccc3n2)cc1F] |
| CYM52755<br>IC | 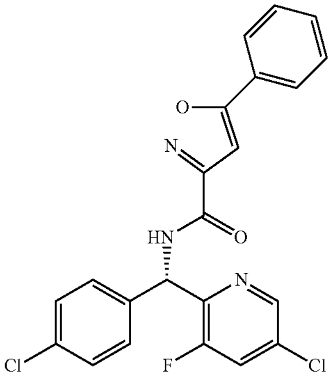 [SMILES: N=C(/C=C(\O)c1ccccc1)C(=O)N[C@@H](c1ccc(Cl)cc1)c1ncc(Cl)cc1F] |

TABLE 1-continued
| Specific Compounds of the Invention | |
|---|---|
| Cpd. ID | Structure |
| CYM 52756<br>IA | 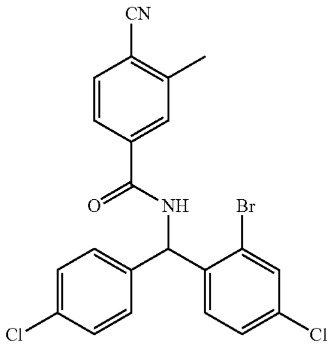 [SMILES: Cc1cc(C(=O)NC(c2ccc(Cl)cc2)c2ccc(Cl)cc2Br)ccc1C#N] |
| CYM 52757<br>IA | 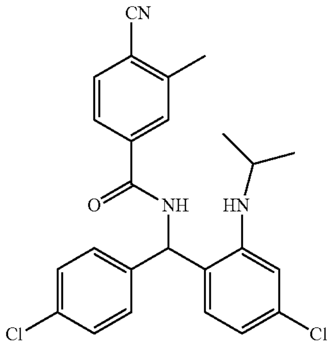 [SMILES: Cc1cc(C(=O)NC(c2ccc(Cl)cc2)c2ccc(Cl)cc2NC(C)C)ccc1C#N] |
| CYM 52758<br>IC | 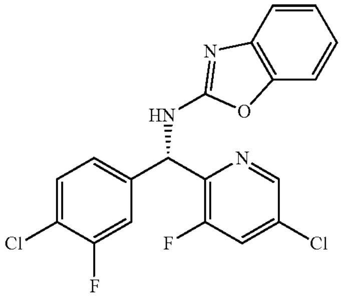 [SMILES: Fc1cc([C@H](Nc2nc3ccccc3o2)c2ncc(Cl)cc2F)ccc1Cl] |
| CYM 52759<br>IC | 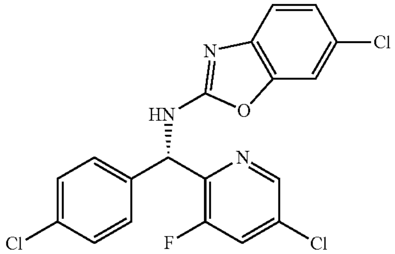 [SMILES: Fc1cc(Cl)cnc1[C@@H](Nc1nc2ccc(Cl)cc2o1)c1ccc(Cl)cc1] |
| CYM 52760<br>IC | 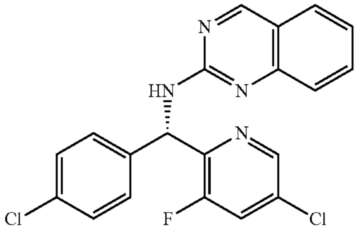 [SMILES: Fc1cc(Cl)cnc1[C@@H](Nc1ncc2ccccc2n1)c1ccc(Cl)cc1] |

TABLE 1-continued
| Specific Compounds of the Invention | |
|---|---|
| Cpd. ID | Structure |
| CYM 52761<br>IC | 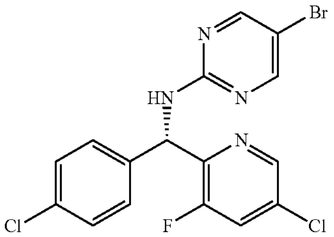 [SMILES: Fc1cc(Cl)cnc1[C@@H](Nc1ncc(Br)cn1)c1ccc(Cl)cc1] |
| CYM 52762<br>IC | 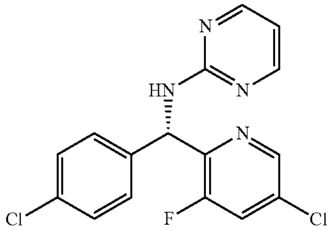 [SMILES: Fc1cc(Cl)cnc1[C@@H](Nc1ncccn1)c1ccc(Cl)cc1] |
| CYM 52763<br>IB | 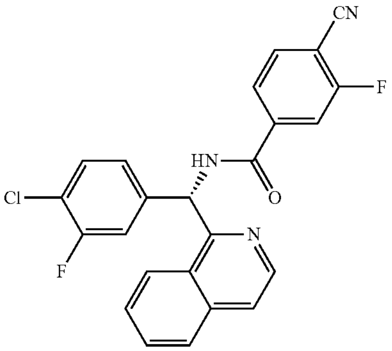 [SMILES: N#Cc1ccc(C(=O)N[C@@H](c2ccc(Cl)c(F)c2)c2nccc3ccccc23)cc1F] |
| CYM 52764<br>IC | 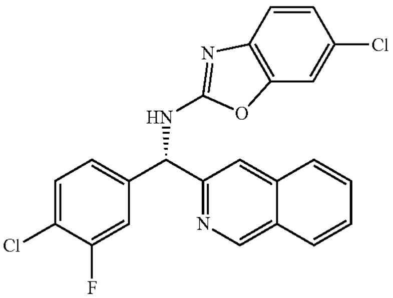 [SMILES: Fc1cc([C@H](Nc2nc3ccc(Cl)cc3o2)c2cc3ccccc3cn2)ccc1Cl] |
| CYM 52765<br>not I | 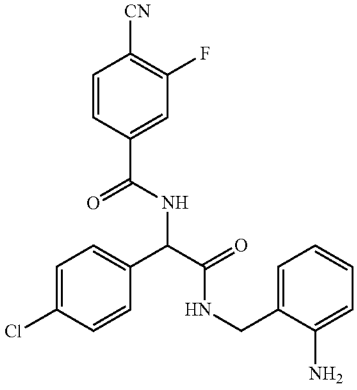 [SMILES: N#Cc1ccc(C(=O)NC(C(=O)NCc2ccccc2N)c2ccc(Cl)cc2)cc1F] |

TABLE 1-continued
| Specific Compounds of the Invention | |
|---|---|
| Cpd. ID | Structure |
| CYM 52766 IC | 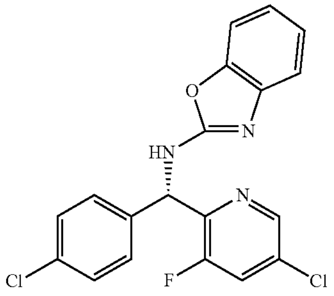 [SMILES: Fc1cc(Cl)cnc1[C@@H](Nc1nc2ccccc2o1)c1ccc(Cl)cc1] |
| CYM 52767 IC | 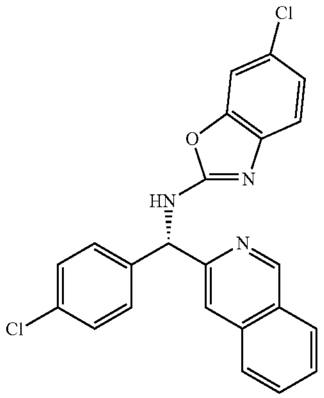 [SMILES: Clc1ccc([C@H](Nc2nc3ccc(Cl)cc3o2)c2cc3ccccc3cn2)cc1] |
| CYM 52768 IC | 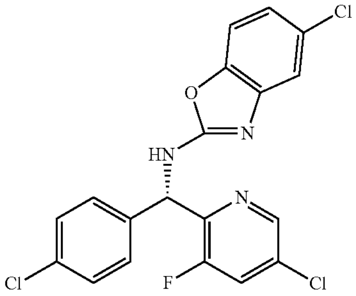 [SMILES: Fc1cc(Cl)cnc1[C@@H](Nc1nc2cc(Cl)ccc2o1)c1ccc(Cl)cc1] |
| CYM 52769 IC | 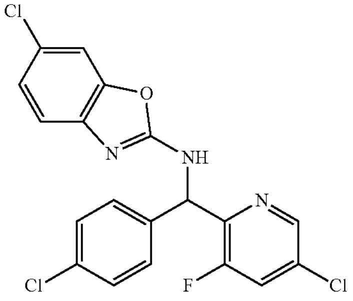 [SMILES: Fc1cc(Cl)cnc1C(Nc1nc2ccc(Cl)cc2o1)c1ccc(Cl)cc1] |

TABLE 1-continued
| Specific Compounds of the Invention | |
|---|---|
| Cpd. ID | Structure |
| CYM 52770<br>IC | 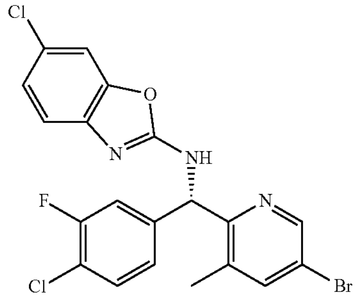 [SMILES: Cc1cc(Br)cnc1[C@@H](Nc1nc2ccc(Cl)cc2o1)c1ccc(Cl)c(F)c1] |
| CYM 52771<br>IC | 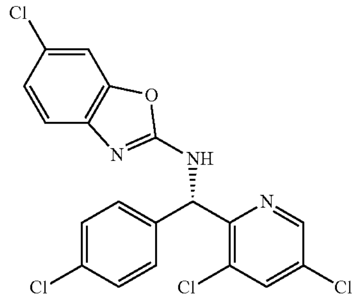 [SMILES: Clc1ccc([C@H](Nc2nc3ccc(Cl)cc3o2)c2ncc(Cl)cc2Cl)cc1] |
| CYM 52772<br>ID | 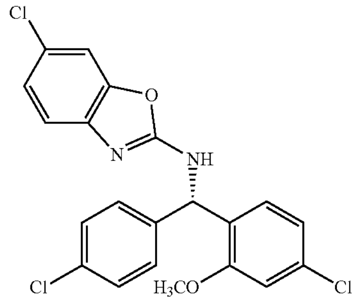 [SMILES: COc1cc(Cl)ccc1[C@@H](Nc1nc2ccc(Cl)cc2o1)c1ccc(Cl)cc1] |
| CYM 52773<br>ID | 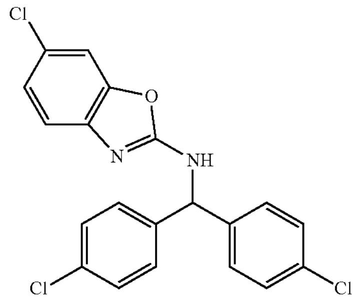 [SMILES: Clc1ccc(C(Nc2nc3ccc(Cl)cc3o2)c2ccc(Cl)cc2)cc1] |
| CYM 52774<br>IC | 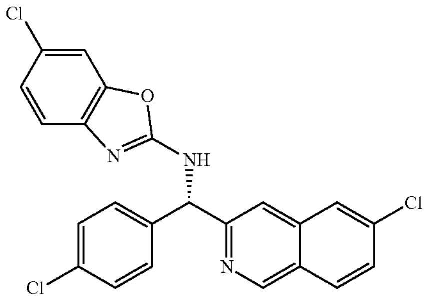 [SMILES: Clc1ccc([C@H](Nc2nc3ccc(Cl)cc3o2)c2cc3cc(Cl)ccc3cn2)cc1] |

TABLE 1-continued
| Specific Compounds of the Invention | |
|---|---|
| Cpd. ID | Structure |
| CYM 52775<br>IB | 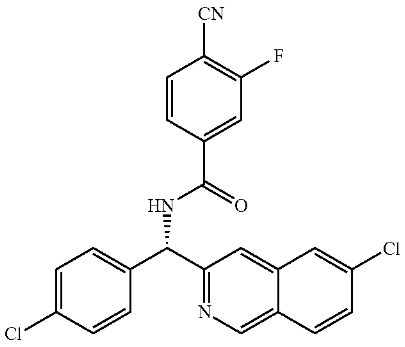 [SMILES: N#Cc1ccc(C(=O)N[C@@H](c2ccc(Cl)cc2)c2cc3cc(Cl)ccc3cn2)cc1F] |
| CYM 52776<br>IC | 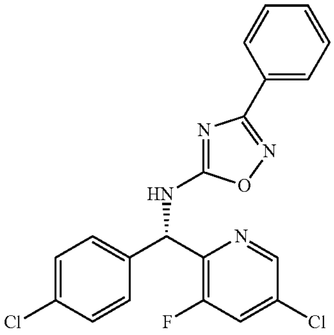 [SMILES: Fc1cc(Cl)cnc1[C@@H](Nc1nc(-c2ccccc2)no1)c1ccc(Cl)cc1] |
| CYM 52777<br>ID | 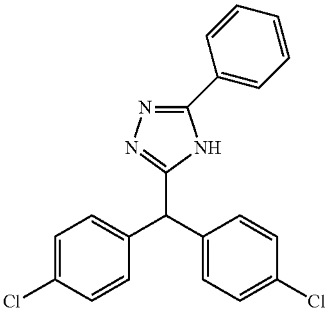 [SMILES: Clc1ccc(C(c2ccc(Cl)cc2)c2nnc(-c3ccccc3)[nH]2)cc1] |
| CYM 52778<br>IC | 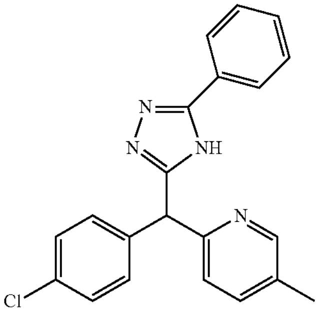 [SMILES: Cc1ccc(C(c2ccc(Cl)cc2)c2nnc(-c3ccccc3)[nH]2)nc1] |

TABLE 1-continued
| Specific Compounds of the Invention | |
|---|---|
| Cpd. ID | Structure |
| CYM 52779 IC | 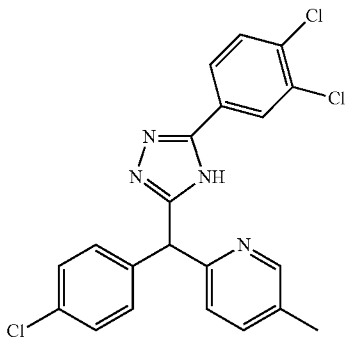 [SMILES: Cc1ccc(C(c2ccc(Cl)cc2)c2nnc(-c3ccc(Cl)c(Cl)c3)[nH]2)nc1] |
| CYM 52780 IB | 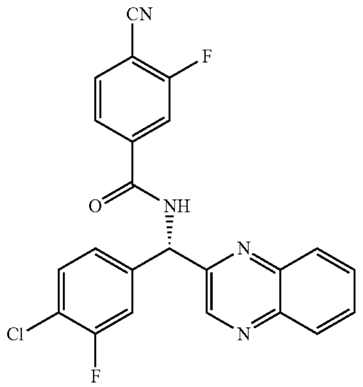 [SMILES: N#Cc1ccc(C(=O)N[C@@H](c2ccc(Cl)c(F)c2)c2cnc3ccccc3n2)cc1F] |
| CYM 52781 IB | 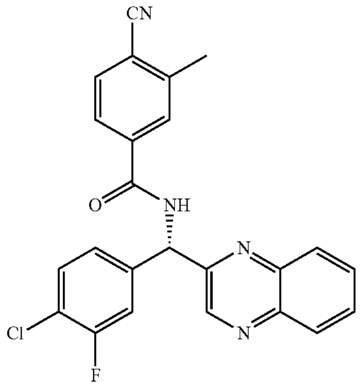 [SMILES: Cc1cc(C(=O)N[C@@H](c2ccc(Cl)c(F)c2)c2cnc3ccccc3n2)ccc1C#N] |
| CYM 52782 IC | 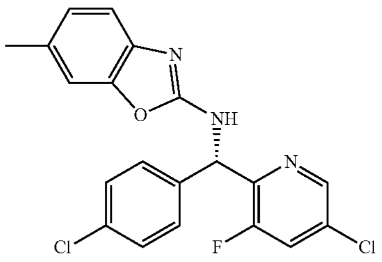 [SMILES: Cc1ccc2nc(N[C@@H](c3ccc(Cl)cc3)c3ncc(Cl)cc3F)oc2c1] |

TABLE 1-continued
| Specific Compounds of the Invention | |
|---|---|
| Cpd. ID | Structure |
| CYM 52783 IC | 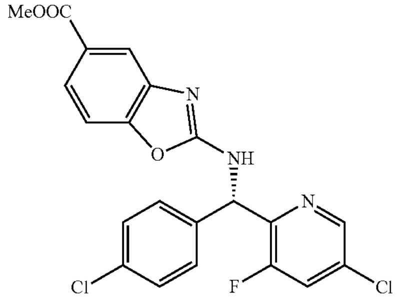 [SMILES: COC(=O)c1ccc2oc(N[C@@H](c3ccc(Cl)cc3)c3ncc(Cl)cc3F)nc2c1] |
| CYM 52784 IC | 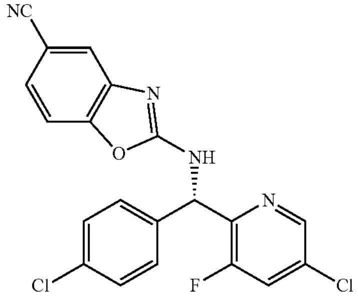 [SMILES: N#Cc1ccc2oc(N[C@@H](c3ccc(Cl)cc3)c3ncc(Cl)cc3F)nc2c1] |
| CYM 52785 IC | 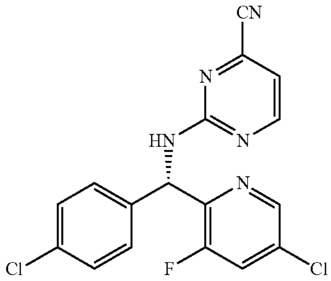 [SMILES: N#Cc1ccnc(N[C@@H](c2ccc(Cl)cc2)c2ncc(Cl)cc2F)n1] |
| CYM 52786 IC | 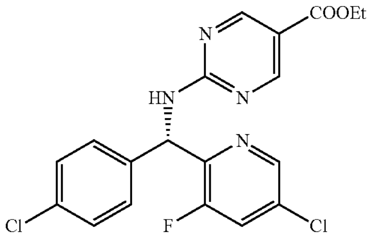 [SMILES: CCOC(=O)c1cnc(N[C@@H](c2ccc(Cl)cc2)c2ncc(Cl)cc2F)nc1] |
| CYM 52787 IC | 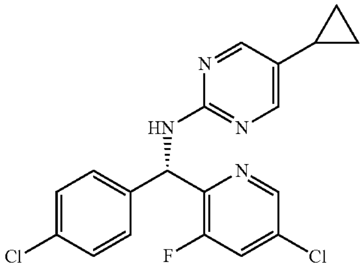 [SMILES: Fc1cc(Cl)cnc1[C@@H](Nc1ncc(C2CC2)cn1)c1ccc(Cl)cc1] |

TABLE 1-continued

| Specific Compounds of the Invention | |
|---|---|
| Cpd. ID | Structure |
| CYM 52788 IC | 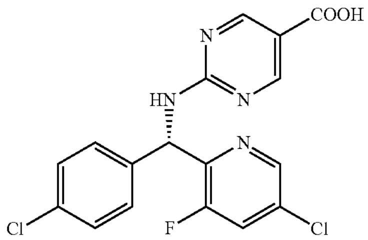 [SMILES: O=C(O)c1cnc(N[C@@H](c2ccc(Cl)cc2)c2ncc(Cl)cc2F)nc1] |
| CYM 52789 IC | 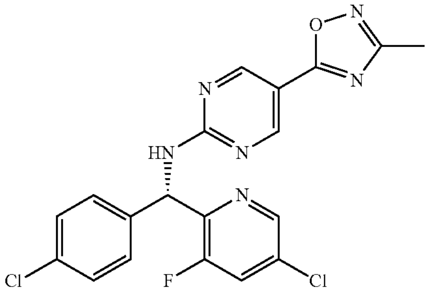 [SMILES: Cc1noc(-c2cnc(N[C@@H](c3ccc(Cl)cc3)c3ncc(Cl)cc3F)nc2)n1] |

Boc = t-butoxycarbonyl

DOCUMENTS CITED

1. Rosen H, Stevens R C, Hanson M, Roberts E, & Oldstone M B A (2013) Sphingosine-1-Phosphate and Its Receptors: Structure, Signaling, and Influence. *Annual Review of Biochemistry* 82(1):null.
2. Hanson M A, et al. (2012) Crystal structure of a lipid G protein-coupled receptor. *Science* 335(6070):851-855.
3. Schmouder R, et al. (2006) FTY720: placebo-controlled study of the effect on cardiac rate and rhythm in healthy subjects. *Journal of clinical pharmacology* 46(8):895-904.
4. Kappos L, et al. (2010) A placebo-controlled trial of oral fingolimod in relapsing multiple sclerosis. *The New England journal of medicine* 362(5):387-401.
5. Kovarik J M, et al. (2008) The ability of atropine to prevent and reverse the negative chronotropic effect of fingolimod in healthy subjects. *British journal of clinical pharmacology* 66(2):199-206.
6. Legangneux E, Gardin A, & Johns D (2013) Dose titration of BAF312 attenuates the initial heart rate reducing effect in healthy subjects. *British journal of clinical pharmacology* 75(3):831-841.
7. Fryer R M, et al. (2012) The clinically-tested S1P receptor agonists, FTY720 and BAF312, demonstrate subtype-specific bradycardia (S1P(1)) and hypertension (S1P(3)) in rat. *PloS one* 7(12):e52985.
8. Shea B S, et al. (2010) Prolonged exposure to sphingosine 1-phosphate receptor-1 agonists exacerbates vascular leak, fibrosis, and mortality after lung injury. *American journal of respiratory cell and molecular biology* 43(6): 662-673.
9. Takuwa N, et al. (2010) S1P3-mediated cardiac fibrosis in sphingosine kinase 1 transgenic mice involves reactive oxygen species. *Cardiovascular research* 85(3):484-493.
10. Ikeda H, et al. (2009) Sphingosine 1-phosphate regulates regeneration and fibrosis after liver injury via sphingosine 1-phosphate receptor 2. *Journal of lipid research* 50(3): 556-564.
11. Sanna M G, et al. (2004) Sphingosine 1-phosphate (S1P) receptor subtypes S1P1 and S1P3, respectively, regulate lymphocyte recirculation and heart rate. *The Journal of biological chemistry* 279(14):13839-13848.
12. Suarez D, et al. (2011) Cost-effectiveness of the Surviving Sepsis Campaign protocol for severe sepsis: a prospective nation-wide study in Spain. *Intensive Care Med* 37(3):444-452.
13. Kumar G, et al. (2011) Nationwide trends of severe sepsis in the 21st century (2000-2007). *Chest* 140(5): 1223-1231.
14. Levy M M, et al. (2010) The Surviving Sepsis Campaign: results of an international guideline-based performance improvement program targeting severe sepsis. *Intensive Care Med* 36(2):222-231.
15. Martin G S (2012) Sepsis, severe sepsis and septic shock: changes in incidence, pathogens and outcomes. *Expert Rev Anti Infect Ther* 10(6):701-706.
16. Angus D C, et al. (2001) Epidemiology of severe sepsis in the United States: analysis of incidence, outcome, and associated costs of care. *Crit Care Med* 29(7):1303-1310.
17. Gaieski D F, et al. (2010) Impact of time to antibiotics on survival in patients with severe sepsis or septic shock in whom early goal-directed therapy was initiated in the emergency department. *Crit Care Med* 38(4):1045-1053.
18. Kumar A (2009) Optimizing antimicrobial therapy in sepsis and septic shock. *Crit Care Clin* 25(4):733-751, viii.
19. Puskarich M A, et al. (2011) Association between timing of antibiotic administration and mortality from septic shock in patients treated with a quantitative resuscitation protocol. *Crit Care Med* 39(9):2066-2071.
20. Rivers E, et al. (2001) Early goal-directed therapy in the treatment of severe sepsis and septic shock. *The New England journal of medicine* 345(19):1368-1377.
21. Boyd J H, Forbes J, Nakada T A, Walley K R, & Russell J A (2011) Fluid resuscitation in septic shock: a positive fluid balance and elevated central venous pressure are associated with increased mortality. *Crit Care Med* 39(2): 259-265.
22. Novotny A R, et al. (2012) Mixed antagonist response and sepsis severity-dependent dysbalance of pro- and anti-inflammatory responses at the onset of postoperative sepsis. *Immunobiology* 217(6):616-621.
23. Walsh K B, Teijaro J R, Rosen H, & Oldstone M B (2011) Quelling the storm: utilization of sphingosine-1-phosphate receptor signaling to ameliorate influenza virus-induced cytokine storm. *Immunol Res* 51(1):15-25.
24. Walsh K B, et al. (2011) Suppression of cytokine storm with a sphingosine analog provides protection against pathogenic influenza virus. *Proc Natl Acad Sci USA* 108(29):12018-12023.
25. Teijaro J R, et al. (2011) Endothelial cells are central orchestrators of cytokine amplification during influenza virus infection. *Cell* 146(6):980-991.
26. Niessen F, et al. (2008) Dendritic cell PAR1-S1P3 signalling couples coagulation and inflammation. *Nature* 452(7187):654-658.
27. Castellheim A, Brekke O L, Espevik T, Harboe M, & Mollnes T E (2009) Innate immune responses to danger signals in systemic inflammatory response syndrome and sepsis. *Scand J Immunol* 69(6):479-491.
28. Cavaillon J M & Annane D (2006) Compartmentalization of the inflammatory response in sepsis and SIRS. *J Endotoxin Res* 12(3):151-170.
29. Rosen H, Sanna M G, Cahalan S M, & Gonzalez-Cabrera P J (2007) Tipping the gatekeeper: S1P regulation of endothelial barrier function. *Trends Immunol* 28(3): 102-107.
30. Rosen H, et al. (2008) Modulating tone: the overture of S1P receptor immunotherapeutics. *Immunol Rev* 223:221-235.
31. Sattler K J, et al. (2010) Sphingosine 1-phosphate levels in plasma and HDL are altered in coronary artery disease. *Basic Res Cardiol* 105(6):821-832.
32. Graler M H (2010) Targeting sphingosine 1-phosphate (SIP) levels and SIP receptor functions for therapeutic immune interventions. *Cell Physiol Biochem* 26(1):79-86.
33. Kulakowska A, et al. (2010) Intrathecal increase of sphingosine 1-phosphate at early stage multiple sclerosis. *Neurosci Lett* 477(3):149-152.
34. Watson L, et al. (2012) Increased serum concentration of sphingosine-1-phosphate in juvenile-onset systemic lupus erythematosus. *J Clin Immunol* 32(5):1019-1025.
35. Christoffersen C, et al. (2011) Endothelium-protective sphingosine-1-phosphate provided by HDL-associated apolipoprotein M. *Proc Natl Acad Sci USA* 108(23):9613-9618.
36. Christoffersen C & Nielsen L B (2012) Apolipoprotein M—a new biomarker in sepsis. *Crit Care* 16(3):126.
37. Dolgin E (2012) Trial failure prompts soul-searching for critical-care specialists. *Nat Med* 18(7):1000.
38. Annane D (2011) Corticosteroids for severe sepsis: an evidence-based guide for physicians. *Ann Intensive Care* 1(1):7.
39. Annane D (2008) Adrenal insufficiency in sepsis. *Curr Pharm Des* 14(19):1882-1886.
40. Pan S, et al. (2006) A monoselective sphingosine-1-phosphate receptor-1 agonist prevents allograft rejection in a stringent rat heart transplantation model. *Chem Biol* 13(11):1227-1234.
41. Zhang Z Y, et al. (2009) AUY954, a selective S1P(1) modulator, prevents experimental autoimmune neuritis. *J Neuroimmunol* 216(1-2):59-65.
42. Bajwa A, et al. (2012) Dendritic cell sphingosine 1-phosphate receptor-3 regulates Th1-Th2 polarity in kidney ischemia-reperfusion injury. *J Immunol* 189(5):2584-2596.
43. Rathinasamy A, Czeloth N, Pabst O, Forster R, & Bernhardt G (2010) The origin and maturity of dendritic cells determine the pattern of sphingosine 1-phosphate receptors expressed and required for efficient migration. *J Immunol* 185(7):4072-4081.
44. Kuehn B M (2013) Guideline promotes early, aggressive sepsis treatment to boost survival. *JAMA* 309(10):969-970.
45. Oliveira C F, et al. (2008) Time- and fluid-sensitive resuscitation for hemodynamic support of children in septic shock: barriers to the implementation of the American College of Critical Care Medicine/Pediatric Advanced Life Support Guidelines in a pediatric intensive care unit in a developing world. *Pediatr Emerg Care* 24(12):810-815.
46. Schurer S C, et al. (2008) Ligand-binding pocket shape differences between sphingosine 1-phosphate (S1P) receptors S1P1 and S1P3 determine efficiency of chemical probe identification by ultrahigh-throughput screening. *ACS chemical biology* 3(8):486-498.
47. Gonzalez-Cabrera P J, et al. (2012) S1P(1) receptor modulation with cyclical recovery from lymphopenia ameliorates mouse model of multiple sclerosis. *Molecular pharmacology* 81(2):166-174.
48. Sanna M G, et al. (2006) Enhancement of capillary leakage and restoration of lymphocyte egress by a chiral S1P1 antagonist in vivo. *Nature chemical biology* 2(8): 434-441.
49. Clemens J J, Davis M D, Lynch K R, & Macdonald T L (2005) Synthesis of 4(5)-phenylimidazole-based analogues of sphingosine-1-phosphate and FTY720: discovery of potent S1P1 receptor agonists. *Bioorganic & medicinal chemistry letters* 15(15):3568-3572.
50. Parrill A L, et al. (2000) Identification of Edg1 receptor residues that recognize sphingosine 1-phosphate. *The Journal of biological chemistry* 275(50):39379-39384.

Examples

Compounds are presented that selectively modify the action(s) of Sphingosine-1-Phosphate Receptors (S1P-R's) and therefore have potential for the treatment(s) of diseases or disorders of the cardiovascular and/or pulmonary systems. These diseases/disorders include but are not limited to:

Cardiovascular disease, hypertension (including malignant hypertension), angina, myocardial infarction, cardiac arrhythmias, congestive heart failure, Coronary heart disease, atherosclerosis, angina pectoris, dysrhythmias, cardiomyothopy (including hypertropic cardiomyothopy), heart failure, cardiac arrest, bronchitis, asthma, chronic obstructive pulmonary disease, cystic fibrosis, croup, emphysema, pleurisy, pulmonary fibrosis, pneumonia, pulmonary embolus, pulmonary hypertension, mesothelioma, Ventricular Conduction abnormalities, Complete Heart Block Adult Respiratory Distress Syndrome and Sepsis Syndrome, Idiopathic Pulmonary fibrosis, scleroderma, systemic sclerosis, retroperitoneal fibrosis, prevention of keloid formation, cirrhosis.

Compounds of the invention below have been shown to demonstrate activity as antagonist/agonist of one or more of the known sphingosine-1-phosphate receptors with $IC_{50}$/$EC_{50}$ values lower than 10 micromolar. Representative examples are given in Tables 2 and 3, below.

TABLE 2
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52274 IB | 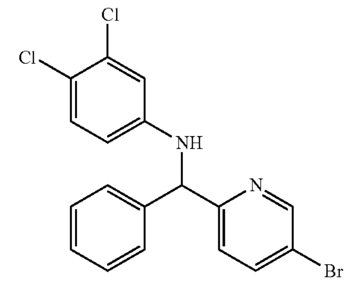 [SMILES: Clc1ccc(NC(c2ccccc2)c2ccc(Br)cn2)cc1Cl] | — | — | 0.772 | 44.0 | — |
| 52276 IB | 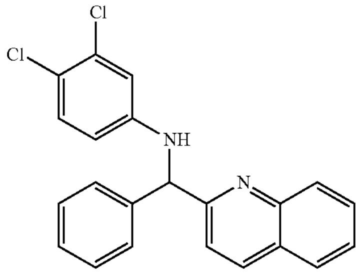 [SMILES: Clc1ccc(NC(c2ccccc2)c2ccc3ccccc3n2)cc1Cl] | — | — | 17.2 | >50 | — |
| 52296 IB | 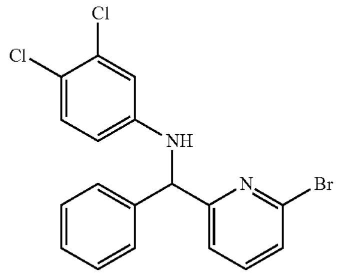 [SMILES: Clc1ccc(NC(c2ccccc2)c2cccc(Br)n2)cc1Cl] | — | 39.7 | 10.3 | 35.4 | — |
| 52297 IB | 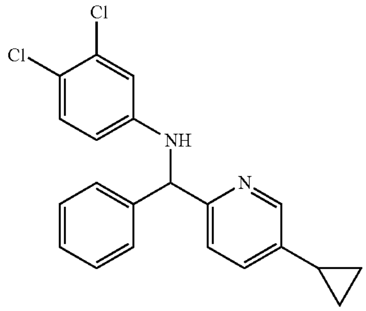 [SMILES: Clc1ccc(NC(c2ccccc2)c2ccc(C3CC3)cn2)cc1Cl] | — | >50 | 1.9 | >50 | — |
| 52298 IB | 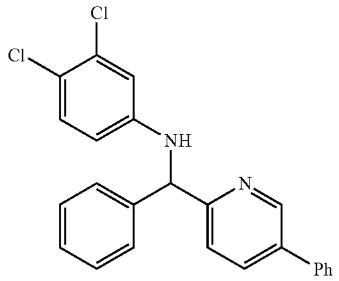 [SMILES: Clc1ccc(NC(c2ccccc2)c2ccc(-c3ccccc3)cn2)cc1Cl] | — | >50 | >50 | >50 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52299 IB | 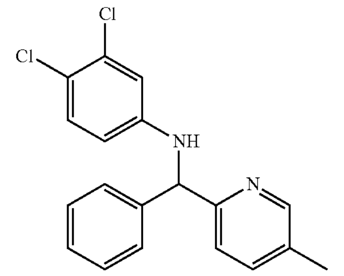 [SMILES: Cc1ccc(C(Nc2ccc(Cl)c(Cl)c2)c2ccccc2)nc1] | — | 29.7 | 2.2 | 39.1 | — |
| 52294 IB | 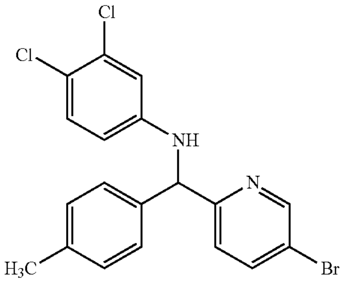 [SMILES: Cc1ccc(C(Nc2ccc(Cl)c(Cl)c2)c2ccc(Br)cn2)cc1] | — | >50 | 1.6 | 5.7 | — |
| 52331 IB | 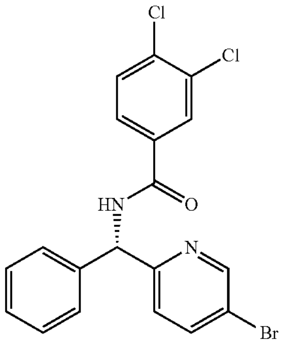 [SMILES: O=C(N[C@@H](c1ccccc1)c1ccc(Br)cn1)c1ccc(Cl)c(Cl)c1] | — | 14.7 | 0.667 | 21.3 | — |
| 52332 IB | 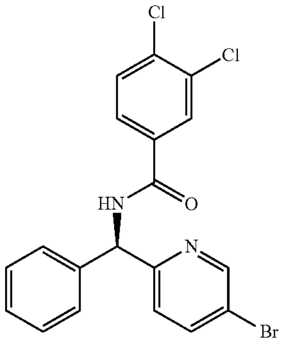 [SMILES: O=C(N[C@H](c1ccccc1)c1ccc(Br)cn1)c1ccc(Cl)c(Cl)c1] | — | 15.9 | 1.5 | 17.9 | — |
| 52351 IB | 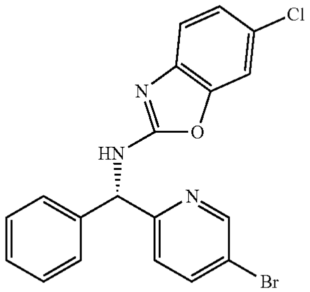 [SMILES: Clc1ccc2nc(N[C@@H](c3ccccc3)c3ccc(Br)cn3)oc2c1] | — | >50 | 4.2 | >50 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52355 IB | 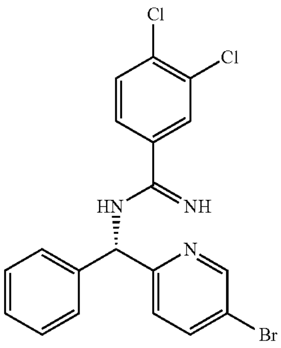 [SMILES: N=C(N[C@@H](c1ccccc1)c1ccc(Br)cn1)c1ccc(Cl)c(Cl)c1] | — | >50 | 26 | >50 | — |
| 52356 IB | 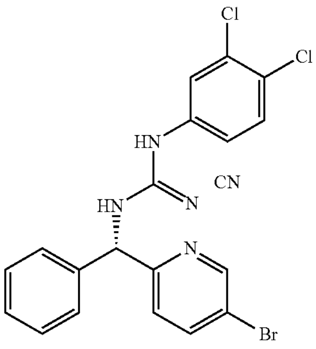 | — | >50 | 9.8 | >50 | — |
| 52394 IB | 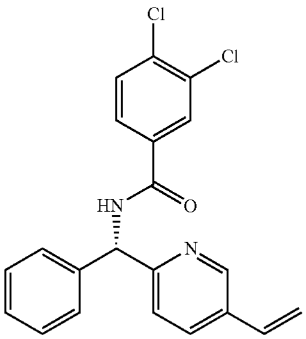 [SMILES: C=Cc1ccc([C@@H](NC(=O)c2ccc(Cl)c(Cl)c2)c2ccccc2)nc1] | — | 1.0 | 0.246 | 0.873 | — |
| 52396 IB | 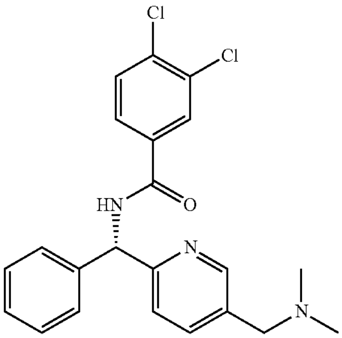 [SMILES: CN(C)Cc1ccc([C@@H](NC(=O)c2ccc(Cl)c(Cl)c2)c2ccccc2)nc1] | — | 44.3 | 30.8 | >50 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52397 IB | 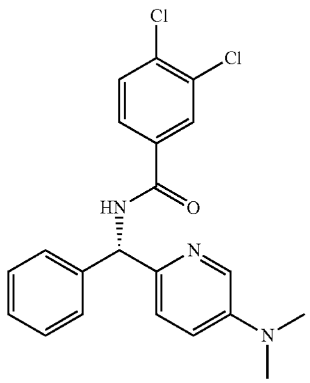 [SMILES: CN(C)c1ccc([C@@H](NC(=O)c2ccc(Cl)c(Cl)c2)c2ccccc2)nc1] | — | 30.8 | 8.8 | 21.6 | — |
| 52398 IB | 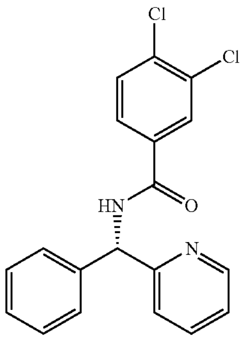 [SMILES: O=C(N[C@@H](c1ccccc1)c1ccccn1)c1ccc(Cl)c(Cl)c1] | — | 21.7 | 3.1 | 12.7 | — |
| 52399 IB | 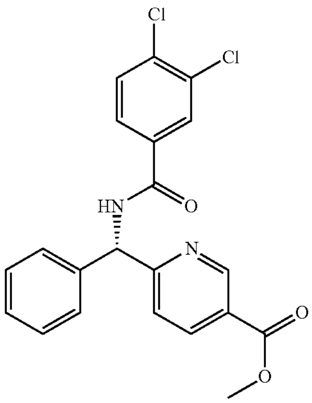 [SMILES: COC(=O)c1ccc([C@@H](NC(=O)c2ccc(Cl)c(Cl)c2)c2ccccc2)nc1] | — | >50 | 8.4 | 28.2 | — |
| 52433 IB | 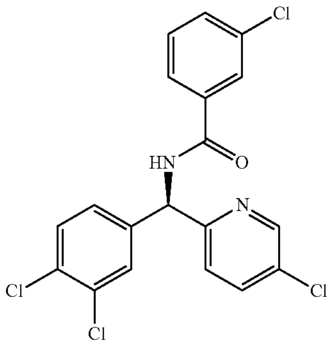 [SMILES: O=C(N[C@H](c1ccc(Cl)c(Cl)c1)c1ccc(Cl)cn1)c1cccc(Cl)c1] | — | >50 | 0.649 | 15.1 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52434 IB | 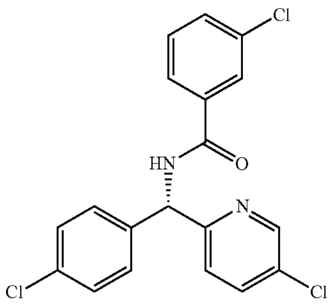 [SMILES: O=C(N[C@@H](c1ccc(Cl)cc1)c1ccc(Cl)cn1)c1cccc(Cl)c1] | — | 29.4 | 0.317 | 9.9 | — |
| 52435 IB | 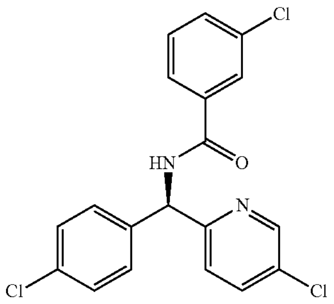 [SMILES: O=C(N[C@H](c1ccc(Cl)cc1)c1ccc(Cl)cn1)c1cccc(Cl)c1] | — | 32.2 | 1.6 | 8.2 | — |
| 52442 IB | 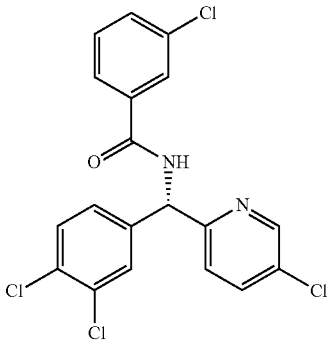 [SMILES: O=C(N[C@@H](c1ccc(Cl)c(Cl)c1)c1ccc(Cl)cn1)c1cccc(Cl)c1] | — | >50 | 0.07 | 9.3 | — |
| 52458 IB | 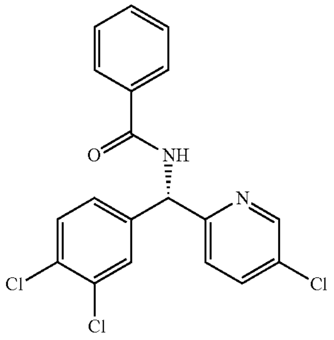 [SMILES: O=C(N[C@@H](c1ccc(Cl)c(Cl)c1)c1ccc(Cl)cn1)c1ccccc1] | — | 38.3 | 0.943 | 9.8 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52459 IB | 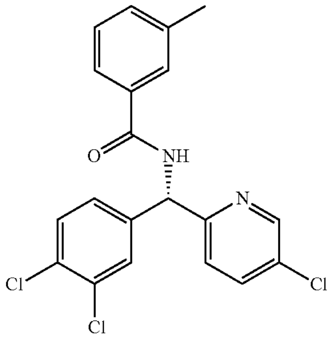 [SMILES: Cc1cccc(C(=O)N[C@@H](c2ccc(Cl)c(Cl)c2)c2ccc(Cl)cn2)c1] | — | 24.6 | 0.236 | 8.2 | — |
| 52460 IB | 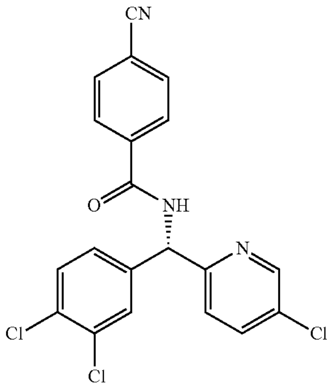 [SMILES: N#Cc1ccc(C(=O)N[C@@H](c2ccc(Cl)c(Cl)c2)c2ccc(Cl)cn2)cc1] | — | >50 | 0.09 | 8.8 | — |
| 52464 IB | 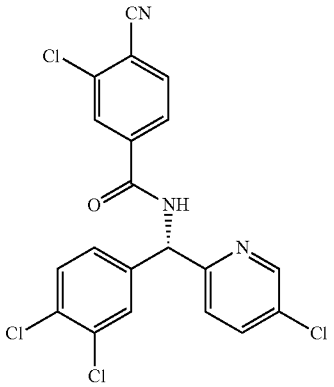 [SMILES: N#Cc1ccc(C(=O)N[C@@H](c2ccc(Cl)c(Cl)c2)c2ccc(Cl)cn2)cc1Cl] | — | >50 | 0.022 | 8.3 | — |
| 52474 IB | 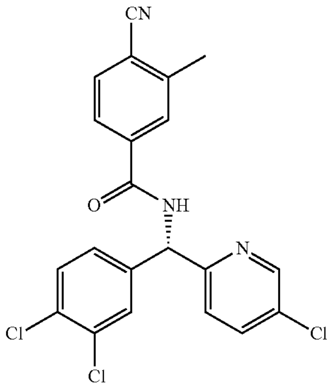 [SMILES: Cc1cc(C(=O)N[C@@H](c2ccc(Cl)c(Cl)c2)c2ccc(Cl)cn2)ccc1C#N] | 0.227 | >50 | 0.014 | >50 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52475 IB | 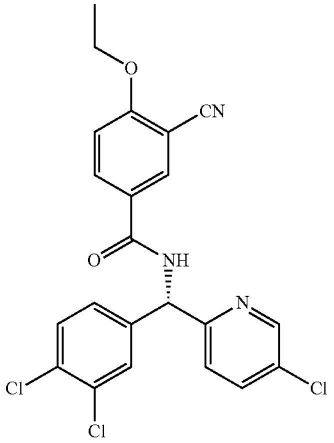 [SMILES: CCOc1ccc(C(=O)N[C@@H](c2ccc(Cl)c(Cl)c2)c2ccc(Cl)cn2)cc1C#N] | 37.2 | 37.3 | 0.082 | >50 | — |
| 52476 IB | 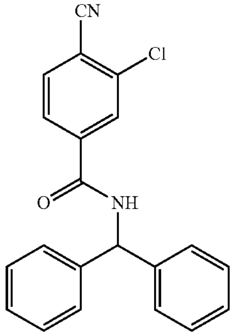 [SMILES: N#Cc1ccc(C(=O)NC(c2ccccc2)c2ccccc2)cc1Cl] | >28 | >50 | 0.906 | >50 | — |
| 52483 IB | 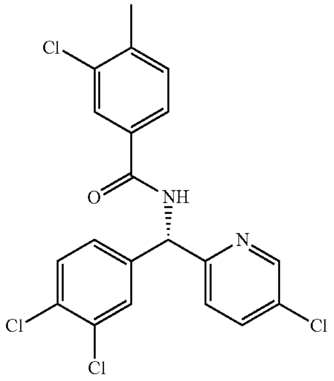 [SMILES: Cc1ccc(C(=O)N[C@@H](c2ccc(Cl)c(Cl)c2)c2ccc(Cl)cn2)cc1Cl] | 0.91 | >50 | 0.097 | 6.5 | — |
| 52484 IB | 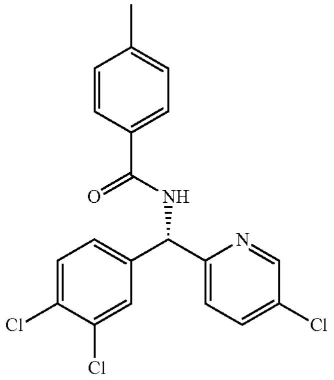 [SMILES: Cc1ccc(C(=O)N[C@@H](c2ccc(Cl)c(Cl)c2)c2ccc(Cl)cn2)cc1] | 9.3 | 43.8 | 0.826 | 11.5 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52486 IB | 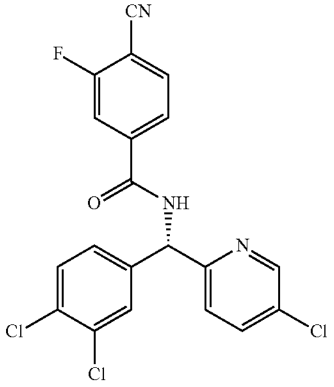 [SMILES: N#Cc1ccc(C(=O)N[C@@H](c2ccc(Cl)c(Cl)c2)c2ccc(Cl)cn2)cc1F] | 1.3 | >50 | 0.028 | >50 | — |
| 52487 IB | 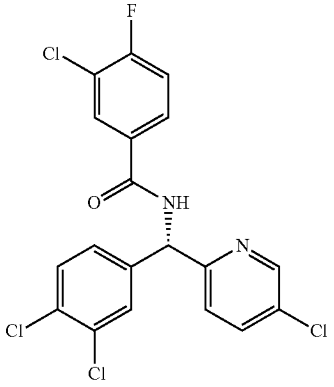 [SMILES: O=C(N[C@@H](c1ccc(Cl)c(Cl)c1)c1ccc(Cl)cn1)c1ccc(F)c(Cl)c1] | 0.347 | >50 | 0.113 | 17.5 | — |
| 52488 IB | 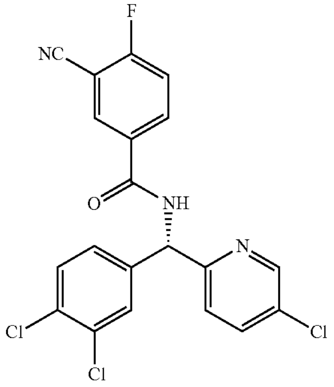 [SMILES: N#Cc1cc(C(=O)N[C@@H](c2ccc(Cl)c(Cl)c2)c2ccc(Cl)cn2)ccc1F] | 0.197 | >50 | 0.079 | 5.6 | — |
| 52489 IC | 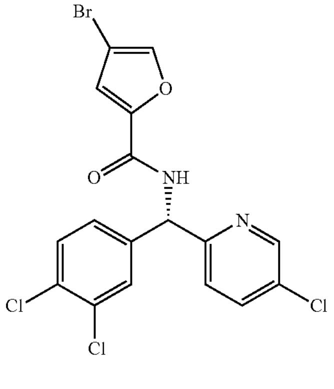 [SMILES: O=C(N[C@@H](c1ccc(Cl)c(Cl)c1)c1ccc(Cl)cn1)c1cc(Br)co1] | 2.7 | >50 | 0.567 | 26.6 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52491 IB | 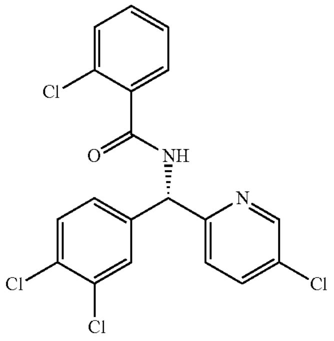 [SMILES: O=C(N[C@@H](c1ccc(Cl)c(Cl)c1)c1ccc(Cl)cn1)c1ccccc1Cl] | >28 | >50 | 3.9 | 30.6 | — |
| 52492 IB | 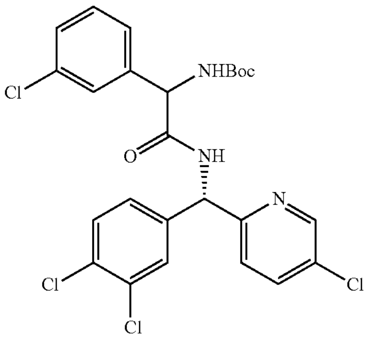 [SMILES: CC(C)(C)OC(=O)NC(C(=O)N[C@@H](c1ccc(Cl)c(Cl)c1)c1ccc(Cl)cn1)c1cccc(Cl)c1] | >28 | >50 | 5.1 | >50 | — |
| 52495 IB | 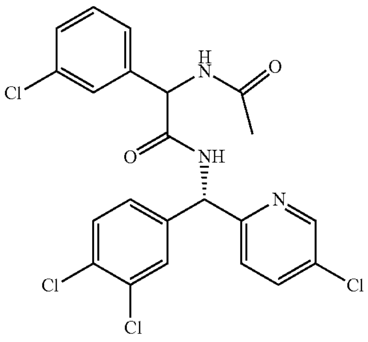 [SMILES: CC(=O)NC(C(=O)N[C@@H](c1ccc(Cl)c(Cl)c1)c1ccc(Cl)cn1)c1cccc(Cl)c1] | >28 | 15.6 | 9.8 | >50 | — |
| 52504 IB | 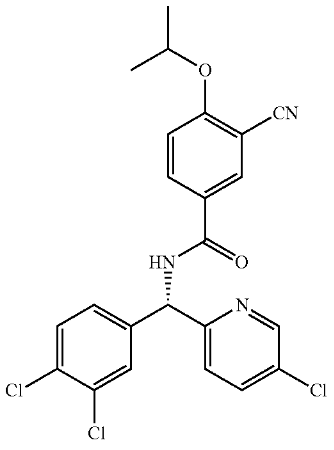 [SMILES: CC(C)Oc1ccc(C(=O)N[C@@H](c2ccc(Cl)c(Cl)c2)c2ccc(Cl)cn2)cc1C#N] | 2.8 | — | 0.152 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52505 IB | 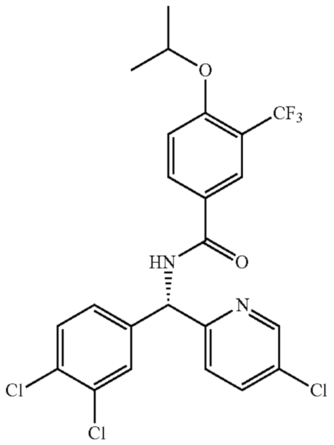 [SMILES: CC(C)Oc1ccc(C(=O)N[C@@H](c2ccc(Cl)c(Cl)c2)c2ccc(Cl)cn2)cc1C(F)(F)F] | >50 | — | 0.576 | — | — |
| 52506 IB | 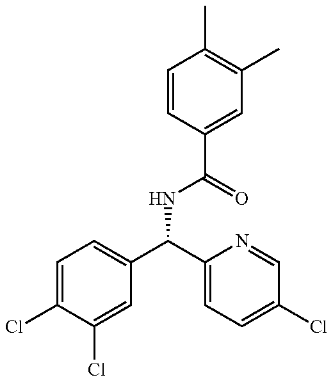 [SMILES: Cc1ccc(C(=O)N[C@@H](c2ccc(Cl)c(Cl)c2)c2ccc(Cl)cn2)cc1C] | 1.5 | — | 0.172 | — | — |
| 52507 IB | 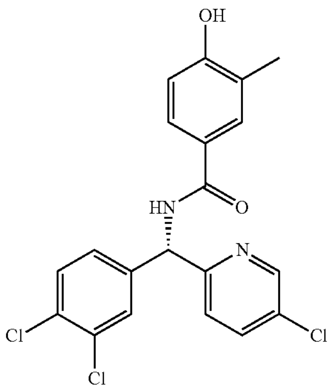 [SMILES: Cc1cc(C(=O)N[C@@H](c2ccc(Cl)c(Cl)c2)c2ccc(Cl)cn2)ccc1O] | 2.2 | — | 0.112 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52508 IB | 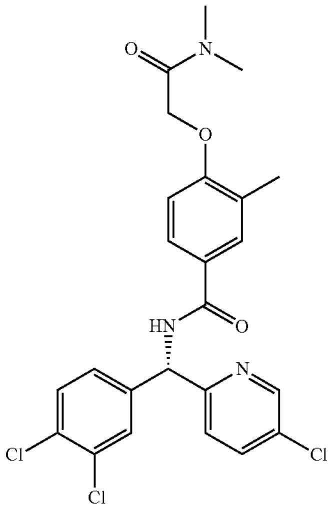 [SMILES: Cc1cc(C(=O)N[C@@H](c2ccc(Cl)c(Cl)c2)c2ccc(Cl)cn2)ccc1OCC(=O)N(C)C] | >50 | — | 0.796 | — | — |
| 52509 IB | 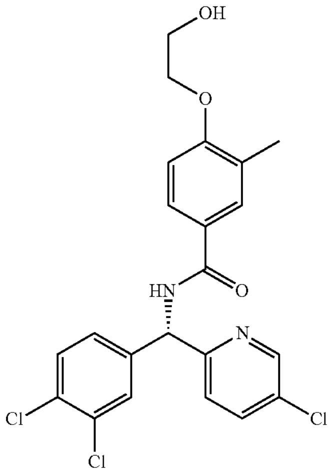 [SMILES: Cc1cc(C(=O)N[C@@H](c2ccc(Cl)c(Cl)c2)c2ccc(Cl)cn2)ccc1OCCO] | >50 | — | 2.5 | — | — |
| 52510 IB | 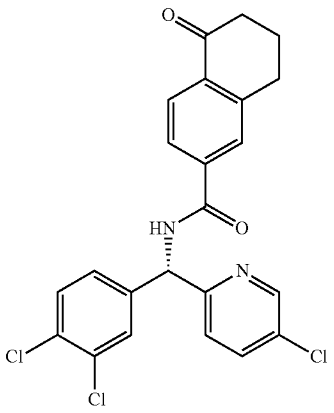 [SMILES: O=C(N[C@@H](c1ccc(Cl)c(Cl)c1)c1ccc(Cl)cn1)c1ccc2c(c1)CCCC2=O] | 0.899 | — | 0.213 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52511 IC | 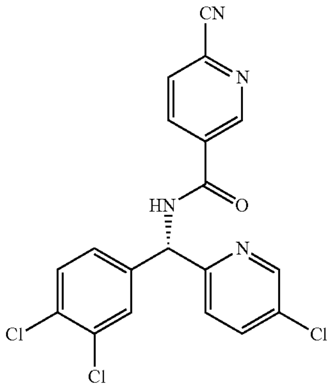 [SMILES: N#Cc1ccc(C(=O)N[C@@H](c2ccc(Cl)c(Cl)c2)c2ccc(Cl)cn2)cn1] | 6.4 | — | 0.308 | — | — |
| 52512 IB | 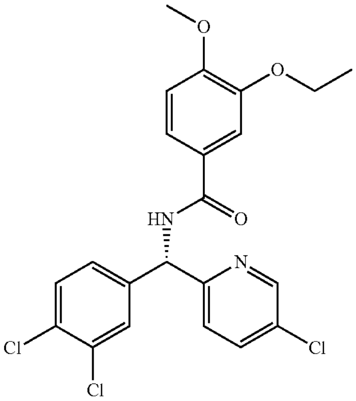 [SMILES: CCOc1cc(C(=O)N[C@@H](c2ccc(Cl)c(Cl)c2)c2ccc(Cl)cn2)ccc1OC] | 25.5 | — | 4.1 | — | — |
| 52514 IB | 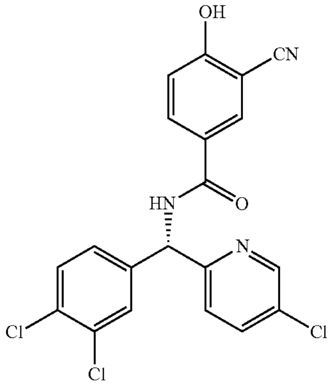 [SMILES: N#Cc1cc(C(=O)N[C@@H](c2ccc(Cl)c(Cl)c2)c2ccc(Cl)cn2)ccc1O] | >50 | — | 29.6 | — | — |
| 52520 IB | 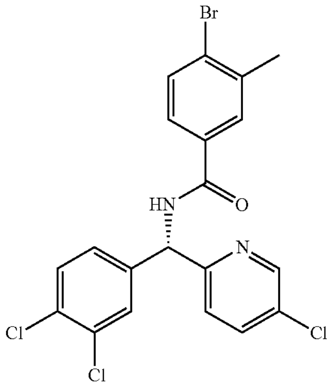 [SMILES: Cc1cc(C(=O)N[C@@H](c2ccc(Cl)c(Cl)c2)c2ccc(Cl)cn2)ccc1Br] | 0.22 | >50 | 0.035 | 16.2 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52522 IB | 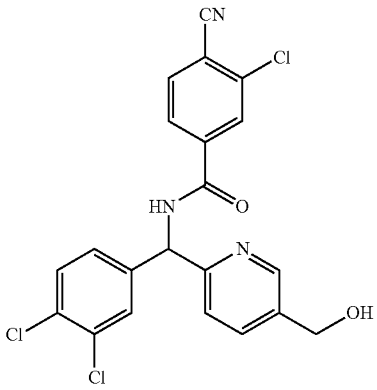 [SMILES: N#Cc1ccc(C(=O)NC(c2ccc(Cl)c(Cl)c2)c2ccc(CO)cn2)cc1Cl] | 3.6 | — | 0.39 | — | — |
| 52523 IB | 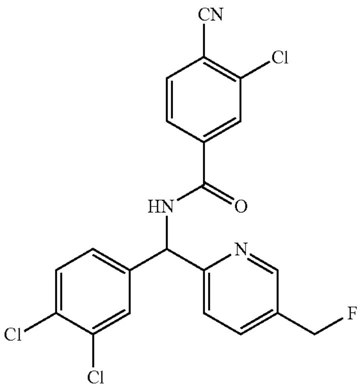 [SMILES: N#Cc1ccc(C(=O)NC(c2ccc(Cl)c(Cl)c2)c2ccc(CF)cn2)cc1Cl] | 7.3 | — | 0.168 | — | — |
| 52524 IB | 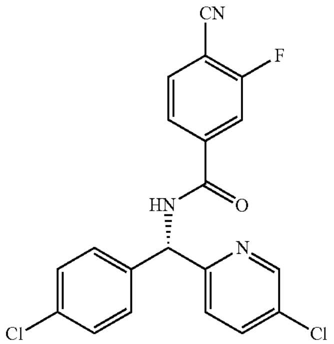 [SMILES: N#Cc1ccc(C(=O)N[C@@H](c2ccc(Cl)cc2)c2ccc(Cl)cn2)cc1F] | >50 | — | 0.065 | — | — |
| 52525 IB | 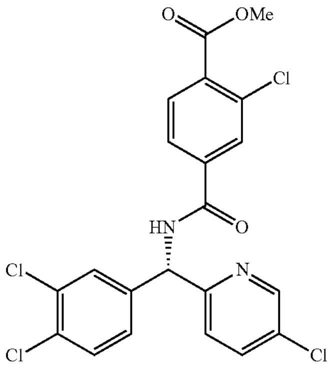 [SMILES: COC(=O)c1ccc(C(=O)N[C@@H](c2ccc(Cl)c(Cl)c2)c2ccc(Cl)cn2)cc1Cl] | 2.0 | — | 0.076 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52526 IB | 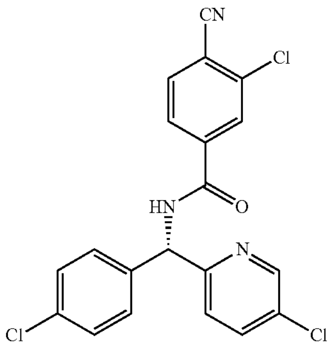 [SMILES: N#Cc1ccc(C(=O)N[C@@H](c2ccc(Cl)cc2)c2ccc(Cl)cn2)cc1Cl] | 1.8 | 6.7 | 0.027 | >50 | — |
| 52527 IB | 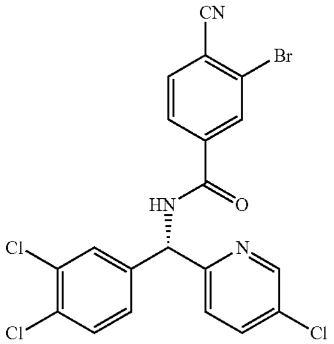 [SMILES: N#Cc1ccc(C(=O)N[C@@H](c2ccc(Cl)c(Cl)c2)c2ccc(Cl)cn2)cc1Br] | 0.204 | — | 0.032 | — | — |
| 52528 IB | 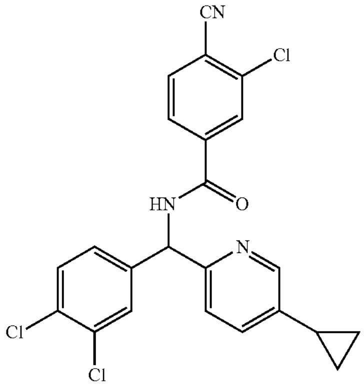 [SMILES: N#Cc1ccc(C(=O)NC(c2ccc(Cl)c(Cl)c2)c2ccc(C3CC3)cn2)cc1Cl] | 1.4 | — | 0.063 | — | — |
| 52529 IB | 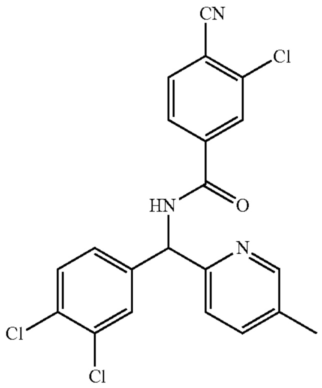 [SMILES: Cc1ccc(C(NC(=O)c2ccc(C#N)c(Cl)c2)c2ccc(Cl)c(Cl)c2)nc1] | 1.4 | 44.9 | 0.041 | 18.8 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52530 IB | 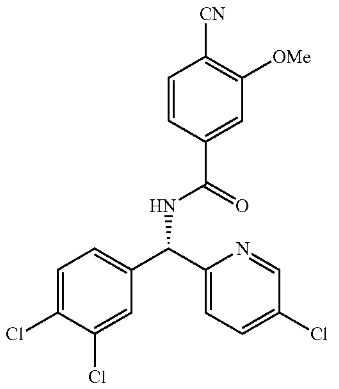 [SMILES: COc1cc(C(=O)N[C@@H](c2ccc(Cl)c(Cl)c2)c2ccc(Cl)cn2)ccc1C#N] | 0.333 | — | 0.040 | — | — |
| 52531 IC | 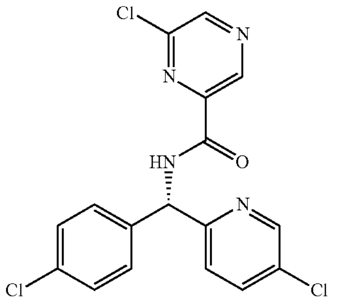 [SMILES: O=C(N[C@@H](c1ccc(Cl)cc1)c1ccc(Cl)cn1)c1cncc(Cl)n1] | >50 | — | 2.7 | — | — |
| 52543 IB | 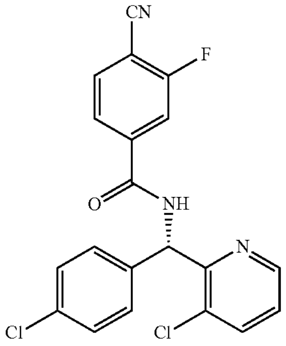 [SMILES: N#Cc1ccc(C(=O)N[C@@H](c2ccc(Cl)cc2)c2ncccc2Cl)cc1F] | 17.6 | — | 0.405 | — | — |
| 52544 IB | 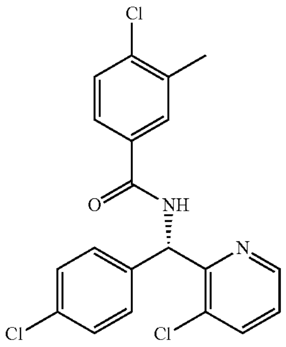 | >28 | — | 9.1 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52545 IB | 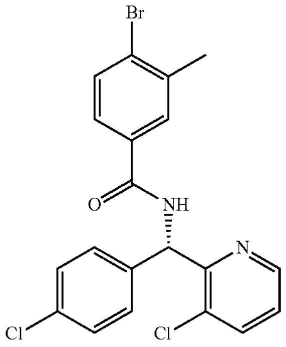 [SMILES: Cc1cc(C(=O)N[C@@H](c2ccc(Cl)cc2)c2ncccc2Cl)ccc1Br] | 3.5 | — | 0.792 | — | — |
| 52547 IB | 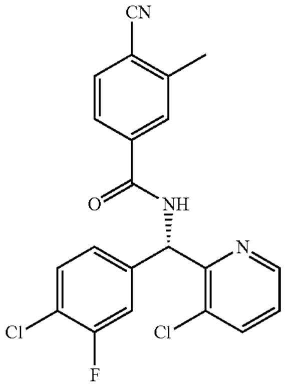 [SMILES: Cc1cc(C(=O)N[C@@H](c2ccc(Cl)c(F)c2)c2ncccc2Cl)ccc1C#N] | 1.9 | — | 0.249 | — | — |
| 52548 IB | 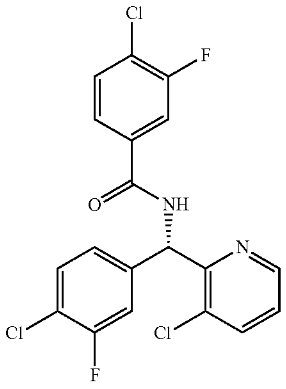 [SMILES: O=C(N[C@@H](c1ccc(Cl)c(F)c1)c1ncccc1Cl)c1ccc(Cl)c(F)c1] | 3.2 | — | 0.13 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52551 IB | 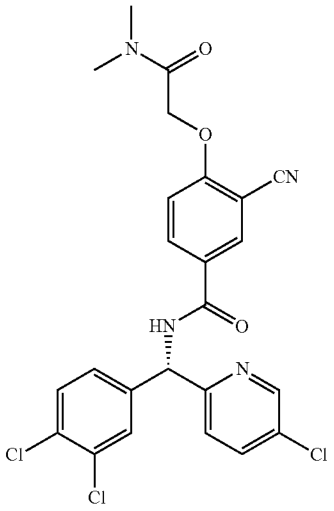 [SMILES: CN(C)C(=O)COc1ccc(C(=O)N[C@@H](c2ccc(Cl)c(Cl)c2)c2ccc(Cl)cn2)cc1C#N] | >28 | — | 0.964 | — | — |
| 52552 IB | 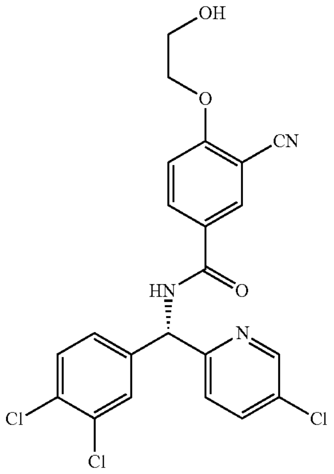 [SMILES: N#Cc1cc(C(=O)N[C@@H](c2ccc(Cl)c(Cl)c2)c2ccc(Cl)cn2)ccc1OCCO] | 10.2 | — | 1.0 | — | — |
| 52553 IB | 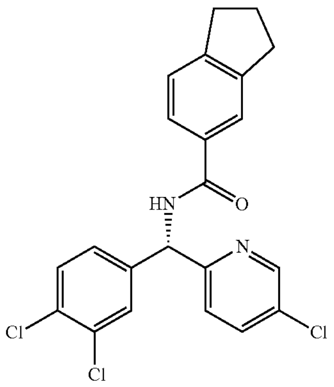 [SMILES: O=C(N[C@@H](c1ccc(Cl)c(Cl)c1)c1ccc(Cl)cn1)c1ccc2c(c1)CCC2] | 0.574 | — | 0.147 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52555 IB | 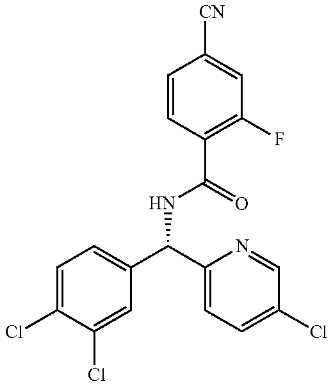 [SMILES: N#Cc1ccc(C(=O)N[C@@H](c2ccc(Cl)c(Cl)c2)c2ccc(Cl)cn2)c(F)c1] | 7.1 | >50 | 0.057 | 8.5 | — |
| 52556 IB | 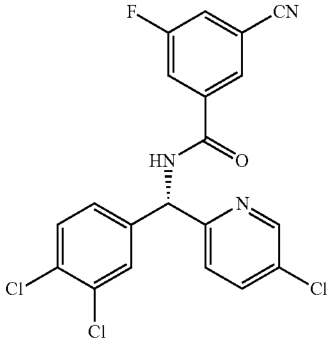 [SMILES: N#Cc1cc(F)cc(C(=O)N[C@@H](c2ccc(Cl)c(Cl)c2)c2ccc(Cl)cn2)c1] | 0.285 | — | 0.061 | — | — |
| 52558 IB | 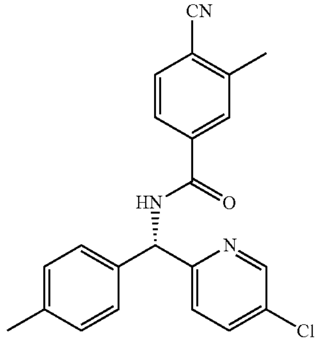 | 1.4 | — | 0.057 | — | — |
| 52559 IB | 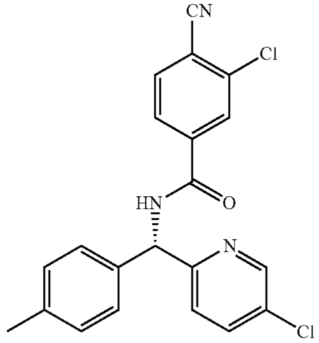 | 0.604 | 44.7 | 0.016 | 14.8 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52560 IB | 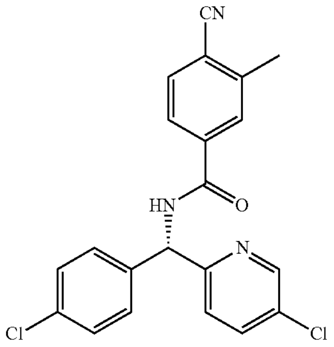 [SMILES: Cc1cc(C(=O)N[C@@H](c2ccc(Cl)cc2)c2ccc(Cl)cn2)ccc1C#N] | 2.3 | 19.9 | 0.038 | 22.1 | — |
| 52562 IB | 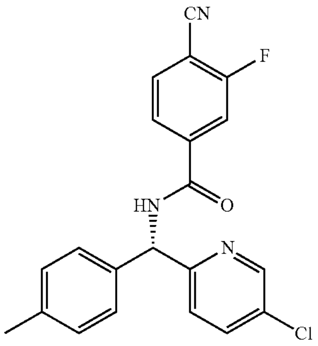 | 5.3 | >50 | 0.042 | 20.9 | — |
| 52563 IB | 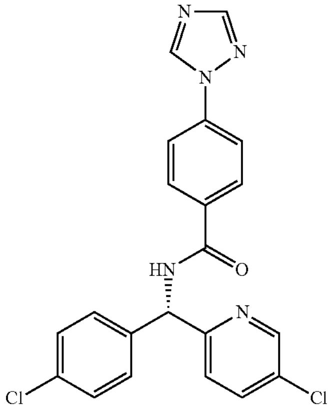 [SMILES: O=C(N[C@@H](c1ccc(Cl)cc1)c1ccc(Cl)cn1)c1ccc(-n2cncn2)cc1] | 17.2 | — | 0.114 | — | — |
| 52564 IB | 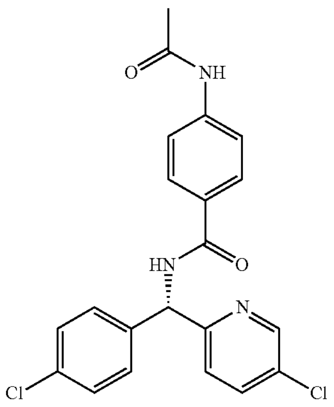 [SMILES: CC(=O)Nc1ccc(C(=O)N[C@@H](c2ccc(Cl)cc2)c2ccc(Cl)cn2)cc1] | >28 | — | 3.7 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52566 IB | 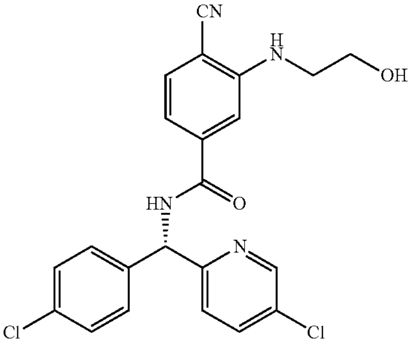 [SMILES: N#Cc1ccc(C(=O)N[C@@H](c2ccc(Cl)cc2)c2ccc(Cl)cn2)cc1NCCO] | >28 | — | 10.3 | | |
| 52568 IC | 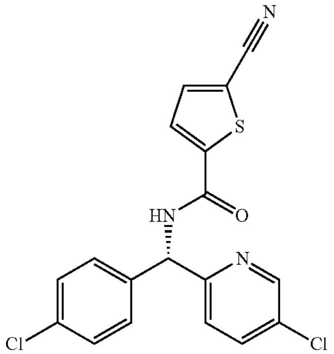 [SMILES: N#Cc1ccc(C(=O)N[C@@H](c2ccc(Cl)cc2)c2ccc(Cl)cn2)s1] | 6.3 | 14.1 | 0.052 | 10.3 | — |
| 52571 IB | 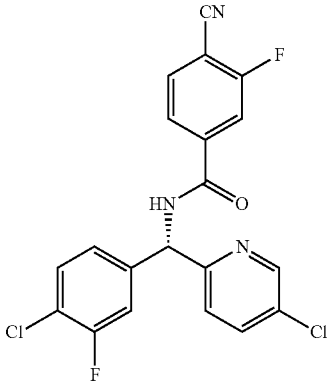 | 4.4 | >50 | 0.29 | 25.4 | — |
| 52572 IB | 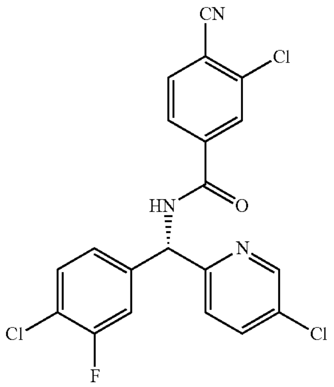 [SMILES: N#Cc1ccc(C(=O)N[C@@H](c2ccc(Cl)c(F)c2)c2ccc(Cl)cn2)cc1Cl] | 0.81 | 18.9 | 0.013 | 34.4 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52573 IB | 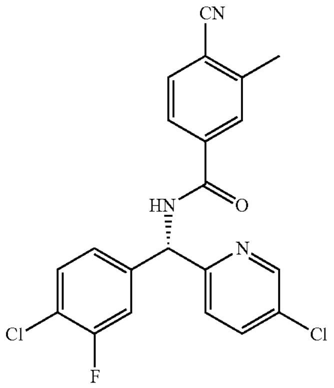 [SMILES: Cc1cc(C(=O)N[C@@H](c2ccc(Cl)c(F)c2)c2ccc(Cl)cn2)ccc1C#N] | 1.1 | 40.0 | 0.032 | 28.8 | — |
| 52574 IB | 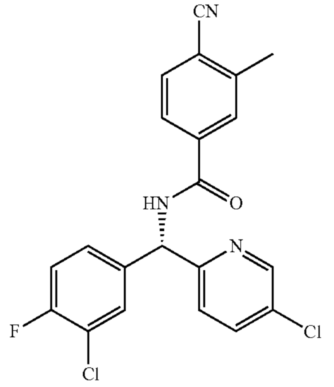 | 2.1 | — | 0.092 | — | — |
| 52575 IB | 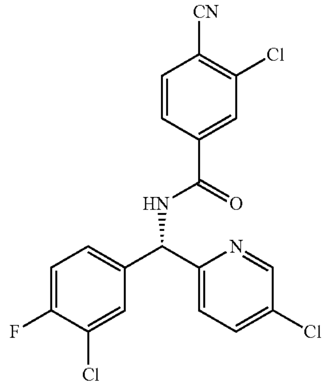 | 1.5 | 24.3 | 0.034 | 21.4 | — |
| 52576 IB | 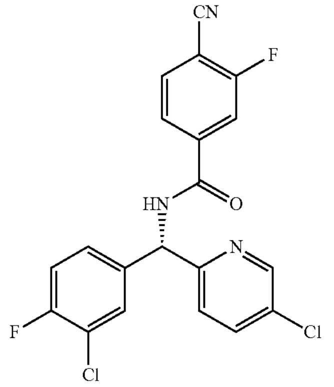 | 7.8 | — | 0.077 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52577 IB | 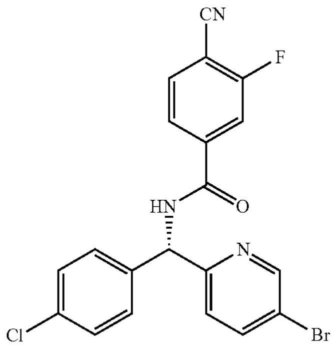 [SMILES: N#Cc1ccc(C(=O)N[C@@H](c2ccc(Cl)cc2)c2ccc(Br)cn2)cc1F] | >28 | >50 | 0.026 | >50 | — |
| 52578 IB | 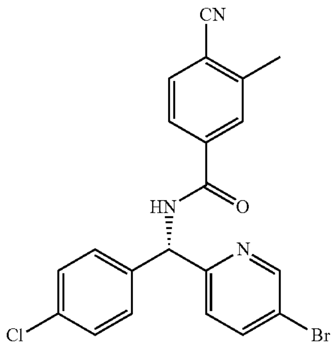 [SMILES: Cc1cc(C(=O)N[C@@H](c2ccc(Cl)cc2)c2ccc(Br)cn2)ccc1C#N] | 1.7 | 32.6 | 0.029 | 13.6 | — |
| 52579 IB | 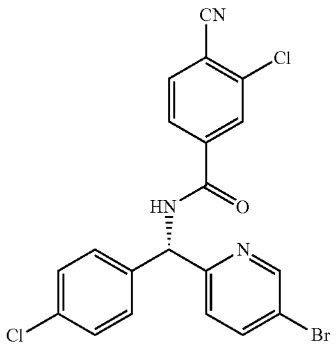 [SMILES: N#Cc1ccc(C(=O)N[C@@H](c2ccc(Cl)cc2)c2ccc(Br)cn2)cc1Cl] | 1.1 | 44.8 | 0.016 | >50 | — |
| 52580 IB | 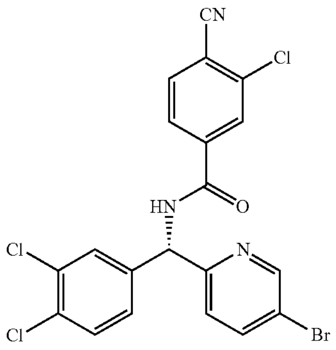 [SMILES: N#Cc1ccc(C(=O)N[C@@H](c2ccc(Cl)c(Cl)c2)c2ccc(Br)cn2)cc1Cl] | 0.141 | >50 | 0.007 | 24.8 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52581 IB | 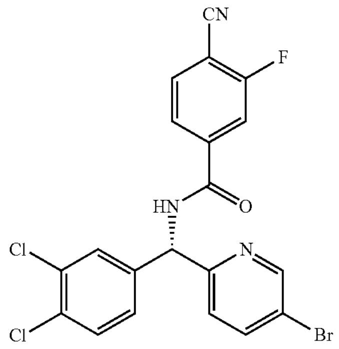 [SMILES: N#Cc1ccc(C(=O)N[C@@H](c2ccc(Cl)c(Cl)c2)c2ccc(Br)cn2)cc1F] | 0.566 | >50 | 0.009 | 14.1 | — |
| 52582 IB | 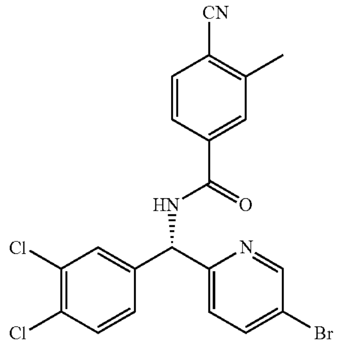 [SMILES: Cc1cc(C(=O)N[C@@H](c2ccc(Cl)c(Cl)c2)c2ccc(Br)cn2)ccc1C#N] | 0.308 | >50 | 0.018 | 27.6 | — |
| 52583 IB | 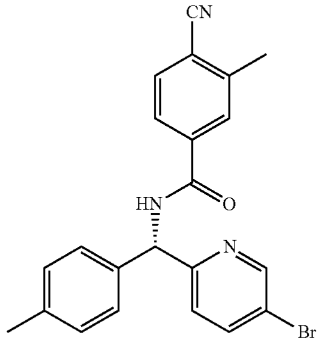 [SMILES: Cc1ccc([C@H](NC(=O)c2ccc(C#N)c(C)c2)c2ccc(Br)cn2)cc1] | 1.1 | >50 | 0.032 | 23.1 | — |
| 52584 IB | 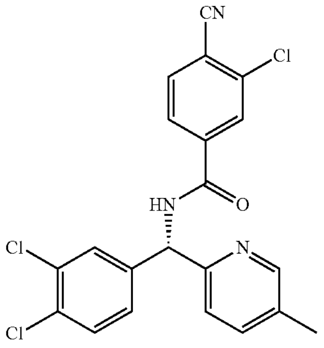 [SMILES: Cc1ccc([C@@H](NC(=O)c2ccc(C#N)c(Cl)c2)c2ccc(Cl)c(Cl)c2)nc1] | 0.505 | >50 | 0.02 | 38.9 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52585 IB | 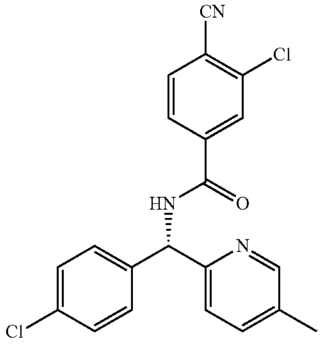 [SMILES: Cc1ccc([C@@H](NC(=O)c2ccc(C#N)c(Cl)c2)c2ccc(Cl)cc2)nc1] | 17.9 | — | 0.21 | — | — |
| 52586 IB | 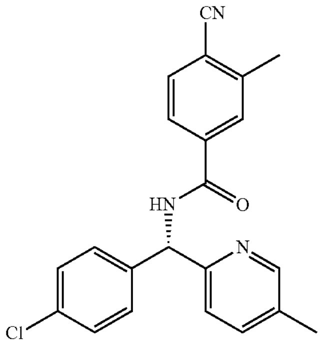 [SMILES: Cc1ccc([C@@H](NC(=O)c2ccc(C#N)c(C)c2)c2ccc(Cl)cc2)nc1] | 10 | — | 0.154 | — | — |
| 52587 IB | 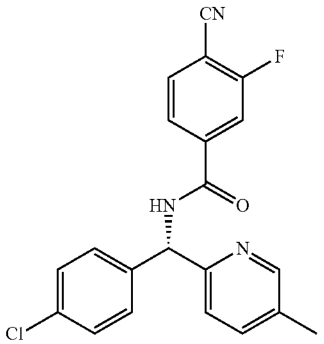 [SMILES: Cc1ccc([C@@H](NC(=O)c2ccc(C#N)c(F)c2)c2ccc(Cl)cc2)nc1] | 19 | — | 0.135 | — | — |
| 52589 IB | 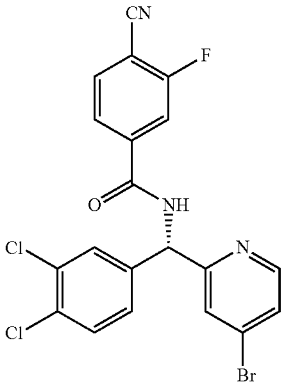 [SMILES: N#Cc1ccc(C(=O)N[C@@H](c2ccc(Cl)c(Cl)c2)c2cc(Br)ccn2)cc1F] | 31.8 | — | 1.1 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52590 IB | 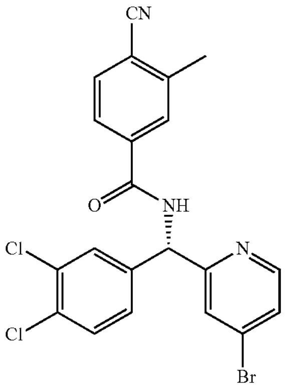 [SMILES: Cc1cc(C(=O)N[C@@H](c2ccc(Cl)c(Cl)c2)c2cc(Br)ccn2)ccc1C#N] | 2.1 | — | 1.0 | — | — |
| 52591 IB | 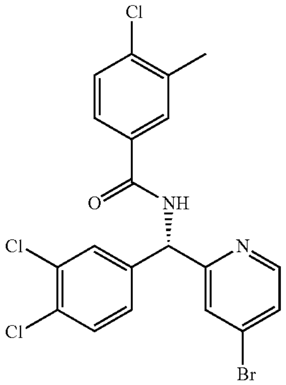 | 1.4 | — | 1.5 | — | — |
| 52592 IB | 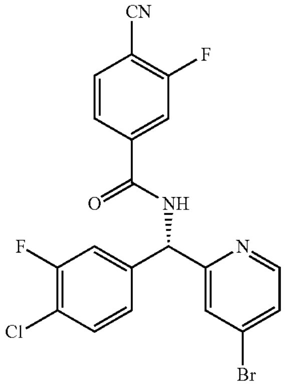 [SMILES: N#Cc1ccc(C(=O)N[C@@H](c2ccc(Cl)c(F)c2)c2cc(Br)ccn2)cc1F] | 10.6 | — | 0.863 | — | — |
| 52593 IB | 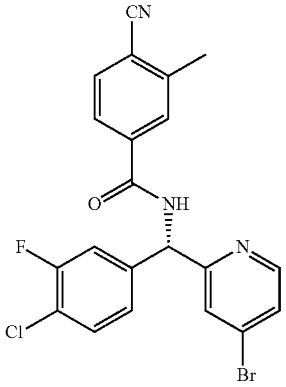 [SMILES: Cc1cc(C(=O)N[C@@H](c2ccc(Cl)c(F)c2)c2cc(Br)ccn2)ccc1C#N] | 9.3 | — | 1.8 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52594 IB | 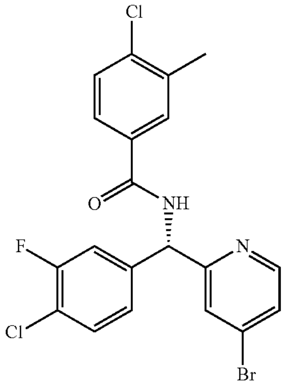 [SMILES: Cc1cc(C(=O)N[C@@H](c2ccc(Cl)c(F)c2)c2cc(Br)ccn2)ccc1Cl] | 2.5 | — | 1.3 | — | — |
| 52595 IB | 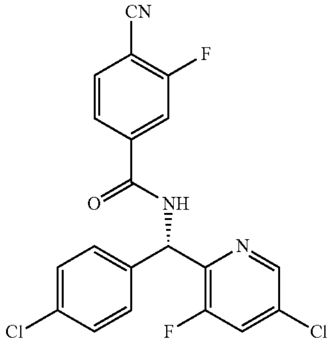 [SMILES: N#Cc1ccc(C(=O)N[C@@H](c2ccc(Cl)cc2)c2ncc(Cl)cc2F)cc1F] | 2.7 | 44.8 | 0.012 | 16.5 | — |
| 52596 IB | 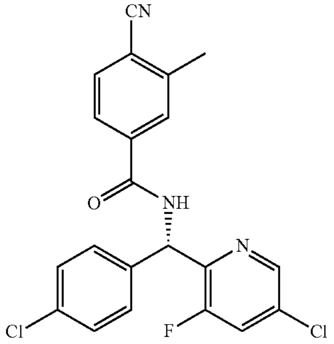 [SMILES: Cc1cc(C(=O)N[C@@H](c2ccc(Cl)cc2)c2ncc(Cl)cc2F)ccc1C#N] | 0.878 | 12.5 | 0.012 | >50 | — |
| 52597 IB | 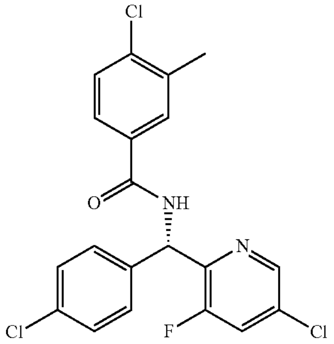 [SMILES: Cc1cc(C(=O)N[C@@H](c2ccc(Cl)cc2)c2ncc(Cl)cc2F)ccc1Cl] | 0.332 | 43.2 | 0.026 | >50 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52598 IB | 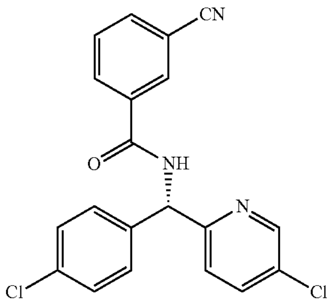 [SMILES: N#Cc1cccc(C(=O)N[C@@H](c2ccc(Cl)cc2)c2ccc(Cl)cn2)c1] | 5.1 | — | 0.350 | — | — |
| 52599 IB | 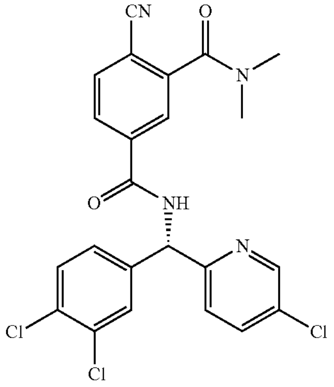 [SMILES: CN(C)C(=O)c1cc(C(=O)N[C@@H](c2ccc(Cl)c(Cl)c2)c2ccc(Cl)cn2)ccc1C#N] | 23.3 | — | 3.5 | — | — |
| 52600 IB | 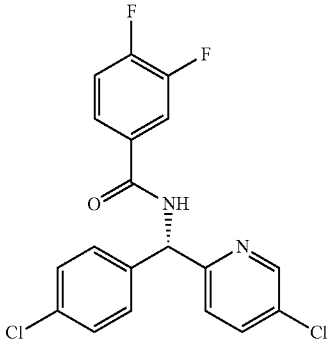 [SMILES: O=C(N[C@@H](c1ccc(Cl)cc1)c1ccc(Cl)cn1)c1ccc(F)c(F)c1] | 6.4 | — | 0.396 | — | — |
| 52601 IB | 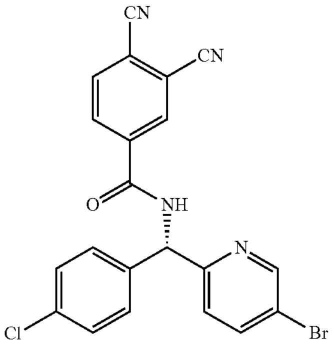 [SMILES: N#Cc1ccc(C(=O)N[C@@H](c2ccc(Cl)cc2)c2ccc(Br)cn2)cc1C#N] | 1.4 | 13.5 | 0.03 | 26.8 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52602 IB | 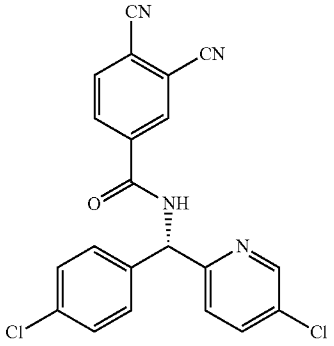 [SMILES: N#Cc1ccc(C(=O)N[C@@H](c2ccc(Cl)cc2)c2ccc(Cl)cn2)cc1C#N] | 3.2 | — | 0.073 | — | — |
| 52603 IB | 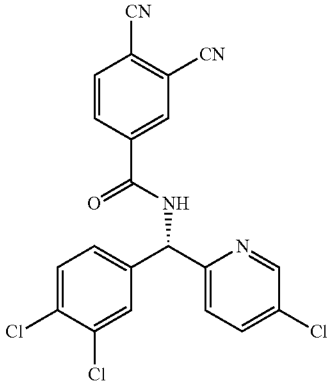 [SMILES: N#Cc1ccc(C(=O)N[C@@H](c2ccc(Cl)c(Cl)c2)c2ccc(Cl)cn2)cc1C#N] | 0.389 | — | 0.048 | — | — |
| 52604 IB | 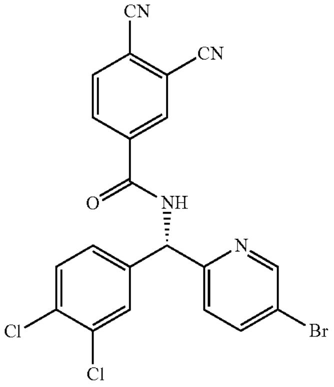 [SMILES: N#Cc1ccc(C(=O)N[C@@H](c2ccc(Cl)c(Cl)c2)c2ccc(Br)cn2)cc1C#N] | 0.099 | 35.4 | 0.010 | 23.5 | — |
| 52605 IB | 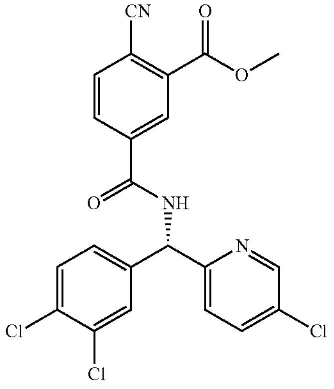 [SMILES: COC(=O)c1cc(C(=O)N[C@@H](c2ccc(Cl)c(Cl)c2)c2ccc(Cl)cn2)ccc1C#N] | 0.4 | — | 0.228 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52606 IB | 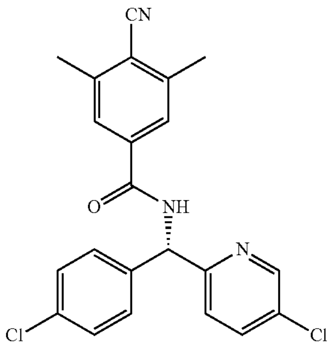 [SMILES: Cc1cc(C(=O)N[C@@H](c2ccc(Cl)cc2)c2ccc(Cl)cn2)cc(C)c1C#N] | >28 | 12.0 | 0.157 | >50 | — |
| 52607 IB | 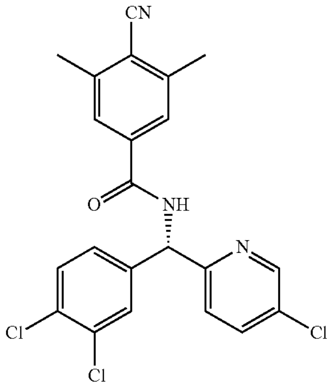 [SMILES: Cc1cc(C(=O)N[C@@H](c2ccc(Cl)c(Cl)c2)c2ccc(Cl)cn2)cc(C)c1C#N] | 0.452 | 12.0 | 0.021 | >50 | — |
| 52608 IB | 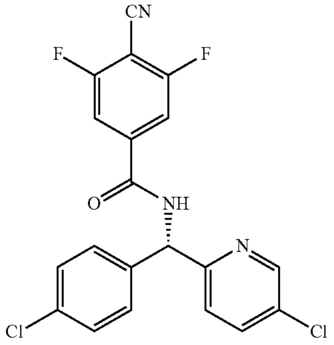 [SMILES: N#Cc1c(F)cc(C(=O)N[C@@H](c2ccc(Cl)cc2)c2ccc(Cl)cn2)cc1F] | >28 | — | 0.253 | — | — |
| 52609 IB | 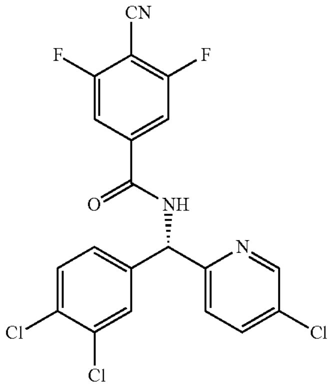 [SMILES: N#Cc1c(F)cc(C(=O)N[C@@H](c2ccc(Cl)c(Cl)c2)c2ccc(Cl)cn2)cc1F] | >28 | 19.6 | 0.042 | 16.1 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52610 IB | 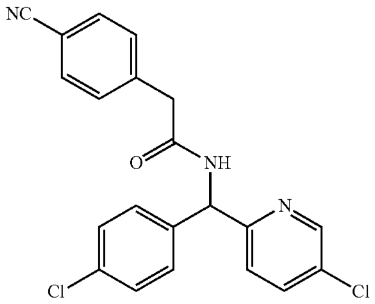 [SMILES: N#Cc1ccc(CC(=O)NC(c2ccc(Cl)cc2)c2ccc(Cl)cn2)cc1] | 5 | — | 0.647 | — | — |
| 52612 IB | 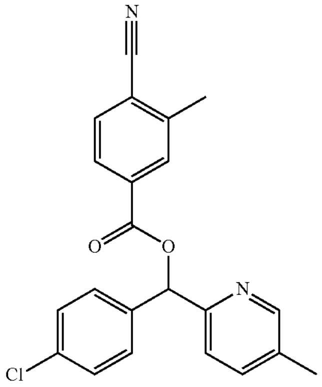 [SMILES: Cc1ccc(C(OC(=O)c2ccc(C#N)c(C)c2)c2ccc(Cl)cc2)nc1] | >28 | — | 0.456 | — | — |
| 52613 IC | 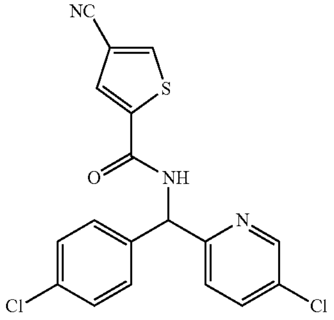 [SMILES: N#Cc1csc(C(=O)NC(c2ccc(Cl)cc2)c2ccc(Cl)cn2)c1] | 10.4 | — | 0.257 | — | — |
| 52614 IB | 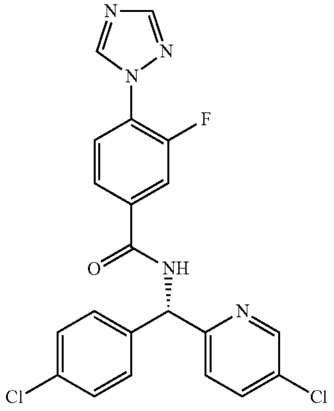 [SMILES: O=C(N[C@@H](c1ccc(Cl)cc1)c1ccc(Cl)cn1)c1ccc(-n2cncn2)c(F)c1] | >28 | — | 0.581 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52615 IC | 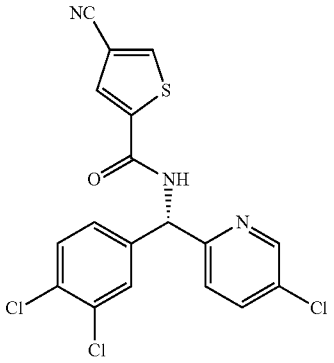 | 1.4 | — | 0.098 | — | — |
| 52616 IB | 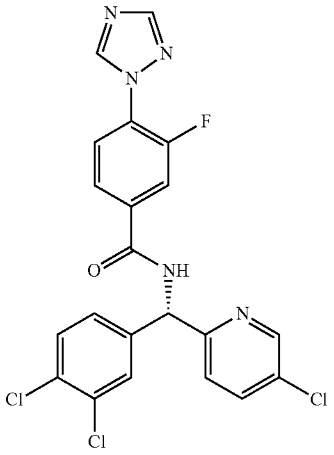 [SMILES: O=C(N[C@@H](c1ccc(Cl)c(Cl)c1)c1ccc(Cl)cn1)c1ccc(-n2cncn2)c(F)c1] | 4.1 | — | 0.15 | — | — |
| 52617 IB | 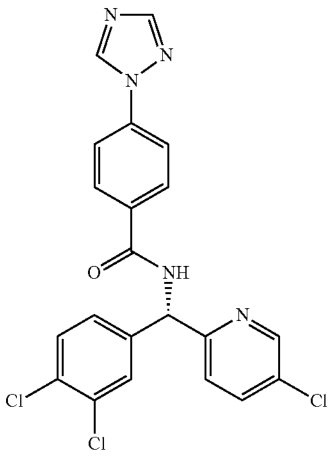 [SMILES: O=C(N[C@@H](c1ccc(Cl)c(Cl)c1)c1ccc(Cl)cn1)c1ccc(-n2cncn2)cc1] | 4.1 | 17.3 | 0.031 | 11.7 | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52618 IB | 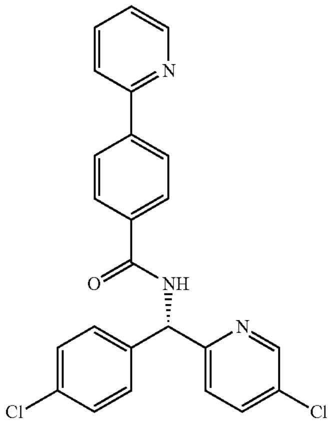 [SMILES: O=C(N[C@@H](c1ccc(Cl)cc1)c1ccc(Cl)cn1)c1ccc(-c2ccccn2)cc1] | >28 | — | 3.2 | — | — |
| 52619 IB | 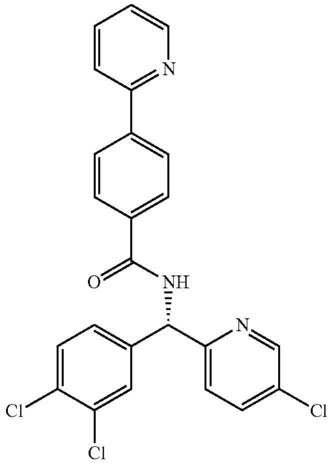 [SMILES: O=C(N[C@@H](c1ccc(Cl)c(Cl)c1)c1ccc(Cl)cn1)c1ccc(-c2ccccn2)cc1] | 7 | — | 0.551 | — | — |
| 52620 IB | 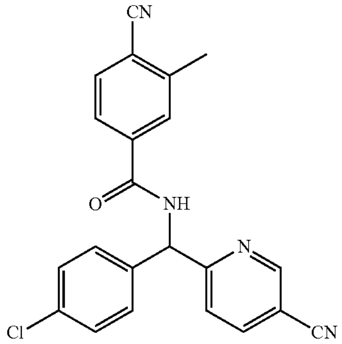 [SMILES: Cc1cc(C(=O)NC(c2ccc(Cl)cc2)c2ccc(C#N)cn2)ccc1C#N] | >28 | — | 1.7 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52621 IB | 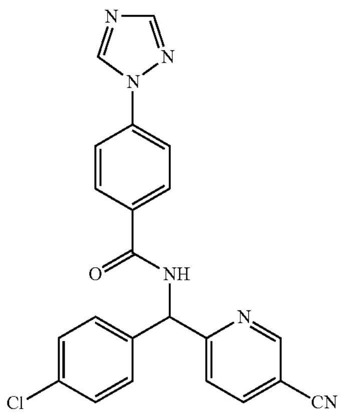 [SMILES: N#Cc1ccc(C(NC(=O)c2ccc(-n3cncn3)cc2)c2ccc(Cl)cc2)nc1] | >28 | — | 19.2 | — | — |
| 52622 IB | 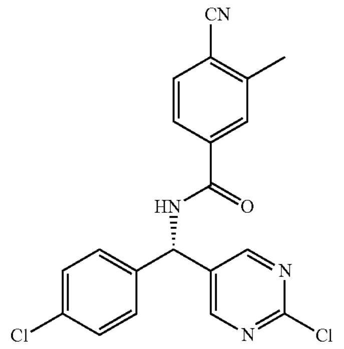 [SMILES: Cc1cc(C(=O)N[C@@H](c2ccc(Cl)cc2)c2cnc(Cl)nc2)ccc1C#N] | >28 | — | 7.6 | — | — |
| 52624 IB | 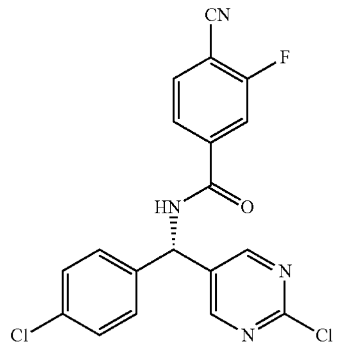 [SMILES: N#Cc1ccc(C(=O)N[C@@H](c2ccc(Cl)cc2)c2cnc(Cl)nc2)cc1F] | >28 | — | 9.2 | — | — |
| 52625 IA | 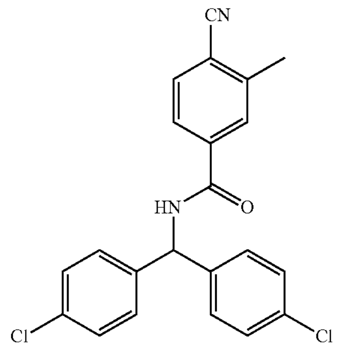 [SMILES: Cc1cc(C(=O)NC(c2ccc(Cl)cc2)c2ccc(Cl)cc2)ccc1C#N] | >28 | — | 0.248 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52626 IA | 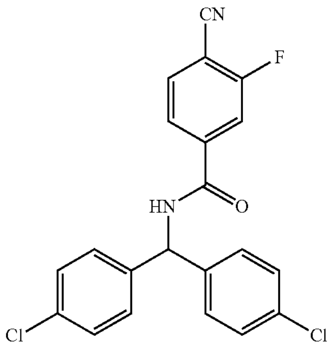 [SMILES: N#Cc1ccc(C(=O)NC(c2ccc(Cl)cc2)c2ccc(Cl)cc2)cc1F] | >28 | — | 0.113 | — | — |
| 52627 IB | 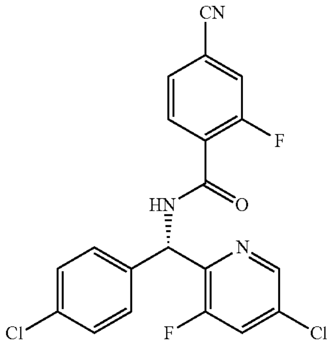 [SMILES: N#Cc1ccc(C(=O)N[C@@H](c2ccc(Cl)cc2)c2ncc(Cl)cc2F)c(F)c1] | >28 | >50 | 0.104 | >50 | — |
| 52628 IB | 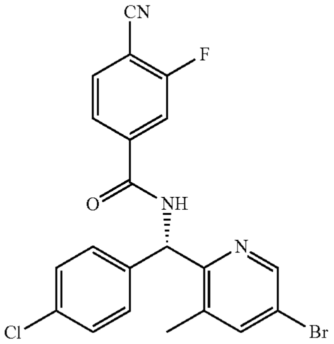 [SMILES: Cc1cc(Br)cnc1[C@@H](NC(=O)c1ccc(C#N)c(F)c1)c1ccc(Cl)cc1] | 4 | — | 0.036 | — | — |
| 52629 IB | 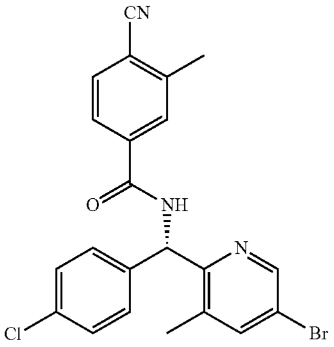 [SMILES: Cc1cc(C(=O)N[C@@H](c2ccc(Cl)cc2)c2ncc(Br)cc2C)ccc1C#N] | 1.1 | — | 0.042 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52630 IB | 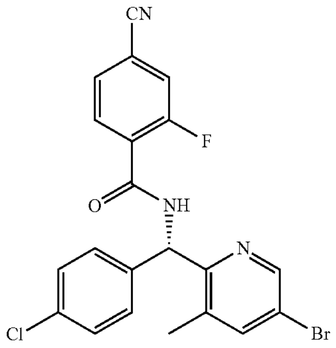 [SMILES: Cc1cc(Br)cnc1[C@@H](NC(=O)c1ccc(C#N)cc1F)c1ccc(Cl)cc1] | >28 | — | 0.416 | — | — |
| 52631 IB | 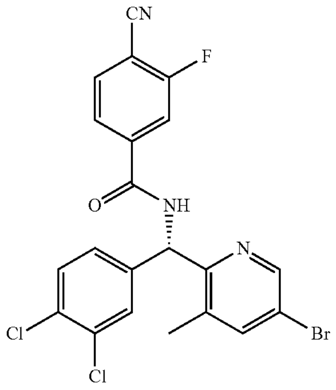 | 1.6 | — | 0.042 | — | — |
| 52632 IB | 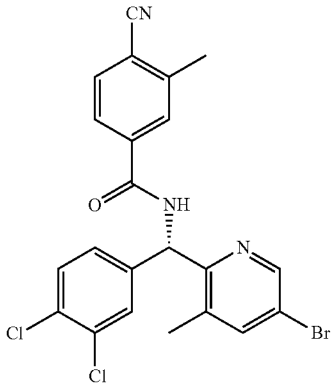 [SMILES: Cc1cc(C(=O)N[C@@H](c2ccc(Cl)c(Cl)c2)c2ncc(Br)cc2C)ccc1C#N] | 0.177 | — | 0.02 | — | — |
| 52633 IB | 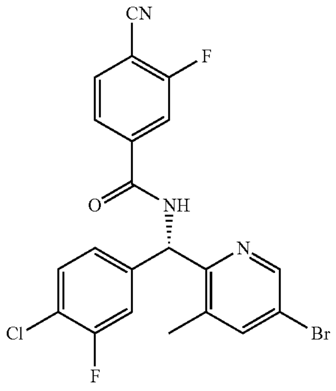 | 1.6 | — | 0.026 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52634 IB | 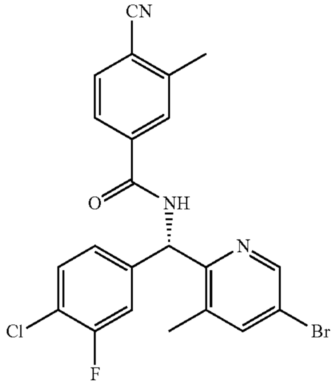 [SMILES: Cc1cc(C(=O)N[C@@H](c2ccc(Cl)c(F)c2)c2ncc(Br)cc2C)ccc1C#N] | 0.133 | — | 0.018 | — | — |
| 52635 IC | 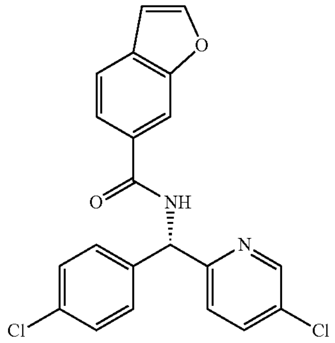 [SMILES: O=C(N[C@@H](c1ccc(Cl)cc1)c1ccc(Cl)cn1)c1ccc2ccoc2c1] | 8.1 | — | 0.122 | — | — |
| 52637 IB | 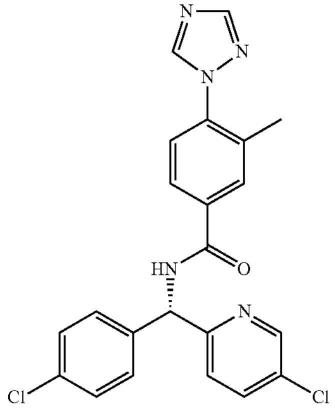 [SMILES: Cc1cc(C(=O)N[C@@H](c2ccc(Cl)cc2)c2ccc(Cl)cn2)ccc1-n1cncn1] | >28 | — | 32.3 | — | — |
| 52638 IB | 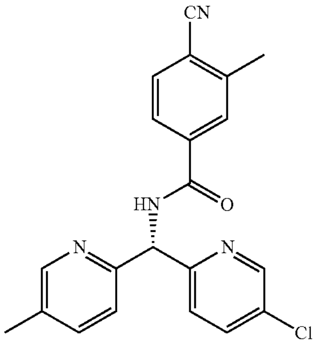 | >28 | — | 0.645 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52639 IB | 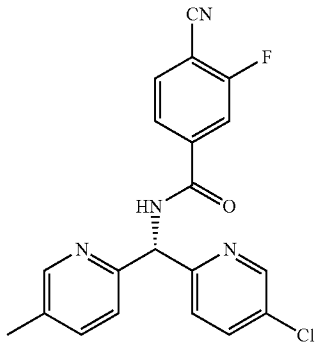 | >28 | — | 0.4 | — | — |
| 52640 IB | 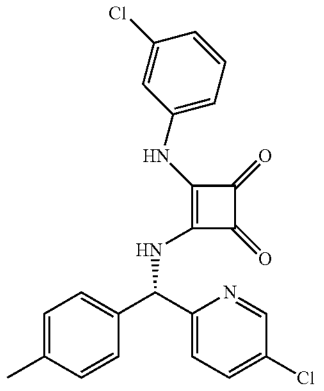 [SMILES: Cc1ccc([C@H](Nc2c(Nc3cccc(Cl)c3)c(=O)c2=O)c2ccc(Cl)cn2)cc1] | >28 | — | 1.7 | — | — |
| 52641 IA | 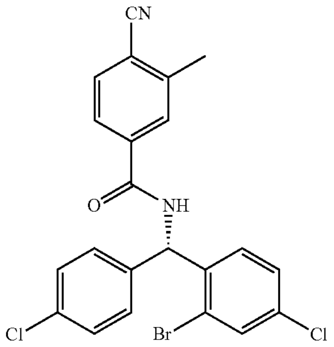 [SMILES: Cc1cc(C(=O)N[C@@H](c2ccc(Cl)cc2)c2ccc(Cl)cc2Br)ccc1C#N] | >28 | — | 0.113 | — | — |
| 52642 ID | 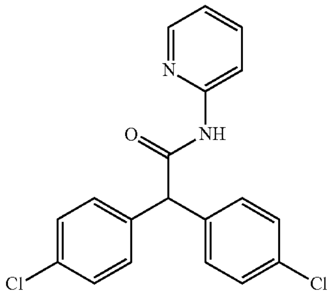 [SMILES: O=C(Nc1ccccn1)C(c1ccc(Cl)cc1)c1ccc(Cl)cc1] | 11.1 | — | 1.7 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52646 IC | 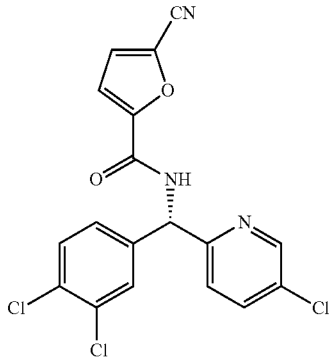 [SMILES: N#Cc1ccc(C(=O)N[C@@H](c2ccc(Cl)c(Cl)c2)c2ccc(Cl)cn2)o1] | 2.5 | — | 0.329 | — | — |
| 52647 IC | 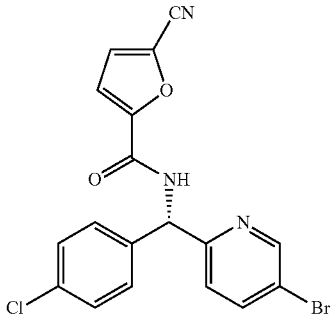 [SMILES: N#Cc1ccc(C(=O)N[C@@H](c2ccc(Cl)cc2)c2ccc(Br)cn2)o1] | 9.5 | — | 0.629 | — | — |
| 52649 IB | 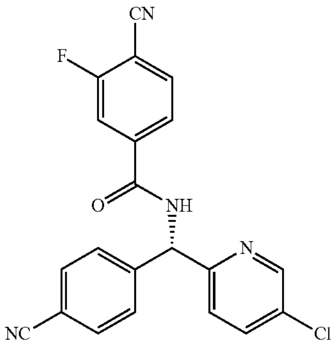 [SMILES: N#Cc1ccc([C@H](NC(=O)c2ccc(C#N)c(F)c2)c2ccc(Cl)cn2)cc1] | >28 | — | 0.95 | — | — |
| 52650 IB | 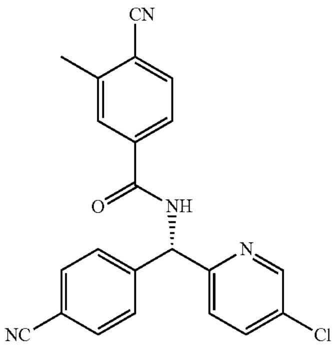 [SMILES: Cc1cc(C(=O)N[C@@H](c2ccc(C#N)cc2)c2ccc(Cl)cn2)ccc1C#N] | >28 | — | 0.834 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52651 IB | 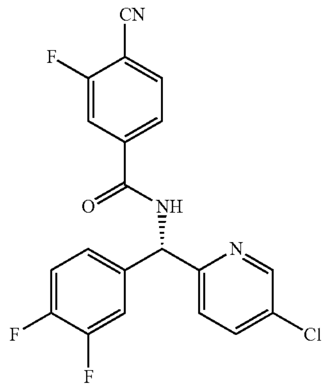 | >28 | — | 0.096 | — | — |
| 52652 IB | 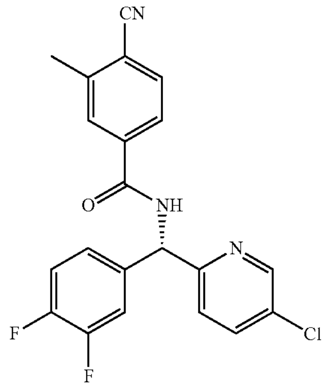 | 3.7 | — | 0.137 | — | — |
| 52653 IB | 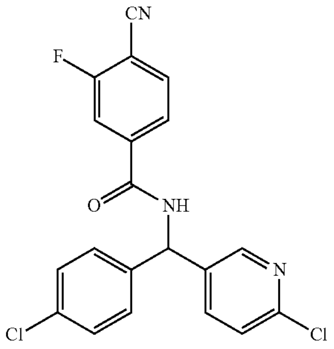 [SMILES: N#Cc1ccc(C(=O)NC(c2ccc(Cl)cc2)c2ccc(Cl)nc2)cc1F] | >28 | — | 1.6 | — | — |
| 52654 IB | 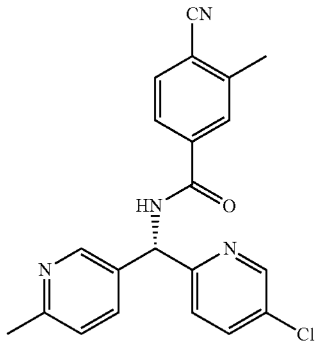 | >28 | — | 2 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52655 IB | 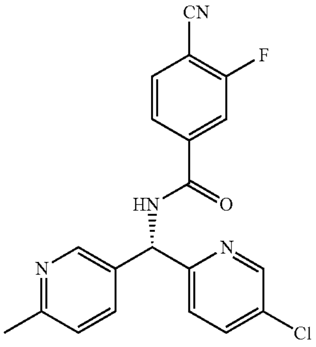 | >28 | — | 2.3 | — | — |
| 52656 IB | 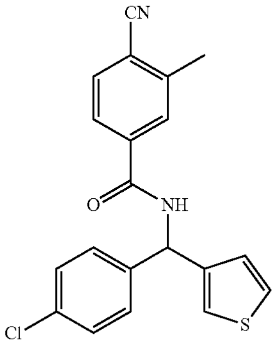 [SMILES: Cc1cc(C(=O)NC(c2ccc(Cl)cc2)c2ccsc2)ccc1C#N] | 4.0 | — | 1.2 | — | — |
| 52657 IB | 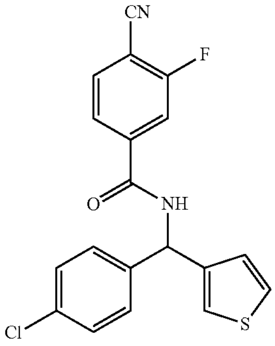 [SMILES: N#Cc1ccc(C(=O)NC(c2ccc(Cl)cc2)c2ccsc2)cc1F] | 4.5 | — | 0.439 | — | — |
| 52660 IE | 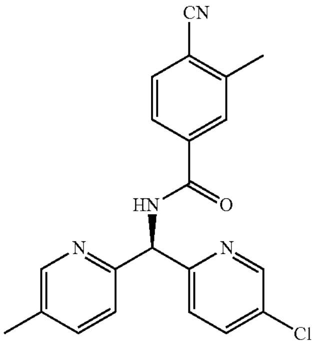 | >28 | — | 0.442 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52661 IE | 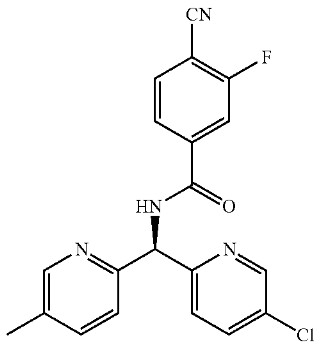 | >28 | — | 0.345 | — | — |
| 52662 IC | 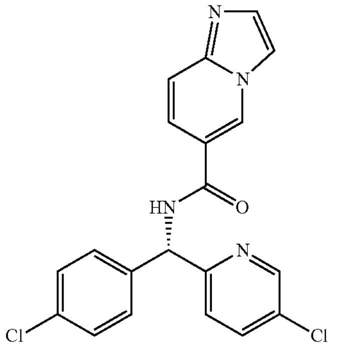 [SMILES: O=C(N[C@@H](c1ccc(Cl)cc1)c1ccc(Cl)cn1)c1ccc2nccn2c1] | >28 | — | 1.1 | — | — |
| 52664 IB | 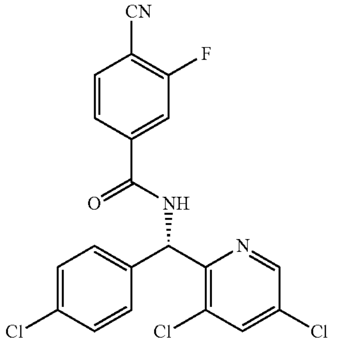 [SMILES: N#Cc1ccc(C(=O)N[C@@H](c2ccc(Cl)cc2)c2ncc(Cl)cc2Cl)cc1F] | 1.4 | — | 0.013 | — | — |
| 52665 IB | 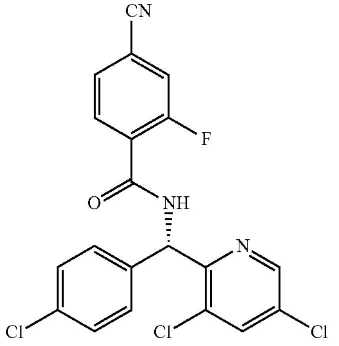 [SMILES: N#Cc1ccc(C(=O)N[C@@H](c2ccc(Cl)cc2)c2ncc(Cl)cc2Cl)c(F)c1] | >28 | — | 0.121 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52666 IB | 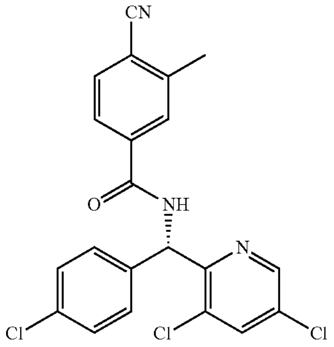 [SMILES: Cc1cc(C(=O)N[C@@H](c2ccc(Cl)cc2)c2ncc(Cl)cc2Cl)ccc1C#N] | 0.528 | — | 0.028 | — | — |
| 52667 IB | 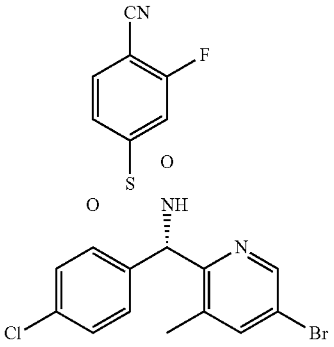 | 6.6 | — | 16.3 | — | — |
| 52668 IA | 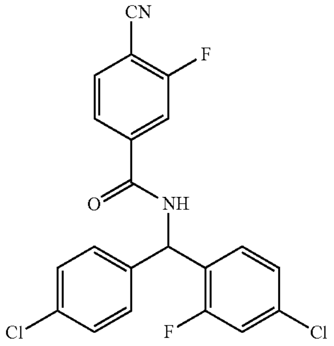 [SMILES: N#Cc1ccc(C(=O)NC(c2ccc(Cl)cc2)c2ccc(Cl)cc2F)cc1F] | >28 | — | 0.679 | — | — |
| 52669 IA | 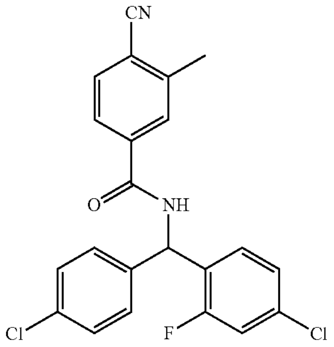 [SMILES: Cc1cc(C(=O)NC(c2ccc(Cl)cc2)c2ccc(Cl)cc2F)ccc1C#N] | 27.5 | — | 2.8 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52670 IB | 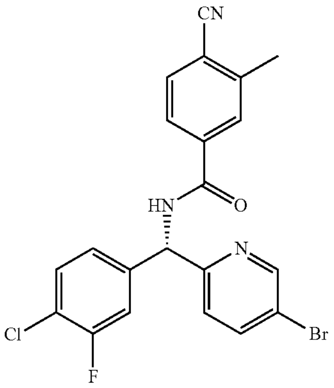 [SMILES: Cc1cc(C(=O)N[C@@H](c2ccc(Cl)c(F)c2)c2ccc(Br)cn2)ccc1C#N] | 0.452 | — | 0.011 | — | — |
| 52671 IB | 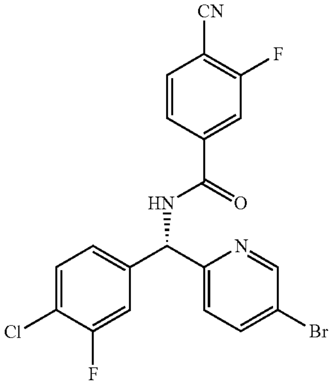 [SMILES: N#Cc1ccc(C(=O)N[C@@H](c2ccc(Cl)c(F)c2)c2ccc(Br)cn2)cc1F] | 1.8 | — | 0.011 | — | — |
| 52672 IB | 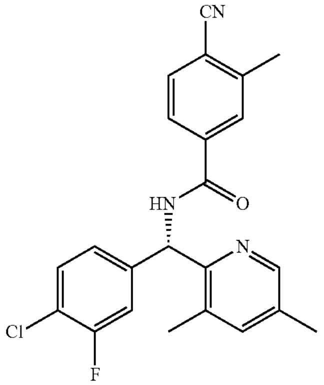 [SMILES: Cc1cnc([C@@H](NC(=O)c2ccc(C#N)c(C)c2)c2ccc(Cl)c(F)c2)c(C)c1] | 1.4 | — | 0.051 | — | — |
| 52673 IB | 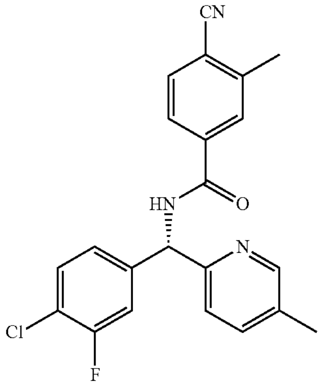 [SMILES: Cc1ccc([C@@H](NC(=O)c2ccc(C#N)c(C)c2)c2ccc(Cl)c(F)c2)nc1] | 3.3 | — | 0.076 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52674 IB | 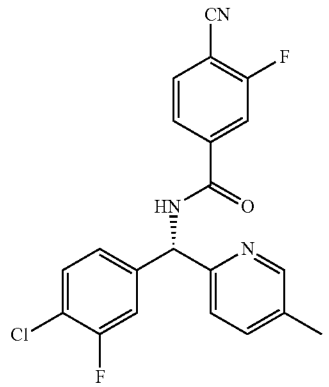 [SMILES: Cc1ccc([C@@H](NC(=O)c2ccc(C#N)c(F)c2)c2ccc(Cl)c(F)c2)nc1] | 6.4 | — | 0.027 | — | — |
| 52675 IB | 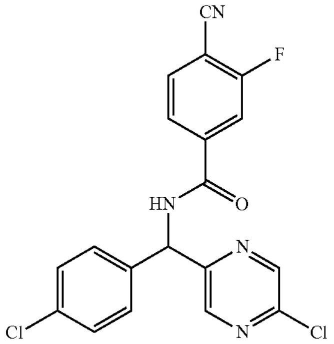 | >28 | — | 0.214 | — | — |
| 62676 IB | 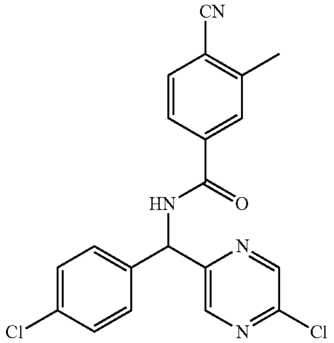 [SMILES: Cc1cc(C(=O)NC(c2ccc(Cl)cc2)c2cnc(Cl)cn2)ccc1C#N] | 12.0 | — | 0.301 | — | — |
| 52677 IB | 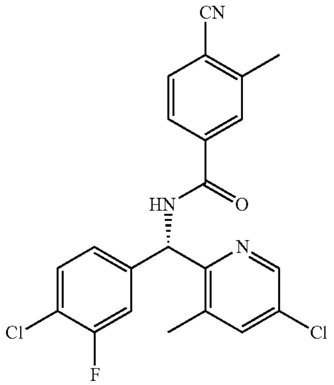 [SMILES: Cc1cc(C(=O)N[C@@H](c2ccc(Cl)c(F)c2)c2ncc(Cl)cc2C)ccc1C#N] | 0.621 | — | 0.033 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52678 IB | 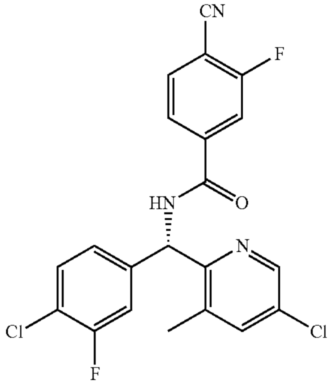 [SMILES: Cc1cc(Cl)cnc1[C@@H](NC(=O)c1ccc(C#N)c(F)c1)c1ccc(Cl)c(F)c1] | 1.5 | — | 0.023 | — | — |
| 52679 IB | 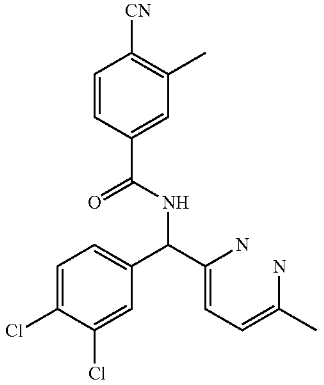 [SMILES: C/C(N)=C/C=C(\N)C(NC(=O)c1ccc(C#N)c(C)c1)c1ccc(Cl)c(Cl)c1] | >28 | — | 3.1 | — | — |
| 52680 IA | 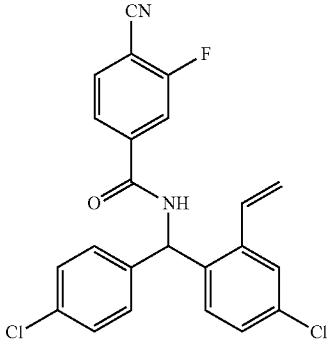 [SMILES: C=Cc1cc(Cl)ccc1C(NC(=O)c1ccc(C#N)c(F)c1)c1ccc(Cl)cc1] | >28 | — | 0.037 | — | — |
| 52682 IA | 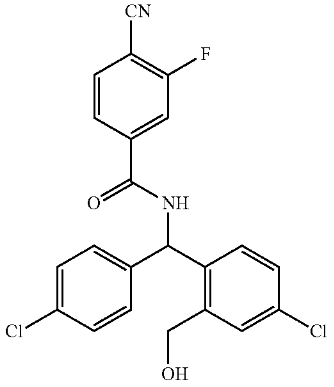 [SMILES: N#Cc1ccc(C(=O)NC(c2ccc(Cl)cc2)c2ccc(Cl)cc2CO)cc1F] | >28 | — | 0.672 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52683 IB | 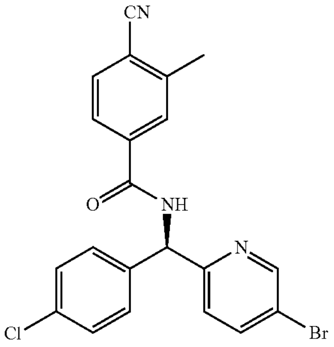 [SMILES: Cc1cc(C(=O)N[C@H](c2ccc(Cl)cc2)c2ccc(Br)cn2)ccc1C#N] | 18.4 | — | 0.124 | — | — |
| 52684 IB | 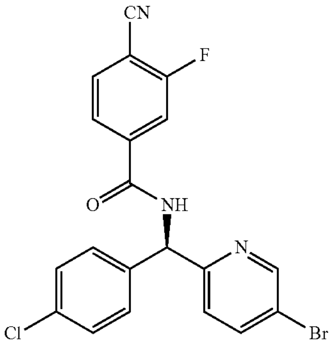 [SMILES: N#Cc1ccc(C(=O)N[C@H](c2ccc(Cl)cc2)c2ccc(Br)cn2)cc1F] | >28 | — | 0.075 | — | — |
| 52685 IB | 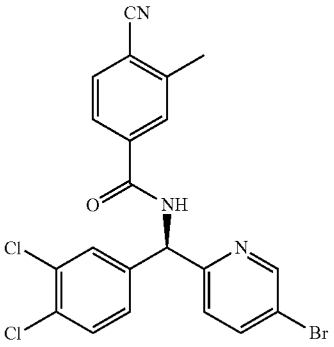 [SMILES: Cc1cc(C(=O)N[C@H](c2ccc(Cl)c(Cl)c2)c2ccc(Br)cn2)ccc1C#N] | 3.3 | — | 0.056 | — | — |
| 52686 IB | 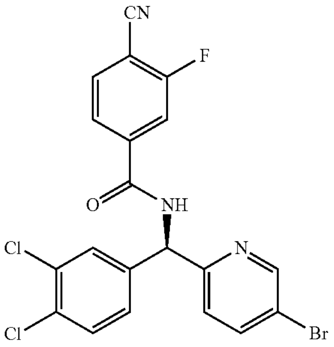 [SMILES: N#Cc1ccc(C(=O)N[C@H](c2ccc(Cl)c(Cl)c2)c2ccc(Br)cn2)cc1F] | 6.6 | — | 0.047 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52687 IA | 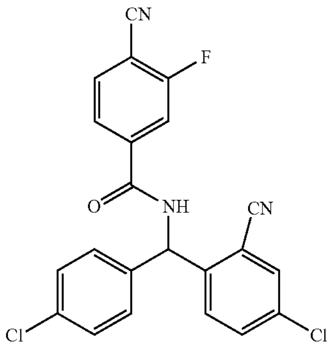 [SMILES: N#Cc1ccc(C(=O)NC(c2ccc(Cl)cc2)c2ccc(Cl)cc2C#N)cc1F] | 22.4 | — | 0.426 | — | — |
| 52688 IA | 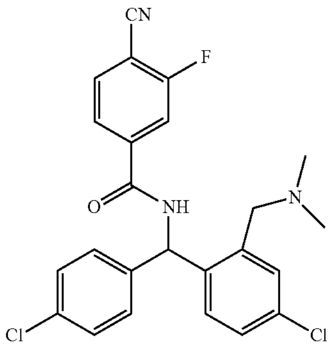 [SMILES: CN(C)Cc1cc(Cl)ccc1C(NC(=O)c1ccc(C#N)c(F)c1)c1ccc(Cl)cc1] | >28 | — | 3.3 | — | — |
| 52689 IB | 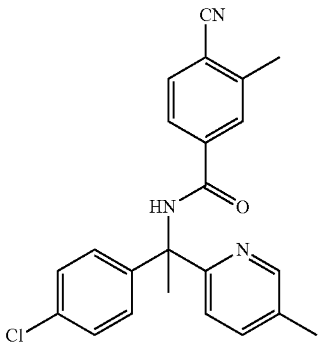 [SMILES: Cc1ccc(C(C)(NC(=O)c2ccc(C#N)c(C)c2)c2ccc(Cl)cc2)nc1] | 10.2 | — | 0.392 | — | — |
| 52690 IB | 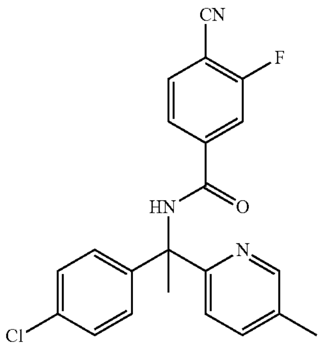 | >28 | — | 0.492 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52691 IB | 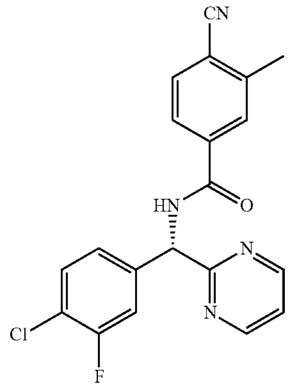 [SMILES: Cc1cc(C(=O)N[C@@H](c2ccc(Cl)c(F)c2)c2ncccn2)ccc1C#N] | >28 | — | 6.8 | — | — |
| 52692 IB | 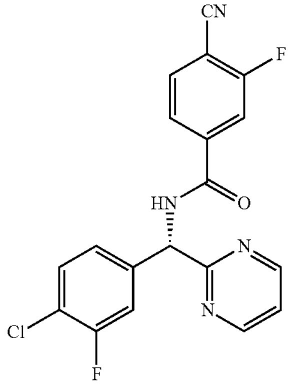 [SMILES: N#Cc1ccc(C(=O)N[C@@H](c2ccc(Cl)c(F)c2)c2ncccn2)cc1F] | >28 | — | 7.3 | — | — |
| 52693 IB | 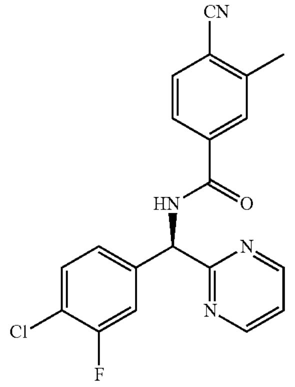 [SMILES: Cc1cc(C(=O)N[C@H](c2ccc(Cl)c(F)c2)c2ncccn2)ccc1C#N] | >28 | — | 2.1 | — | — |
| 52694 IB | 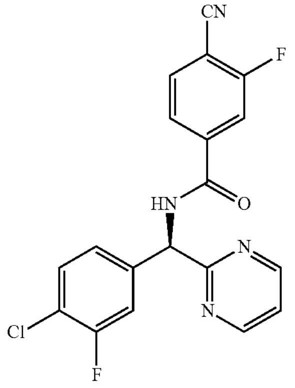 [SMILES: N#Cc1ccc(C(=O)N[C@H](c2ccc(Cl)c(F)c2)c2ncccn2)cc1F] | >28 | — | 1.4 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52695 IB | 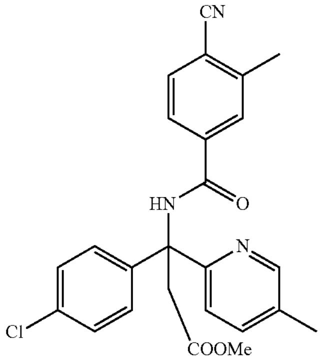 [SMILES: COC(=O)CC(NC(=O)c1ccc(C#N)c(C)c1)(c1ccc(Cl)cc1)c1ccc(C)cn1] | >28 | — | 2.1 | — | — |
| 52696 IB | 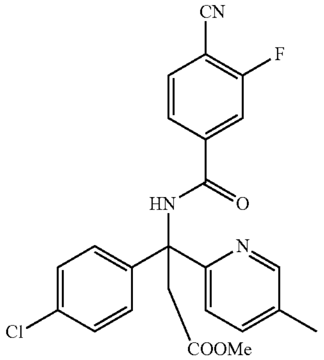 [SMILES: COC(=O)CC(NC(=O)c1ccc(C#N)c(F)c1)(c1ccc(Cl)cc1)c1ccc(C)cn1] | >28 | — | 2.2 | — | — |
| 52697 IB | 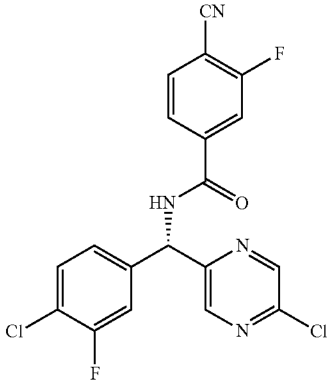 [SMILES: N#Cc1ccc(C(=O)N[C@@H](c2ccc(Cl)c(F)c2)c2cnc(Cl)cn2)cc1F] | >28 | — | 0.049 | — | — |
| 52698 IB | 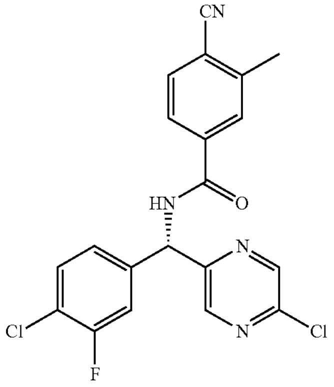 [SMILES: Cc1cc(C(=O)N[C@@H](c2ccc(Cl)c(F)c2)c2cnc(Cl)cn2)ccc1C#N] | 4 | — | 0.063 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52699 IB | 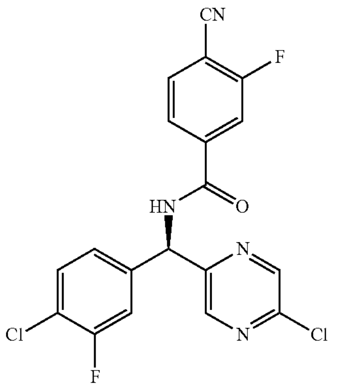 [SMILES: N#Cc1ccc(C(=O)N[C@H](c2ccc(Cl)c(F)c2)c2cnc(Cl)cn2)cc1F] | >28 | — | 0.447 | — | — |
| 52700 IB | 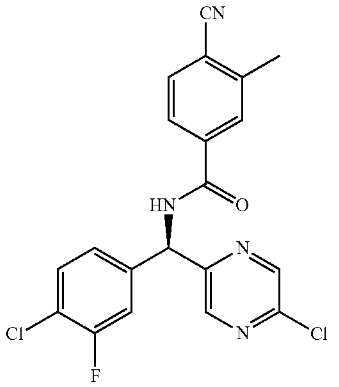 [SMILES: Cc1cc(C(=O)N[C@H](c2ccc(Cl)c(F)c2)c2cnc(Cl)cn2)ccc1C#N] | >28 | — | 0.627 | — | — |
| 52702 IB | 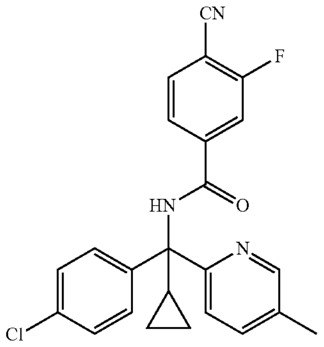 [SMILES: Cc1ccc(C(NC(=O)c2ccc(C#N)c(F)c2)(c2ccc(Cl)cc2)C2CC2)nc1] | >28 | — | 0.542 | — | — |
| 52703 IB | 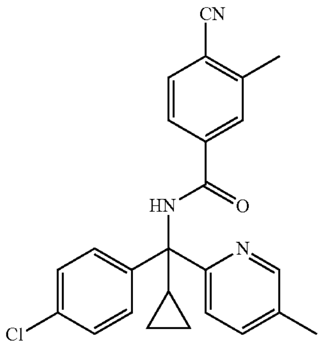 [SMILES: Cc1ccc(C(NC(=O)c2ccc(C#N)c(C)c2)(c2ccc(Cl)cc2)C2CC2)nc1] | >28 | — | 0.641 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52705 IB | 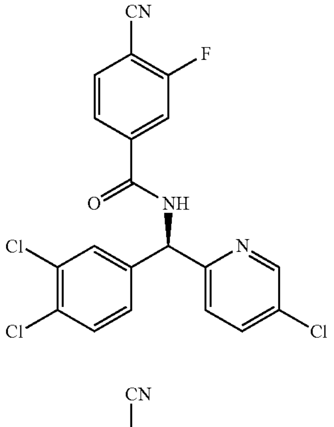 | 4.7 | — | 0.048 | — | — |
| 52706 IB | 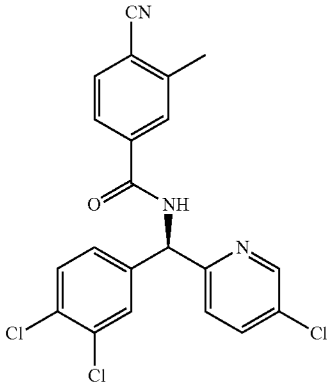 [SMILES: Cc1cc(C(=O)N[C@H](c2ccc(Cl)c(Cl)c2)c2ccc(Cl)cn2)ccc1C#N] | 4.5 | — | 0.153 | — | — |
| 52707 IB | 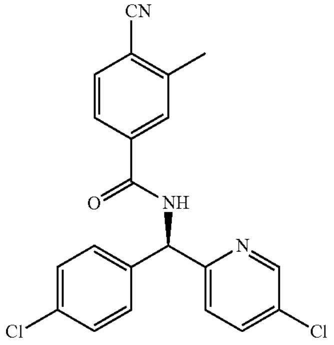 [SMILES: Cc1cc(C(=O)N[C@H](c2ccc(Cl)cc2)c2ccc(Cl)cn2)ccc1C#N] | 26.2 | — | 0.511 | — | — |
| 52708 IB | 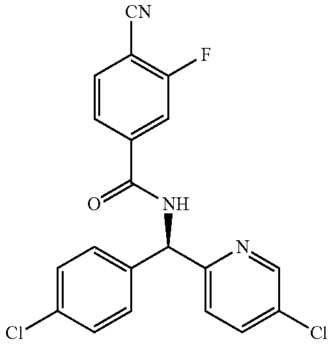 | >28 | — | 0.527 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52709 IB | 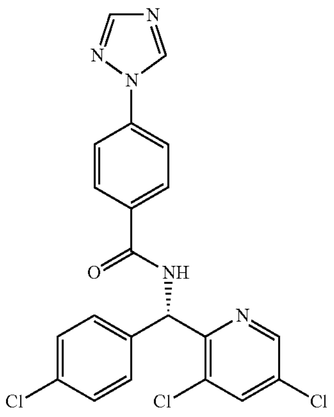 [SMILES: O=C(N[C@@H](c1ccc(Cl)cc1)c1ncc(Cl)cc1Cl)c1ccc(-n2cncn2)cc1] | 3.7 | — | 0.035 | — | — |
| 52710 IB | 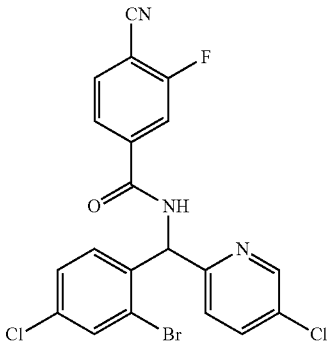 [SMILES: N#Cc1ccc(C(=O)NC(c2ccc(Cl)cn2)c2ccc(Cl)cc2Br)cc1F] | 16.1 | — | 5.3 | — | — |
| 52711 IB | 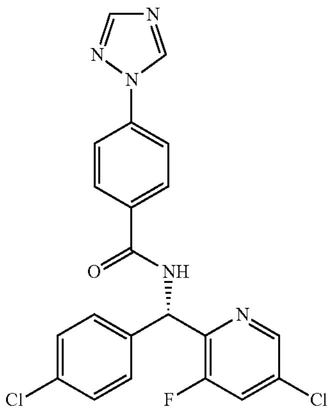 [SMILES: O=C(N[C@@H](c1ccc(Cl)cc1)c1ncc(Cl)cc1F)c1ccc(-n2cncn2)cc1] | 5.3 | — | 0.04 | — | — |
| 52713 IC | 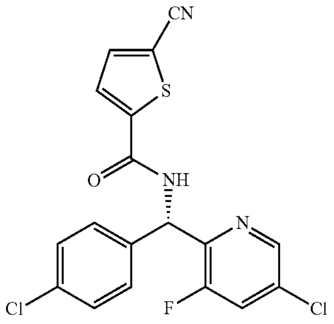 [SMILES: N#Cc1ccc(C(=O)N[C@@H](c2ccc(Cl)cc2)c2ncc(Cl)cc2F)s1] | 0.923 | — | 0.014 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52715 IB | 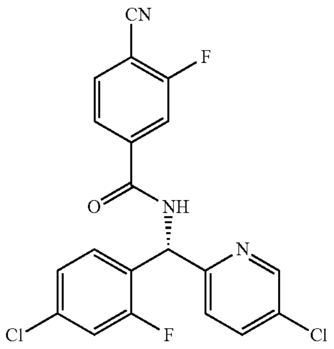 [SMILES: N#Cc1ccc(C(=O)N[C@H](c2ccc(Cl)cn2)c2ccc(Cl)cc2F)cc1F] | >28 | — | 1.6 | — | — |
| 52716 IB | 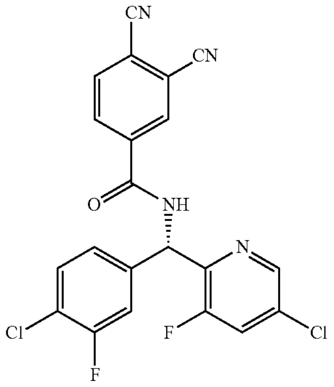 | 0.21 | — | 0.018 | — | — |
| 52717 IB | 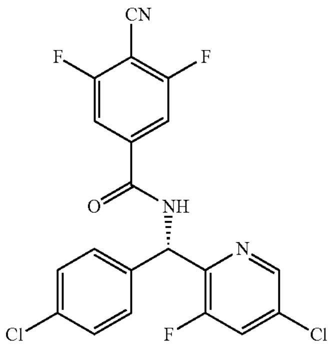 [SMILES: N#Cc1c(F)cc(C(=O)N[C@@H](c2ccc(Cl)cc2)c2ncc(Cl)cc2F)cc1F] | 12.7 | — | 0.096 | — | — |
| 52718 IB | 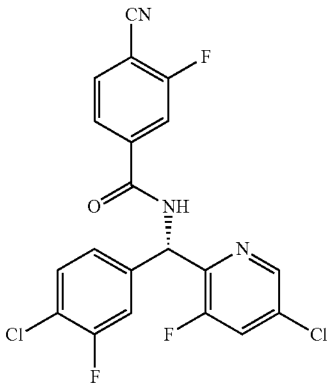 [SMILES: N#Cc1ccc(C(=O)N[C@@H](c2ccc(Cl)c(F)c2)c2ncc(Cl)cc2F)cc1F] | 0.86 | — | 0.006 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 5271IB | 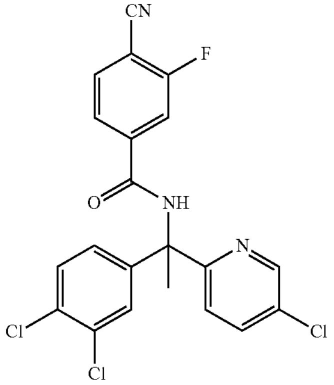 [SMILES: CC(NC(=O)c1ccc(C#N)c(F)c1)(c1ccc(Cl)c(Cl)c1)c1ccc(Cl)cn1] isomer 1 | >28 | — | 11.9 | — | — |
| 52720 IB | 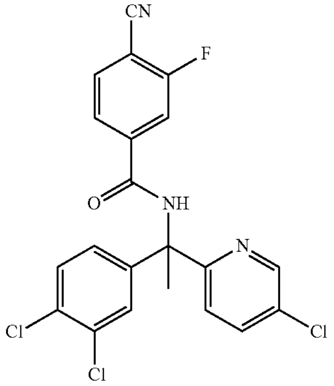 [SMILES: CC(NC(=O)c1ccc(C#N)c(F)c1)(c1ccc(Cl)c(Cl)c1)c1ccc(Cl)cn1] isomer 2 | 5.1 | — | 0.211 | — | — |
| 52721 IB | 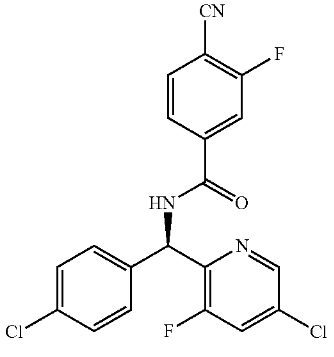 | 10 | — | 0.068 | — | — |
| 52722 IB | 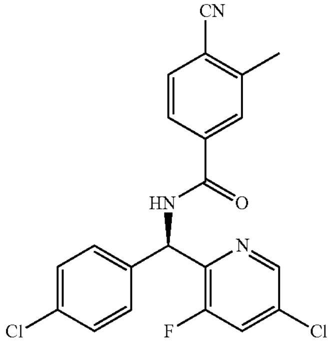 [SMILES: Cc1cc(C(=O)N[C@H](c2ccc(Cl)cc2)c2ncc(Cl)cc2F)ccc1C#N] | 2.6 | — | 0.057 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52723 IB | 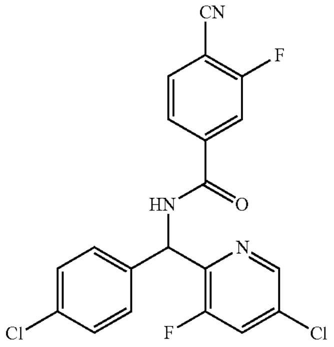 | 3.1 | — | 0.021 | — | — |
| 52724 IB | 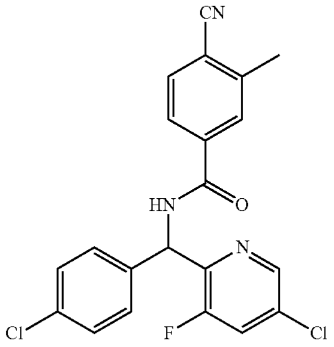 [SMILES: Cc1cc(C(=O)NC(c2ccc(Cl)cc2)c2ncc(Cl)cc2F)ccc1C#N] | 1.3 | — | 0.033 | — | — |
| 52725 IB | 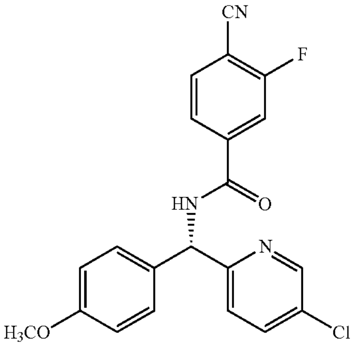 [SMILES: COc1ccc([C@H](NC(=O)c2ccc(C#N)c(F)c2)c2ccc(Cl)cn2)cc1] | >28 | — | 1.0 | — | — |
| 52726 IA | 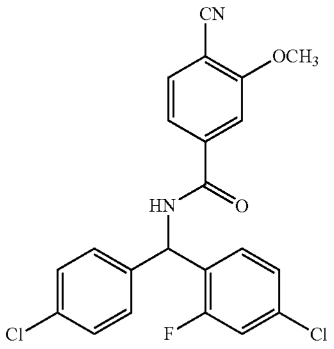 [SMILES: COc1cc(C(=O)NC(c2ccc(Cl)cc2)c2ccc(Cl)cc2F)ccc1C#N] | 22.3 | — | 2.0 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52727 IB | 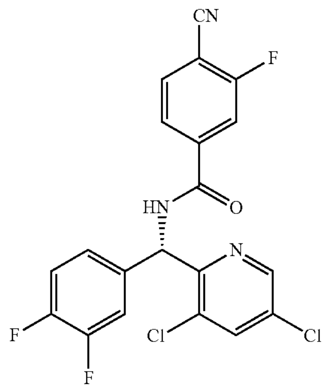 [SMILES: N#Cc1ccc(C(=O)N[C@@H](c2ccc(F)c(F)c2)c2ncc(Cl)cc2Cl)cc1F] | 3.6 | — | 0.057 | — | — |
| 52728 IA | 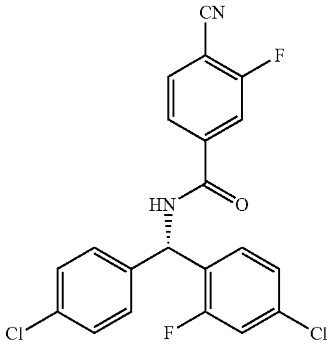 [SMILES: N#Cc1ccc(C(=O)N[C@@H](c2ccc(Cl)cc2)c2ccc(Cl)cc2F)cc1F] | >28 | — | 0.304 | — | — |
| 52729 IB | 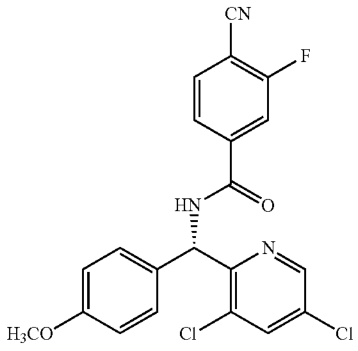 [SMILES: COc1ccc([C@H](NC(=O)c2ccc(C#N)c(F)c2)c2ncc(Cl)cc2Cl)cc1] | 27.4 | — | 0.151 | — | — |
| 52730 IB | 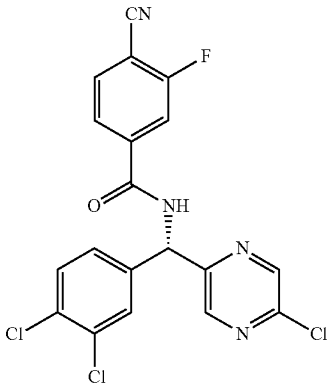 [SMILES: N#Cc1ccc(C(=O)N[C@@H](c2ccc(Cl)c(Cl)c2)c2cnc(Cl)cn2)cc1F] | 9.5 | — | 0.039 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52731 IB | 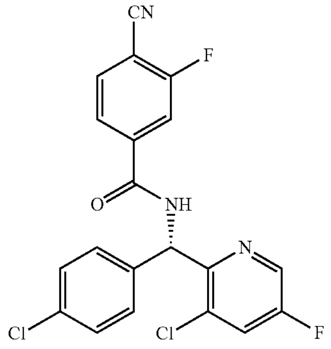 [SMILES: N#Cc1ccc(C(=O)N[C@@H](c2ccc(Cl)cc2)c2ncc(F)cc2Cl)cc1F] | 22.1 | — | 0.231 | — | — |
| 52732 IB | 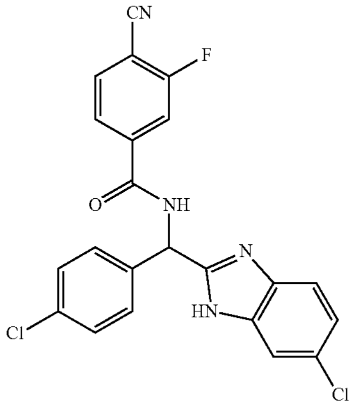 [SMILES: N#Cc1ccc(C(=O)NC(c2ccc(Cl)cc2)c2nc3ccc(Cl)cc3[nH]2)cc1F] | 0.886 | — | 1.1 | — | — |
| 52733 IA | 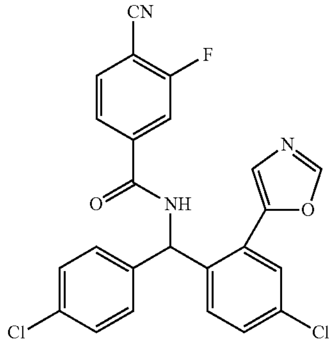 [SMILES: N#Cc1ccc(C(=O)NC(c2ccc(Cl)cc2)c2ccc(Cl)cc2-c2cnco2)cc1F] | >28 | — | 3.1 | — | — |
| 52734 IB | 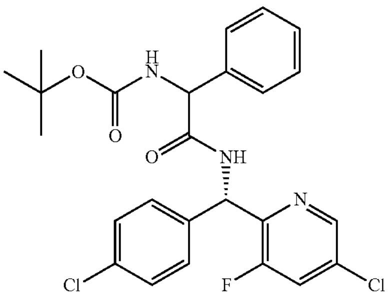 [SMILES: CC(C)(C)OC(=O)NC(C(=O)N[C@@H](c1ccc(Cl)cc1)c1ncc(Cl)cc1F)c1ccccc1] | >28 | — | 1.5 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52735 IB | 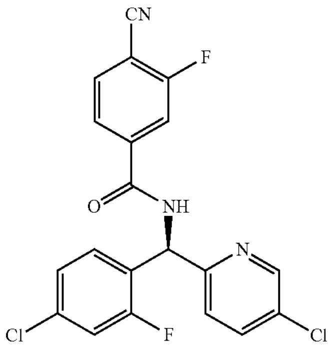 [SMILES: N#Cc1ccc(C(=O)N[C@@H](c2ccc(Cl)cn2)c2ccc(Cl)cc2F)cc1F] | >28 | — | 20.4 | — | — |
| 52736 IB | 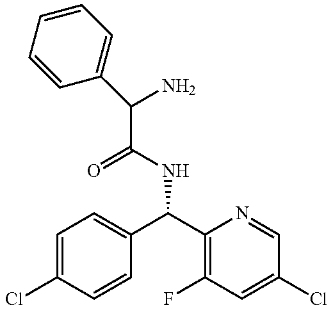 [SMILES: NC(C(=O)N[C@@H](c1ccc(Cl)cc1)c1ncc(Cl)cc1F)c1ccccc1] | 14.2 | — | 3.5 | — | — |
| 52737 IB | 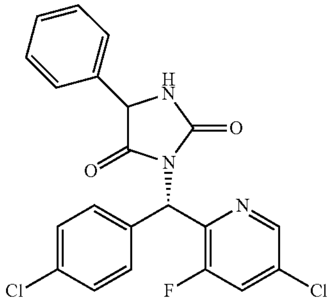 [SMILES: O=C1NC(c2ccccc2)C(=O)N1[C@@H](c1ccc(Cl)cc1)c1ncc(Cl)cc1F] | 13.5 | — | 12.1 | — | — |
| 52739 IB | 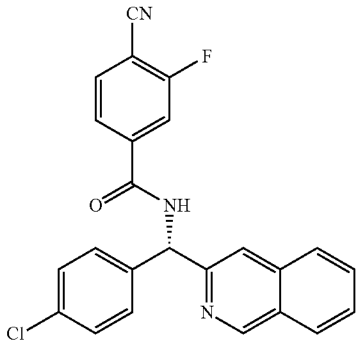 [SMILES: N#Cc1ccc(C(=O)N[C@@H](c2ccc(Cl)cc2)c2cc3ccccc3cn2)cc1F] | 18.5 | — | 0.079 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52740 IB | 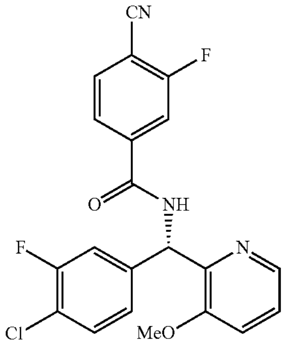 [SMILES: COc1cccnc1[C@@H](NC(=O)c1ccc(C#N)c(F)c1)c1ccc(Cl)c(F)c1] | 10.1 | — | 0.927 | — | — |
| 52741 IA | 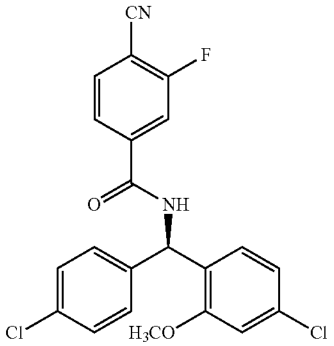 [SMILES: COc1cc(Cl)ccc1[C@H](NC(=O)c1ccc(C#N)c(F)c1)c1ccc(Cl)cc1] | >28 | — | 0.396 | — | — |
| 52742 IA | 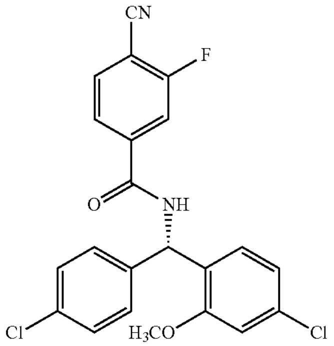 [SMILES: COc1cc(Cl)ccc1[C@@H](NC(=O)c1ccc(C#N)c(F)c1)c1ccc(Cl)cc1] | >28 | — | 0.342 | — | — |
| 52743 IA | 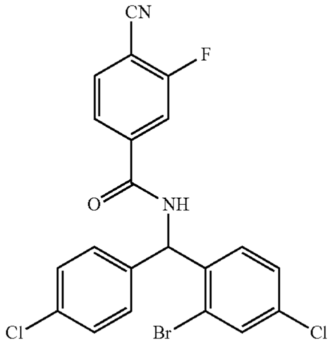 [SMILES: N#Cc1ccc(C(=O)NC(c2ccc(Cl)cc2)c2ccc(Cl)cc2Br)cc1F] | >28 | — | 0.33 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52744 IB | 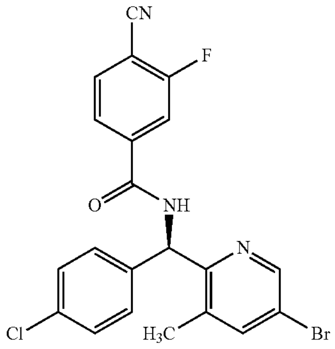 [SMILES: Cc1cc(Br)cnc1[C@H](NC(=O)c1ccc(C#N)c(F)c1)c1ccc(Cl)cc1] | >28 | — | 0.349 | — | — |
| 52745 IA | 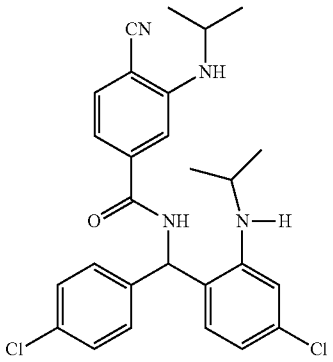 [SMILES: CC(C)Nc1cc(C(=O)NC(c2ccc(Cl)cc2)c2ccc(Cl)cc2NC(C)C)ccc1C#N] | >28 | — | 2.2 | — | — |
| 52749 | 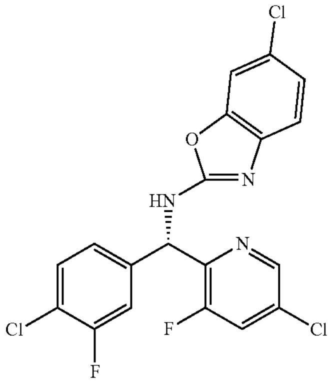 [SMILES: Fc1cc([C@H](Nc2nc3ccc(Cl)cc3o2)c2ncc(Cl)cc2F)ccc1Cl] | 0.199 | — | 0.019 | — | — |
| 52750 | 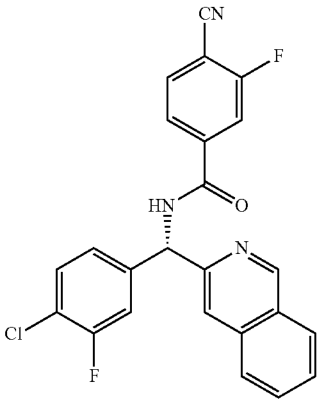 [SMILES: N#Cc1ccc(C(=O)N[C@@H](c2ccc(Cl)c(F)c2)c2cc3ccccc3cn2)cc1F] | 4.3 | — | 0.046 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52751 | 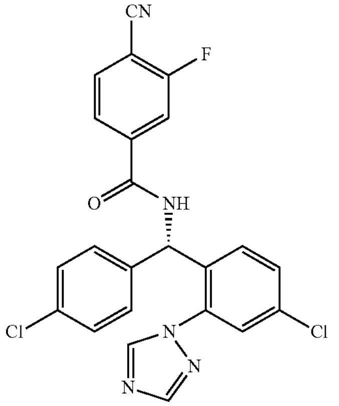 [SMILES: N#Cc1ccc(C(=O)N[C@@H](c2ccc(Cl)cc2)c2ccc(Cl)cc2-n2cncn2)cc1F] | >28 | — | 4.4 | — | — |
| 52752 | 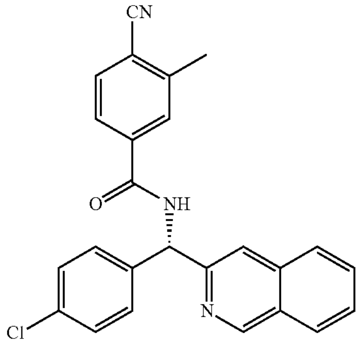 [SMILES: Cc1cc(C(=O)N[C@@H](c2ccc(Cl)cc2)c2cc3ccccc3cn2)ccc1C#N] | 7.8 | — | 0.164 | — | — |
| 52754 | 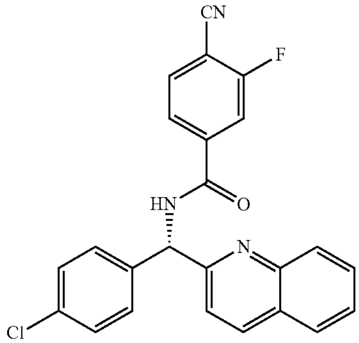 [SMILES: N#Cc1ccc(C(=O)N[C@@H](c2ccc(Cl)cc2)c2ccc3ccccc3n2)cc1F] | 6.0 | — | 0.189 | — | — |
| 52755 | 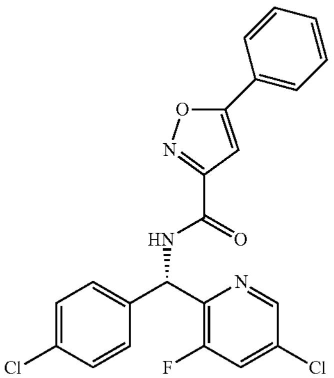 [SMILES: O=C(N[C@@H](c1ccc(Cl)cc1)c1ncc(Cl)cc1F)c1cc(-c2ccccc2)on1] | 3.9 | — | 2.7 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52756 | 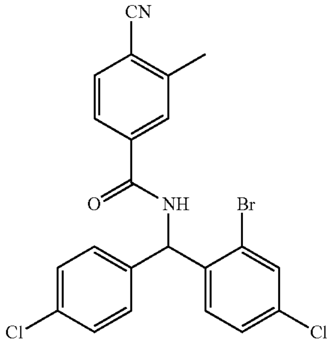 [SMILES: Cc1cc(C(=O)NC(c2ccc(Cl)cc2)c2ccc(Cl)cc2Br)ccc1C#N] | >28 | — | 0.489 | — | — |
| 52759 | 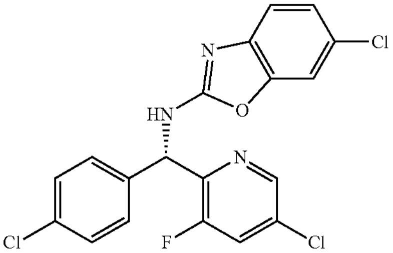 [SMILES: Fc1cc(Cl)cnc1[C@@H](Nc1nc2ccc(Cl)cc2o1)c1ccc(Cl)cc1] | 0.352 | — | 0.027 | — | — |
| 52760 | 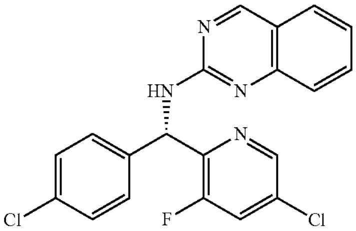 [SMILES: Fc1cc(Cl)cnc1[C@@H](Nc1ncc2ccccc2n1)c1ccc(Cl)cc1] | >28 | — | 0.439 | — | — |
| 52761 | 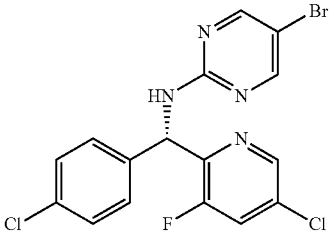 [SMILES: Fc1cc(Cl)cnc1[C@@H](Nc1ncc(Br)cn1)c1ccc(Cl)cc1] | 1.5 | — | 0.133 | — | — |
| 52763 | 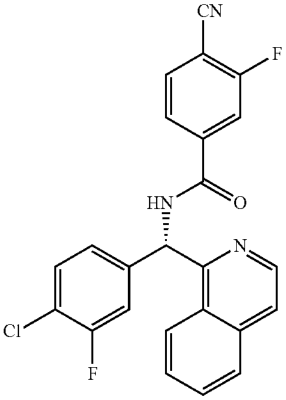 [SMILES: N#Cc1ccc(C(=O)N[C@@H](c2ccc(Cl)c(F)c2)c2nccc3ccccc23)cc1F] | 3.0 | — | 0.682 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52764 | 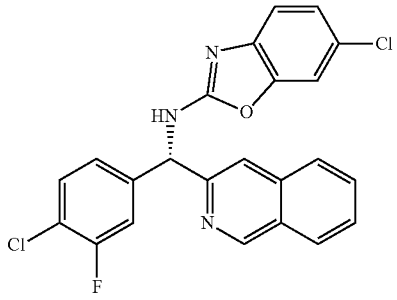 [SMILES: Fc1cc([C@H](Nc2nc3ccc(Cl)cc3o2)c2cc3ccccc3cn2)ccc1Cl] | 4.3 | — | 0.251 | — | — |
| 52766 | 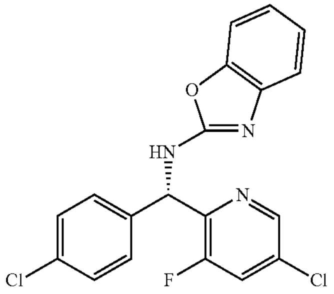 [SMILES: Fc1cc(Cl)cnc1[C@@H](Nc1nc2ccccc2o1)c1ccc(Cl)cc1] | 1.6 | — | 0.112 | — | — |
| 52767 | 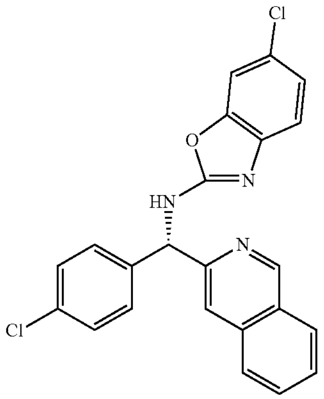 [SMILES: Clc1ccc([C@H](Nc2nc3ccc(Cl)cc3o2)c2cc3ccccc3cn2)cc1] | 15.4 | — | 0.445 | — | — |
| 52768 | 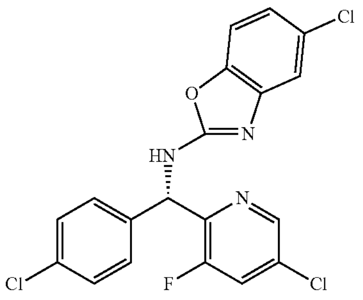 [SMILES: Fc1cc(Cl)cnc1[C@@H](Nc1nc2cc(Cl)ccc2o1)c1ccc(Cl)cc1] | 1.2 | — | 0.088 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52770 | 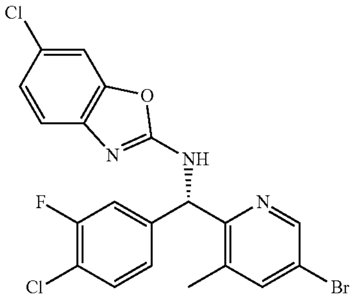 [SMILES: Cc1cc(Br)cnc1[C@@H](Nc1nc2ccc(Cl)cc2o1)c1ccc(Cl)c(F)c1] | 0.636 | — | 0.040 | — | — |
| 52771 | 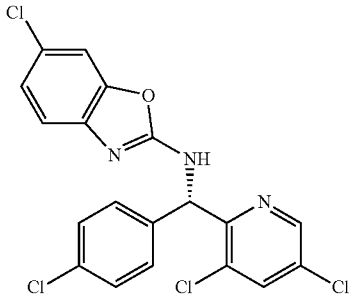 [SMILES: Clc1ccc([C@H](Nc2nc3ccc(Cl)cc3o2)c2ncc(Cl)cc2Cl)cc1] | 0.268 | — | 0.036 | — | — |
| 52772 | 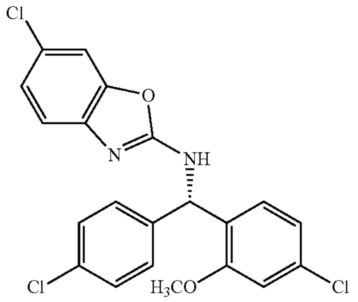 [SMILES: COc1cc(Cl)ccc1[C@@H](Nc1nc2ccc(Cl)cc2o1)c1ccc(Cl)cc1] | >28 | — | 1.2 | — | — |
| 52773 | 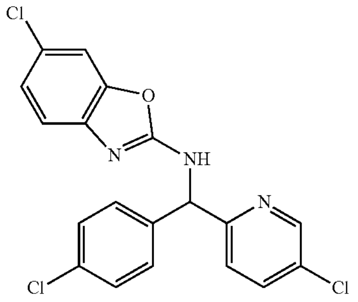 | >28 | — | 0.485 | — | — |
| 52774 | 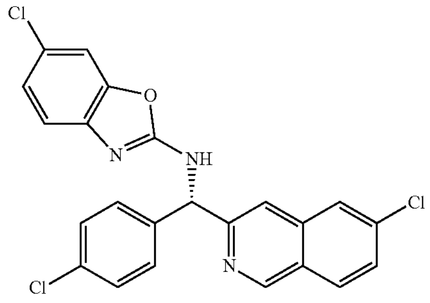 [SMILES: Clc1ccc([C@H](Nc2nc3ccc(Cl)cc3o2)c2cc3cc(Cl)ccc3cn2)cc1] | >28 | — | 1.1 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52776 | 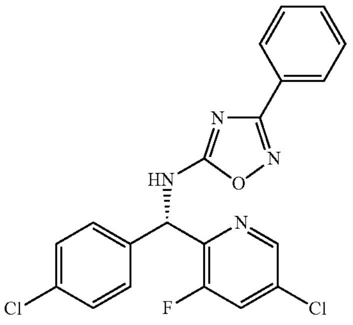 [SMILES: Fc1cc(Cl)cnc1[C@@H](Nc1nc(-c2ccccc2)no1)c1ccc(Cl)cc1] | 0.858 | — | 3.5 | — | — |
| 52777 | 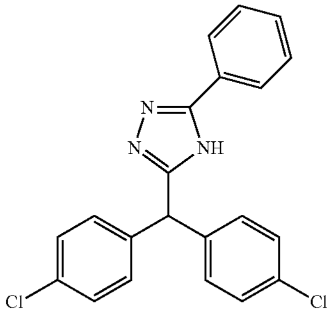 [SMILES: Clc1ccc(C(c2ccc(Cl)cc2)c2nnc(-c3ccccc3)[nH]2)cc1] | 3.2 | — | 3.2 | — | — |
| 52780 | 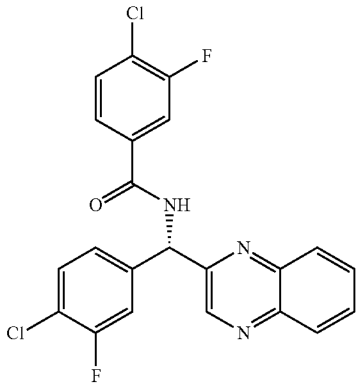 | 5.6 | — | 0.091 | — | — |
| 52781 | 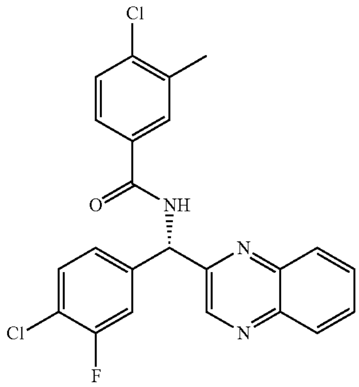 [SMILES: Cc1cc(C(=O)N[C@@H](c2ccc(Cl)c(F)c2)c2cnc3ccccc3n2)ccc1Cl] | 0.939 | — | 0.105 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52782 | 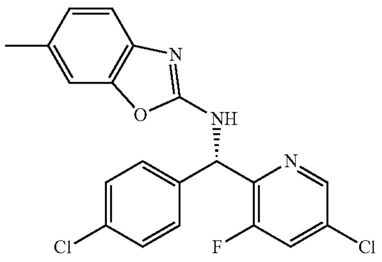 [SMILES: Cc1ccc2nc(N[C@@H](c3ccc(Cl)cc3)c3ncc(Cl)cc3F)oc2c1] | 1.5 | — | 0.105 | — | — |
| 52783 | 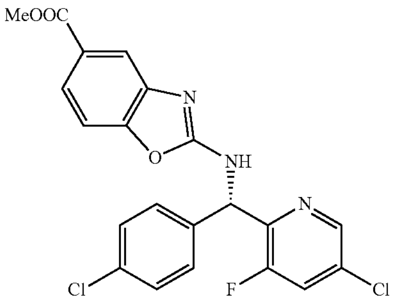 [SMILES: COC(=O)c1ccc2oc(N[C@@H](c3ccc(Cl)cc3)c3ncc(Cl)cc3F)nc2c1] | 0.537 | — | 0.048 | — | — |
| 52784 | 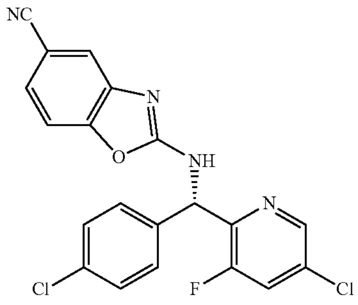 [SMILES: N#Cc1ccc2oc(N[C@@H](c3ccc(Cl)cc3)c3ncc(Cl)cc3F)nc2c1] | 0.088 | — | 0.030 | — | — |
| 52785 | 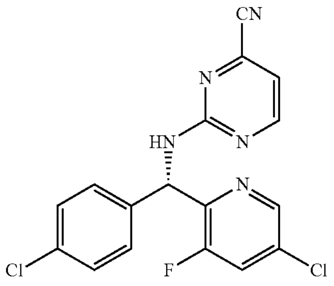 [SMILES: N#Cc1ccnc(N[C@@H](c2ccc(Cl)cc2)c2ncc(Cl)cc2F)n1] | 9.2 | — | 2.4 | — | — |
| 52786 | 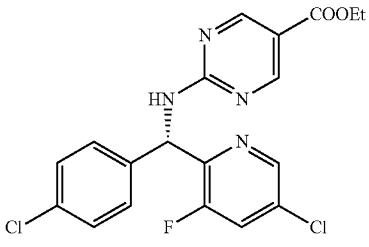 [SMILES: CCOC(=O)c1cnc(N[C@@H](c2ccc(Cl)cc2)c2ncc(Cl)cc2F)nc1] | 5.8 | — | 0.540 | — | — |

TABLE 2-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52787 | 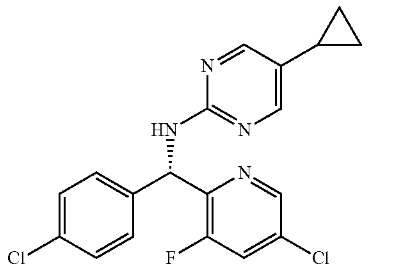 [SMILES: Fc1cc(Cl)cnc1[C@@H](Nc1ncc(C2CC2)cn1)c1ccc(Cl)cc1] | 14.3 | — | 0.438 | — | — |
| 52789 | 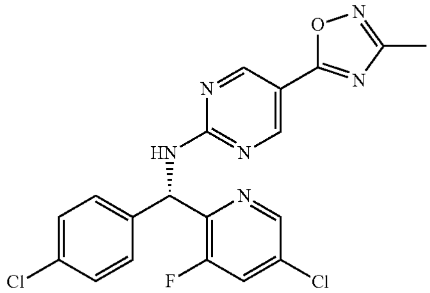 [SMILES: Cc1noc(-c2cnc(N[C@@H](c3ccc(Cl)cc3)c3ncc(Cl)cc3F)nc2)n1] | 3.8 | — | 0.451 | — | — |
TABLE 3
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52167 IB | 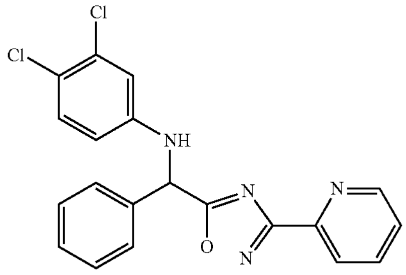 [SMILES: N=C(/N=C(\O)C(Nc1ccc(Cl)c(Cl)c1)c1ccccc1)c1ccccn1] | — | — | 0.7 | 5.2 | — |
| 52205 IB | 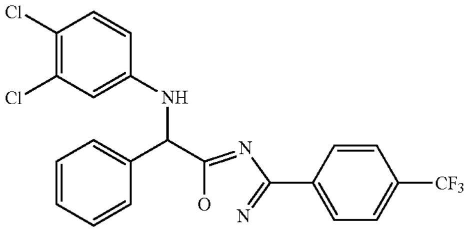 [SMILES: N=C(/N=C(\O)C(Nc1ccc(Cl)c(Cl)c1)c1ccccc1)c1ccc(C(F)(F)F)cc1] | — | — | 4.3 | 34 | — |
| 52207 IB | 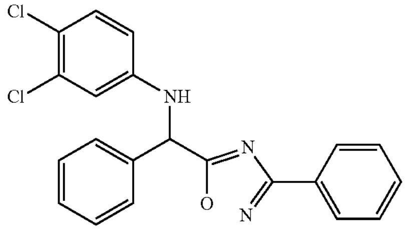 [SMILES: N=C(/N=C(\O)C(Nc1ccc(Cl)c(Cl)c1)c1ccccc1)c1ccccc1] | — | — | 1.3 | 30.4 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52304 IB | 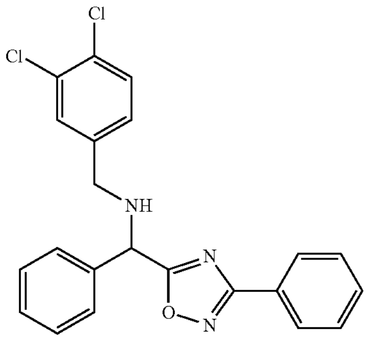 [SMILES: Clc1ccc(CNC(c2ccccc2)c2nc(-c3ccccc3)no2)cc1Cl] | 7.9 | >50 | 1.2 | 7.8 | 21.8 |
| 52305 IB | 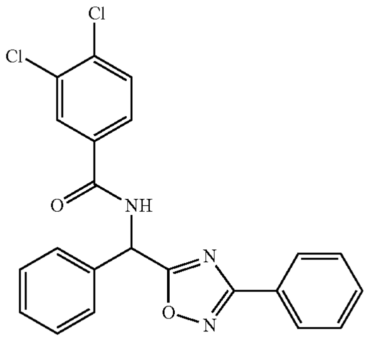 [SMILES: O=C(NC(c1ccccc1)c1nc(-c2ccccc2)no1)c1ccc(Cl)c(Cl)c1] | 1.6 | >50 | 0.521 | >50 | >50 |
| 52306 IB | 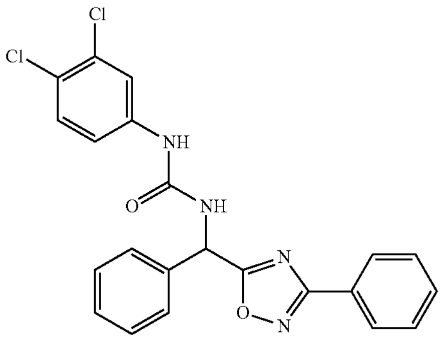 [SMILES: O=C(Nc1ccc(Cl)c(Cl)c1)NC(c1ccccc1)c1nc(-c2ccccc2)no1] | 0.881 | 2.8 | 0.586 | 2.6 | 5.1 |
| 52307 IC | 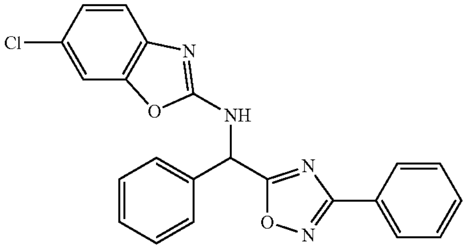 [SMILES: Clc1ccc2nc(NC(c3ccccc3)c3nc(-c4ccccc4)no3)oc2c1] | — | >50 | 0.899 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52308 IB | 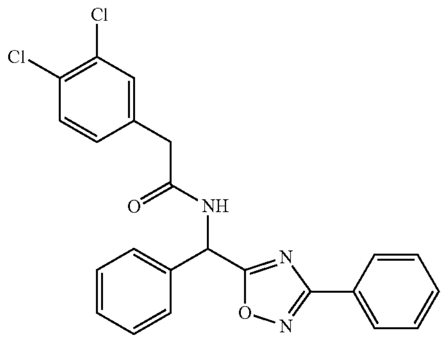 [SMILES: O=C(Cc1ccc(Cl)c(Cl)c1)NC(c1ccccc1)c1nc(-c2ccccc2)no1] | >50 | >50 | 3.9 | >50 | >50 |
| 52310 IB | 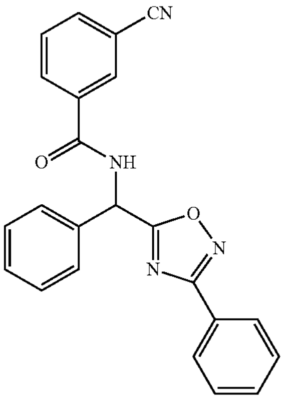 [SMILES: N#Cc1cccc(C(=O)NC(c2ccccc2)c2nc(-c3ccccc3)no2)c1] | — | >50 | 3.5 | >50 | — |
| 52311 IB | 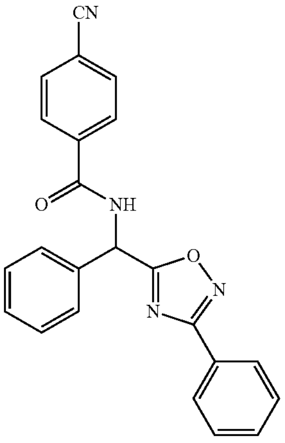 [SMILES: N#Cc1ccc(C(=O)NC(c2ccccc2)c2nc(-c3ccccc3)no2)cc1] | — | >50 | 2.3 | 30.2 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52312 IB | 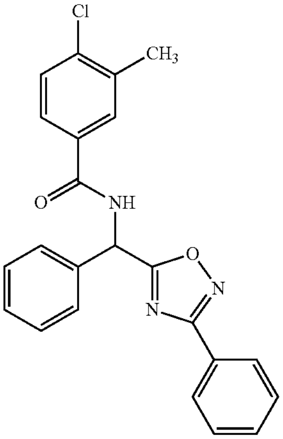 [SMILES: Cc1cc(C(=O)NC(c2ccccc2)c2nc(-c3ccccc3)no2)ccc1Cl] | — | >50 | 3.1 | >50 | — |
| 52313 IB | 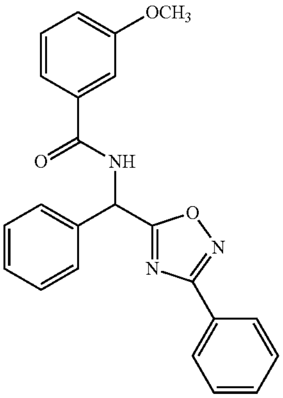 [SMILES: COc1cccc(C(=O)NC(c2ccccc2)c2nc(-c3ccccc3)no2)c1] | — | >50 | 2.2 | >50 | — |
| 52321 IB | 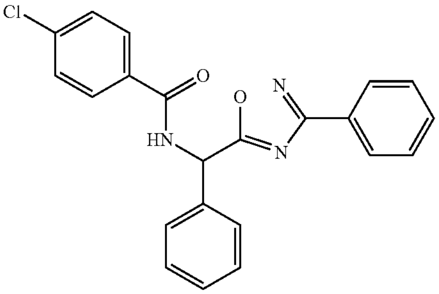 [SMILES: N=C(/N=C(\O)C(NC(=O)c1ccc(Cl)cc1)c1ccccc1)c1ccccc1] | — | >50 | 2.4 | 39.7 | >50 |
| 52325 IB | 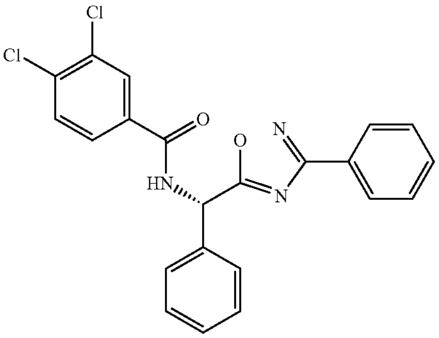 [SMILES: N=C(/N=C(\O)[C@@H](NC(=O)c1ccc(Cl)c(Cl)c1)c1ccccc1)c1ccccc1] | — | >50 | 2.8 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52326 IB | 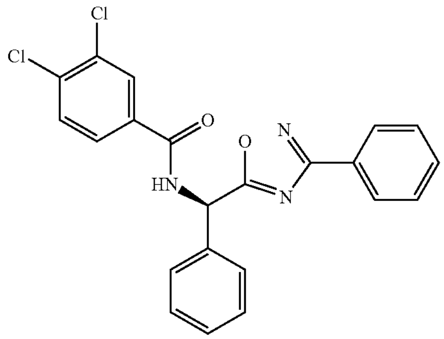 [SMILES: N=C(/N=C(\O)[C@H](NC(=O)c1ccc(Cl)c(Cl)c1)c1ccccc1)c1ccccc1] | — | >50 | 3.4 | >50 | — |
| 52333 IB | 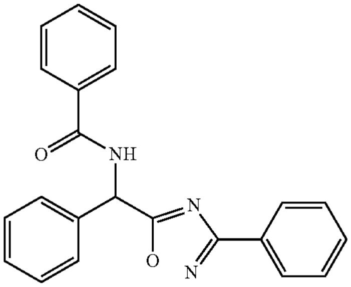 [SMILES: N=C(/N=C(\O)C(NC(=O)c1ccccc1)c1ccccc1)c1ccccc1] | — | >50 | 3.8 | >50 | — |
| 52335 IB | 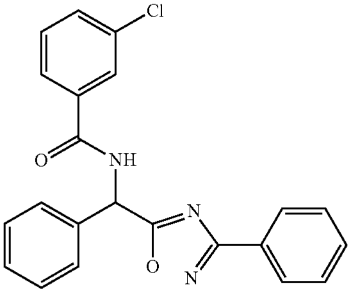 [SMILES: N=C(/N=C(\O)C(NC(=O)c1cccc(Cl)c1)c1ccccc1)c1ccccc1] | 1.6 | >50 | 0.415 | >50 | >50 |
| 52336 IB | 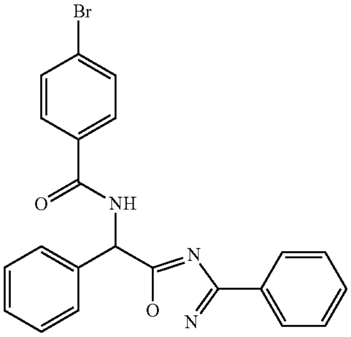 [SMILES: N=C(/N=C(\O)C(NC(=O)c1ccc(Br)cc1)c1ccccc1)c1ccccc1] | — | >50 | 1.7 | >50 | — |

TABLE 3-continued
| CYM Generic formula | Structure | S1P1 AA $IC_{50}$ µM | S1P2 AA $IC_{50}$ µM | S1P3AA $IC_{50}$ µM | S1P4AA $IC_{50}$ µM | S1P5AA $IC_{50}$ µM |
|---|---|---|---|---|---|---|
| 52337 IC | 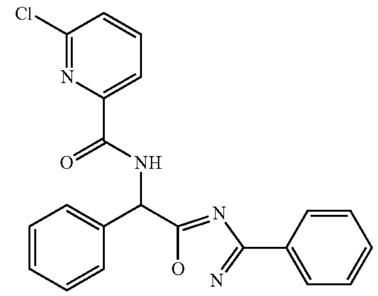 [SMILES: N=C(/N=C(\O)C(NC(=O)c1cccc(Cl)n1)c1ccccc1)c1ccccc1] | 7.3 | >50 | 2.8 | >50 | 25.1 |
| 52339 IC | 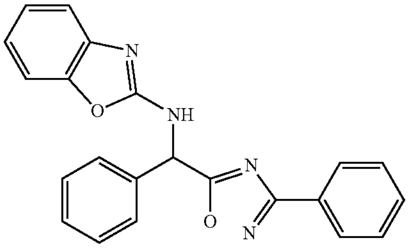 [SMILES: N=C(/N=C(\O)C(Nc1nc2ccccc2o1)c1ccccc1)c1ccccc1] | — | 23.4 | 1.2 | 5.9 | — |
| 52341 IB | 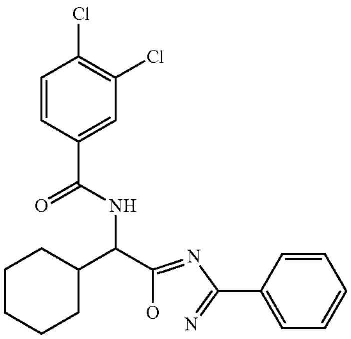 [SMILES: N=C(/N=C(\O)C(NC(=O)c1ccc(Cl)c(Cl)c1)C1CCCCC1)c1ccccc1] | 1.8 | >50 | 3.3 | >50 | >50 |
| 52346 IB | 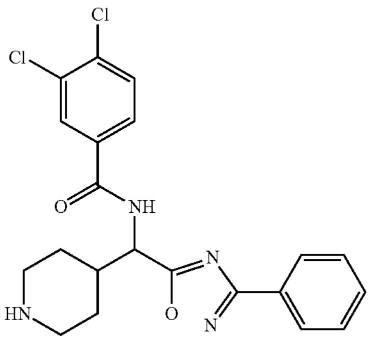 [SMILES: N=C(/N=C(\O)C(NC(=O)c1ccc(Cl)c(Cl)c1)C1CCNCC1)c1ccccc1] | — | 5.2 | 5.7 | 5.1 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52357 IB | 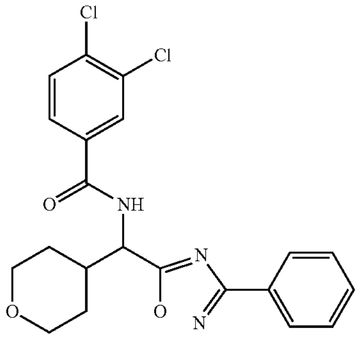 [SMILES: N=C(/N=C(\O)C(NC(=O)c1ccc(Cl)c(Cl)c1)C1CCOCC1)c1ccccc1] | 2.1 | >50 | 2.8 | 12.9 | >50 |
| 52364 IB | 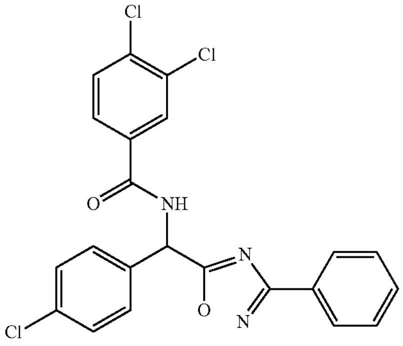 [SMILES: N=C(/N=C(\O)C(NC(=O)c1ccc(Cl)c(Cl)c1)c1ccc(Cl)cc1)c1ccccc1] | 17.5 | >50 | 0.368 | >50 | >50 |
| 52365 IB | 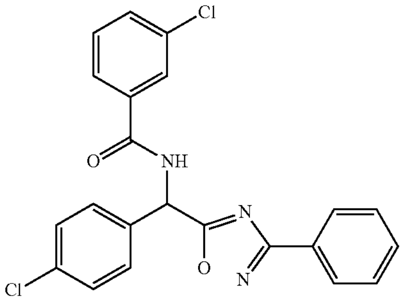 | >50 | >50 | 0.214 | 14.3 | >50 |
| 52379 IB | 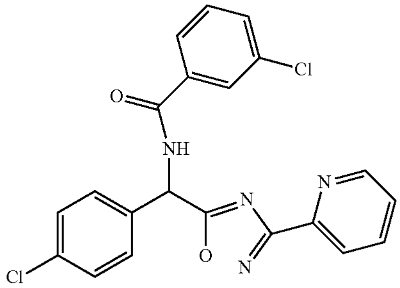 [SMILES: N=C(/N=C(\O)C(NC(=O)c1cccc(Cl)c1)c1ccc(Cl)cc1)c1ccccn1] | >50 | >50 | 2.9 | >50 | >50 |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52386 IB | 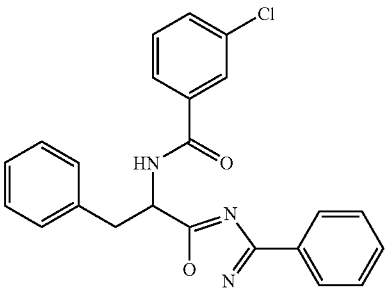 [SMILES: N=C(/N=C(\O)C(Cc1ccccc1)NC(=O)c1cccc(Cl)c1)c1ccccc1] | >50 | 43.7 | 5.7 | 21.6 | 12.4 |
| 52387 IB | 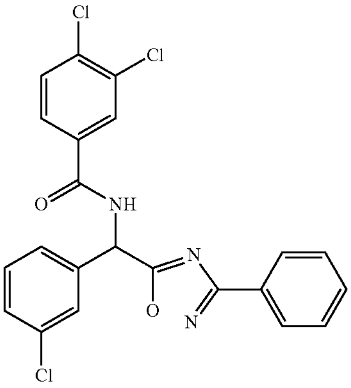 [SMILES: N=C(/N=C(\O)C(NC(=O)c1ccc(Cl)c(Cl)c1)c1cccc(Cl)c1)c1ccccc1] | 0.392 | >50 | 0.229 | >50 | >50 |
| 52388 IB | 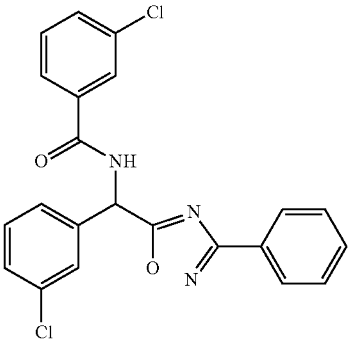 [SMILES: N=C(/N=C(\O)C(NC(=O)c1cccc(Cl)c1)c1cccc(Cl)c1)c1ccccc1] | 0.456 | >50 | 0.104 | 5.2 | 5.1 |
| 52389 IB | 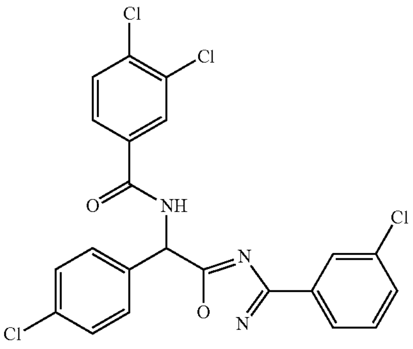 [SMILES: N=C(/N=C(\O)C(NC(=O)c1ccc(Cl)c(Cl)c1)c1ccc(Cl)cc1)c1cccc(Cl)c1] | — | >50 | 5.3 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52390 IB | 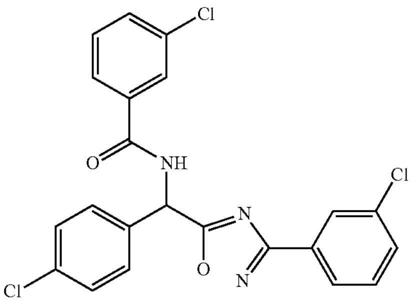 [SMILES: N=C(/N=C(\O)C(NC(=O)c1cccc(Cl)c1)c1ccc(Cl)cc1)c1cccc(Cl)c1] | >50 | >50 | 1.1 | >50 | >50 |
| 52391 IB | 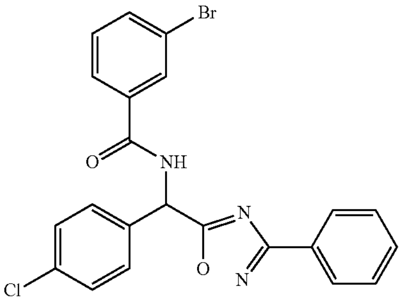 | 9.5 | >50 | 0.278 | 30.5 | 16.1 |
| 52392 IB | 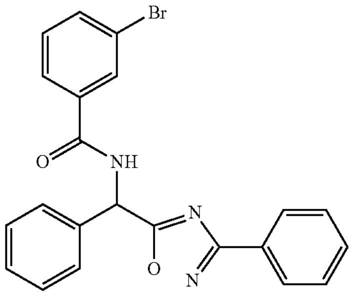 | 0.564 | >50 | 0.108 | >50 | >50 |
| 52393 IC | 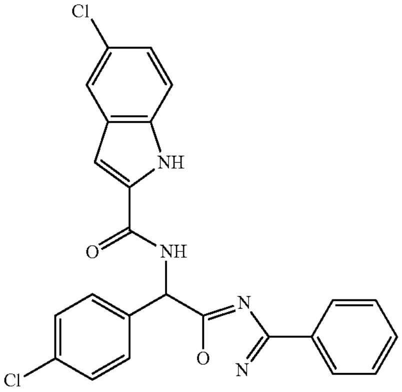 [SMILES: N=C(/N=C(\O)C(NC(=O)c1cc2cc(Cl)ccc2[nH]1)c1ccc(Cl)cc1)c1ccccc1] | — | >50 | 6.4 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52401 IB | 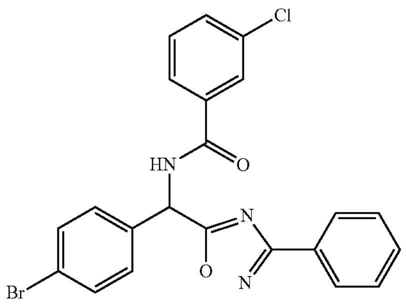 | — | >50 | 0.226 | 21.2 | — |
| 52402 IB | 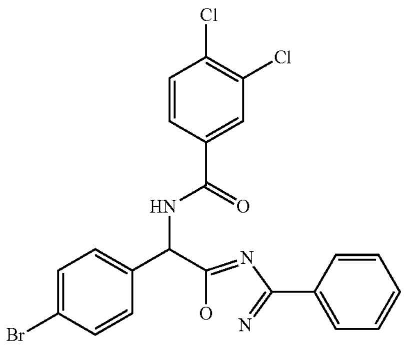 [SMILES: N=C(/N=C(\O)C(NC(=O)c1ccc(Cl)c(Br)c1)c1ccc(Cl)cc1)c1ccccc1] | >50 | >50 | 0.214 | >50 | >50 |
| 52403 IB | 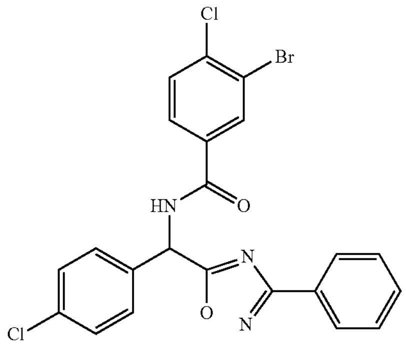 | 10.1 | >50 | 0.39 | >50 | >50 |
| 52404 IB | 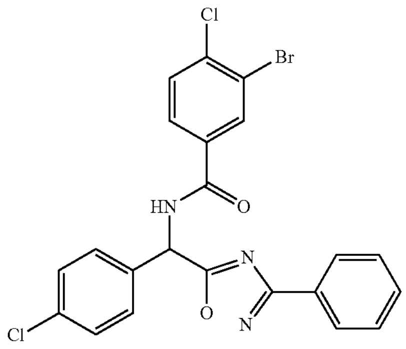 [SMILES: N=C(/N=C(\O)C(NC(=O)c1ccc(Cl)c(Br)c1)c1ccc(Cl)cc1)c1ccccc1] | — | >50 | 0.376 | 37.9 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52405 IB | 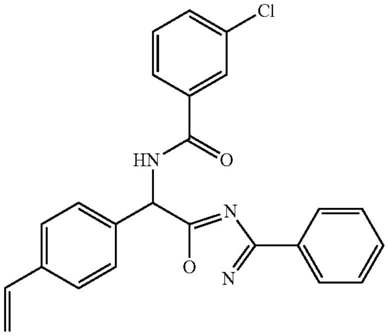 [SMILES: C=Cc1ccc(C(NC(=O)c2cccc(Cl)c2)/C(O)=N/C(=N)c2ccccc2)cc1] | — | >50 | 2.0 | >50 | — |
| 542406 IB | 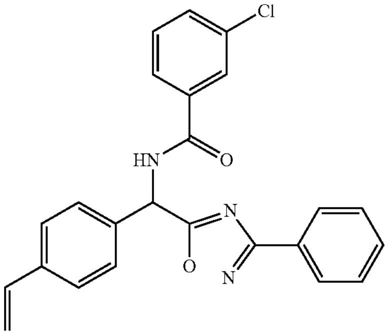 [SMILES: C=Cc1ccc(C(NC(=O)c2cccc(Cl)c2)/C(O)=N/C(=N)c2ccccc2)cc1] | >50 | >50 | 0.406 | >50 | >50 |
| 52407 IB | 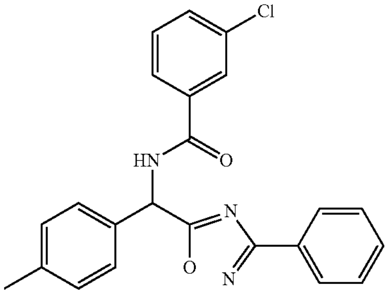 [SMILES: Cc1ccc(C(NC(=O)c2cccc(Cl)c2)/C(O)=N/C(=N)c2ccccc2)cc1] | 4.0 | >50 | 0.219 | >50 | 39.4 |
| 52408 IB | 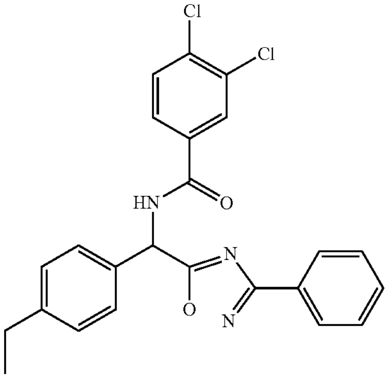 [SMILES: CCc1ccc(C(NC(=O)c2ccc(Cl)c(Cl)c2)/C(O)=N/C(=N)c2ccccc2)cc1] | — | >50 | 0.898 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52409 IB | 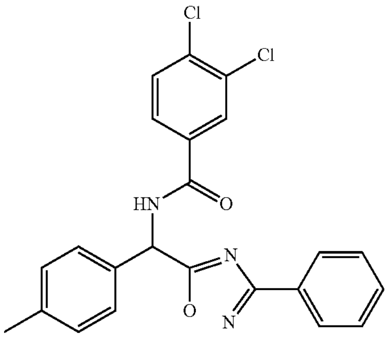 [SMILES: Cc1ccc(C(NC(=O)c2ccc(Cl)c(Cl)c2)/C(O)=N/C(=N)c2ccccc2)cc1] | — | >50 | 0.381 | >50 | — |
| 52412 IB | 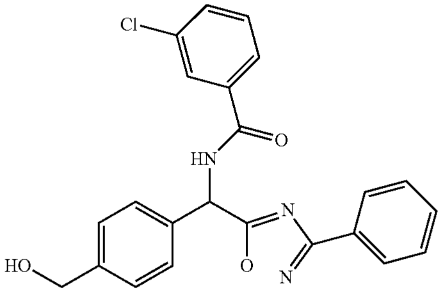 [SMILES: N=C(/N=C(\O)C(NC(=O)c1cccc(Cl)c1)c1ccc(CO)cc1)c1ccccc1] | — | >50 | 3.7 | 24.2 | — |
| 52415 IC | 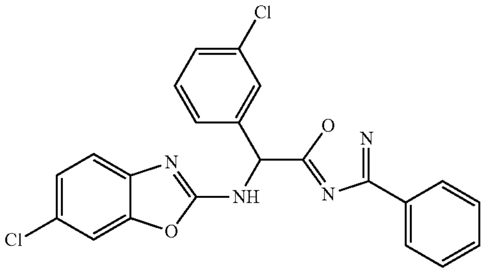 [SMILES: N=C(/N=C(\O)C(Nc1nc2ccc(Cl)cc2o1)c1cccc(Cl)c1)c1ccccc1] | — | >50 | 0.556 | 25.4 | — |
| 52416 IC | 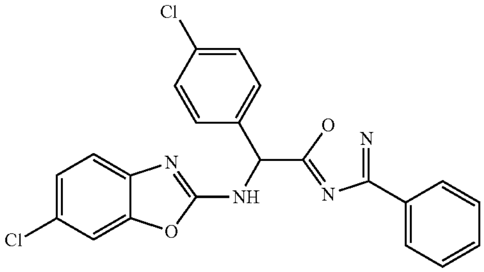 [SMILES: N=C(/N=C(\O)C(Nc1nc2ccc(Cl)cc2o1)c1ccc(Cl)cc1)c1ccccc1] | — | >50 | 0.411 | 22.2 | — |
| 52419 IB | 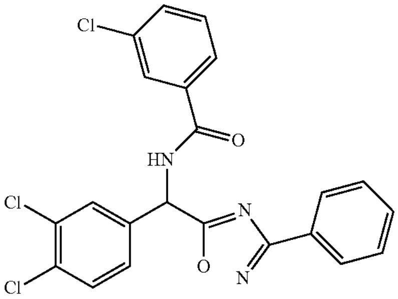 [SMILES: N=C(/N=C(\O)C(NC(=O)c1cccc(Cl)c1)c1ccc(Cl)c(Cl)c1)c1ccccc1] | 0.823 | >50 | 0.053 | 34.6 | 20 |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52420 IB | 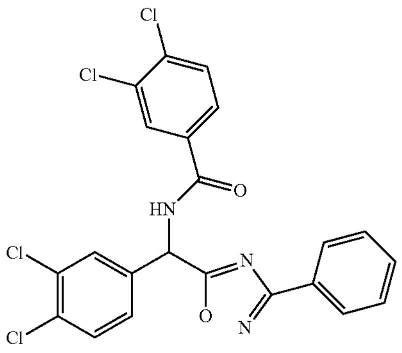 [SMILES: N=C(/N=C(\O)C(NC(=O)c1ccc(Cl)c(Cl)c1)c1ccc(Cl)c(Cl)c1)c1ccccc1] | 0.426 | >50 | 0.066 | >50 | >50 |
| 52421 IB | 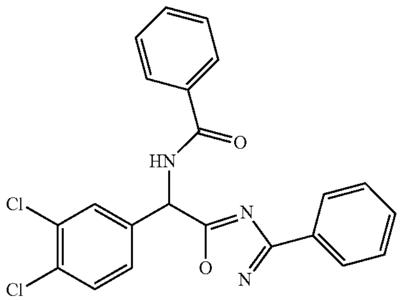 [SMILES: N=C(/N=C(\O)C(NC(=O)c1ccccc1)c1ccc(Cl)c(Cl)c1)c1ccccc1] | 2.7 | >50 | 0.211 | >50 | >50 |
| 52426 IB | 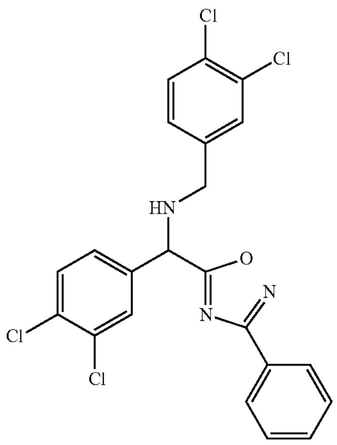 [SMILES: N=C(/N=C(\O)C(NCc1ccc(Cl)c(Cl)c1)c1ccc(Cl)c(Cl)c1)c1ccccc1] | — | >50 | 2.15 | >50 | — |
| 52427 IB | 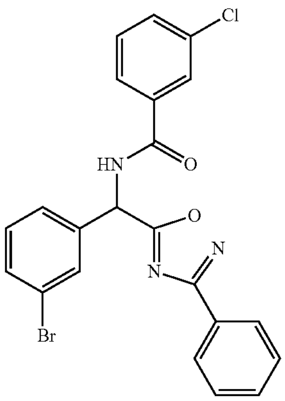 [SMILES: N=C(/N=C(\O)C(NC(=O)c1cccc(Cl)c1)c1cccc(Br)c1)c1ccccc1] | — | >50 | 0.111 | 17.5 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52428 IB | 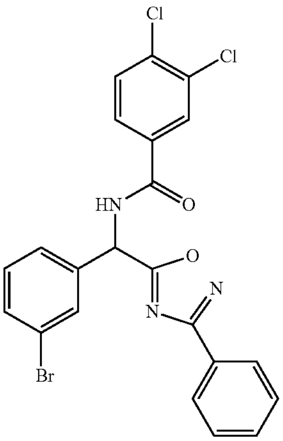 [SMILES: N=C(/N=C(\O)C(NC(=O)c1ccc(Cl)c(Cl)c1)c1cccc(Br)c1)c1ccccc1] | — | >50 | 0.198 | 23.3 | — |
| 52429 IB | 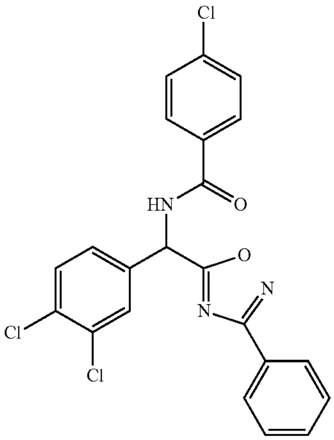 [SMILES: N=C(/N=C(\O)C(NC(=O)c1ccc(Cl)cc1)c1ccc(Cl)c(Cl)c1)c1ccccc1] | 1.2 | >50 | 0.076 | 38.5 | 16.2 |
| 52430 IB | 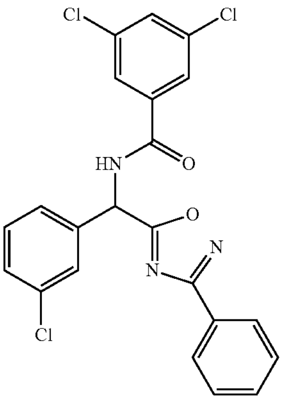 [SMILES: N=C(/N=C(\O)C(NC(=O)c1cc(Cl)cc(Cl)c1)c1cccc(Cl)c1)c1ccccc1] | 0.112 | >50 | 0.033 | >50 | >50 |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52436 IB | 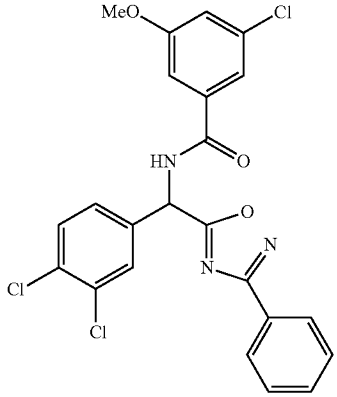 [SMILES: COc1cc(Cl)cc(C(=O)NC(/C(O)=N/C(=N)c2ccccc2)c2ccc(Cl)c(Cl)c2)c1] | — | >50 | 0.264 | >50 | — |
| 52438 IB | 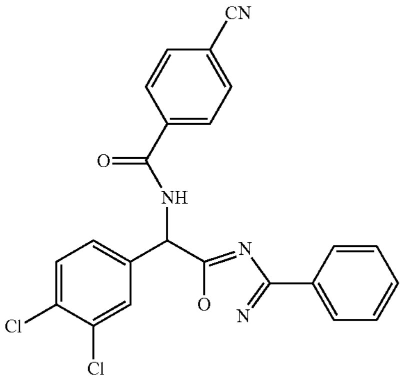 [SMILES: N#Cc1ccc(C(=O)NC(/C(O)=N/C(=N)c2ccccc2)c2ccc(Cl)c(Cl)c2)cc1] | 9.6 | >50 | 0.32 | 3.1 | 17.1 |
| 52439 IB | 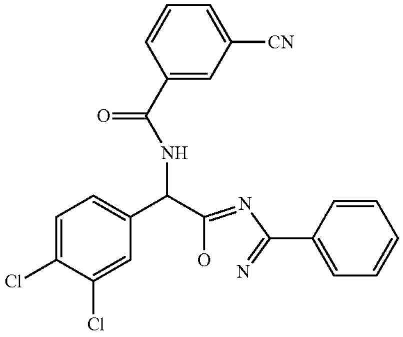 [SMILES: N#Cc1cccc(C(=O)NC(/C(O)=N/C(=N)c2ccccc2)c2ccc(Cl)c(Cl)c2)c1] | — | >50 | 0.584 | 44.8 | — |
| 52440 IB | 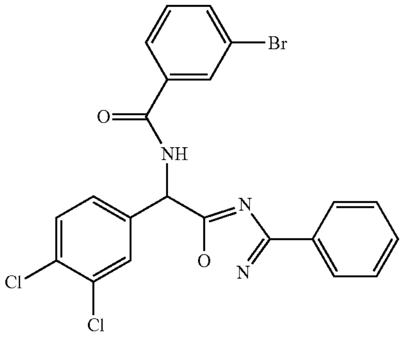 [SMILES: N=C(/N=C(\O)C(NC(=O)c1cccc(Br)c1)c1ccc(Cl)c(Cl)c1)c1ccccc1] | — | >20 | 0.086 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52441 IB | 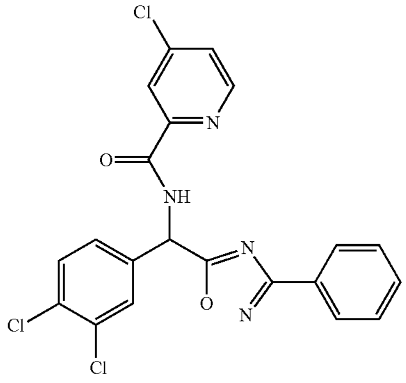 [SMILES: N=C(/N=C(\O)C(NC(=O)c1cc(Cl)ccn1)c1ccc(Cl)c(Cl)c1)c1ccccc1] | — | >30 | 2.5 | 20.3 | — |
| 52445 IB | 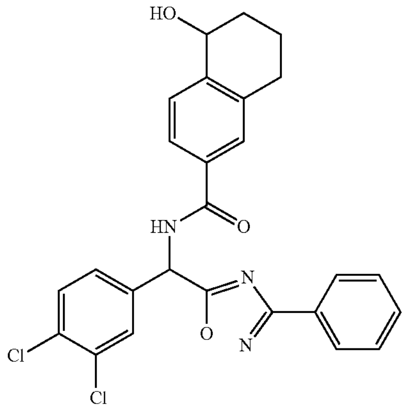 [SMILES: N=C(/N=C(\O)C(NC(=O)c1ccc2c(c1)CCCC2O)c1ccc(Cl)c(Cl)c1)c1ccccc1] | — | >50 | 1.5 | 17.1 | — |
| 52446 IC | 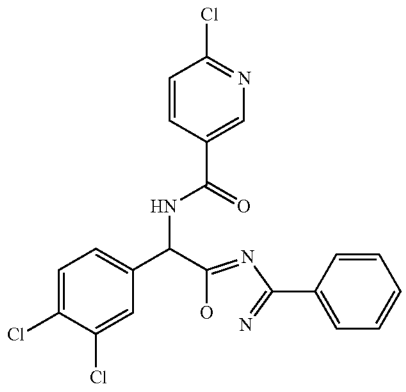 [SMILES: N=C(/N=C(\O)C(NC(=O)c1ccc(Cl)nc1)c1ccc(Cl)c(Cl)c1)c1ccccc1] | — | 22.7 | 0.370 | 9.2 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52447 IB | 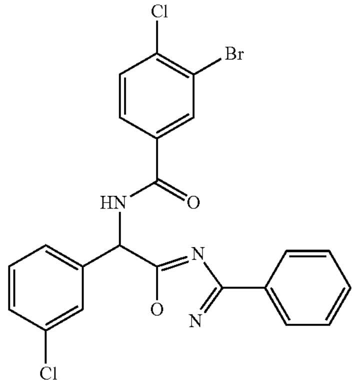 [SMILES: N=C(/N=C(\O)C(NC(=O)c1ccc(Cl)c(Br)c1)c1cccc(Cl)c1)c1ccccc1] | — | >50 | 0.26 | >50 | — |
| 52449 IB | 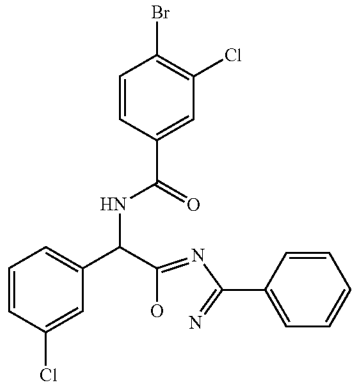 | — | >50 | 0.219 | 16.3 | — |
| 52450 IB | 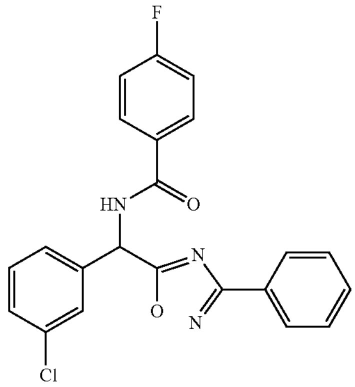 [SMILES: N=C(/N=C(\O)C(NC(=O)c1ccc(F)cc1)c1cccc(Cl)c1)c1ccccc1] | — | >50 | 0.184 | 19.2 | — |
| 52451 IB | 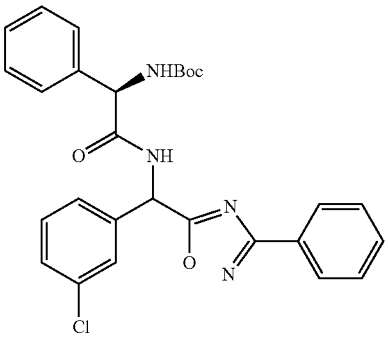 [SMILES: CC(C)(C)OC(=O)N[C@@H](C(=O)NC(/C(O)=N/C(=N)c1ccccc1)c1cccc(Cl)c1)c1ccccc1] | — | 8.7 | 0.475 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52453 IB | 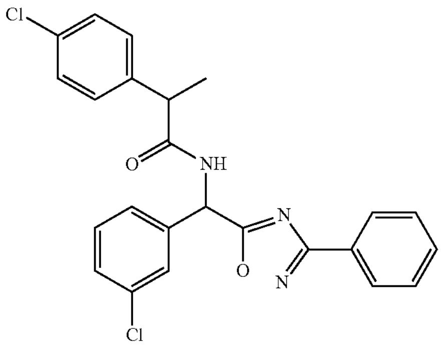 [SMILES: CC(C(=O)NC(/C(O)=N/C(=N)c1ccccc1)c1cccc(Cl)c1)c1ccc(Cl)cc1] | — | 10.9 | 0.215 | 6.7 | — |
| 52454 IB | 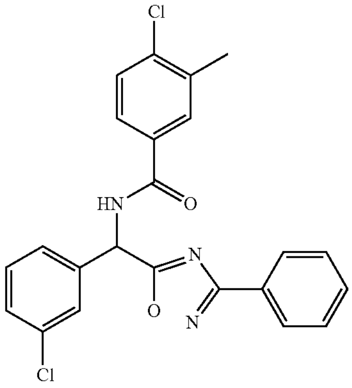 [SMILES: Cc1cc(C(=O)NC(/C(O)=N/C(=N)c2ccccc2)c2cccc(Cl)c2)ccc1Cl] | — | >50 | 0.24 | >50 | — |
| 52455 IB | 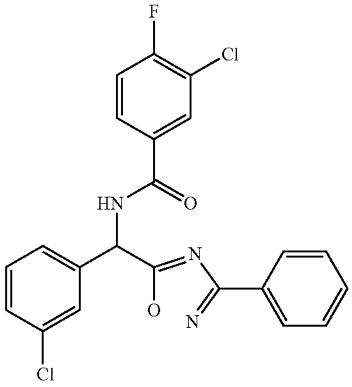 [SMILES: N=C(/N=C(\O)C(NC(=O)c1ccc(F)c(Cl)c1)c1cccc(Cl)c1)c1ccccc1] | — | >50 | 0.091 | 12.4 | — |
| 52456 IB | 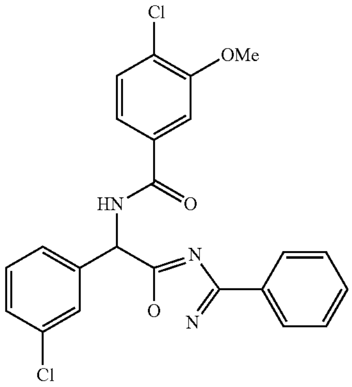 [SMILES: COc1cc(C(=O)NC(/C(O)=N/C(=N)c2ccccc2)c2cccc(Cl)c2)ccc1Cl] | — | >50 | 0.201 | 38.4 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52457 IB | 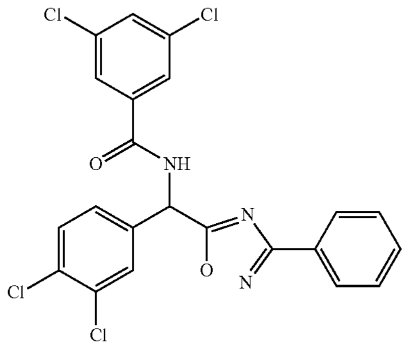 [SMILES: N=C(/N=C(\O)C(NC(=O)c1cc(Cl)cc(Cl)c1)c1ccc(Cl)c(Cl)c1)c1ccccc1] | — | >50 | 0.06 | >50 | — |
| 52461 IC | 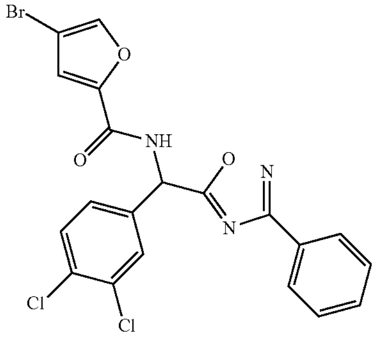 [SMILES: N=C(/N=C(\O)C(NC(=O)c1cc(Br)co1)c1ccc(Cl)c(Cl)c1)c1ccccc1] | — | >50 | 0.045 | 19.9 | — |
| 52462 IC | 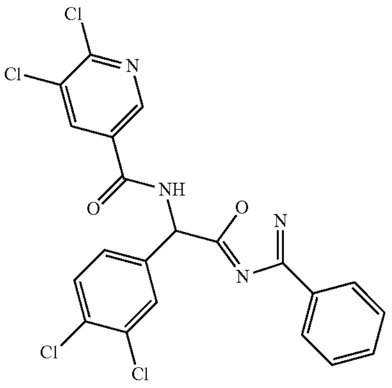 [SMILES: N=C(/N=C(\O)C(NC(=O)c1cnc(Cl)c(Cl)c1)c1ccc(Cl)c(Cl)c1)c1ccccc1] | — | 35 | 6.6 | 42.3 | 29.5 |
| 52463 IB | 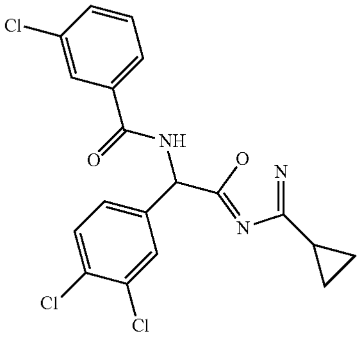 [SMILES: N=C(/N=C(\O)C(NC(=O)c1cccc(Cl)c1)c1ccc(Cl)c(Cl)c1)C1CC1] | — | 43.1 | 0.341 | 15.5 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52465 IB | 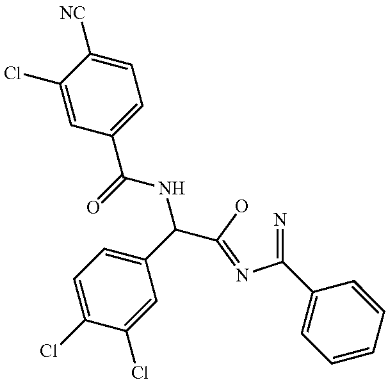 [SMILES: N#Cc1ccc(C(=O)NC(/C(O)=N/C(=N)c2ccccc2)c2ccc(Cl)c(Cl)c2)cc1Cl] | — | 44.5 | 0.175 | 8.6 | — |
| 52466 IC | 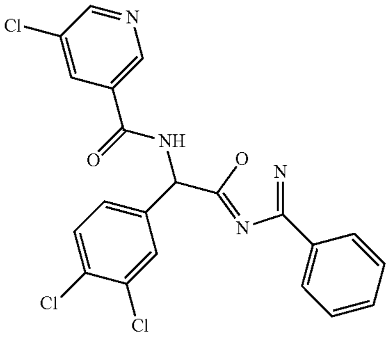 [SMILES: N=C(/N=C(\O)C(NC(=O)c1cncc(Cl)c1)c1ccc(Cl)c(Cl)c1)c1ccccc1] | — | >50 | 1.1 | 28.7 | — |
| 52469 IB | 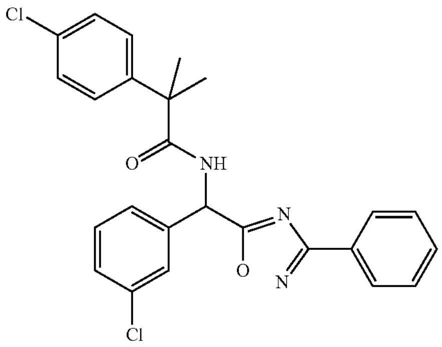 [SMILES: CC(C)(C(=O)NC(/C(O)=N/C(=N)c1ccccc1)c1cccc(Cl)c1)c1ccc(Cl)cc1] | 6.2 | 10.5 | 1.4 | 15.7 | — |
| 52470 IB | 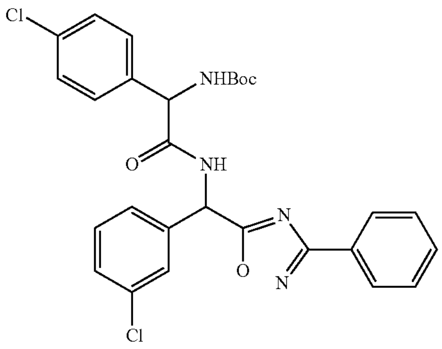 [SMILES: CC(C)(C)OC(=O)NC(C(=O)NC(/C(O)=N/C(=N)c1ccccc1)c1cccc(Cl)c1)c1ccc(Cl)cc1] | 20.1 | >50 | 0.382 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52471 IB | 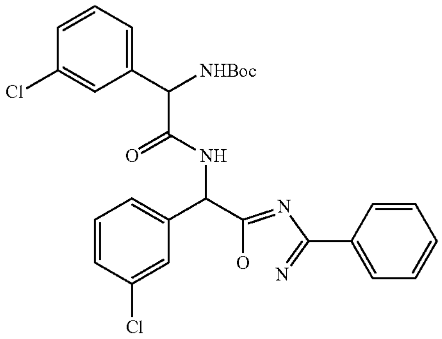 [SMILES: CC(C)(C)OC(=O)NC(C(=O)NC(/C(O)=N/C(=N)c1ccccc1)c1cccc(Cl)c1)c1cccc(Cl)c1] | 0.475 | 31.1 | 0.214 | >50 | — |
| 52472 IB | 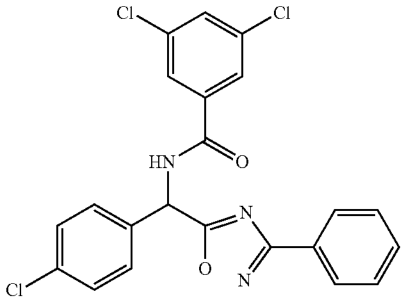 [SMILES: N=C(/N=C(\O)C(NC(=O)c1cc(Cl)cc(Cl)c1)c1ccc(Cl)cc1)c1ccccc1] | >28 | >50 | 0.113 | >50 | — |
| 52473 IB | 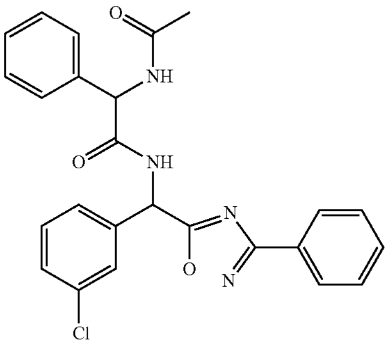 [SMILES: CC(=O)NC(C(=O)NC(/C(O)=N/C(=N)c1ccccc1)c1cccc(Cl)c1)c1ccccc1] | >28 | >50 | 1.7 | >50 | — |
| 52477 IB | 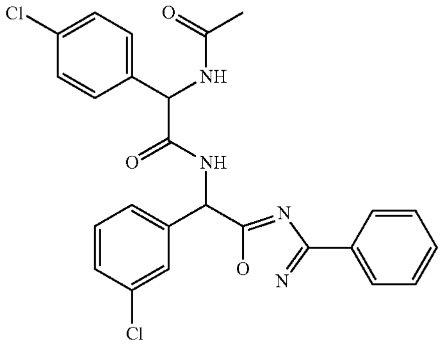 [SMILES: CC(=O)NC(C(=O)NC(/C(O)=N/C(=N)c1ccccc1)c1cccc(Cl)c1)c1ccc(Cl)cc1] | >28 | >50 | 3.2 | >50 | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52478 IB | 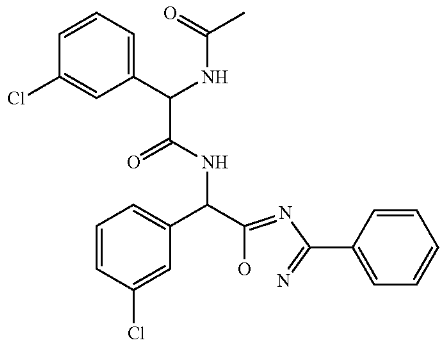 [SMILES: CC(=O)NC(C(=O)NC(/C(O)=N/C(=N)c1ccccc1)c1cccc(Cl)c1)c1cccc(Cl)c1] | 17.9 | >50 | 1.1 | >50 | — |
| 52479 IB | 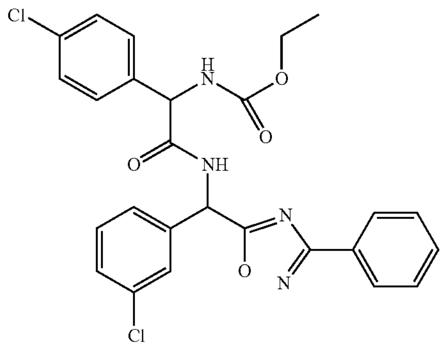 [SMILES: CCOC(=O)NC(C(=O)NC(/C(O)=N/C(=N)c1ccccc1)c1cccc(Cl)c1)c1ccc(Cl)cc1] | 1.2 | >50 | 0.31 | >50 | — |
| 52480 IB | 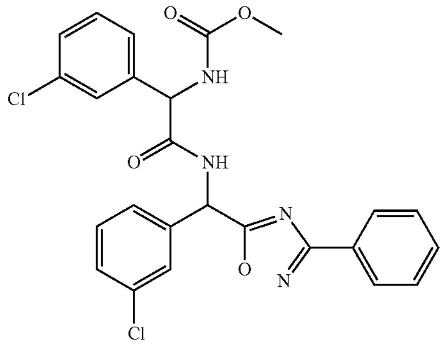 [SMILES: COC(=O)NC(C(=O)NC(/C(O)=N/C(=N)c1ccccc1)c1cccc(Cl)c1)c1cccc(Cl)c1] | 0.39 | >50 | 0.147 | >50 | — |
| 52481 IB | 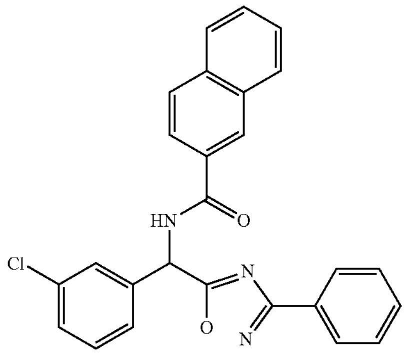 [SMILES: N=C(/N=C(\O)C(NC(=O)c1ccc2ccccc2c1)c1cccc(Cl)c1)c1ccccc1] | 1.5 | >50 | 0.425 | >50 | — |

TABLE 3-continued
| CYM Generic formula | Structure | S1P1 AA IC50 μM | S1P2 AA IC50 μM | S1P3AA IC50 μM | S1P4AA IC50 μM | S1P5AA IC50 μM |
|---|---|---|---|---|---|---|
| 52482 IB | 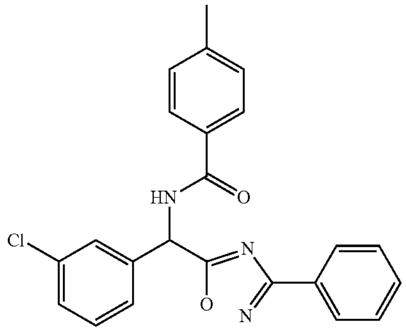 [SMILES: Cc1ccc(C(=O)NC(/C(O)=N/C(=N)c2ccccc2)c2cccc(Cl)c2)cc1] | 3.5 | >50 | 0.319 | >50 | — |
| 52485 IC | 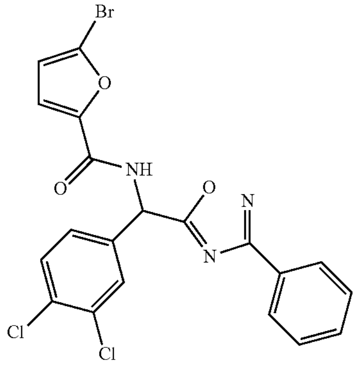 [SMILES: N=C(/N=C(\O)C(NC(=O)c1ccc(Br)o1)c1ccc(Cl)c(Cl)c1)c1ccccc1] | 3.5 | >50 | 0.984 | >50 | — |
| 52498 IB | 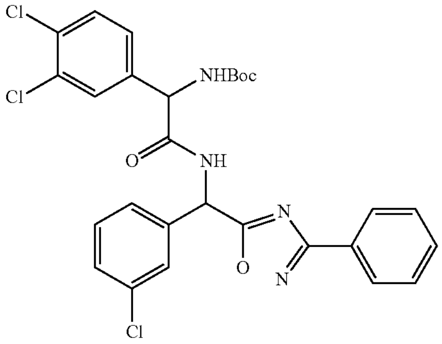 [SMILES: CC(C)(C)OC(=O)NC(C(=O)NC(/C(O)=N/C(=N)c1ccccc1)c1cccc(Cl)c1)c1ccc(Cl)c(Cl)c1] | 34.3 | — | 0.166 | — | — |
| 52499 IB | 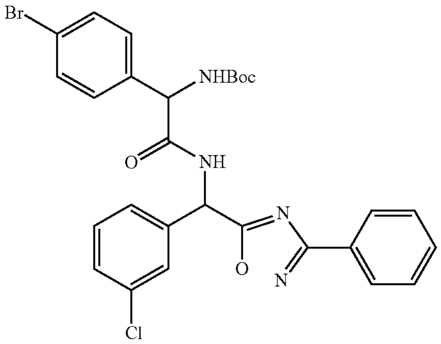 | 40.5 | — | 0.429 | — | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52500 IB | 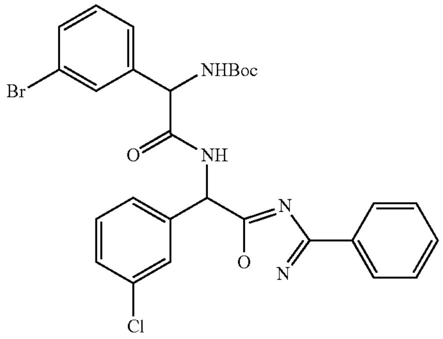 | 0.959 | — | 0.095 | — | — |
| 52501 IB | 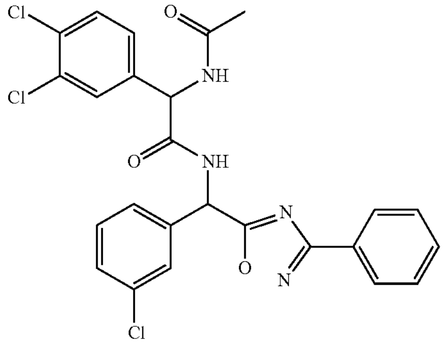 [SMILES: CC(=O)NC(C(=O)NC(/C(O)=N/C(=N)c1ccccc1)c1cccc(Cl)c1)c1ccc(Cl)c(Cl)c1] | 22.2 | — | 0.839 | — | — |
| 52502 IB | 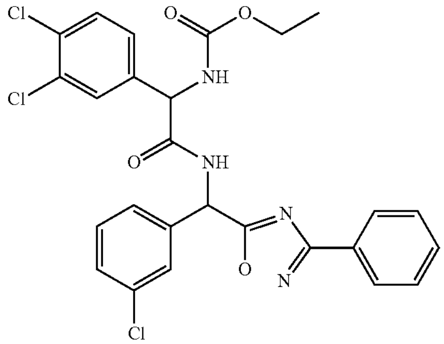 [SMILES: CCOC(=O)NC(C(=O)NC(/C(O)=N/C(=N)c1ccccc1)c1cccc(Cl)c1)c1ccc(Cl)c(Cl)c1] | 1.4 | — | 0.109 | — | — |
| 52503 IB | 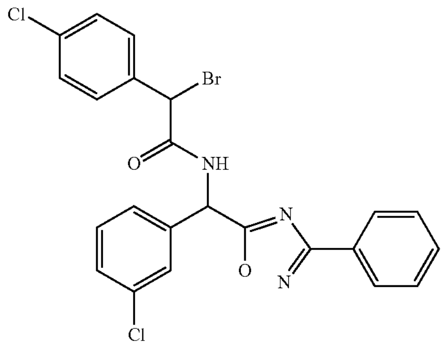 | 0.527 | — | 0.147 | — | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52515 IB | 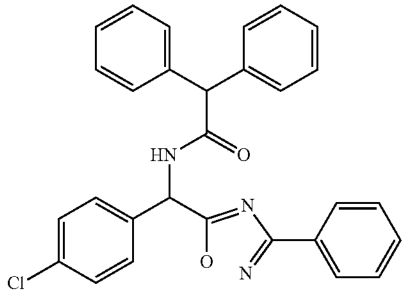 [SMILES: N=C(/N=C(\O)C(NC(=O)C(c1ccccc1)c1ccccc1)c1ccc(Cl)cc1)c1ccccc1] | >50 | — | 0.685 | — | — |
| 52518 IC | 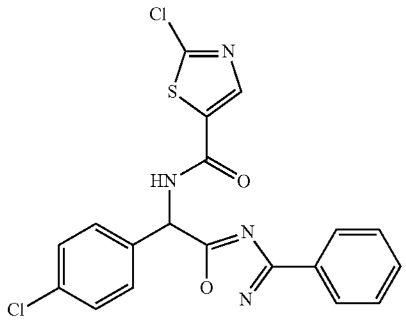 [SMILES: N=C(/N=C(\O)C(NC(=O)c1cnc(Cl)s1)c1ccc(Cl)cc1)c1ccccc1] | 9.8 | — | 1.5 | — | — |
| 52519 IB | 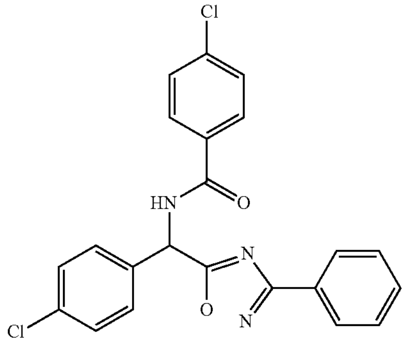 [SMILES: N=C(/N=C(\O)C(NC(=O)c1ccc(Cl)cc1)c1ccc(Cl)cc1)c1ccccc1] | >50 | — | 0.194 | — | — |
| 52532 IB | 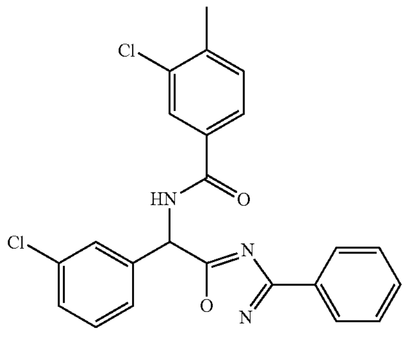 [SMILES: Cc1ccc(C(=O)NC(/C(O)=N/C(=N)c2ccccc2)c2cccc(Cl)c2)cc1Cl] | 2.0 | — | 0.405 | — | — |

TABLE 3-continued
| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52534 IB | 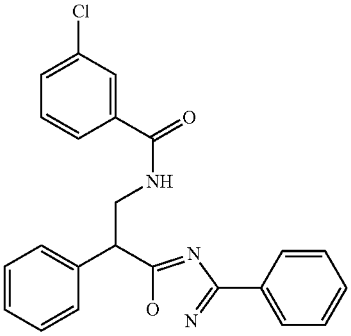 [SMILES: N=C(/N=C(\O)C(CNC(=O)c1cccc(Cl)c1)c1ccccc1)c1ccccc1] | 8.4 | — | 2.2 | — | — |
| 52536 IC | 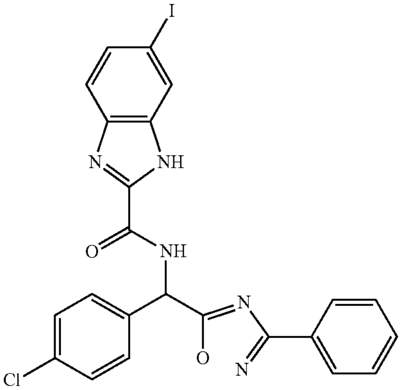 [SMILES: N=C(/N=C(\O)C(NC(=O)c1nc2ccc(I)cc2[nH]1)c1ccc(Cl)cc1)c1ccccc1] | >50 | — | 4.9 | — | — |
| 52569 IB | 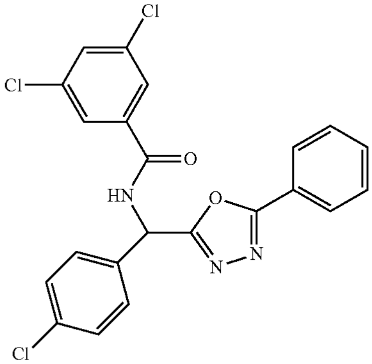 [SMILES: O=C(NC(c1ccc(Cl)cc1)c1nnc(-c2ccccc2)o1)c1cc(Cl)cc(Cl)c1] | >28 | — | 2.2 | — | — |
| 52636 IB | 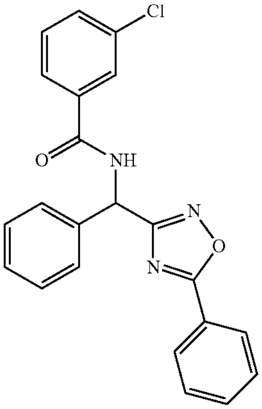 [SMILES: O=C(NC(c1ccccc1)c1noc(-c2ccccc2)n1)c1cccc(Cl)c1] | 1.9 | — | 0.098 | — | — |

TABLE 3-continued

| CYM Generic formula | Structure | S1P1 AA $IC_{50}$ μM | S1P2 AA $IC_{50}$ μM | S1P3AA $IC_{50}$ μM | S1P4AA $IC_{50}$ μM | S1P5AA $IC_{50}$ μM |
|---|---|---|---|---|---|---|
| 52648 IB | 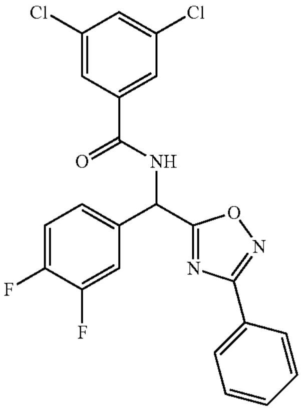 | 0.401 | — | 0.046 | — | — |
| 52588 IB | 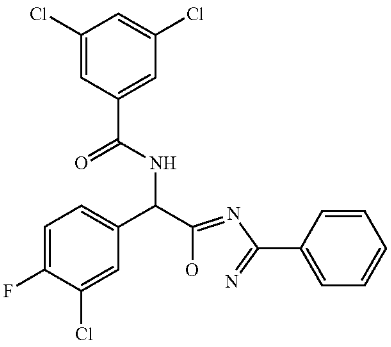 [SMILES: N=C(/N=C(\O)C(NC(=O)c1cc(Cl)cc(Cl)c1)c1ccc(F)c(Cl)c1)c1ccccc1] | 0.392 | — | 0.047 | — | — |

Boc = t-butoxycarbonyl
Ph = phenyl
Rac = racemate; all compounds as shown include all stereoisomers unless otherwise indicated.
Isomer 1, isomer 2; indicates separated stereoisomers of a structure, but absolute configuration unstated.

General Synthetic Schemes:

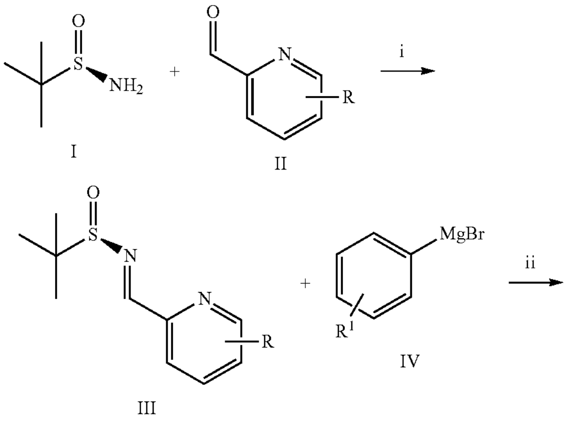

-continued

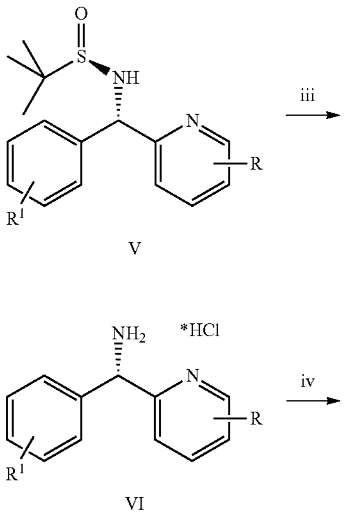

-continued

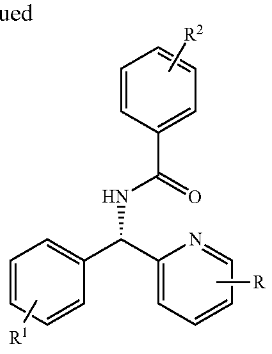

VII

Reagents and conditions: i) I (1.2 equiv.), II (1 equiv.), $Ti(OEt)_4$, 70° C., 30 min; ii) III (1 equiv.), IV (3 equiv.), -78° C., 2 h; iii) HCl (2 equiv.), MeOH, rt, 30 min; iv) VI (1 equiv.), carboxylic acid derivative (1.2 equiv.), EDCI (1.2 equiv.), HOBt (1.2 equiv.), DIPEA (1.2 equiv.), $CH_2Cl_2$, rt, 2 h.

A mixture of I, II and $Ti(OEt)_4$ in a sealed tube was heated at 70° C. for 30 min. The mixture was dissolved in EtOAc and washed with brine. The organic phase was dried over anhydrous $Na_2SO_4$ and concentrated under reduced pressure. The product III was used without further purification. To a solution of III in THF at −78° C. was slowly added aryl magnesium bromide IV and the reaction was stirred for 2 h. The mixture was quenched with a saturated solution of ammonium chloride and the product extracted with EtOAc. The organic phase was dried over anhydrous $Na_2SO_4$ and concentrated in vacuo, followed by the purification of product V by column chromatography (CC) using hexanes/EtOAc. To a solution of V in MeOH was added a 4M solution of HCl in dioxane and the reaction was stirred for 30 min at room temperature (rt). The mixture was concentrated under reduced pressure and the product VI used without further purification. A solution of VI, the appropriated carboxylic acid, EDCI, HOBt and DIPEA in dichloromethane was stirred at rt for 2 h. The mixture was concentrated under reduced pressure and the product VII purified by HPLC.

A mixture of the appropriate aryl chloride (VIII or X), VI and DIPEA in EtOH was heated with microwave irradiation at 130° C. for 30 minutes to afford the corresponding products (IX or XI) that were purified by HPLC.

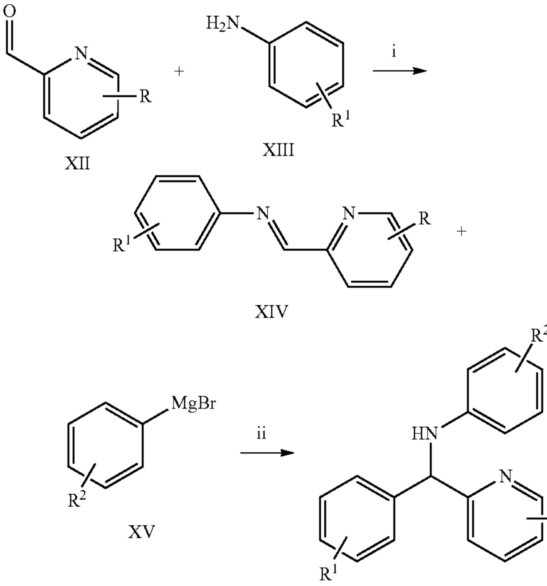

XII XIII XIV XV XVI

Reagents and conditions: i) XII (1 equiv.), XIII (1 equiv.), $HCO_2H$ (cat.), EtOH, 60° C., overnight; ii) XIV (1 equiv.), XV (1 equiv.), THF, 0° C. to rt, overnight A mixture of XII, XIII and catalytic amount of formic acid in EtOH was heated at 60° C. overnight. The crude was concentrated and purified by CC using hexanes/EtOAc. To a solution of XIV in THF at 0° C. was added dropwise a solution of XV in $Et_2O$; the reaction mixture was stirred overnight at it. The mixture was quenched with a saturated solution of ammonium chloride and the product extracted

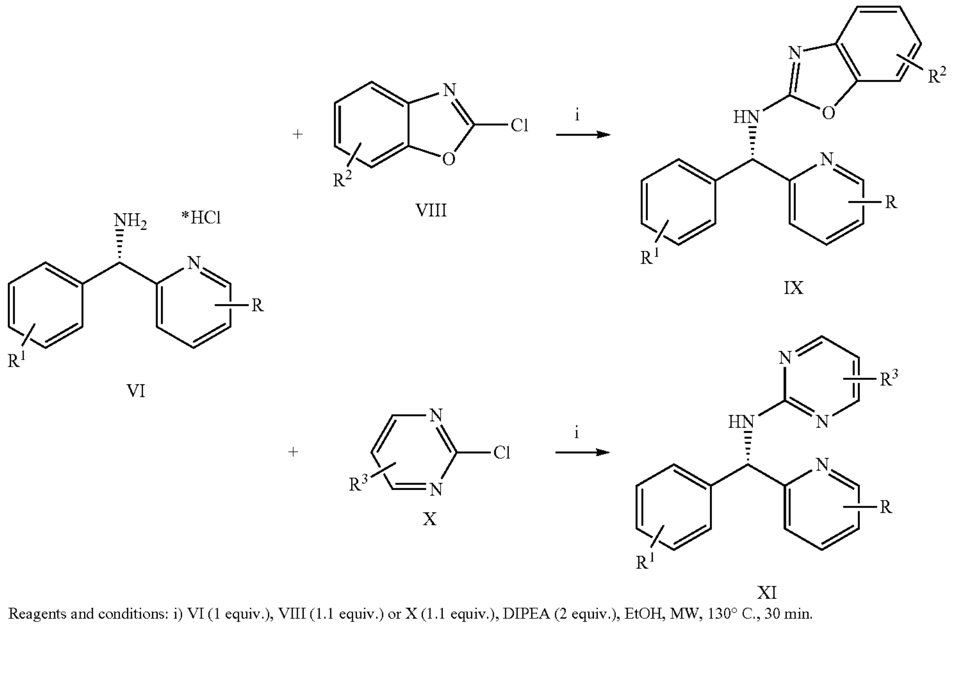

VIII IX VI X XI

Reagents and conditions: i) VI (1 equiv.), VIII (1.1 equiv.) or X (1.1 equiv.), DIPEA (2 equiv.), EtOH, MW, 130° C., 30 min.

with EtOAc. The organic phase was dried over anhydrous $Na_2SO_4$ and concentrated under reduced pressure. The product XVI was purified by CC using hexanes/EtOAc or HPLC.

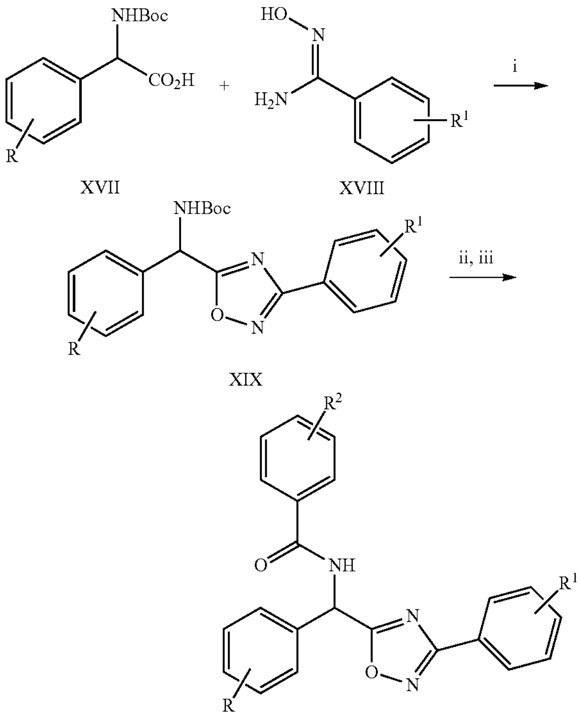

Reagents and conditions: i) XVII (1 equiv.), XVIII (1.2 equiv.), EDCI (1.2 equiv.), HOBt (1.2 equiv.), dioxane, MW, 110° C., 30 min; ii) XIX (1 equiv.), TFA (20 equiv.) $CH_2Cl_2$, rt, 20 min; iii) carboxylic acid derivative (1.2 equiv.), EDCI (1.2 equiv.), HOBt (1.2 equiv.), DIPEA (1.2 equiv.), $CH_2Cl_2$, rt, 2 h.

In a microwave vial a stirring solution of XVII in dioxane was treated with HOBt and EDCI at rt. The reaction was stirred for 10 minutes followed by the addition of XVIII. The reaction was stirred for additional 30 minutes at rt, then heated to 110° C. under microwave irradiation for 30 minutes. To the reaction was added brine and the product was extracted with EtOAc (3×). The organic phase was dried over anhydrous $Na_2SO_4$ and concentrated under reduced pressure. The product XIX was purified by CC using hexanes/EtOAc. A solution of XIX in dichloromethane was stirred with TFA at rt for 20 minutes. The mixture was concentrated under reduced pressure and the product used without further purification. A solution of the TFA salt, the appropriate carboxylic acid, EDCI, HOBt and DIPEA in dichloromethane was stirred at rt for 2 h. The mixture was concentrated under reduced pressure and the product XX purified by HPLC.

What is claimed is:

1. A compound of formula (TB)

(IB)

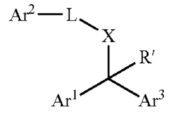

wherein $Ar^1$ and $Ar^2$ are each independently selected (C6-C10)aryl and $Ar^3$ is a (5- to 10-membered)heteroaryl;

wherein any aryl or heteroaryl ring system of AO, $Ar^2$, or $Ar^3$ is optionally fused with a cycloalkyl or a heterocyclyl ring;

wherein any aryl or heteroaryl of $Ar^1$, $Ar^2$, or $Ar^3$ is each optionally independently mono- or multi-substituted with up to three substituents selected from the group consisting of (C1-C4)alkyl, (C2-C4)alkenyl, halo, halo (C1-C4)alkyl, monohydroxy(C1-C4)alkyl, dihydroxy (C2-C4)alkyl, monohydroxy(C1-C4)alkoxy, dihydroxy (C2-C4)alkoxy, (C2-C6)acyl, (C1-C6)alkoxycarbonyl $(CH_2)_{0-2}$, carboxy$(CH_2)_{0-2}$, oxo, cyano, $NR_2(CH_2)_{0-2}$, $NR_2C(=O)(CH_2)_{0-2}$, $NR_2C(=O)(CH_2)_{0-2}O(CH_2)_{0-2}$, (C1-C4)C(=O)N(R), (C1-C4)OC(=O)N(R), C=NOR, (C3-C10)cycloalkyl, (5- to 10-membered) heterocyclyl, (C6-C10)aryl, and (5- to 10-membered) heteroaryl; wherein any cycloalkyl, heterocyclyl, aryl or heteroaryl substituent of AO, $Ar^2$, or $Ar^3$ is itself optionally substituted with up to three secondary substituents selected from the group consisting of (C1-C4) alkyl, (C2-C4)alkenyl, halo, halo(C1-C4)alkyl, OH, monohydroxy(C1-C4)alkyl, dihydroxy(C2-C4)alkyl, monohydroxy(C1-C4)alkoxy, dihydroxy(C2-C4) alkoxy, (C1-C4)alkoxy, (C2-C6)acyl, (C1-C6)alkoxycarbonyl$(CH_2)_{0-2}$, carboxy$(CH_2)_{0-2}$, oxo, cyano, $NR_2$ $(CH_2)_{0-2}$, $NR_2C(=O)(CH_2)_{0-2}$, $NR_2C(=O)(CH_2)_{0-2}O$ $(CH_2)_{0-2}$, (C1-C4)C(=O)N(R), (C1-C4)OC(=O)N (R), and C=NOR;

each R is independently H, (C1-C4)alkyl, hydroxy(C2-C4)alkyl, cyano, or ((C1-C4)alkyl-O)$_{1-2}$(C1-C4)alkyl, or two R groups together with an atom to which they are both joined can form a ring;

each R' is independently H, (C1-C4)alkyl, hydroxy(C2-C4)alkyl, $(CH_2)_{0-2}C(=O)O$(C1-C4)alkyl, or (C3-C6) cycloalkyl;

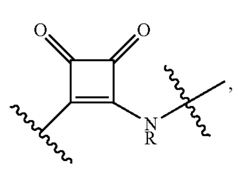, or 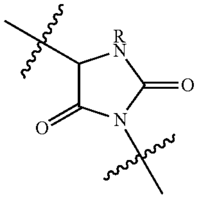

wherein X is NR and L is a bond or is C(=O), or a pharmaceutically acceptable salt thereof.

2. The compound of claim 1, wherein $Ar^3$ is pyridyl or quinolyl.

3. The compound of claim 1, wherein $Ar^1$ and $Ar^2$ are phenyl.

4. A pharmaceutical composition comprising a compound of claim 1 and a pharmaceutically acceptable excipient.

5. A method of treatment of a cardiopulmonary disease in a patient afflicted therewith, comprising administering an effective amount of a compound of claim 1.

6. The method of claim 5, wherein the disease is asthma or a chronic obstructive pulmonary disease.

7. The method of claim 5, wherein the disease comprises sepsis.

8. The method of claim 5, wherein the disease is coronary atherosclerosis.

9. The method of claim 5, wherein the disease comprises a clinical syndrome characterized by bronchoconstriction, pulmonary fibrosis, coronary artery constriction, cytokine amplification by dendritic cells, or the generation of disseminated intravascular coagulopathy.

10. The method of claim 5, wherein the disease comprises inflammation by influenza infection.

11. The method of claim 5, wherein the disease is cardiovascular disease, hypertension (including malignant hypertension), angina, myocardial infarction, cardiac arrhythmias, congestive heart failure, coronary heart disease, atherosclerosis, angina pectoris, dysrhythmias, cardiomyothopy (including hypertropic cardiomyothopy), heart failure, cardiac arrest, bronchitis, asthma, chronic obstructive pulmonary disease, cystic fibrosis, croup, emphysema, pleurisy, pulmonary fibrosis, pneumonia, pulmonary embolus, pulmonary hypertension, mesothelioma, ventricular conduction abnormalities, complete heart block, adult respiratory distress syndrome, sepsis syndrome, idiopathic pulmonary fibrosis, scleroderma, systemic sclerosis, retroperitoneal fibrosis, prevention of keloid formation, or cirrhosis.

12. A compound, comprising any one of the following:

CYM 52167

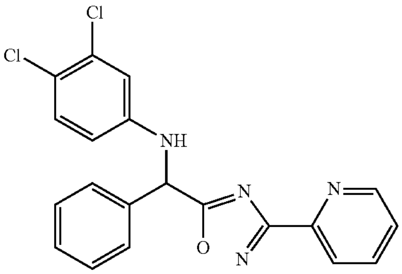

CYM 52205

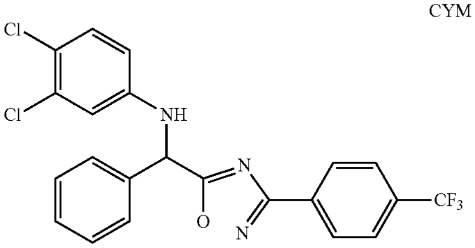

CYM 52207

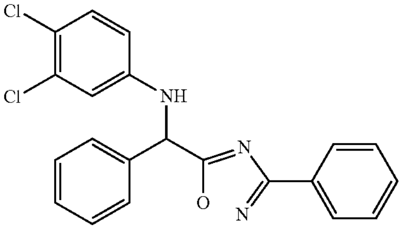

CYM 52246

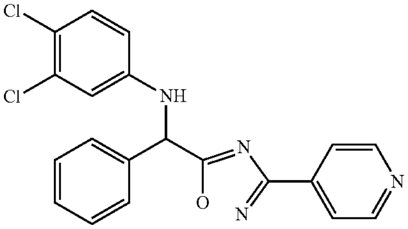

-continued

CYM 52247

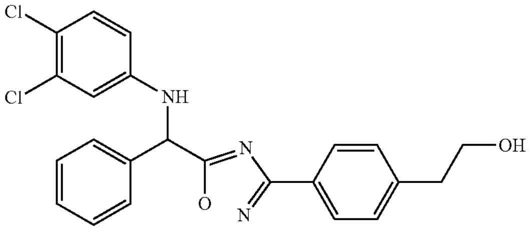

CYM 52248

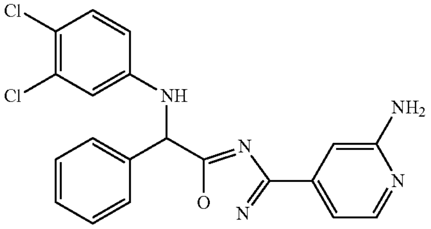

CYM 52249

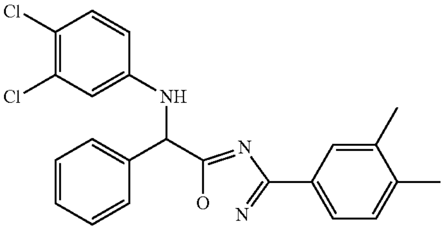

CYM 52250

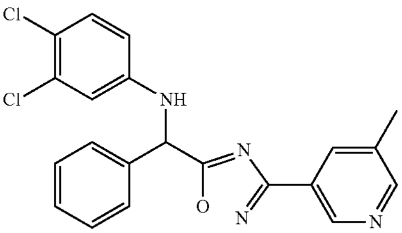

CYM 52251

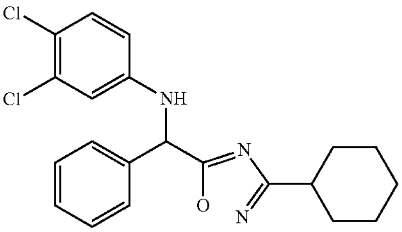

CYM 52255

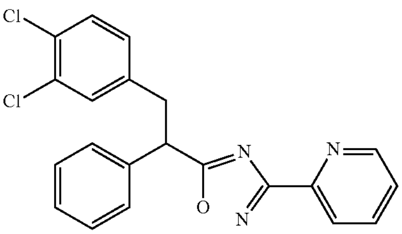

-continued
CYM 52256
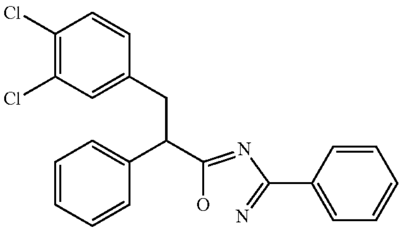
CYM 52257
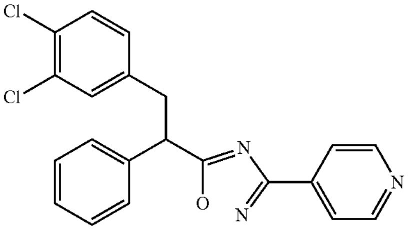
CYM 52258
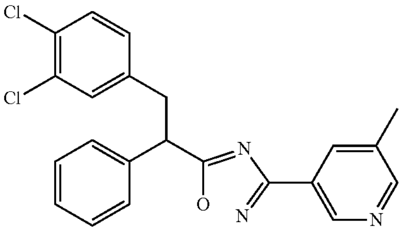
CYM 52264
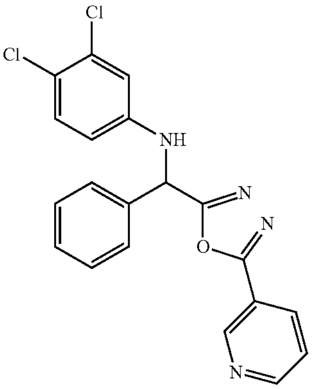
CYM 52266
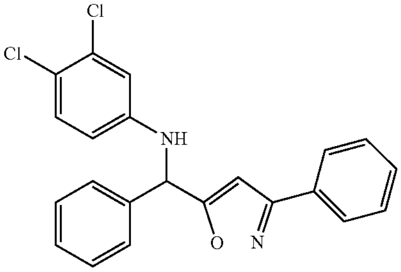
-continued
CYM 52267
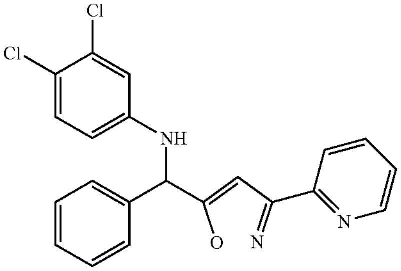
CYM 52268
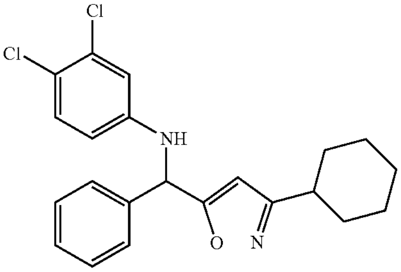
CYM 52274
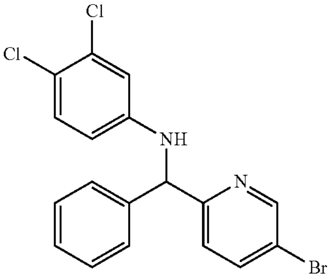
CYM 52276
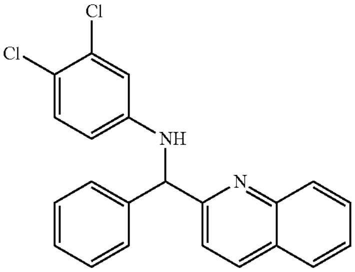
CYM 52289
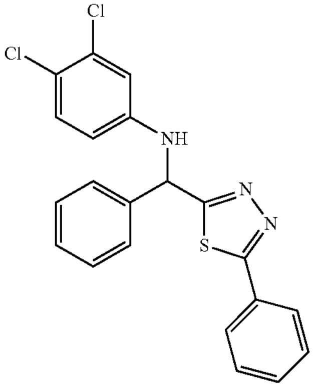

-continued
CYM 52294
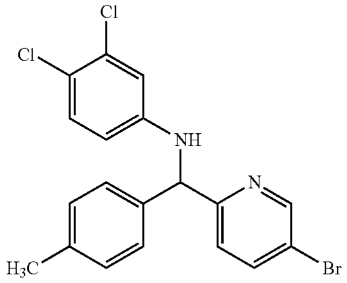
CYM 52296
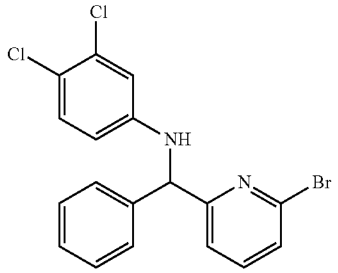
CYM 52297
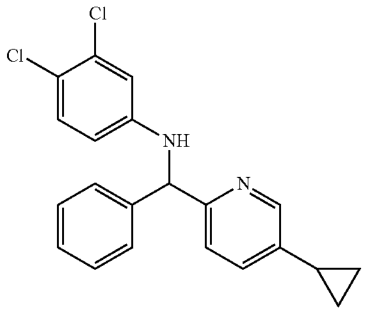
CYM 52298
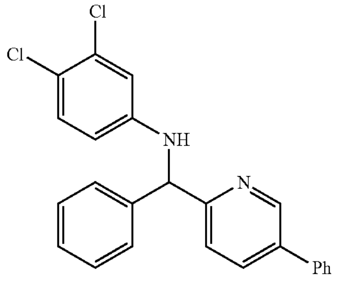
CYM 52299
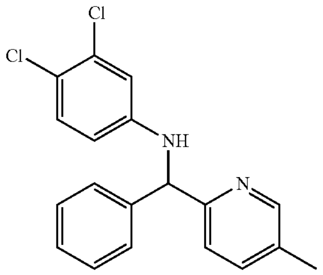
-continued
CYM 52300
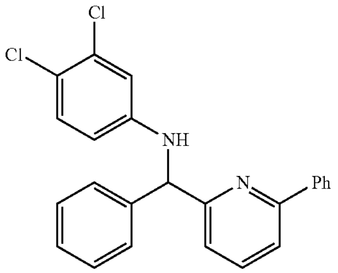
CYM 52301
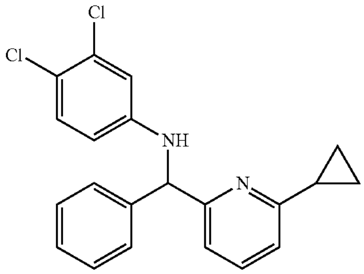
CYM 52302
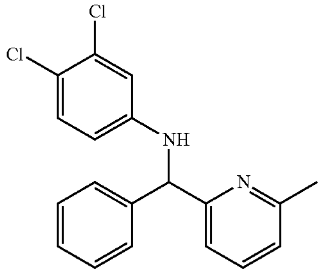
CYM 52304
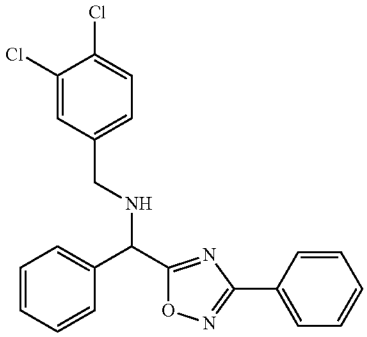
CYM 52305
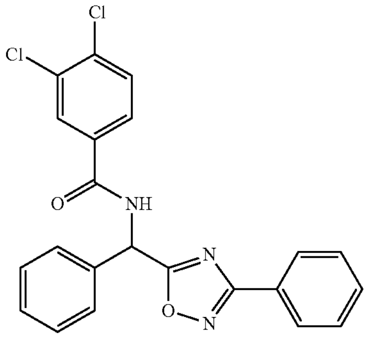

-continued
CYM 52306
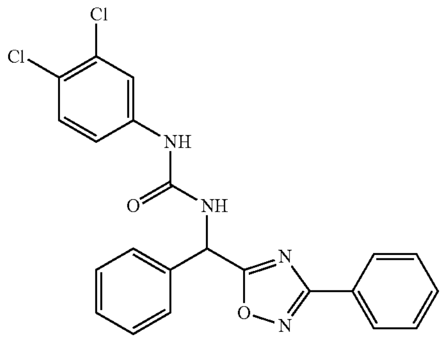
CYM 52308
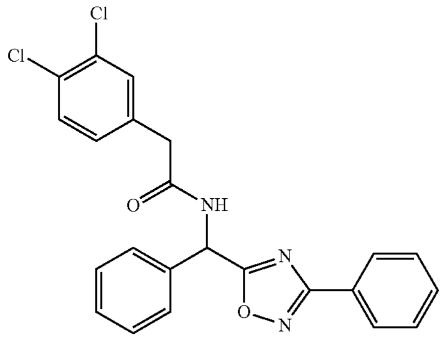
CYM 52310
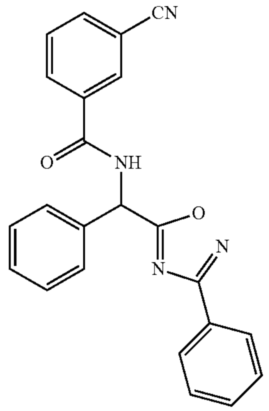
CYM 52311
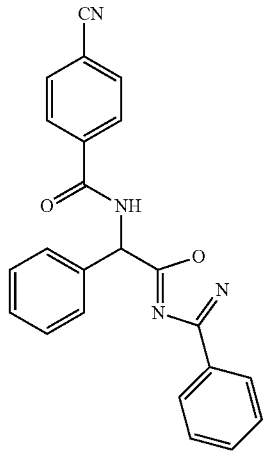
-continued
CYM 52312
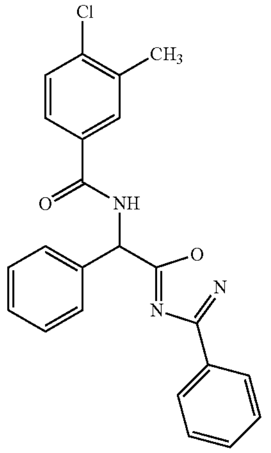
CYM 52313
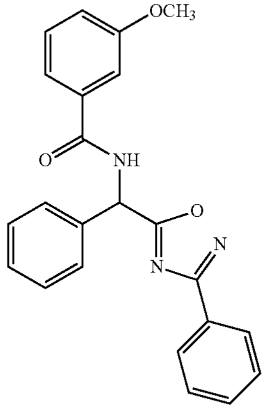
CYM 52314
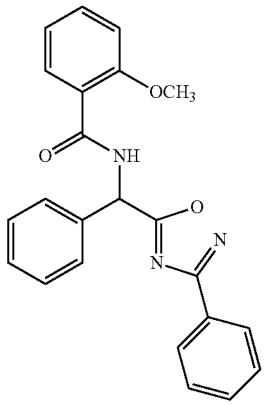
CYM 52320
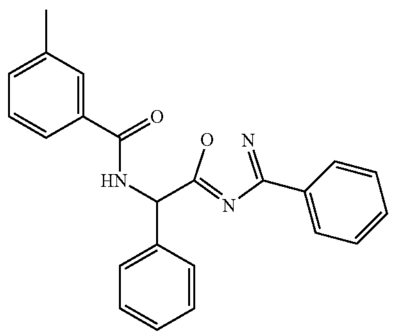

CYM 52321
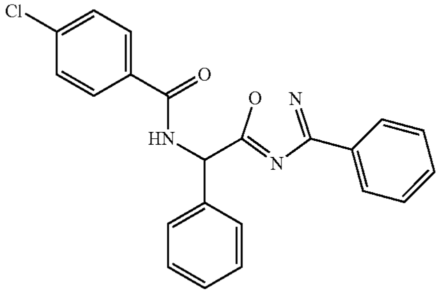
CYM 52323
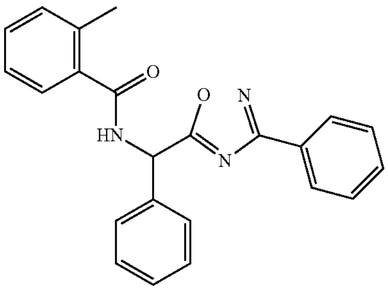
CYM 52325
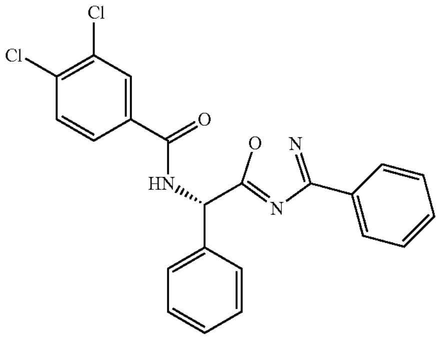
CYM 52326
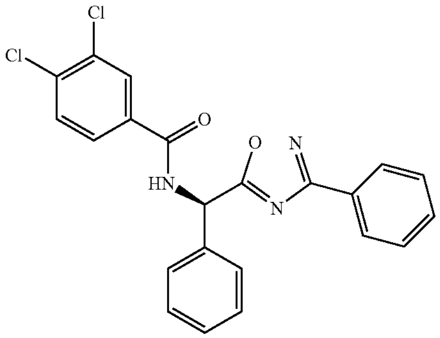
CYM 52329
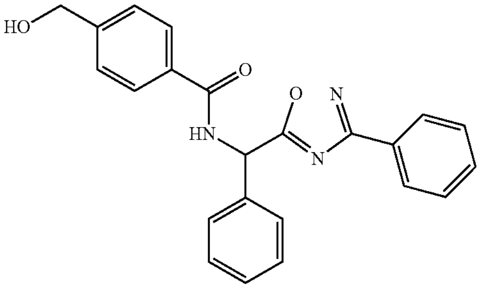
CYM 52330
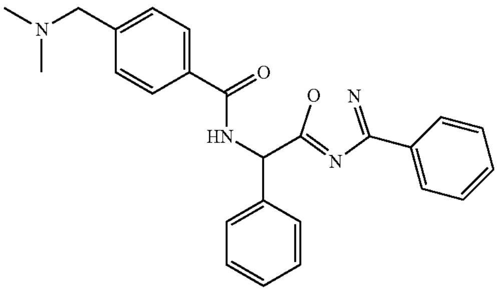
CYM 52331
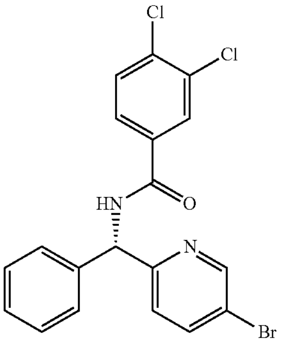
CYM 52332
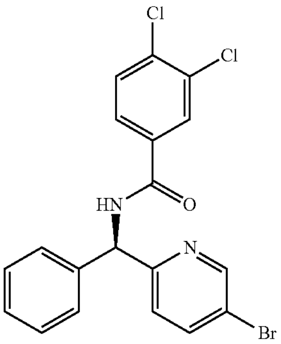
CYM 52333
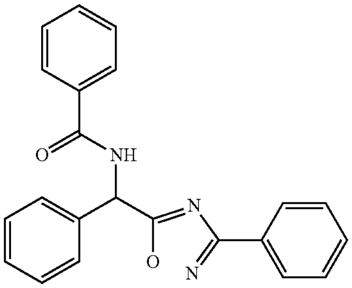
CYM 52334
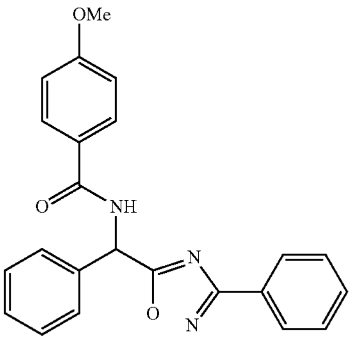

-continued
CYM 52335
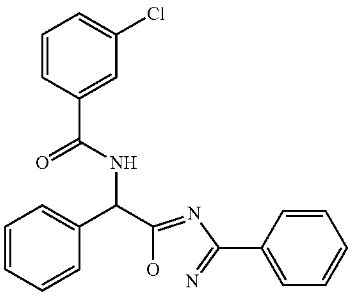
CYM 52336
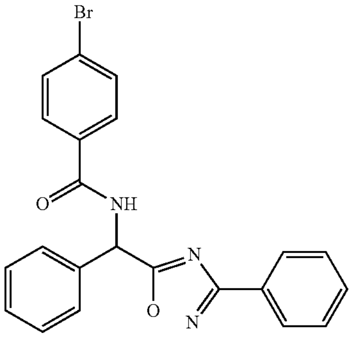
CYM 52343
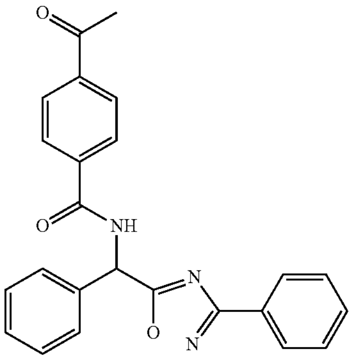
CYM 52344
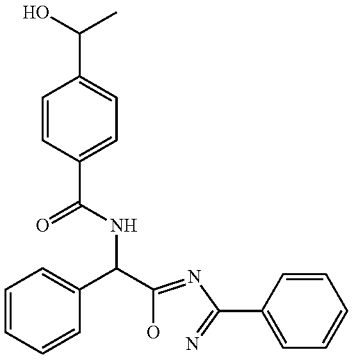
-continued
CYM 52353
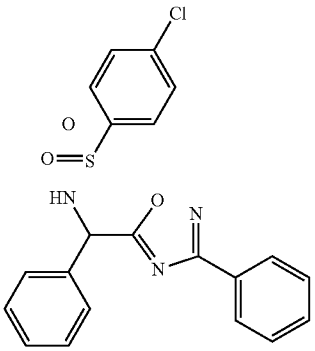
CYM 52355
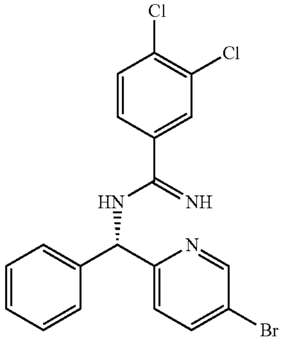
CYM 52356
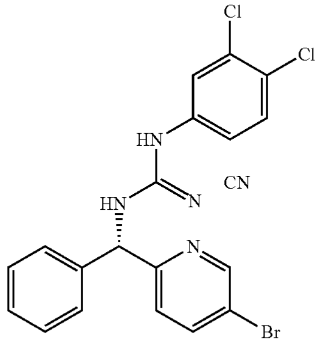
CYM 52359
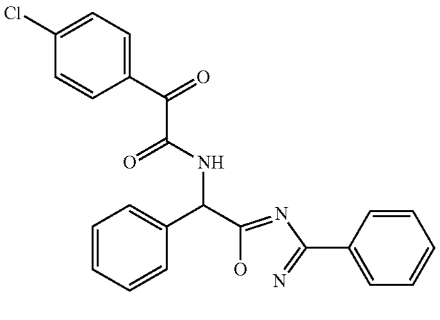

CYM 52364
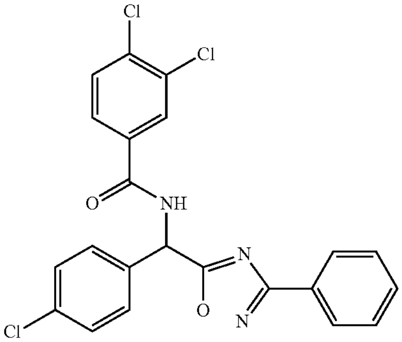
CYM 52365
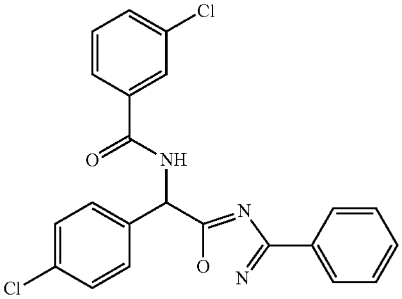
CYM 52372
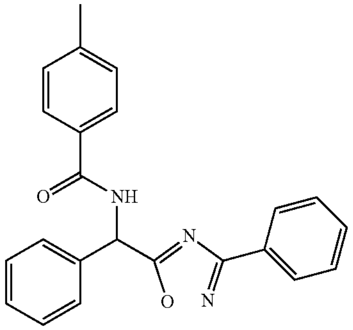
CYM 52375
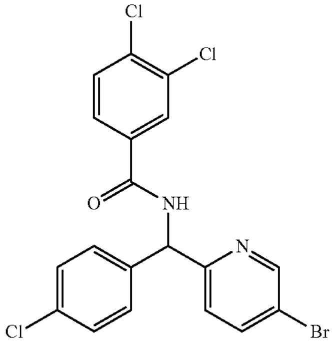
CYM 52378
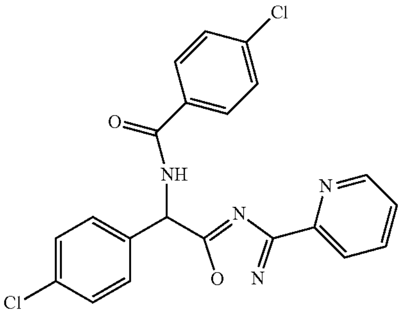
CYM 52379
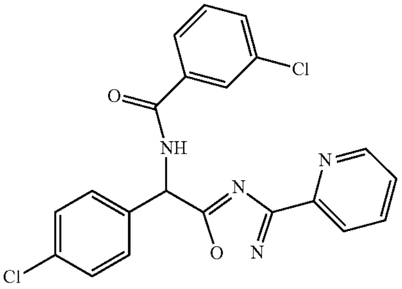
CYM 52380
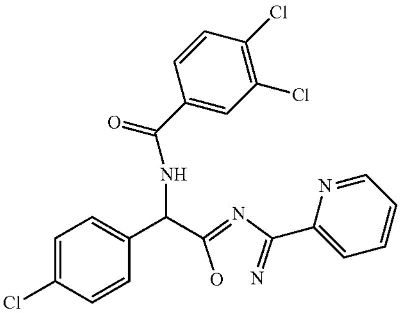
CYM 52381
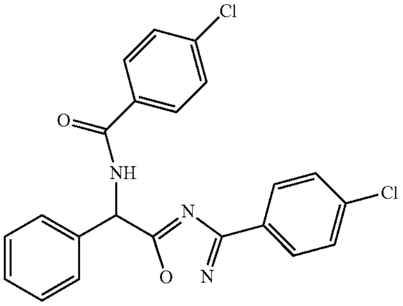
CYM 52382
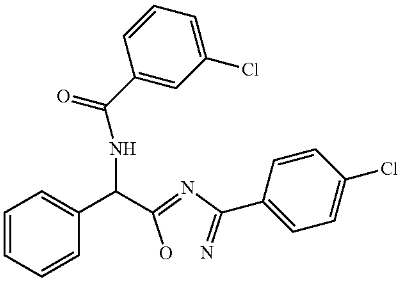
CYM 52383
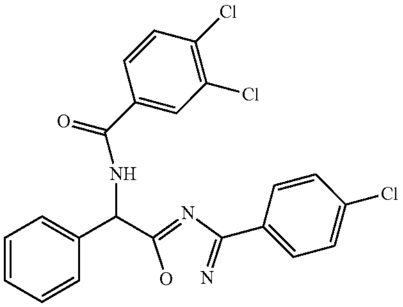

-continued
CYM 52387
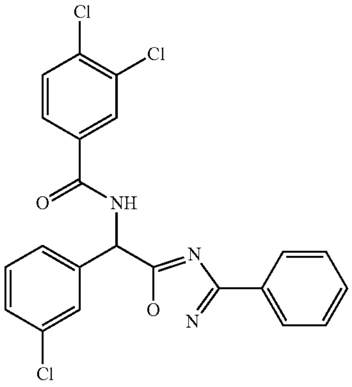
CYM 52388
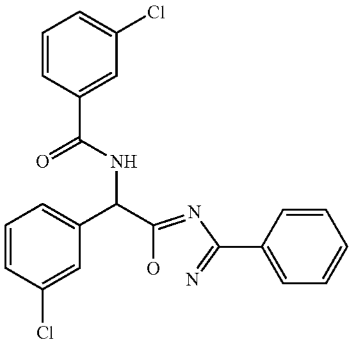
CYM 52389
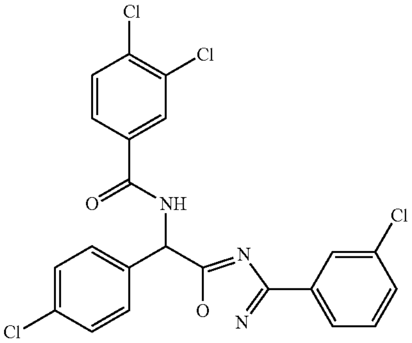
CYM 52390
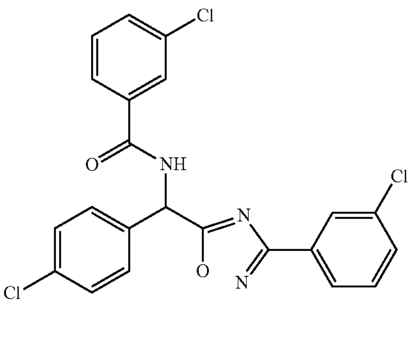
-continued
CYM 52391
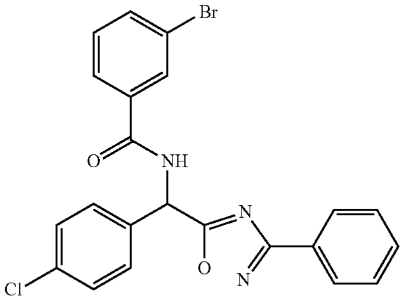
CYM 52392
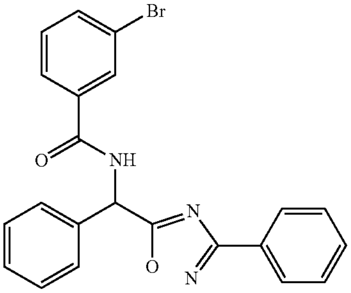
CYM 52394
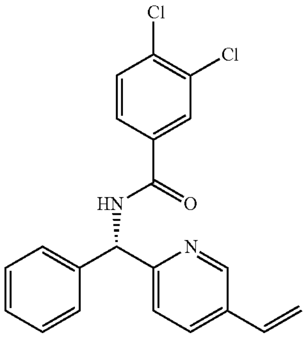
CYM 52395
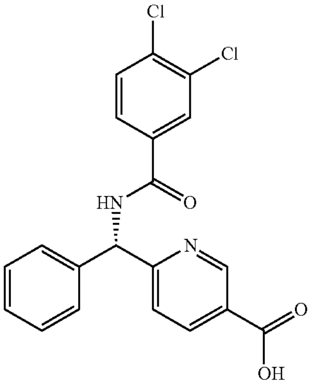

-continued
CYM 52396
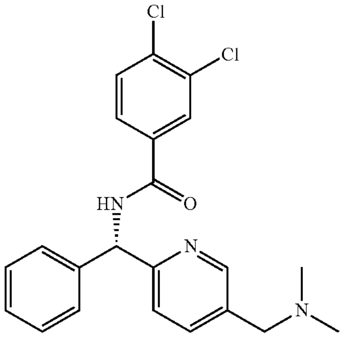
CYM 52397
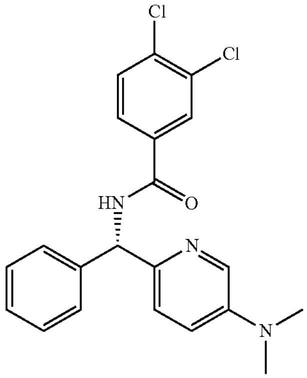
CYM 52398
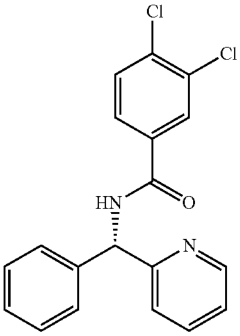
CYM 52399
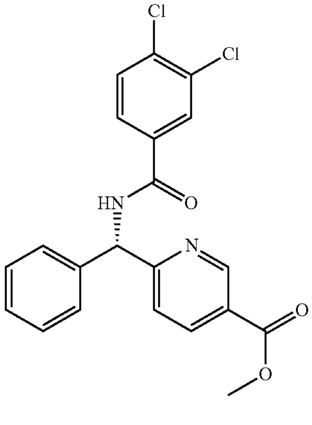
-continued
CYM 52400
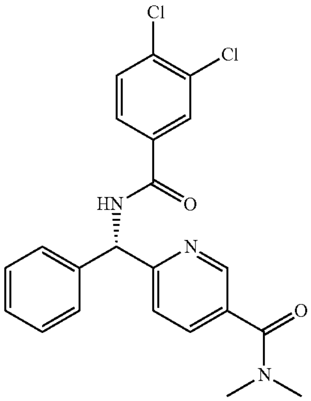
CYM 52401
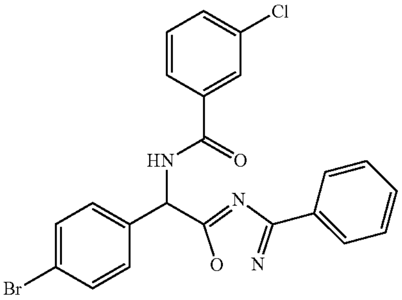
CYM 52402
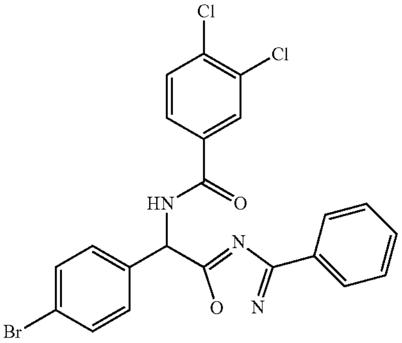
CYM 52403
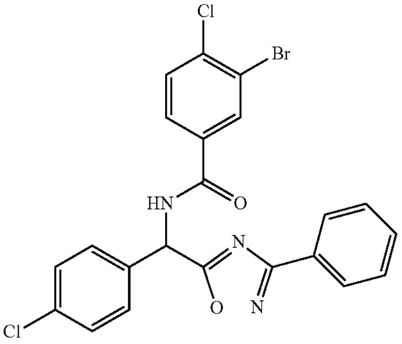

-continued
CYM 52404
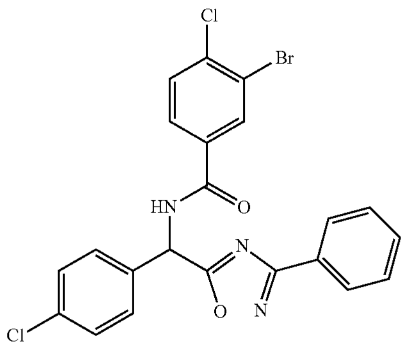
CYM 52405
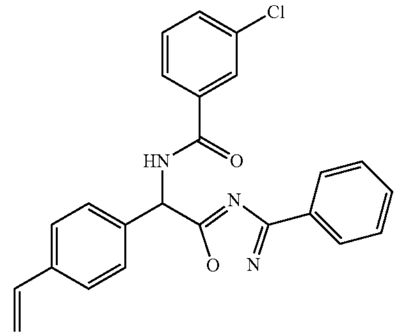
CYM 52406
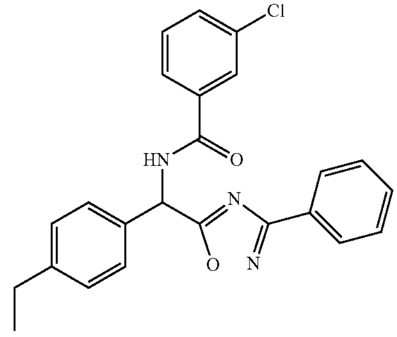
CYM 52407
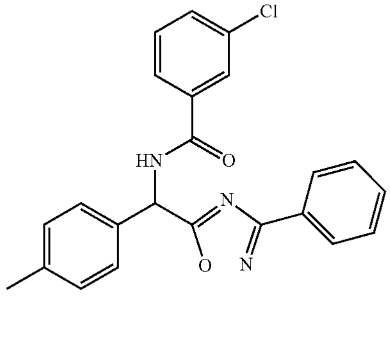
-continued
CYM 52408
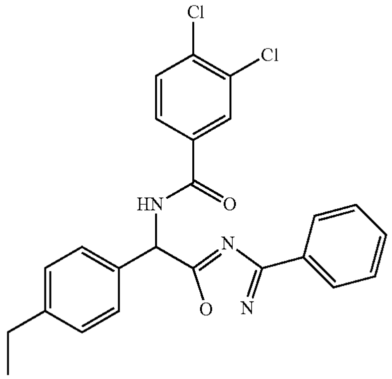
CYM 52409
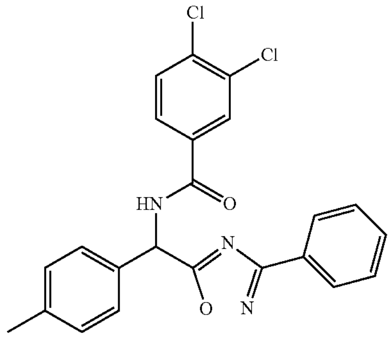
CYM 52410
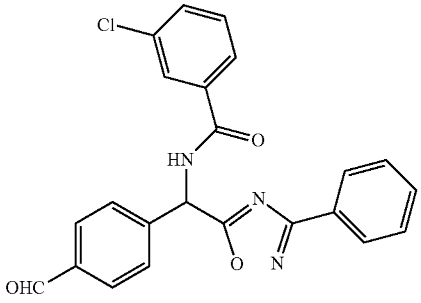
CYM 52411
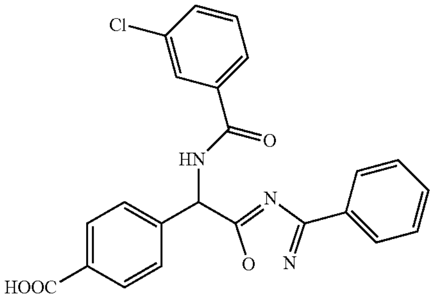
CYM 52412
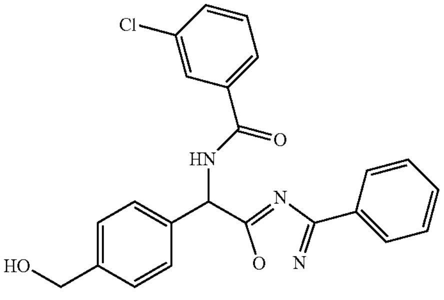

-continued
CYM 52413
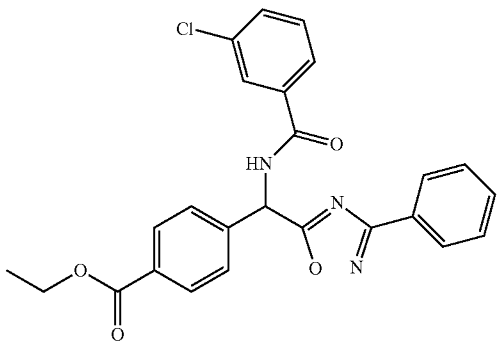
CYM 52414
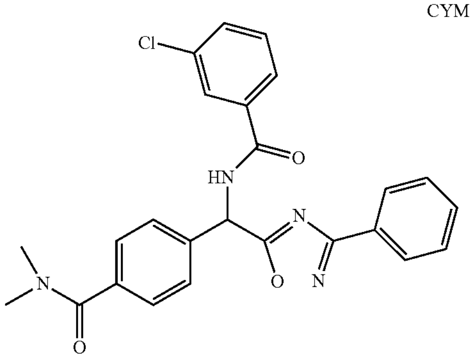
CYM 52417
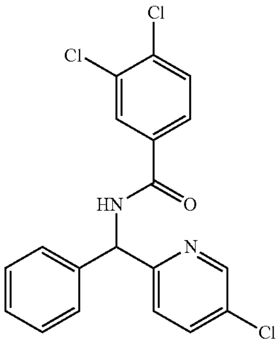
CYM 52418
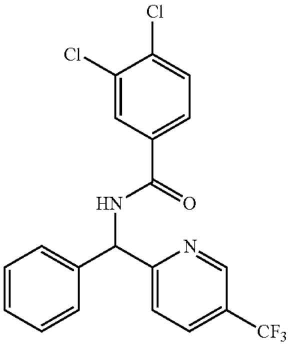
-continued
CYM 52419
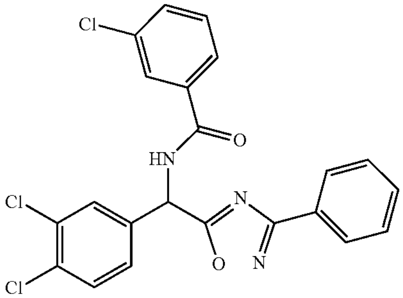
CYM 52420
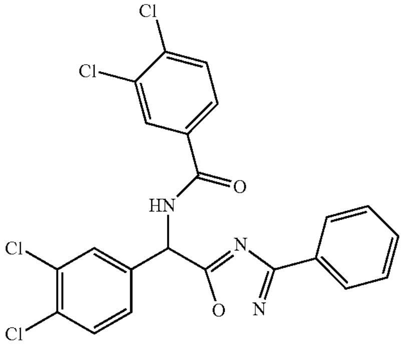
CYM 52421
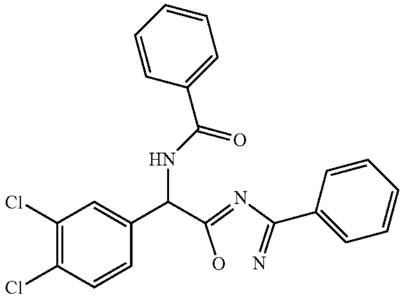
CYM 52426
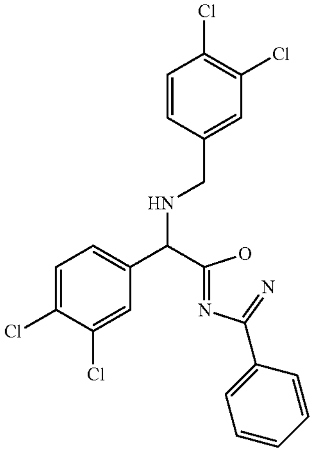

-continued
CYM 52427
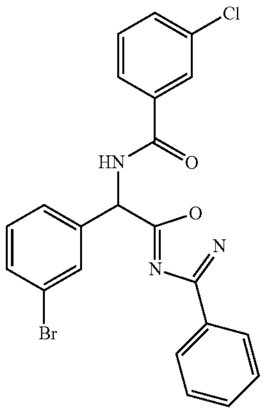
CYM 52428
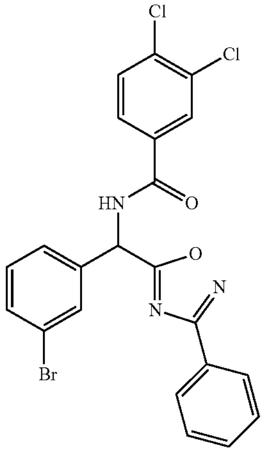
CYM 52429
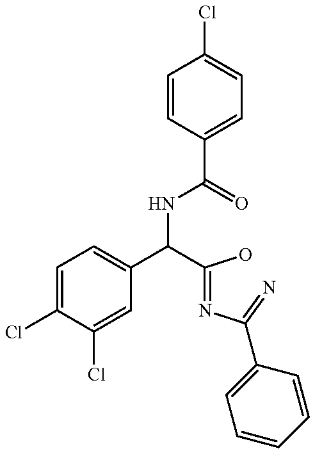
-continued
CYM 52430
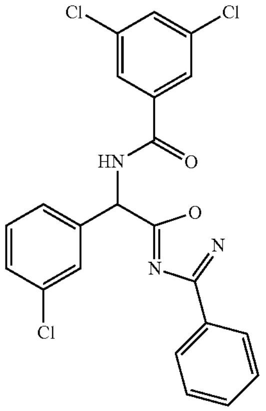
CYM 52431
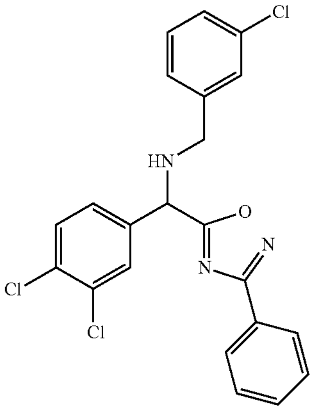
CYM 52432
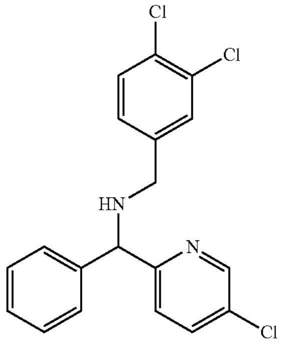
CYM 52433
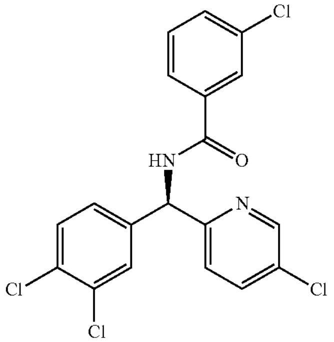

CYM 52434
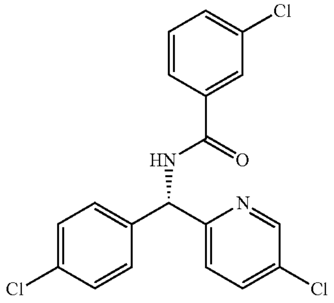
CYM 52435
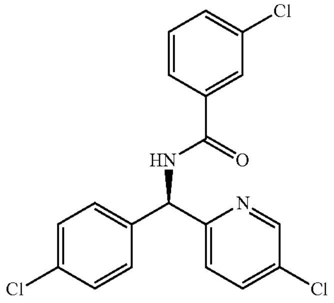
CYM 52436
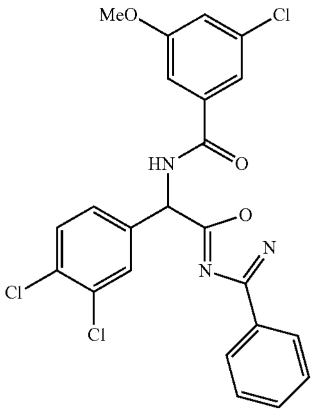
CYM 52437
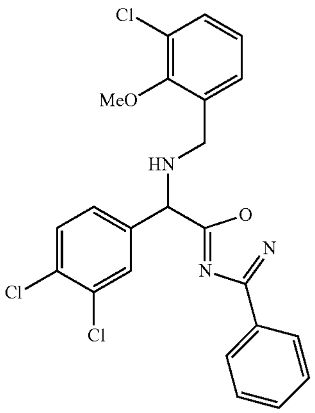
CYM 52438
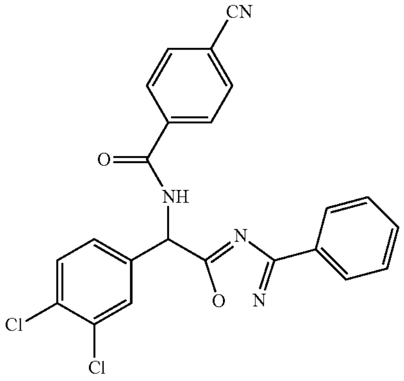
CYM 52439
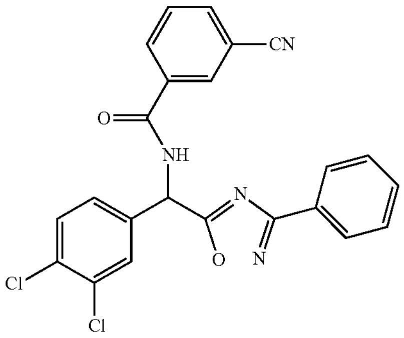
CYM 52440
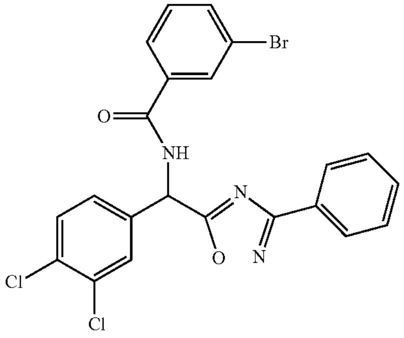
CYM 52442
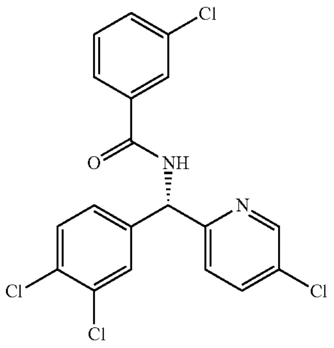

CYM 52443
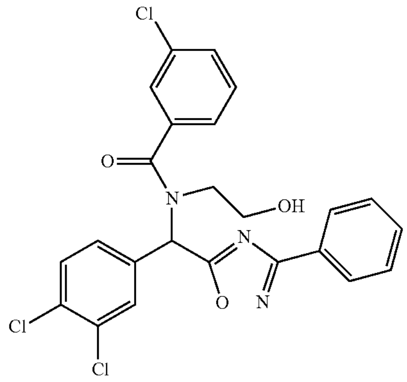
CYM 52444
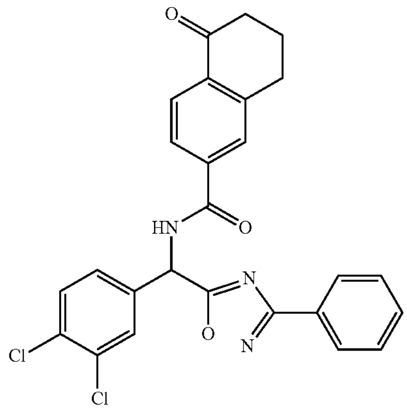
CYM 52445
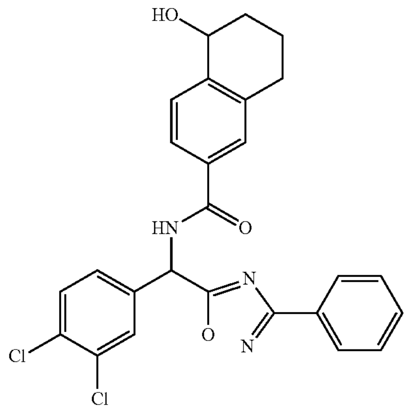
CYM 52447
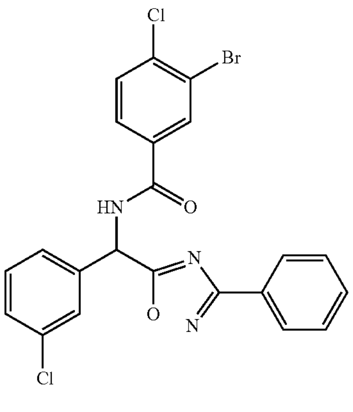
CYM 52448
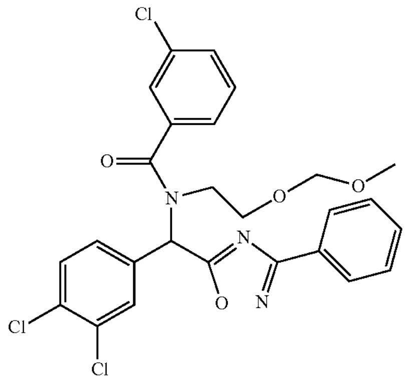
CYM 52449
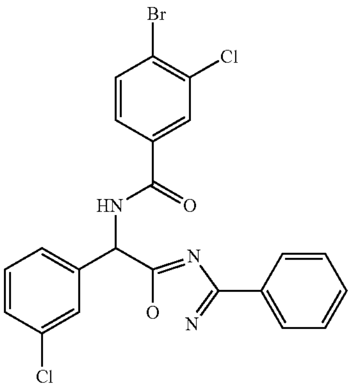
CYM 52450
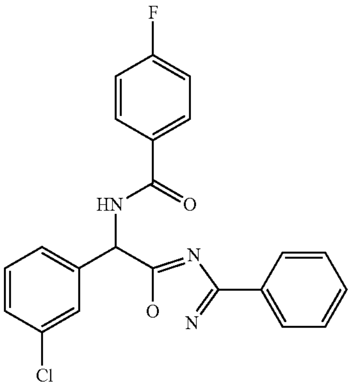
CYM 52451
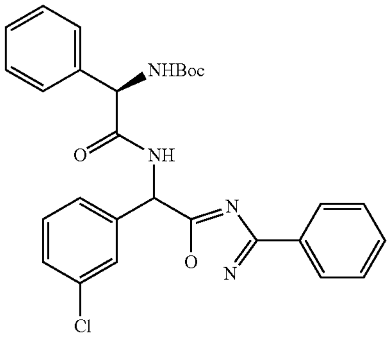

-continued
CYM 52452
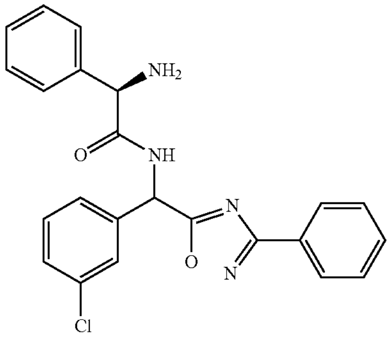
CYM 52453
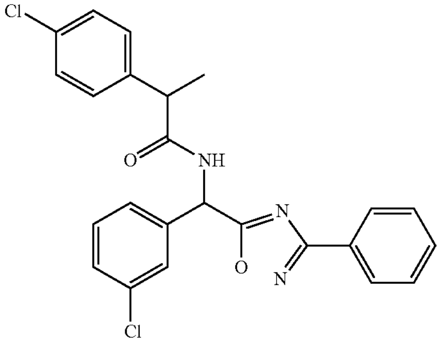
CYM 52454
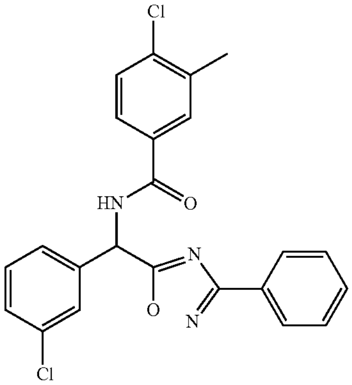
CYM 52455
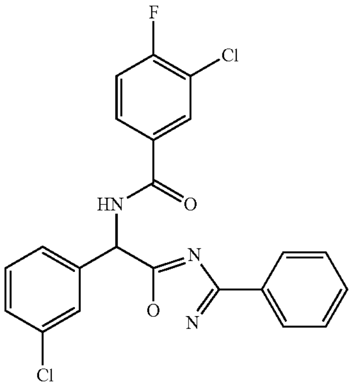
-continued
CYM 52456
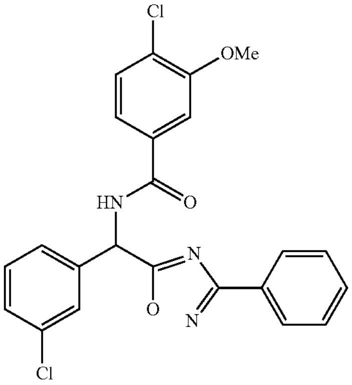
CYM 52457
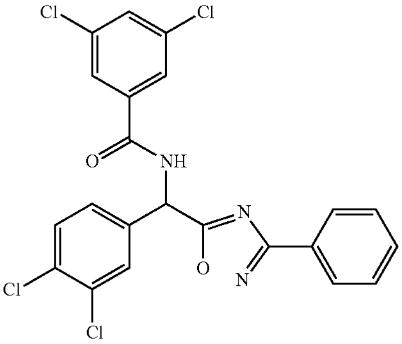
CYM 52458
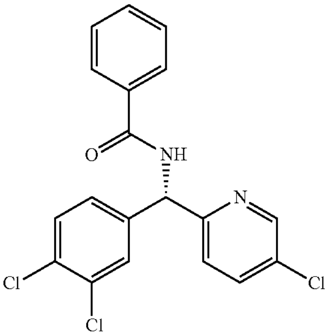
CYM 52459
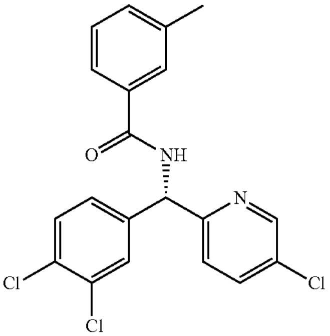

CYM 52460
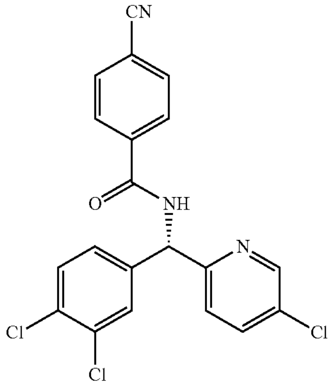
CYM 52463
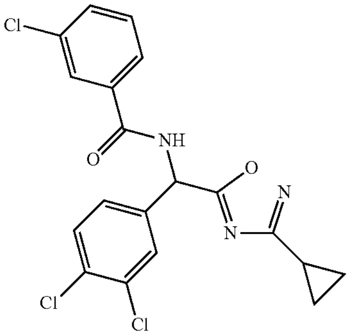
CYM 52464
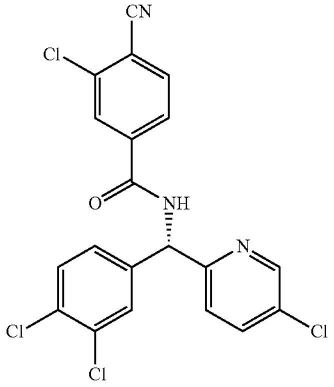
CYM 52465
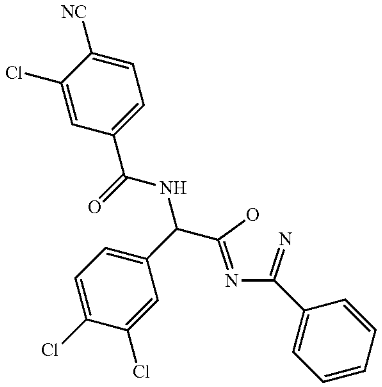
CYM 52469
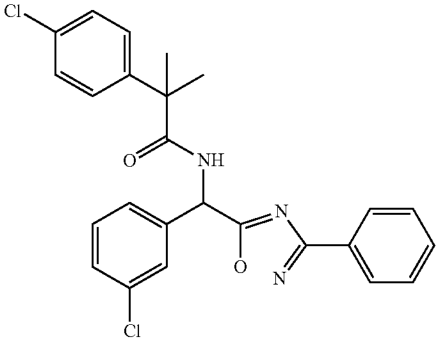
CYM 52470
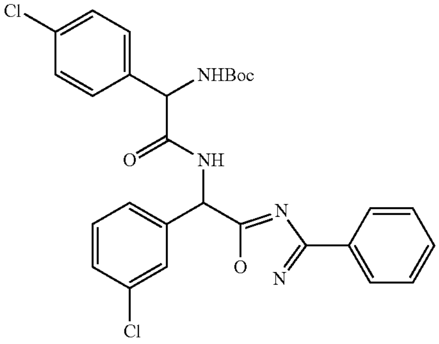
CYM 52471
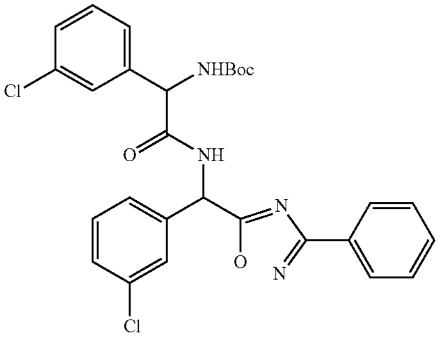
CYM 52472
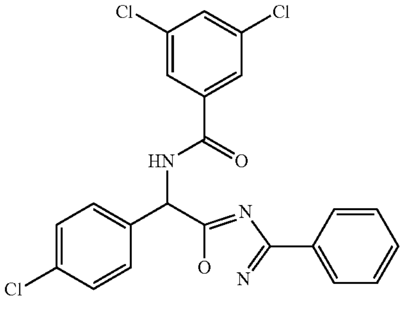

-continued
CYM 52473
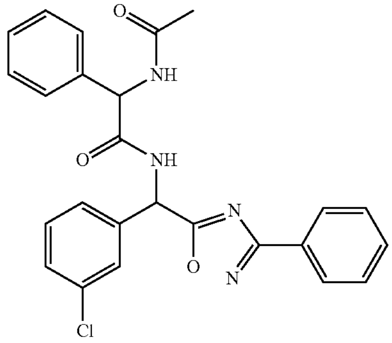
CYM 52474
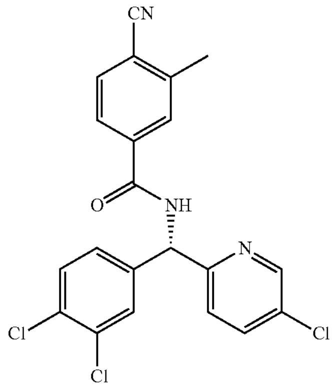
CYM 52475
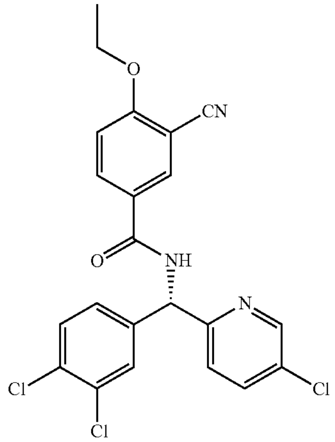
CYM 52477
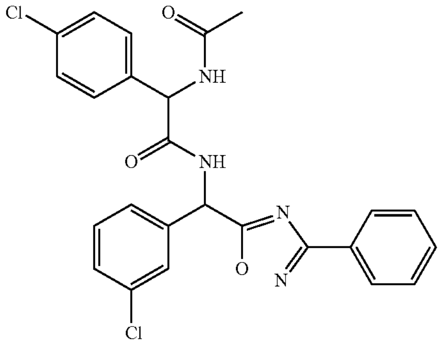
-continued
CYM 52478
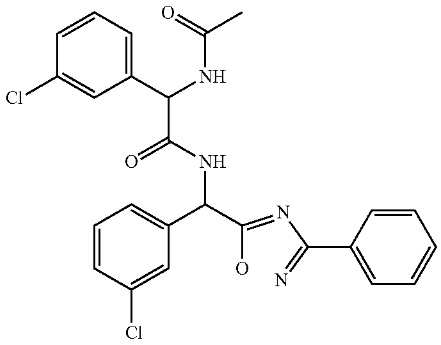
CYM 52479
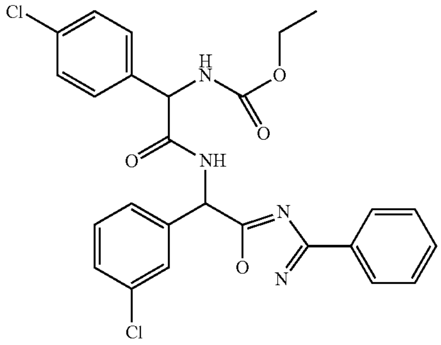
CYM 52480
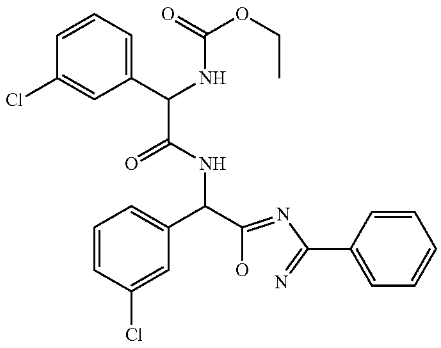
CYM 52481
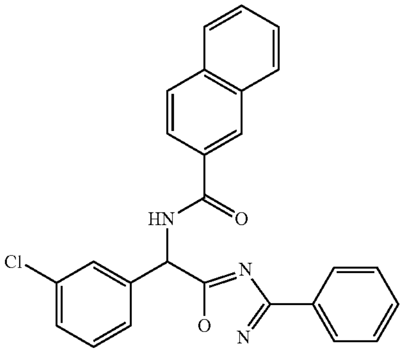

-continued
CYM 52482
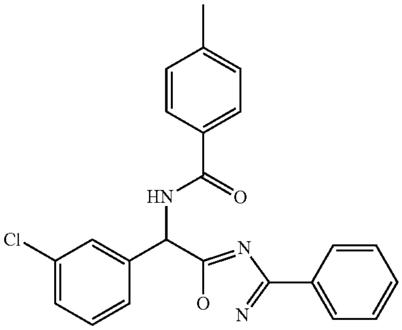
CYM 52483
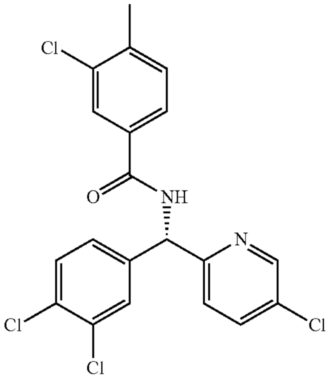
CYM 52484
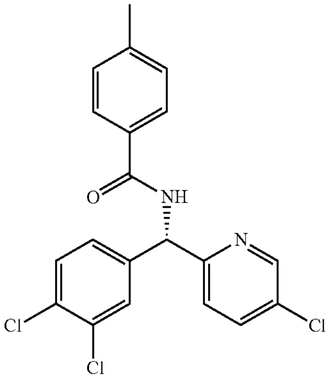
CYM 52486
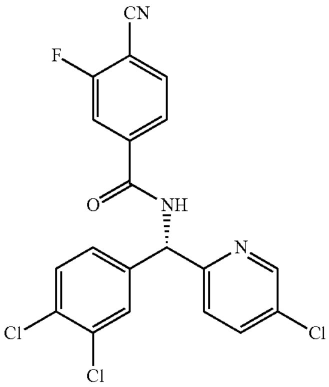
-continued
CYM 52487
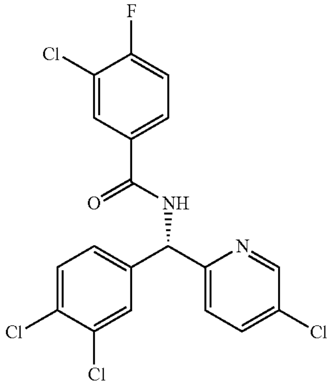
CYM 52488
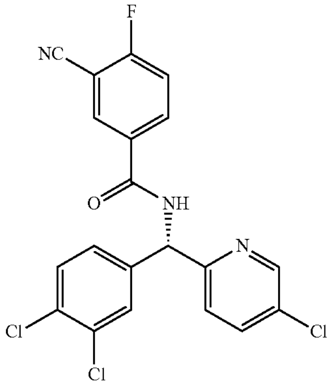
CYM 52490
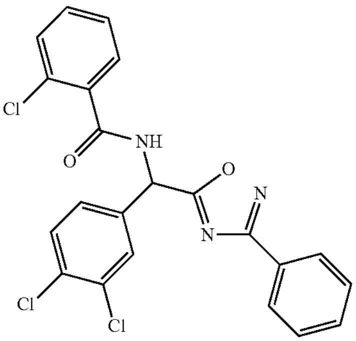
CYM 52491
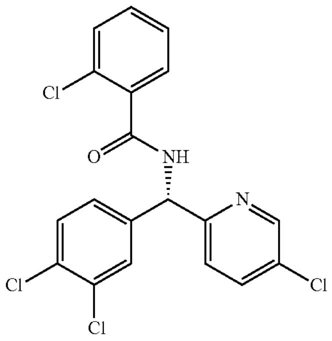

CYM 52492
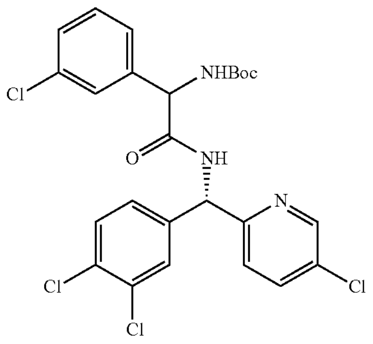
CYM 52493
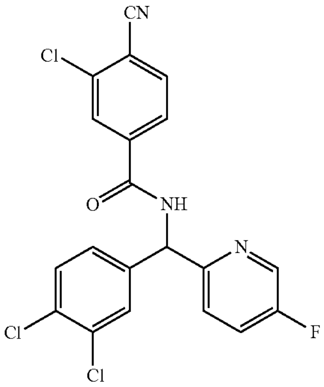
CYM 52494
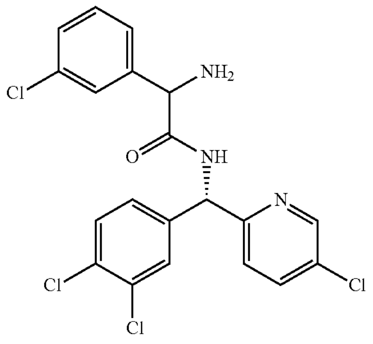
CYM 52495
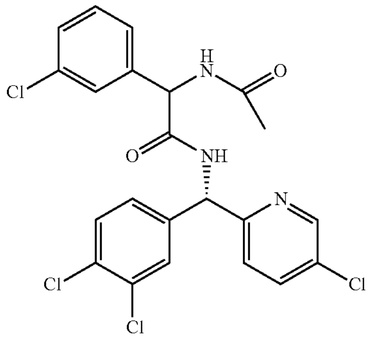
CYM 52496
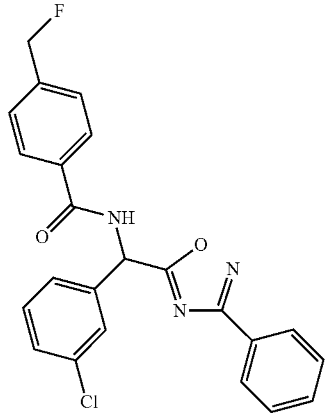
CYM 52497
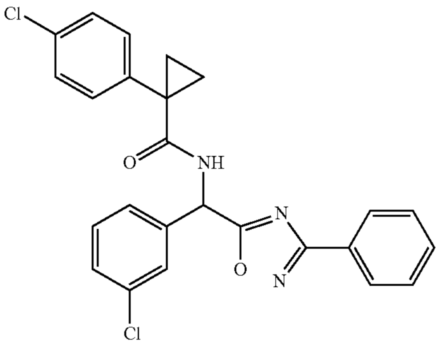
CYM 52498
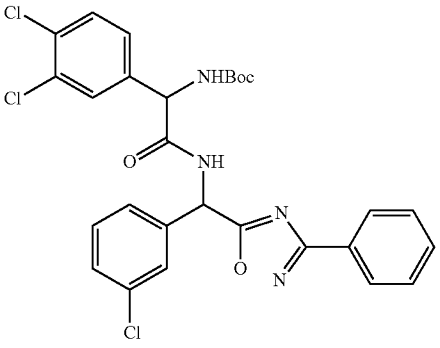
CYM 52499
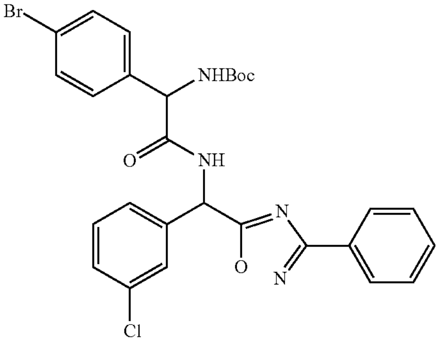

-continued
CYM 52500
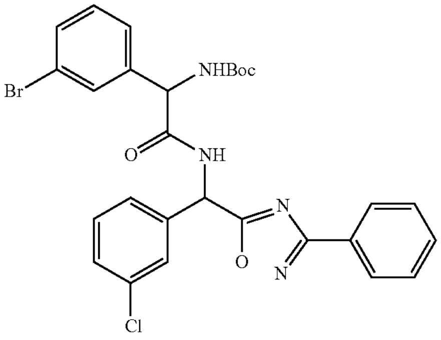
CYM 52501
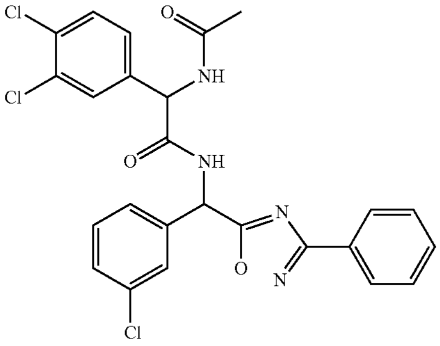
CYM 52502
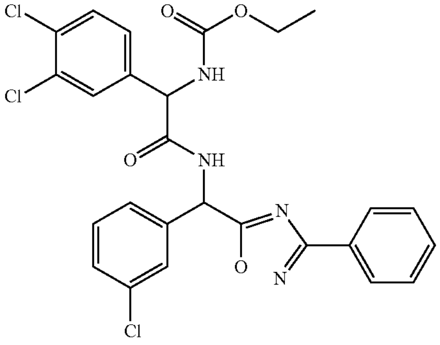
CYM 52503
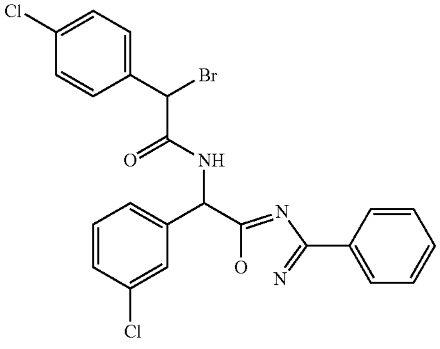
-continued
CYM 52504
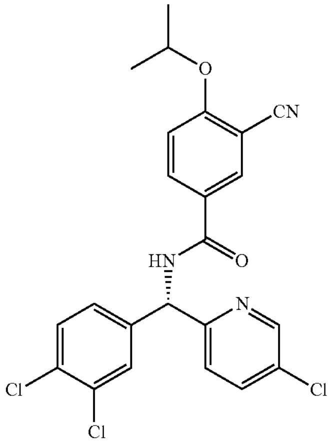
CYM 52505
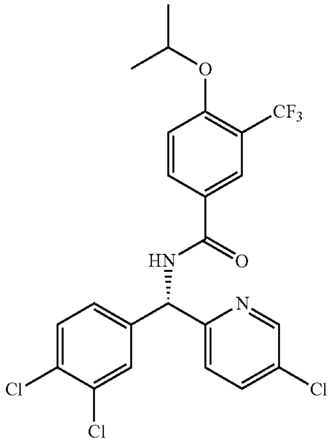
CYM 52506
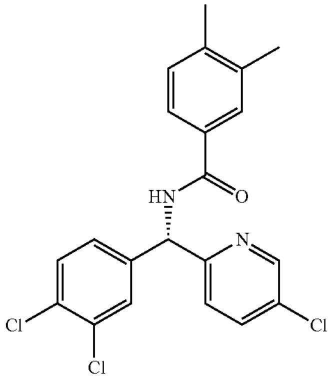
CYM 52507
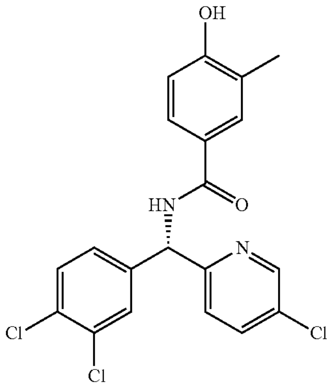

-continued
CYM 52508
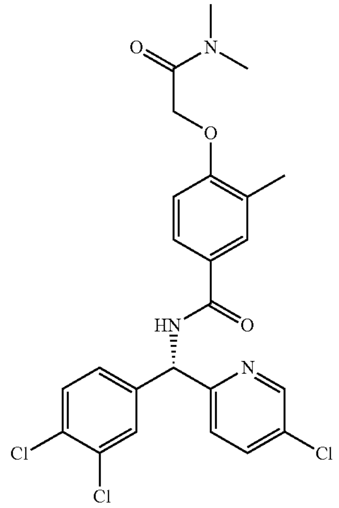
CYM 52509
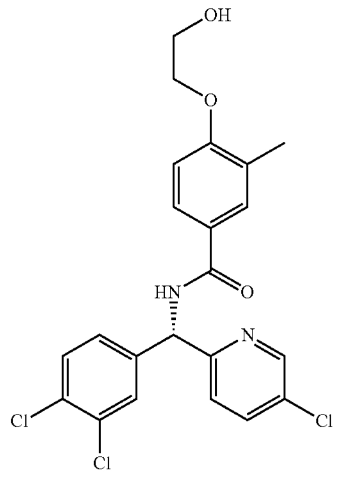
CYM 52510
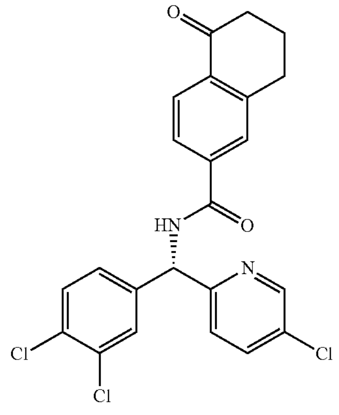
-continued
CYM 52512
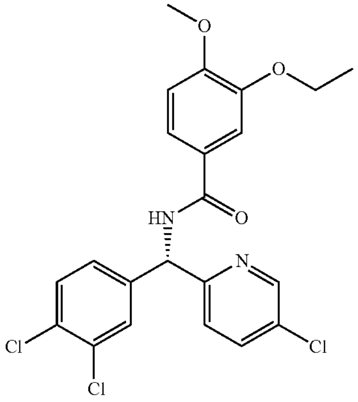
CYM 52514
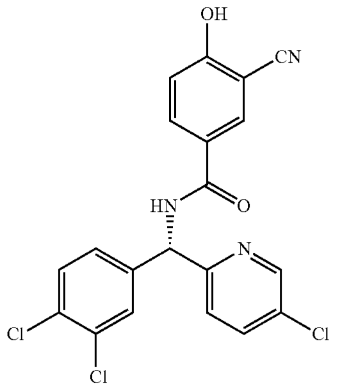
CYM 52515
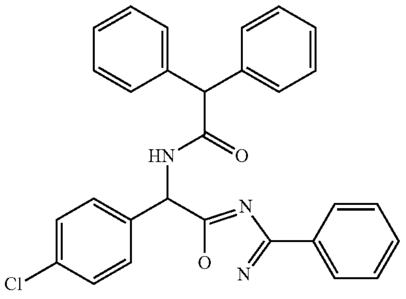
CYM 52516
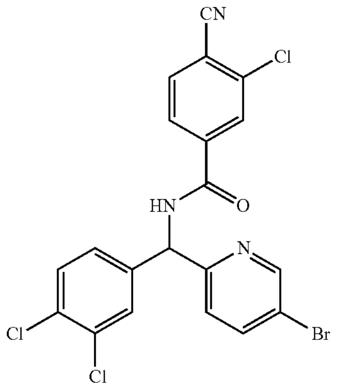

-continued
CYM 52519
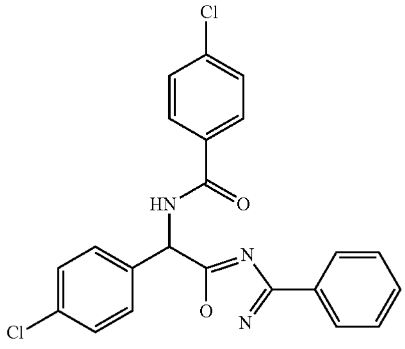
CYM 52520
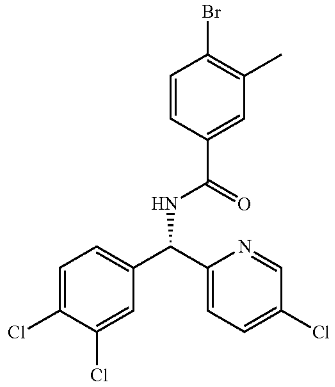
CYM 52521
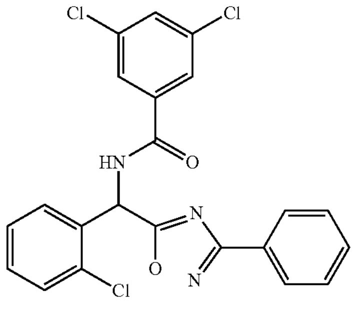
CYM 52522
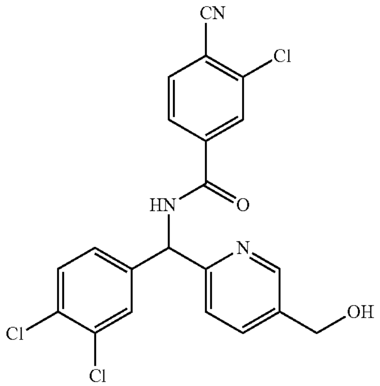
-continued
CYM 52523
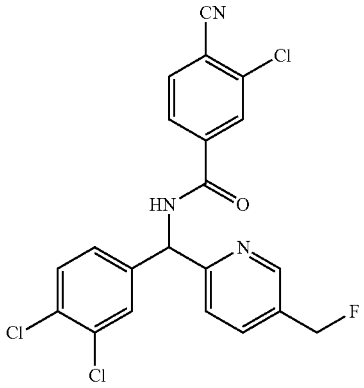
CYM 52524
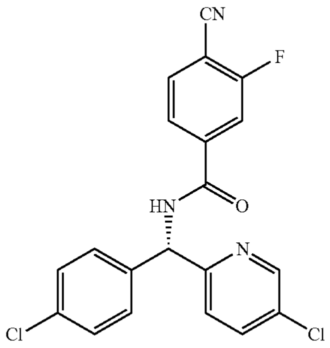
CYM 52525
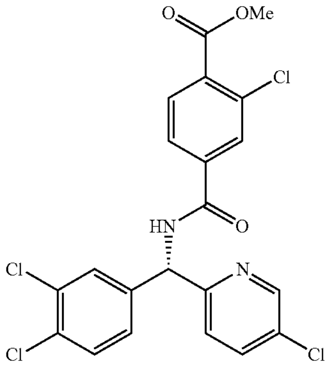
CYM 52526
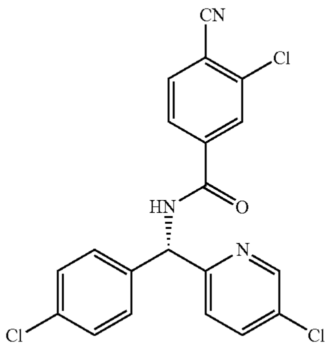

-continued
CYM 52527
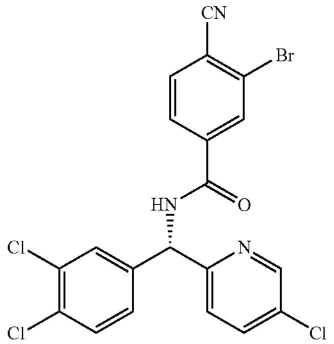
CYM 52528
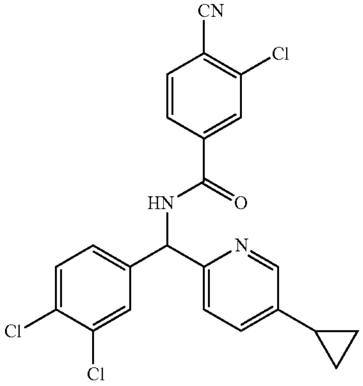
CYM 52529
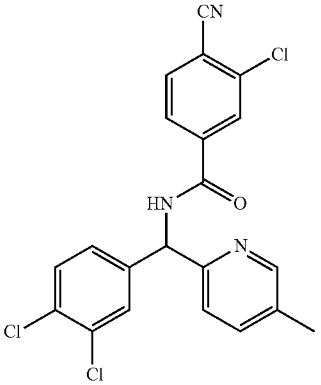
CYM 52530
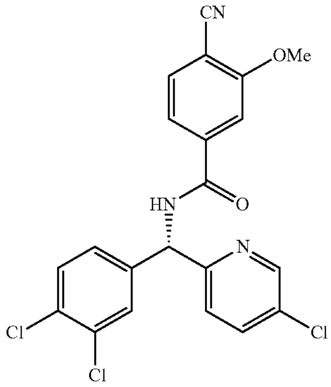
-continued
CYM 52532
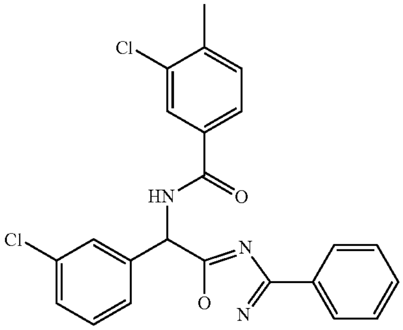
CYM 52533
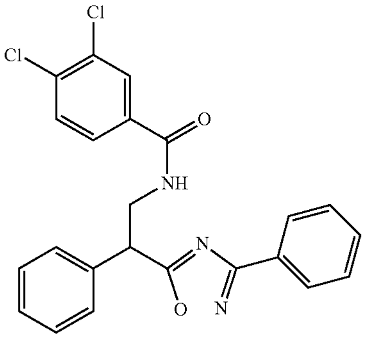
CYM 52534
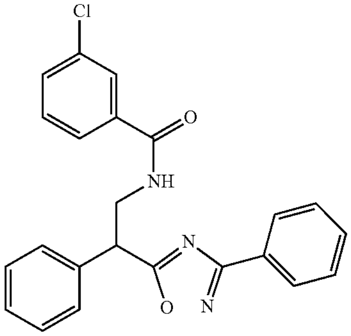
CYM 52535
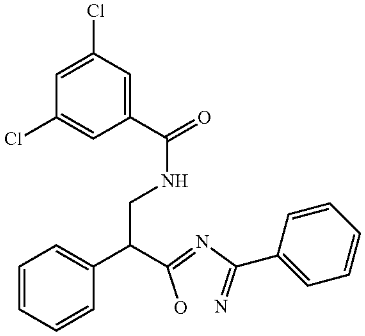

-continued
CYM 52542
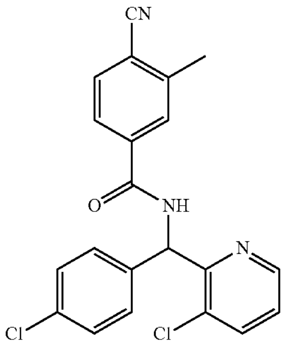
CYM 52543
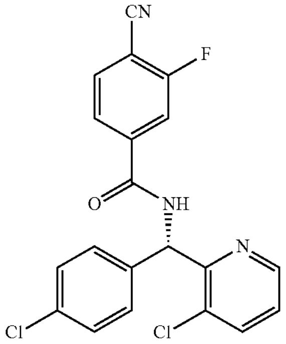
CYM 52544
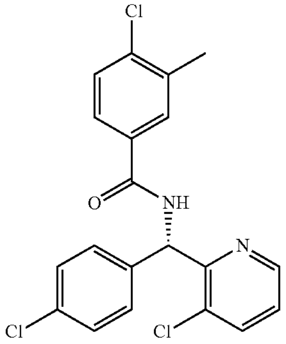
CYM 52545
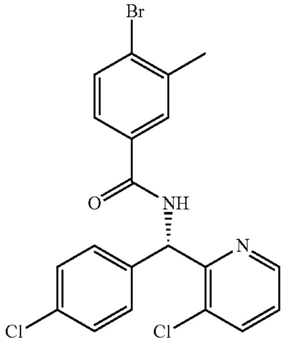
-continued
CYM 52546
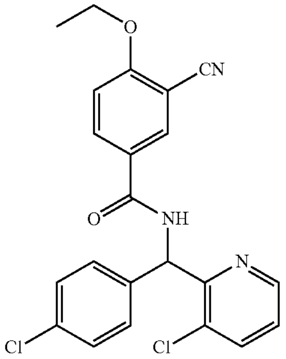
CYM 52547
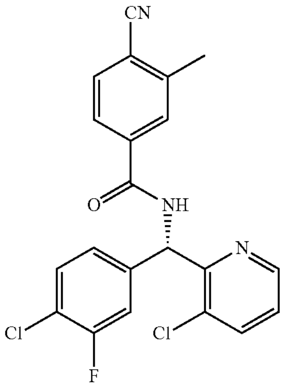
CYM 52548
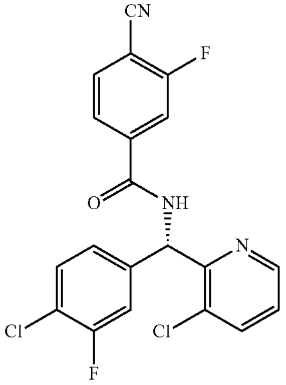
CYM 52549
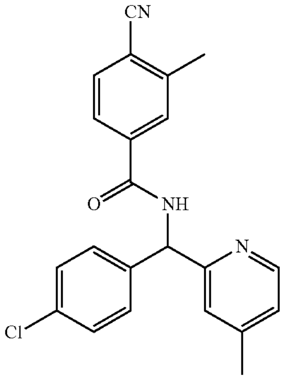

-continued
CYM 52550
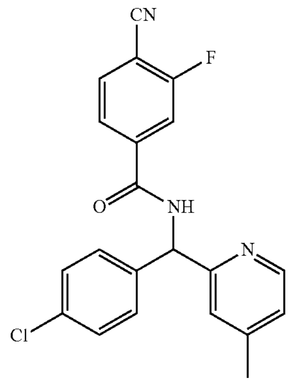
CYM 52551
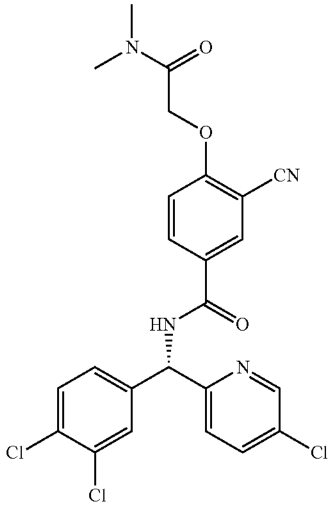
CYM 52552
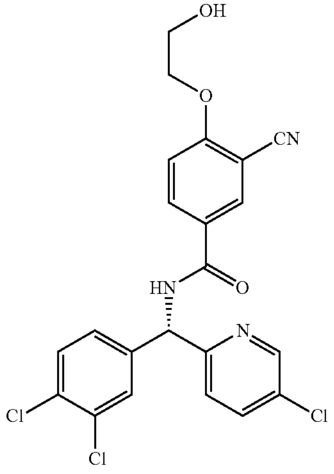
-continued
CYM 52553
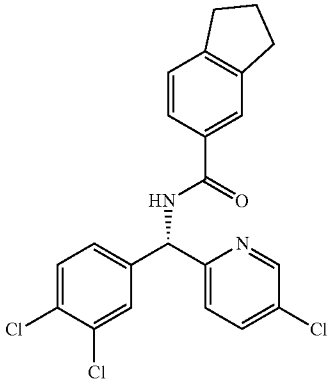
CYM 52555
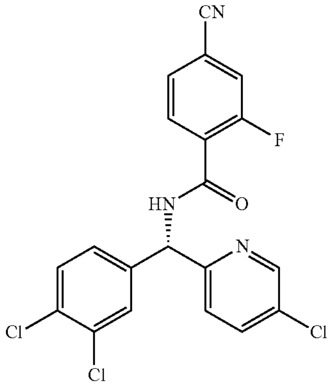
CYM 52556
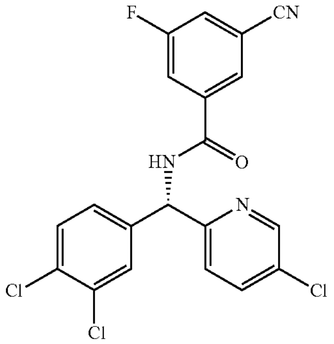
CYM 52557
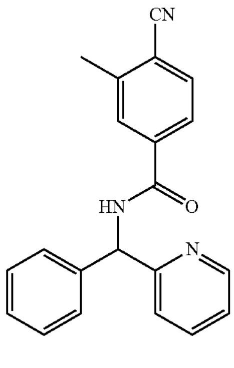

-continued
CYM 52558
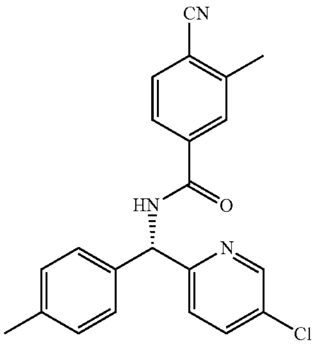
CYM 52559
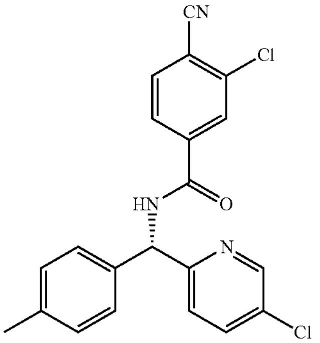
CYM 52560
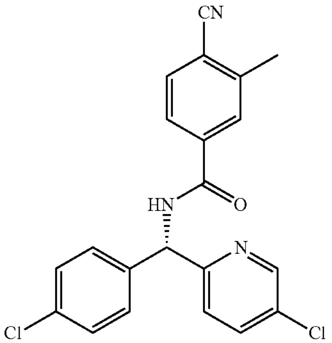
CYM 52562
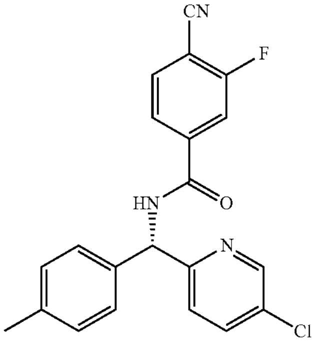
-continued
CYM 52563
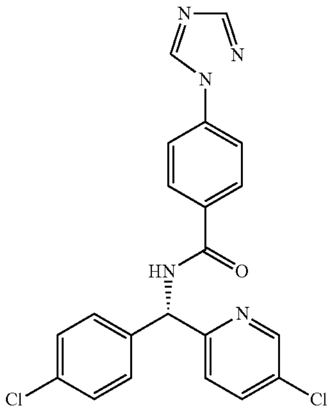
CYM 52564
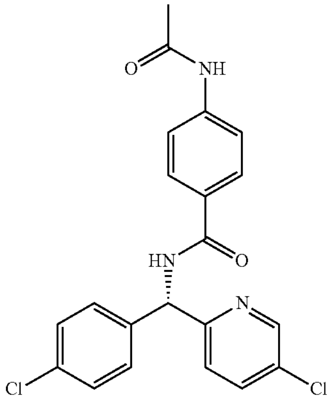
CYM 52565
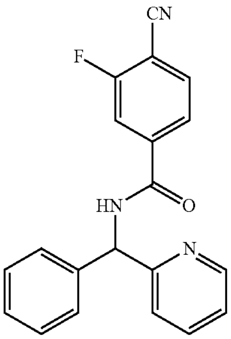
CYM 52566
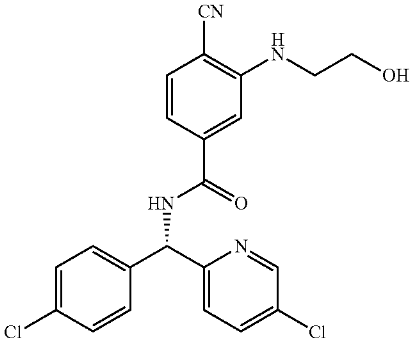

CYM 52567
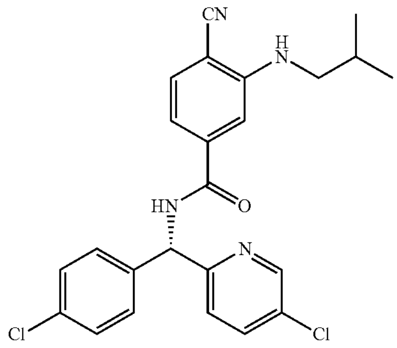
CYM 52569
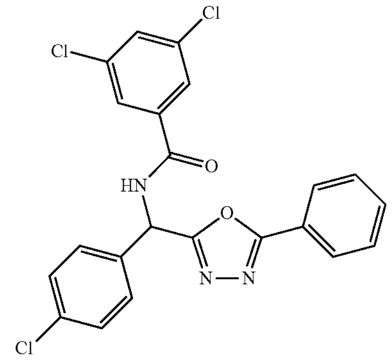
CYM 52570
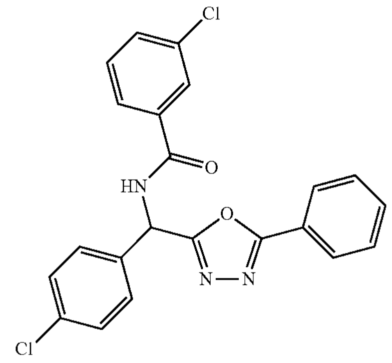
CYM 52571
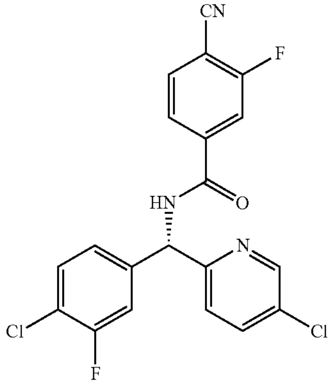
CYM 52572
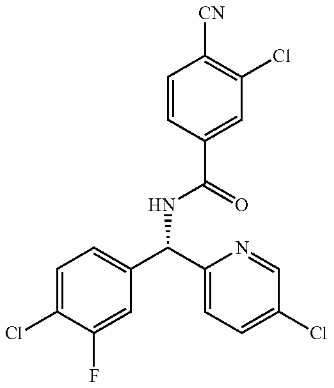
CYM 52573
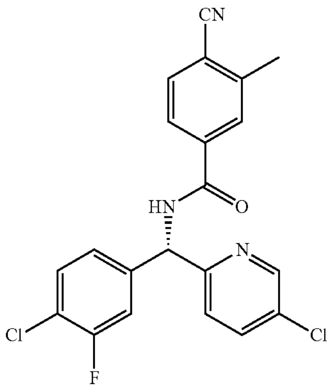
CYM 52574
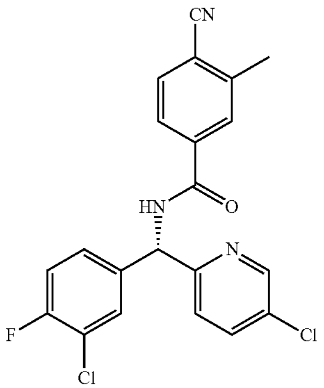
CYM 52575
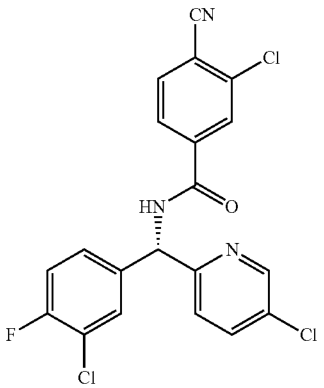

-continued
CYM 52576
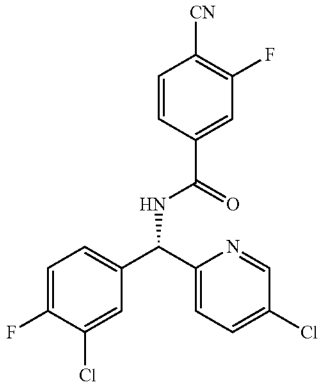
CYM 52577
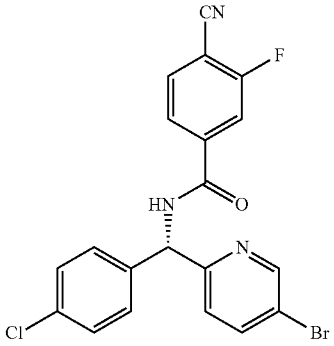
CYM 52578
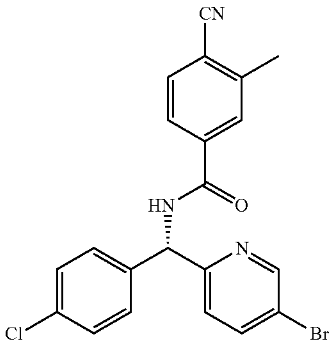
CYM 52579
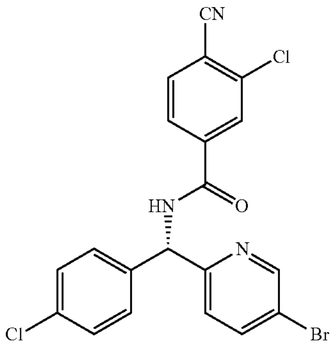
-continued
CYM 52580
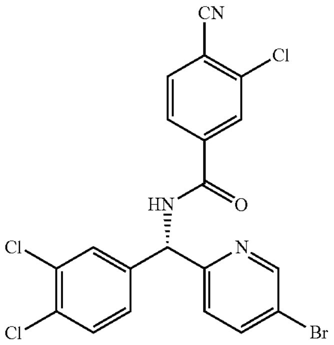
CYM 52581
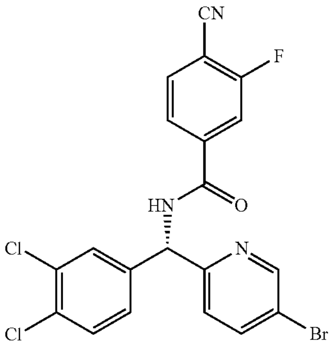
CYM 52582
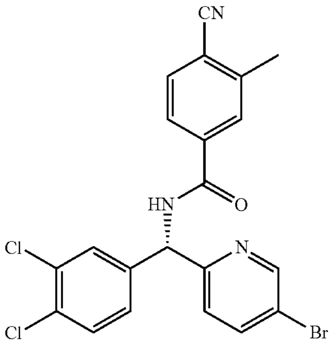
CYM 52583
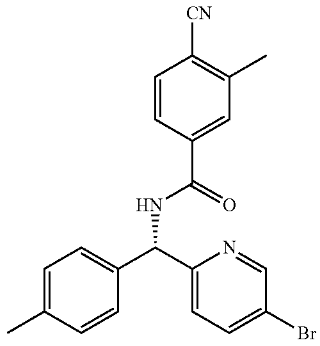

-continued
CYM 52584
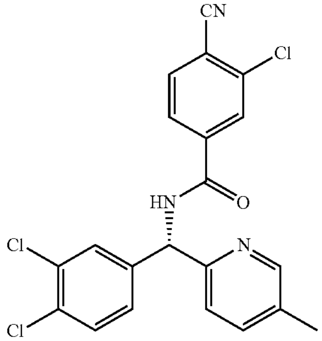
CYM 52585
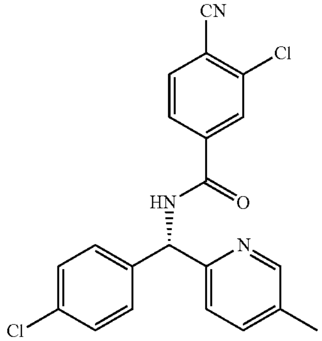
CYM 52586
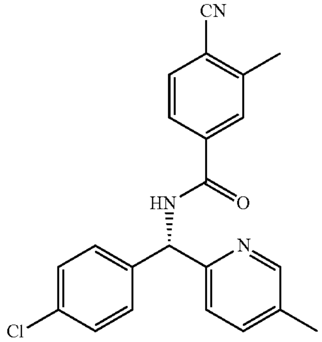
CYM 52587
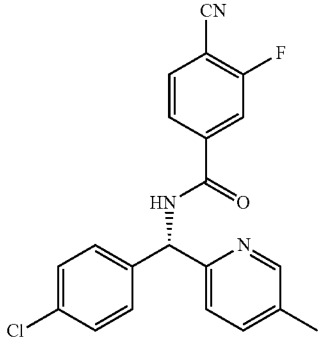
-continued
CYM 52588
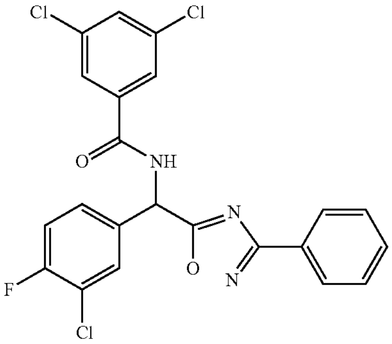
CYM 52589
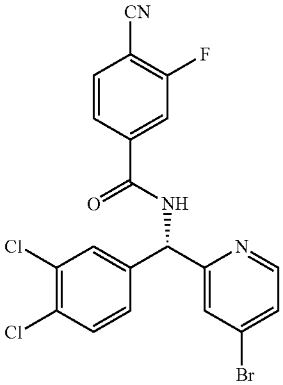
CYM 52590
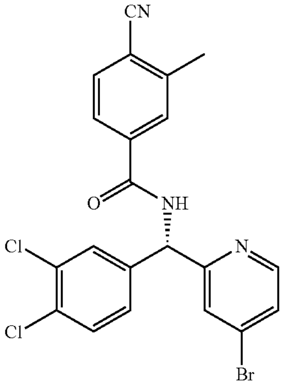
CYM 52591
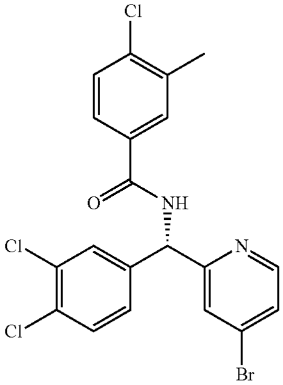

-continued
CYM 52592
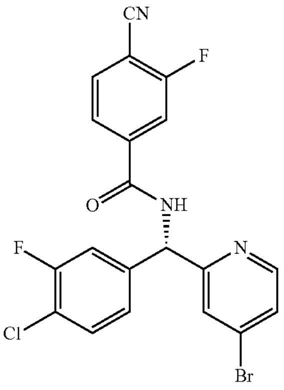
CYM 52593
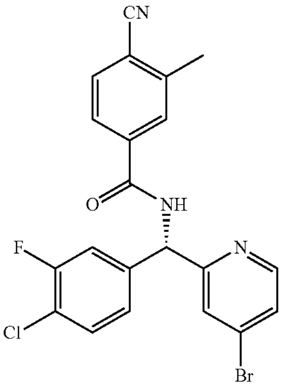
CYM 52594
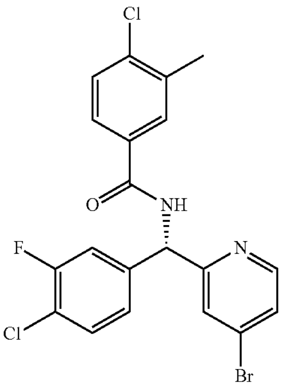
CYM 52595
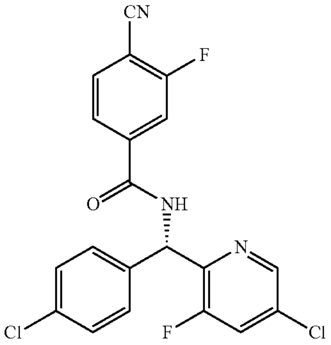
-continued
CYM 52596
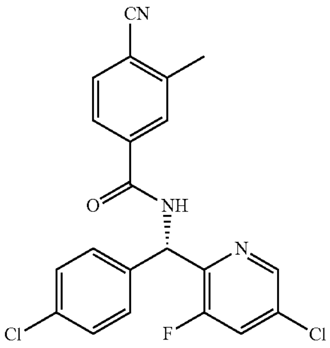
CYM 52597
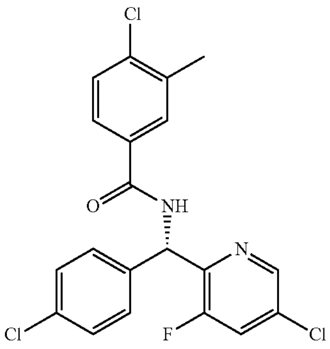
CYM 52598
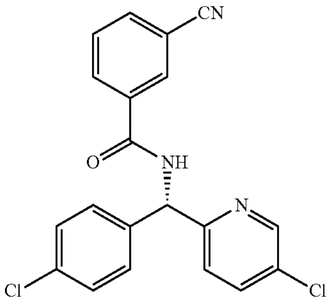
CYM 52599
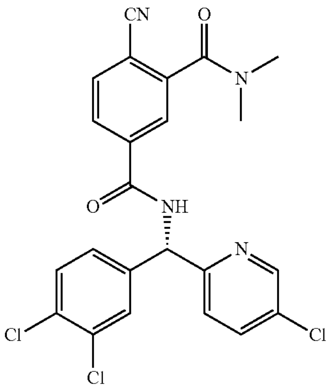

-continued
CYM 52600
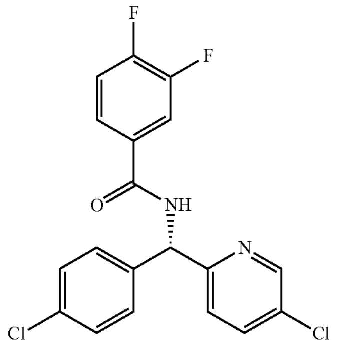
CYM 52601
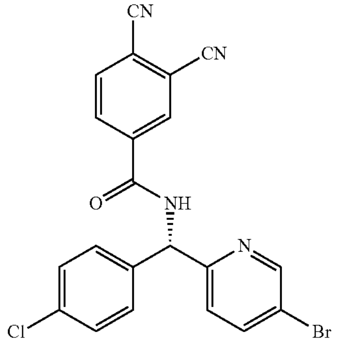
CYM 52602
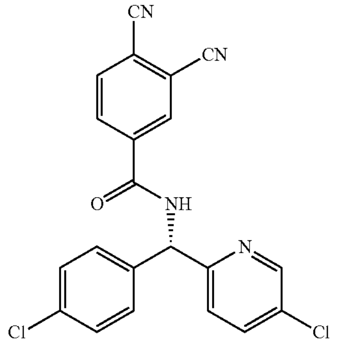
CYM 52603
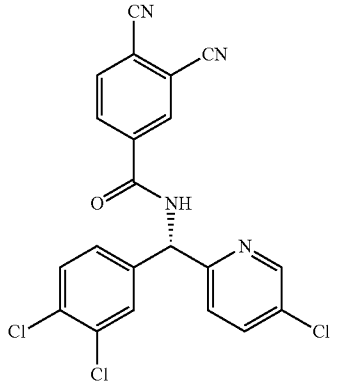
-continued
CYM 52604
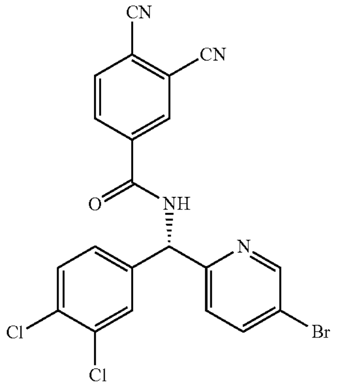
CYM 52605
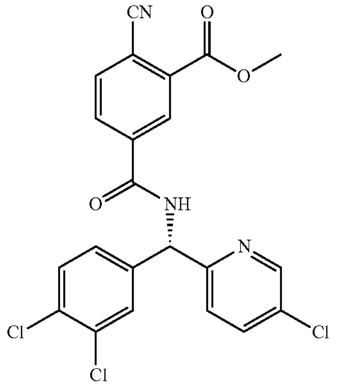
CYM 52606
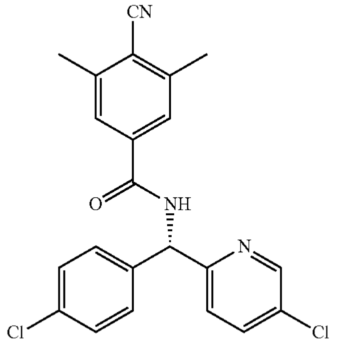
CYM 52607
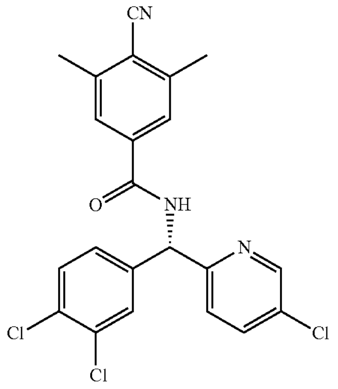

-continued
CYM 52608
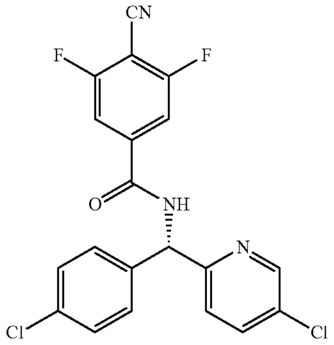
CYM 52609
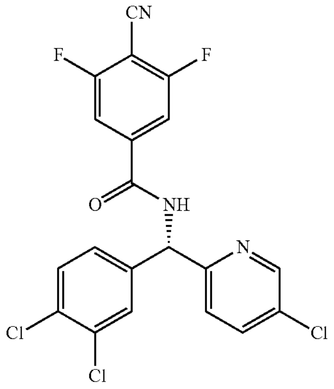
CYM 52610
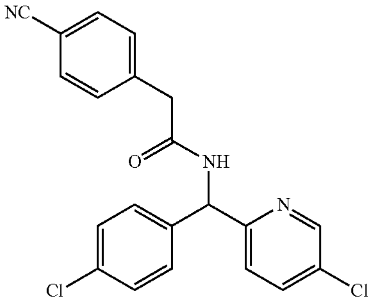
CYM 52612
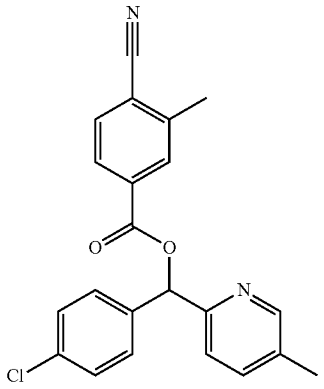
-continued
CYM 52614
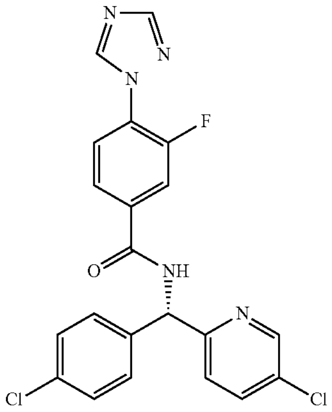
CYM 52616
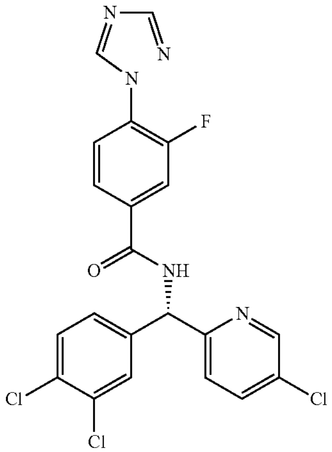
CYM 52617
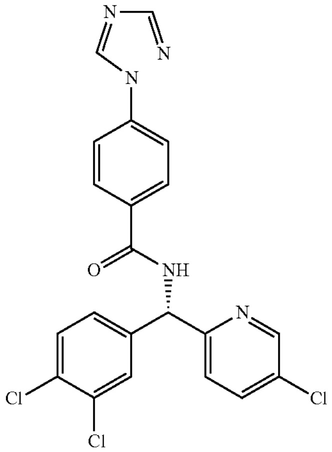

-continued
CYM 52618
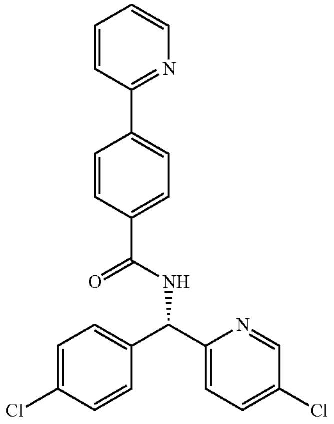
CYM 52619
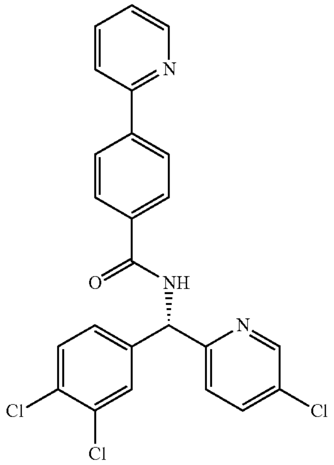
CYM 52620
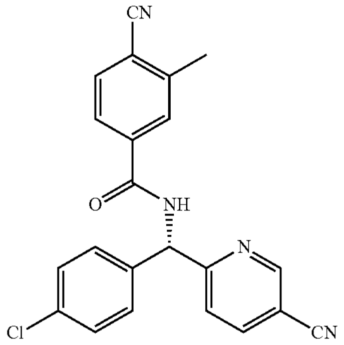
CYM 52621
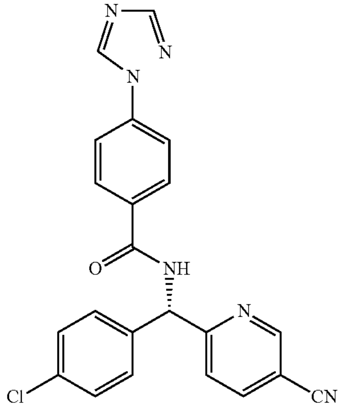
-continued
CYM 52622
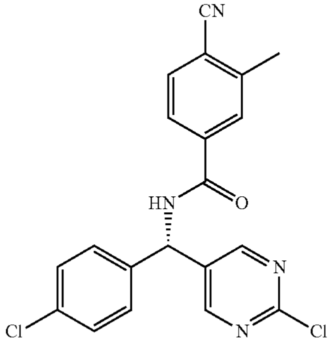
CYM 52623
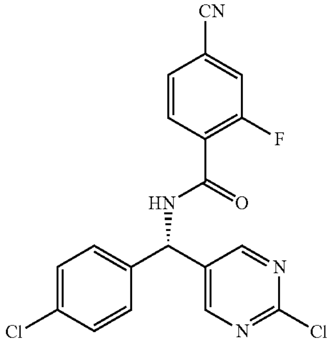
CYM 52624
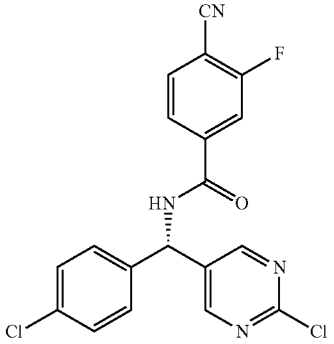
CYM 52627
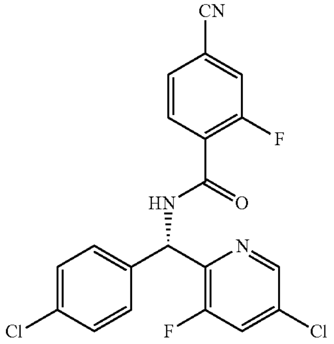

CYM 52628
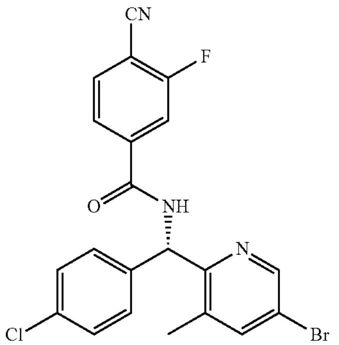
CYM 52629
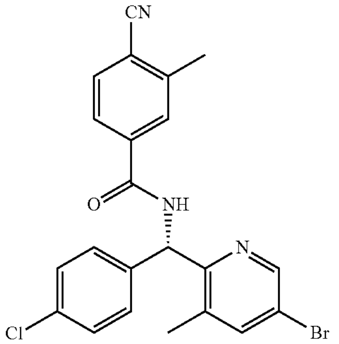
CYM 52630
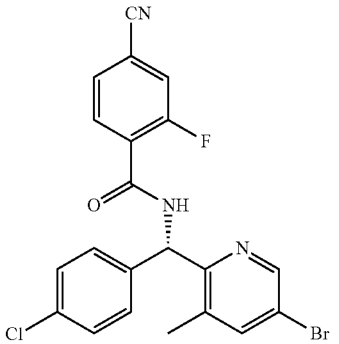
CYM 52631
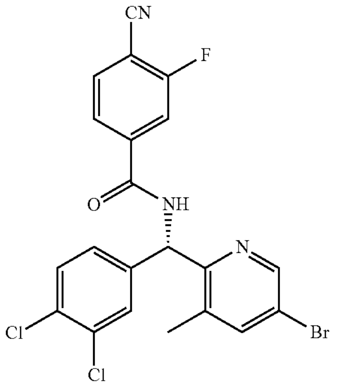
CYM 52632
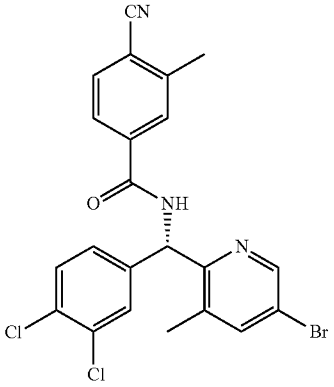
CYM 52633
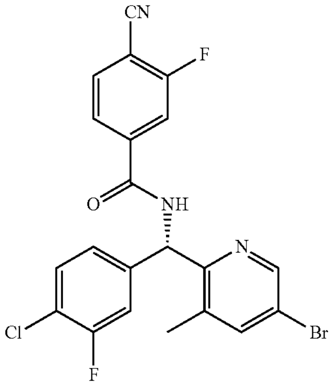
CYM 52634
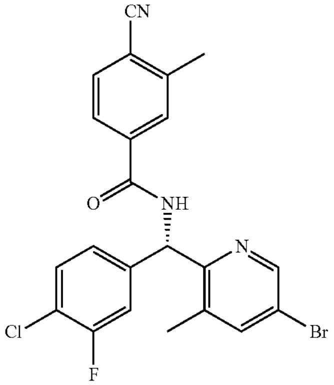
CYM 52636
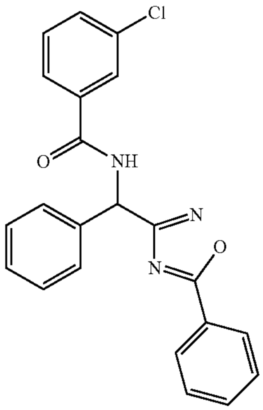

-continued
CYM 52637
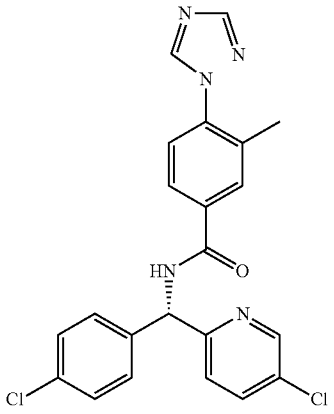
CYM 52640
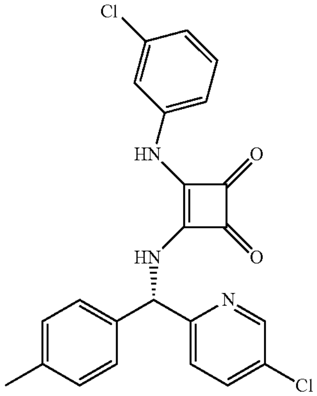
CYM 52643
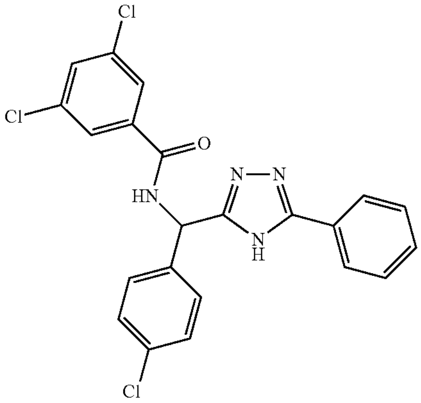
CYM 52648
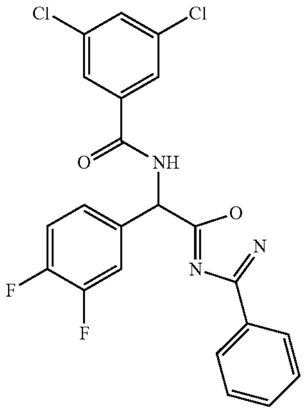
-continued
CYM 52649
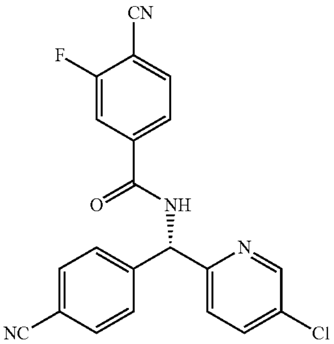
CYM 52650
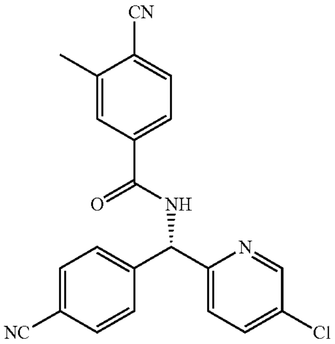
CYM 52651
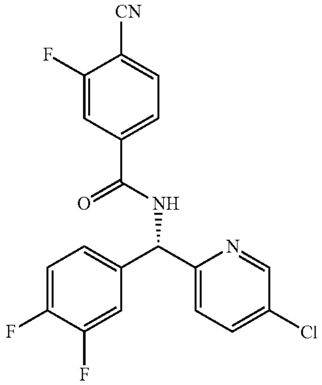
CYM 52652
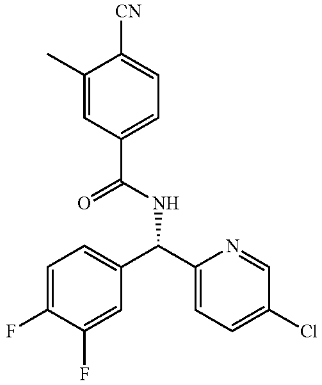

-continued
CYM 52653
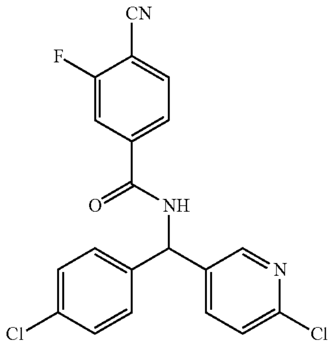
CYM 52656
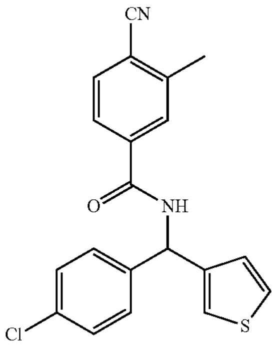
CYM 52657
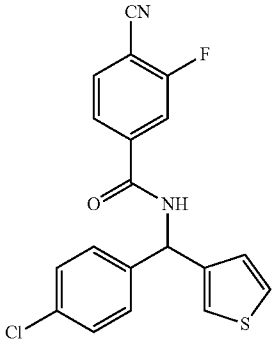
CYM 52658
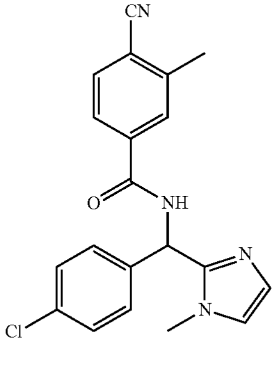
-continued
CYM 52659
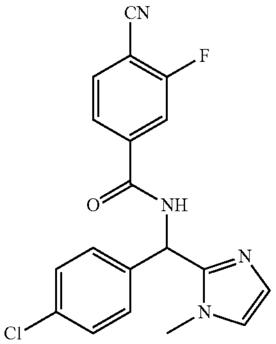
CYM 52663
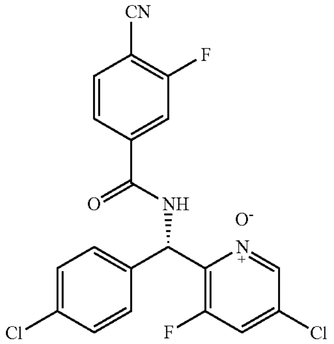
CYM 52664
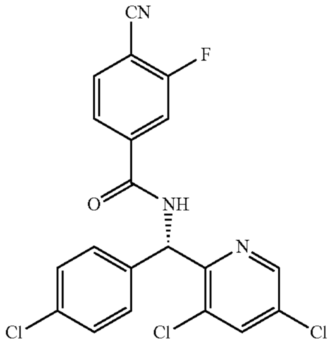
CYM 52665
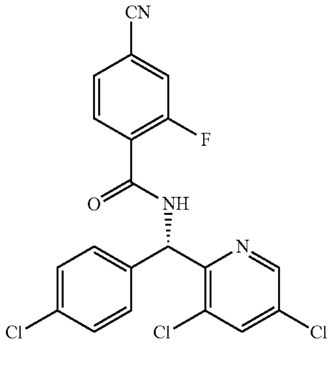

-continued
CYM 52666
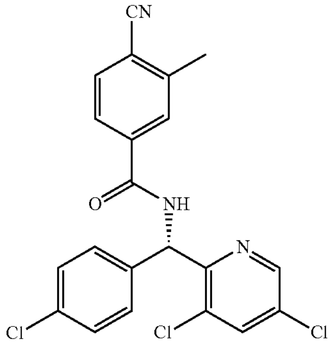
CYM 52667
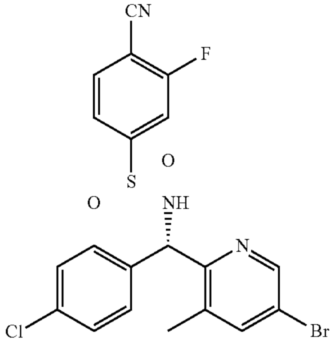
CYM 52670
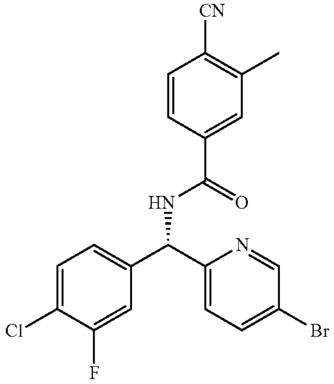
CYM 52671
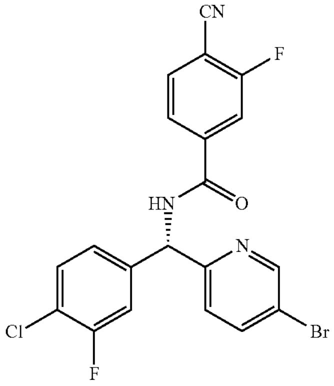
-continued
CYM 52672
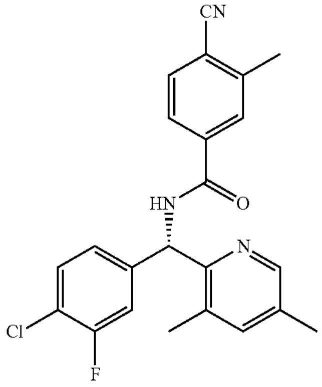
CYM 52673
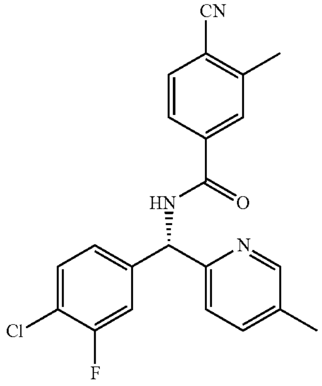
CYM 52674
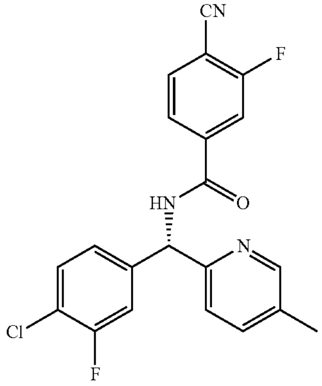
CYM 52675
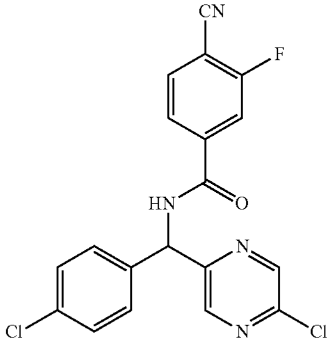

-continued
CYM 52676
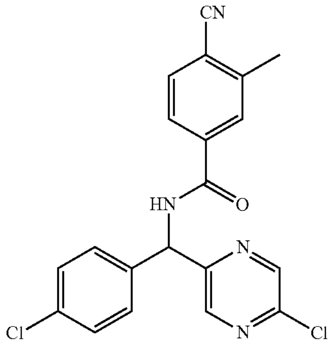
CYM 52677
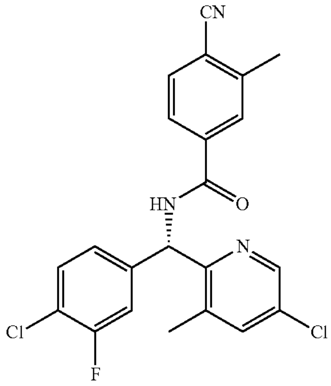
CYM 52678
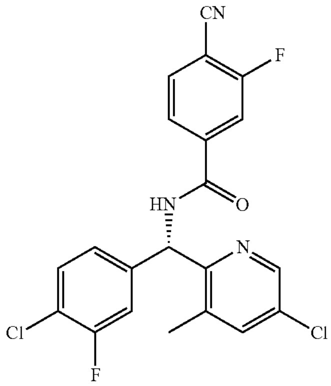
CYM 52679
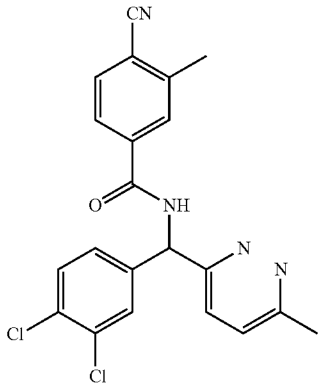
-continued
CYM 52683
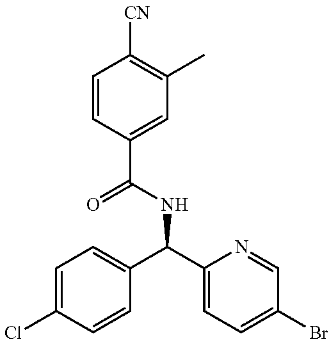
CYM 52684
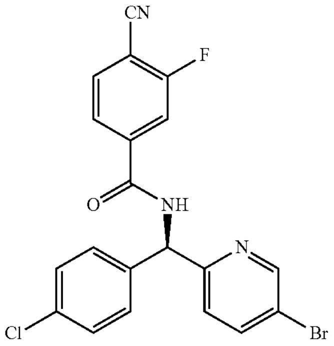
CYM 52685
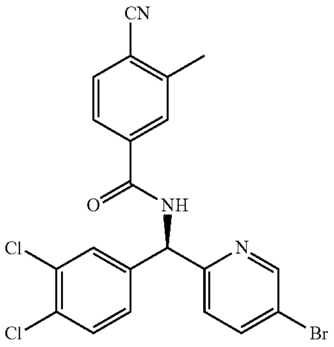
CYM 52686
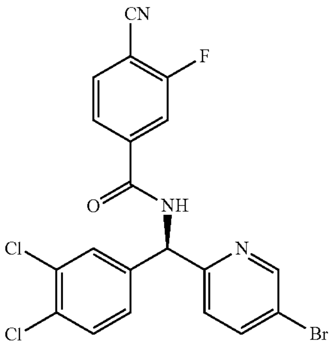

-continued
CYM 52689
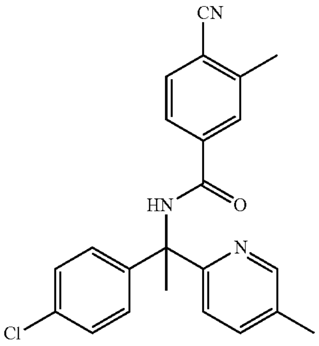
CYM 52690
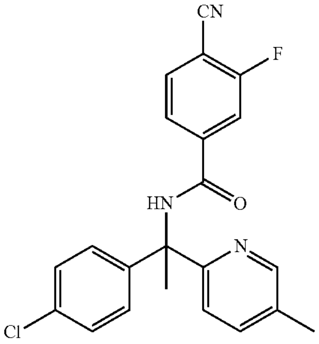
CYM 52691
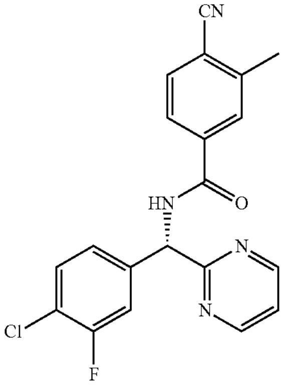
CYM 52692
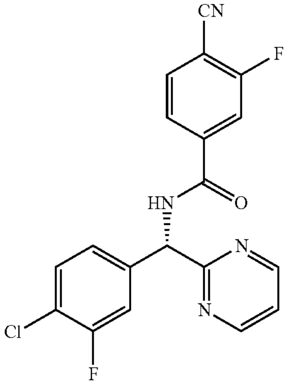
-continued
CYM 52693
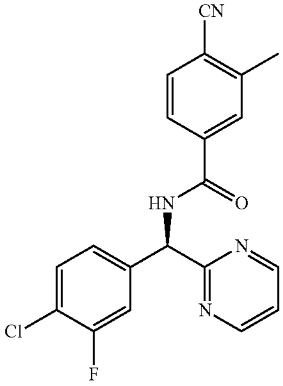
CYM 52694
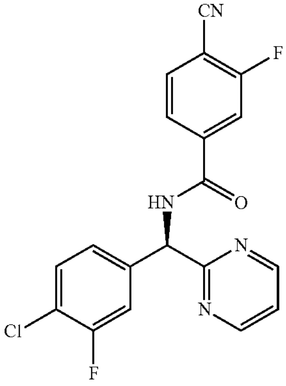
CYM 52695
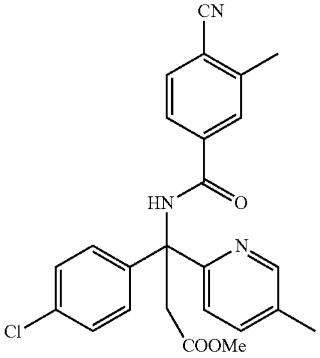
CYM 52696
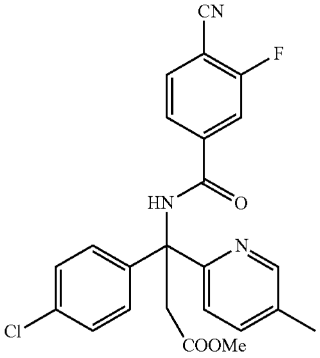

-continued
CYM 52697
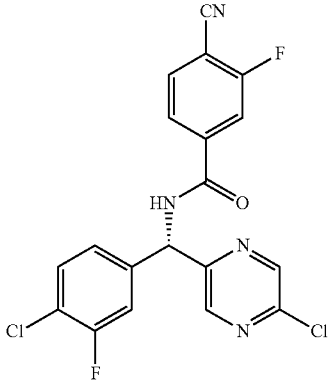
CYM 52698
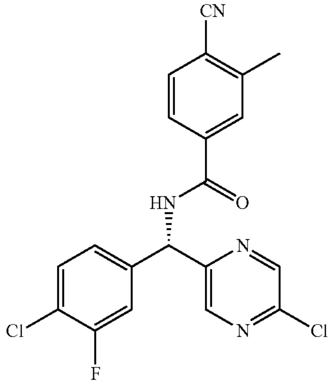
CYM 52699
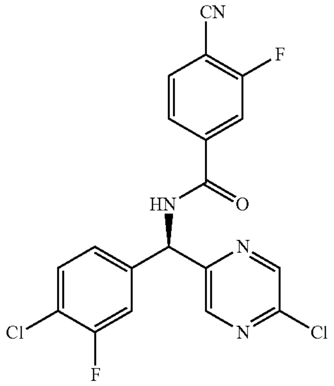
CYM 52700
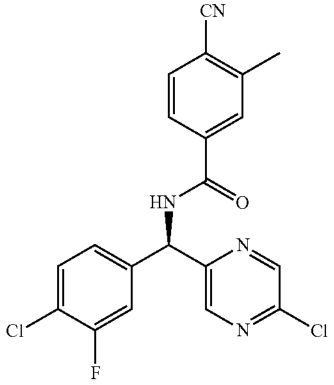
-continued
CYM 52701
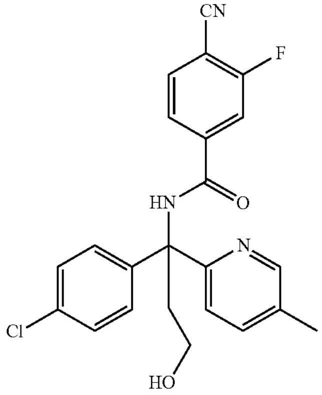
CYM 52702
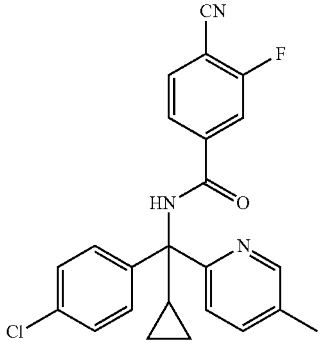
CY 52703
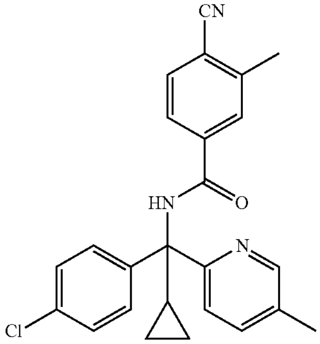
CYM 52705
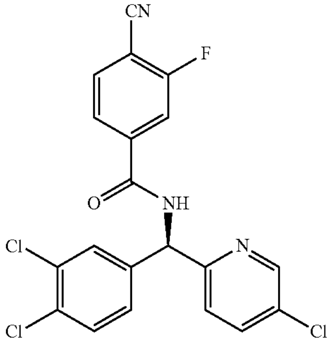

-continued
CYM 52706
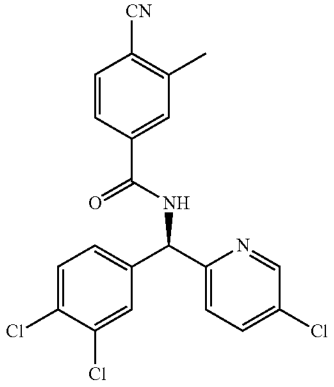
CYM 52707
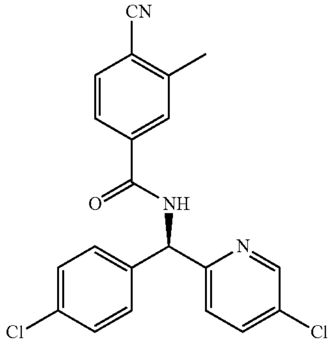
CYM 52708
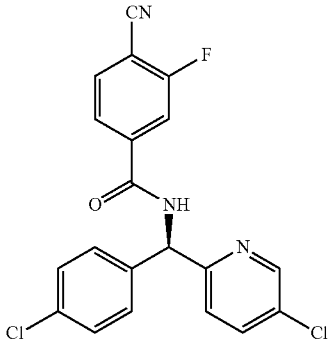
CYM 52709
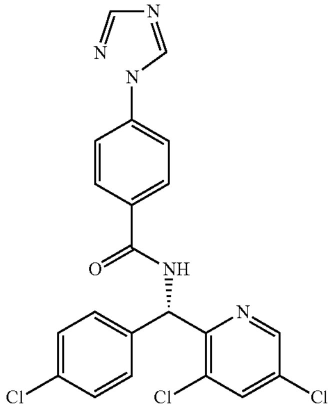
-continued
CYM 52710
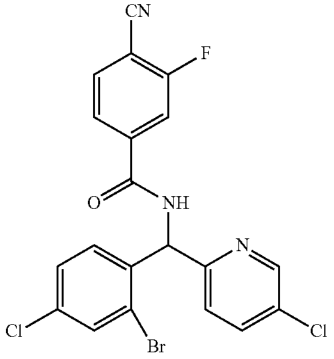
CYM 52711
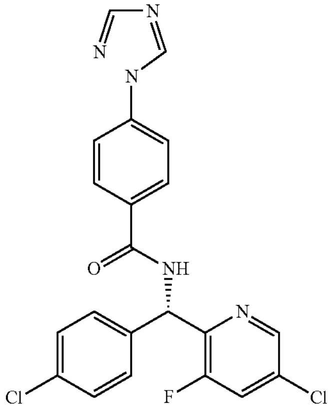
CYM 52714
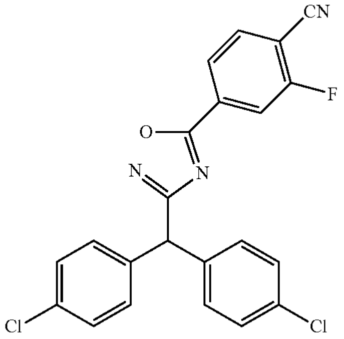
CYM 52715
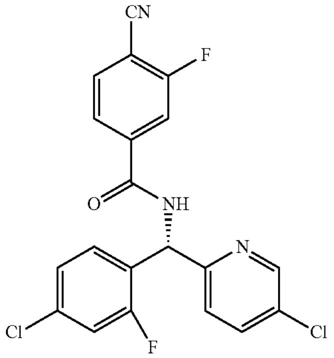

-continued
CYM 52716
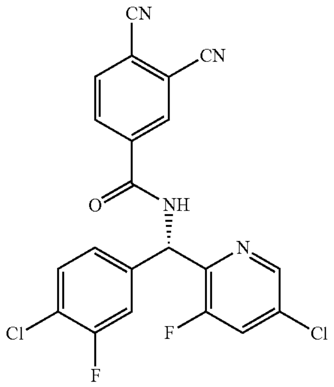
CYM 52717
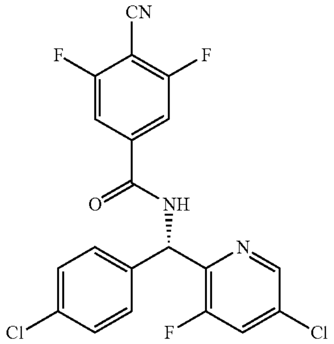
CYM 52718
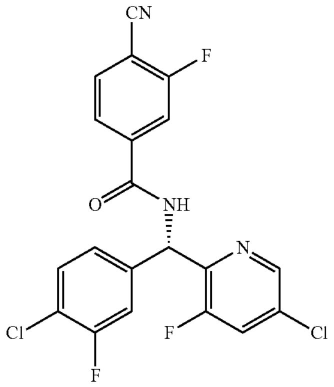
CYM 52719
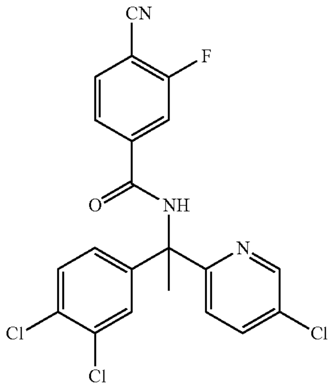
-continued
CYM 52720
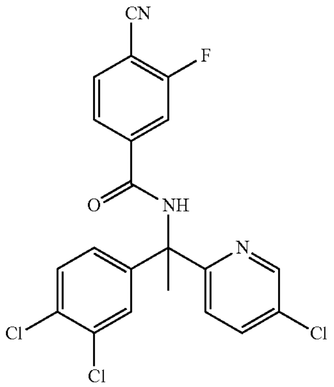
CYM 52721
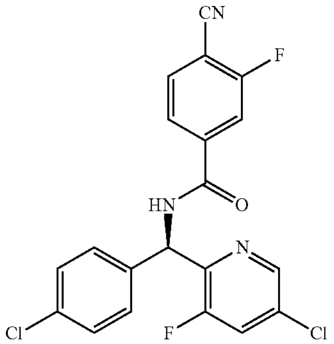
CYM 52722
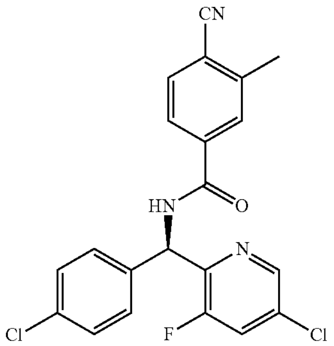
CYM 52723
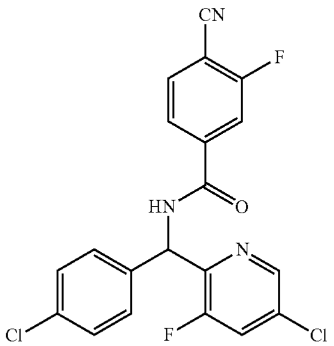

-continued
CYM 52724
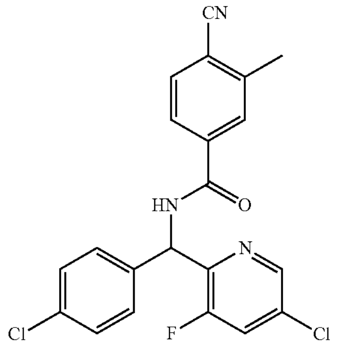
CYM 52725
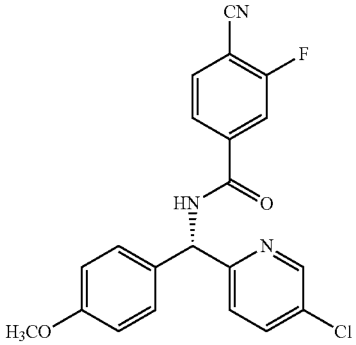
CYM 52727
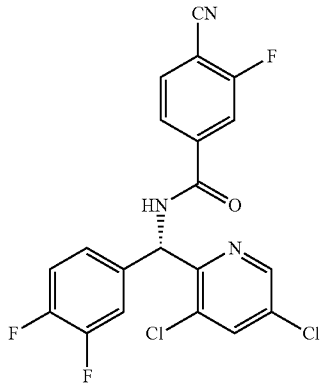
CYM 52729
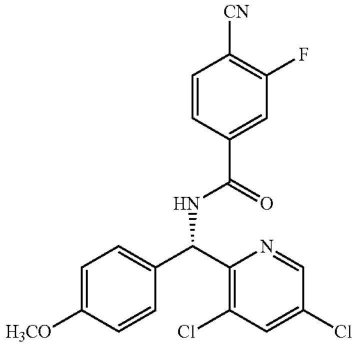
-continued
CYM 52730
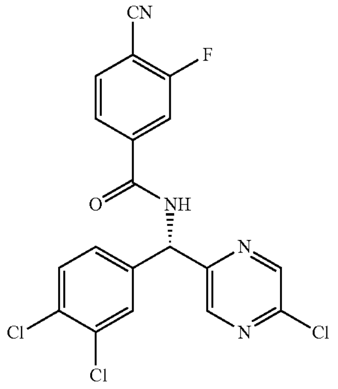
CYM 52731
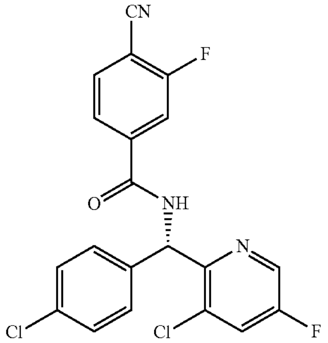
CYM 52732
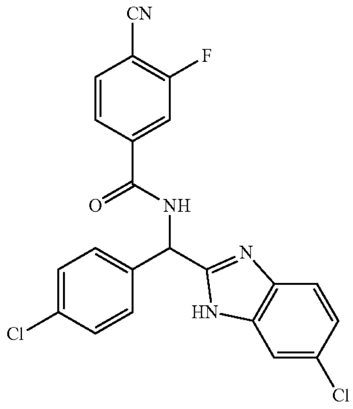
CYM 52734
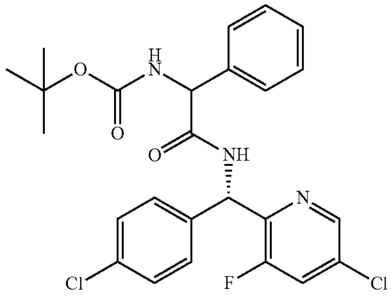

-continued
CYM 52735
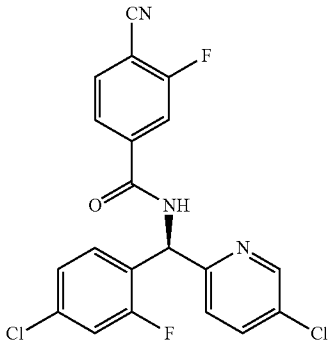
CYM 52736
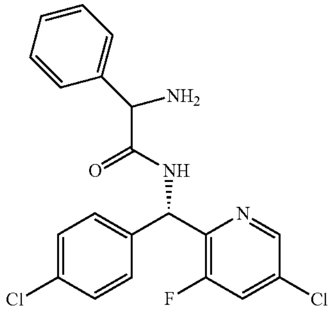
CYM 52737
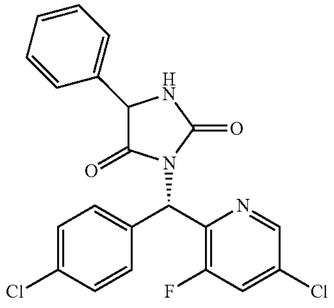
CYM 52739
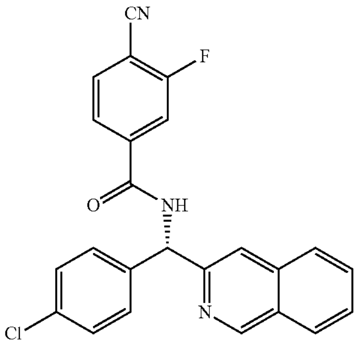
-continued
CYM 52740
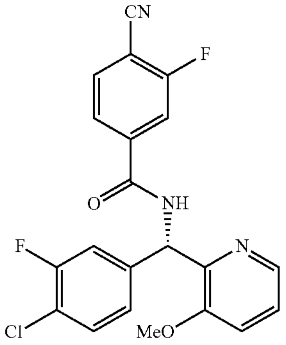
CYM 52744
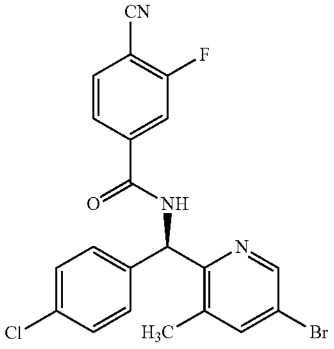
CYM 52746
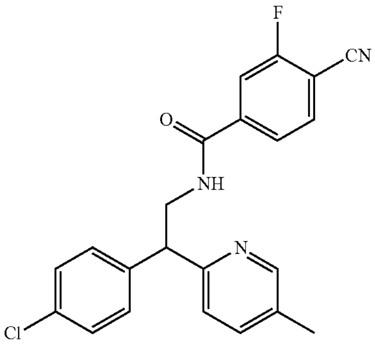
CYM 52747
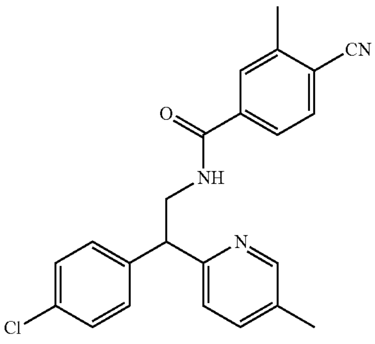

-continued
CYM 52748
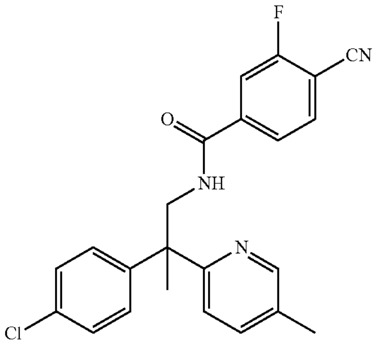
CYM 52750
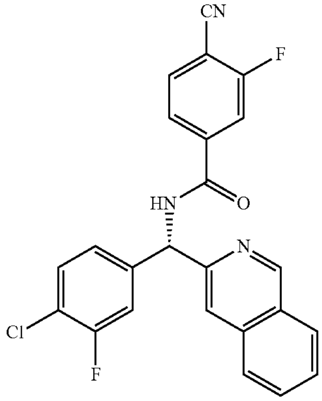
CYM 52752
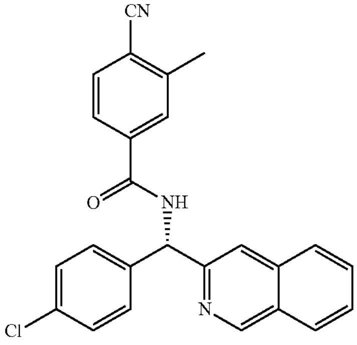
CYM 52754
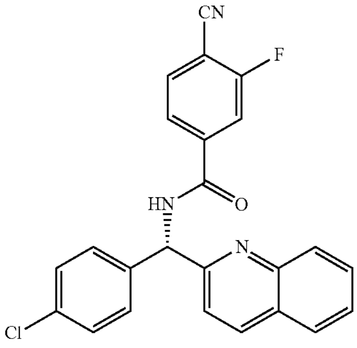
-continued
CYM 52763
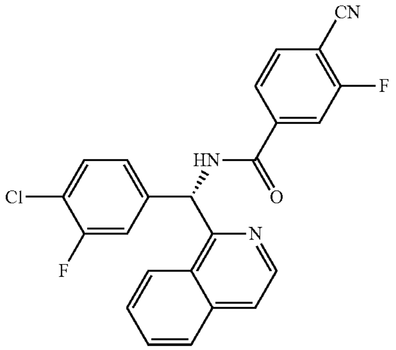
CYM 52775
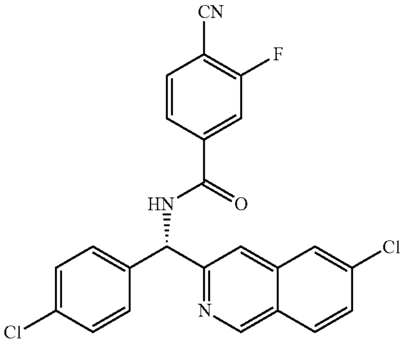
CYM 52780
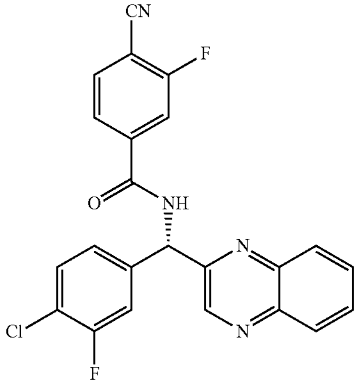
, or
CYM 52781
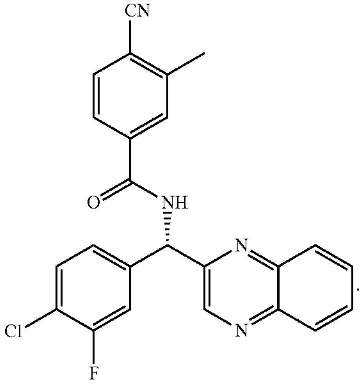
* * * * *